US012540330B2

(12) United States Patent
Erickson et al.

(10) Patent No.: US 12,540,330 B2
(45) Date of Patent: Feb. 3, 2026

(54) STEM-LOOP COMPOSITIONS AND METHODS FOR INHIBITING VASCULAR ENDOTHELIAL GROWTH FACTOR

(71) Applicants: DRIVE THERAPEUTICS LLC, Chapel Hill, NC (US); ALBERT EINSTEIN COLLEGE OF MEDICINE, INC., Bronx, NY (US)

(72) Inventors: Carl Erickson, Corte Madera, CA (US); Christopher P. Rusconi, Durham, NC (US); Matthew Levy, Chapel Hill, NC (US); Keith E. Maier, Durham, NC (US); Sarah E. Thacker, Fuquay-Varina, NC (US); Derek Parks, Raleigh, NC (US)

(73) Assignees: DRIVE THERAPEUTICS LLC, Chapel Hill, NC (US); ALBERT EINSTEIN COLLEGE OF MEDICINE, Bronx, NY (US)

( * ) Notice: Subject to any disclaimer, the term of this patent is extended or adjusted under 35 U.S.C. 154(b) by 1059 days.

(21) Appl. No.: 17/422,034

(22) PCT Filed: Jan. 10, 2020

(86) PCT No.: PCT/US2020/013192

§ 371 (c)(1),
(2) Date: Jul. 9, 2021

(87) PCT Pub. No.: WO2020/146801

PCT Pub. Date: Jul. 16, 2020

(65) Prior Publication Data

US 2022/0098591 A1 Mar. 31, 2022

Related U.S. Application Data

(60) Provisional application No. 62/791,611, filed on Jan. 11, 2019.

(51) Int. Cl.
*C12N 15/115* (2010.01)
*C12Q 1/68* (2018.01)

(52) U.S. Cl.
CPC ........ *C12N 15/115* (2013.01); *C12N 2310/16* (2013.01); *C12N 2310/3183* (2013.01); *C12N 2310/531* (2013.01)

(58) Field of Classification Search
None
See application file for complete search history.

(56) References Cited

U.S. PATENT DOCUMENTS

2015/0037889 A1 2/2015 Cochran et al.

OTHER PUBLICATIONS

Nonaka, Y., et al., "Screening and Improvement of an Anti-VEGF DNA Aptamer," Molecules 2010, 15:215-225; doi:10.3390/molecules15010215.
International Search Report for PCT/US20/13192 mailed Jun. 23, 2020, 3 pages.

*Primary Examiner* — Sean Mcgarry
(74) *Attorney, Agent, or Firm* — Rothwell, Figg, Ernst & Manbeck, P.C.

(57) ABSTRACT

The application discloses methods and compositions for inhibiting functions associated with vascular endothelial growth factor-A (VEGF-A). The methods and compositions may involve the use of pan-variant specific aptamers for binding to VEGF-A, and preventing or reducing association of VEGF-A with Flt-1, KDR, or Nrp-1. The methods and compositions may include one or more aptamers that bind to receptor binding face of VEGF-A. The methods and compositions may include one or more aptamers that bind to a receptor binding domain of VEGF-A. The application further provides anti-VEGF-A aptamers for the treatment of ocular diseases or disorders. In some cases, the anti-VEGF-A aptamers may have a stem-loop secondary structure.

19 Claims, 30 Drawing Sheets

Specification includes a Sequence Listing.

FIG. 1A
GGGAGUGUGUACGAGGCAUU-AGGCCGCC-N30-GGCGGCUU-UGAUACUUGAUCGCCCUAGAAGC
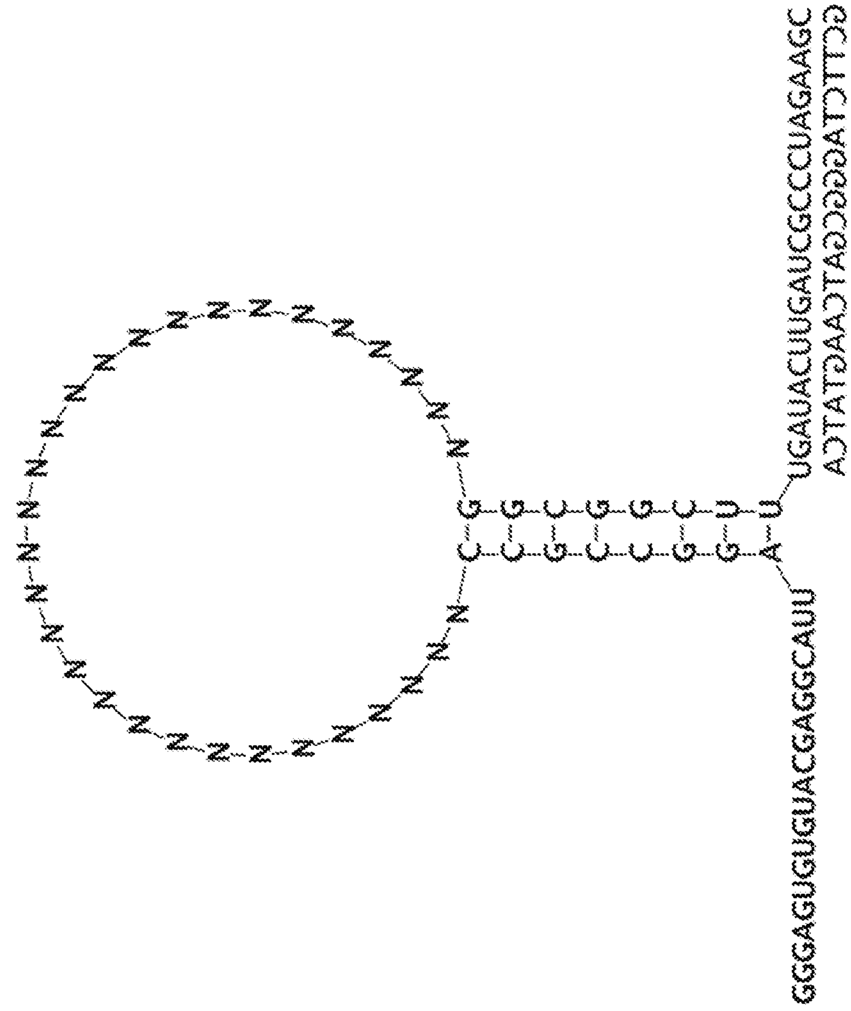
FIG. 1B
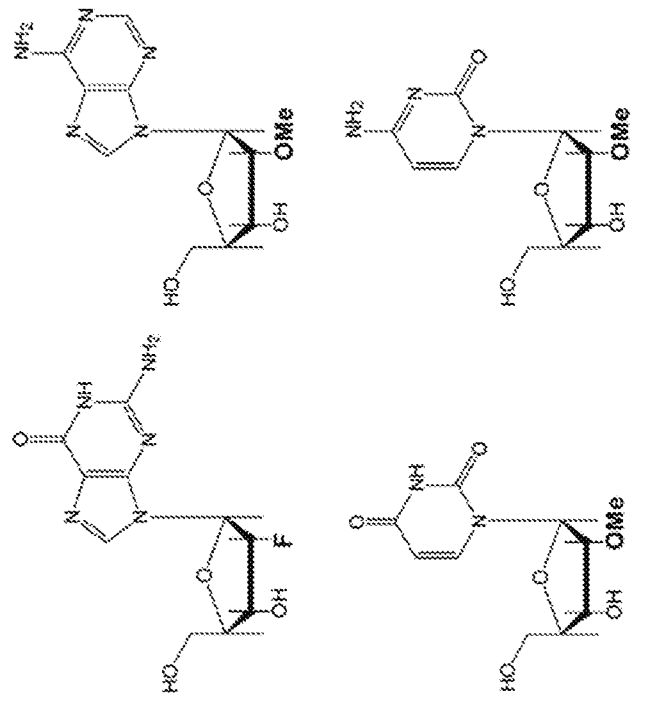
FIG. 1C

| Structure: | S1 | | | | | | | | L1 | S2 | | L2 | | | | S2 | | L3 | S3 | | | | |
|---|---|---|---|---|---|---|---|---|---|---|---|---|---|---|---|---|---|---|---|---|---|---|---|
| Position: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| Aptamer 26: | A | U | G | C | C | G | C | C | U | C | C | G | C | G | C | G | G | A | G | G | G | G | U |
| A | 96.6% | 32.5% | 0.0% | 0.0% | 14.8% | 1.6% | 0.0% | 0.0% | 0.0% | 0.0% | 0.0% | 0.0% | 0.0% | 0.0% | 0.0% | 0.0% | 0.0% | 100.0% | 0.0% | 0.0% | 0.0% | 23.5% | 0.0% |
| C | 0.8% | 1.3% | 0.1% | 97.7% | 83.6% | 0.0% | 100.0% | 100.0% | 0.0% | 100.0% | 100.0% | 0.0% | 100.0% | 0.0% | 100.0% | 0.0% | 0.0% | 0.0% | 0.0% | 0.0% | 0.0% | 0.0% | 0.0% |
| G | 0.0% | 19.3% | 95.5% | 0.0% | 0.0% | 91.6% | 0.0% | 0.0% | 0.0% | 0.0% | 0.0% | 100.0% | 0.0% | 100.0% | 0.0% | 100.0% | 100.0% | 0.0% | 100.0% | 100.0% | 100.0% | 76.5% | 0.0% |
| U | 2.5% | [illegible] | 4.4% | 2.3% | 21.7% | 6.9% | 0.0% | 0.0% | 100.0% | 0.0% | 0.0% | 0.0% | 0.0% | 0.0% | 0.0% | 0.0% | 0.0% | 0.0% | 0.0% | 0.0% | 0.0% | 0.0% | 100.0% |

| Structure: | L4 | | | | | | S3 | | | | | L5 | | | | S1 | | | | | | | |
|---|---|---|---|---|---|---|---|---|---|---|---|---|---|---|---|---|---|---|---|---|---|---|---|
| Position: | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 |
| Aptamer 26: | U | U | C | A | U | U | A | U | C | C | C | G | U | U | U | G | G | C | G | G | C | U | U |
| A | 13.9% | 11.6% | 1.4% | 99.2% | 0.3% | 14.9% | 99.6% | 0.0% | 0.0% | 0.0% | 0.0% | 0.0% | 0.0% | 0.0% | 0.0% | 0.0% | 0.0% | 0.0% | 0.8% | 0.0% | 0.5% | 34.2% | 0.2% |
| C | 0.0% | 0.0% | 96.8% | 0.0% | 3.8% | 1.1% | 0.0% | 1.1% | 100.0% | 100.0% | 100.0% | 0.0% | 0.3% | 0.0% | 0.0% | 0.0% | 0.0% | 97.4% | 4.9% | 0.0% | 99.1% | 6.0% | 0.0% |
| G | 1.1% | 2.6% | 1.1% | 0.3% | 0.0% | 0.0% | 0.0% | 0.0% | 0.0% | 0.0% | 0.0% | 100.0% | 0.0% | 0.0% | 0.0% | 100.0% | 95.8% | 0.0% | 25.9% | 98.8% | 0.1% | 0.6% | 0.0% |
| U | 85.0% | 85.2% | 0.7% | 0.4% | 95.9% | 84.0% | 0.4% | 98.9% | 0.0% | 0.0% | 0.0% | 0.0% | 99.7% | 100.0% | 100.0% | 0.0% | 4.2% | 2.6% | 68.4% | 1.2% | 0.0% | 59.1% | 99.8% |

FIG. 6

STEM-LOOP COMPOSITIONS AND METHODS FOR INHIBITING VASCULAR ENDOTHELIAL GROWTH FACTOR

CROSS REFERENCE TO RELATED APPLICATION

This application is a 35 U.S.C. 371 National Phase Entry Application from PCT/US2020/013192, filed Jan. 10, 2020, which claims priority to U.S. provisional Application No. 62/791,611, filed Jan. 11, 2019, the disclosures of which are incorporated herein by reference in their entireties, and priority is claimed to each of the foregoing.

BACKGROUND OF THE INVENTION

Visual impairment is a national and global health concern that has a negative impact on physical and mental health. The number of people with visual impairment and blindness is increasing due to an overall aging population. Visual impairment and blindness can be caused by any one of a large number of eye diseases and disorders affecting people of all ages.

Vascular endothelial growth factor-A (VEGF-A) is thought to be the most significant regulator of angiogenesis in the VEGF family. VEGF-A promotes growth of vascular endothelial cells, which leads to the formation of capillary-like structures and may be necessary for the survival of newly formed blood vessels. VEGF-A is thought to play a role in various ocular diseases and disorders. Previous attempts at developing aptamers that inhibit VEGF-A have proven difficult because such aptamers have been unable to target multiple isoforms and variants of VEGF-A. Therefore, there is an un-met need for pan-variant specific aptamers that demonstrate high specificity and potency towards multiple isoforms and variants of VEGF-A.

These needs may be met by the aptamers provided in the present disclosure.

SUMMARY OF THE INVENTION

In one aspect, an aptamer is provided having a nucleic acid sequence, wherein the aptamer comprises a stem-loop secondary structure which specifically binds to and inhibits at least one of VEGF-$A_{121}$ and VEGF-$A_{110}$. In some cases, the aptamer comprises up to five loops. In some cases, the aptamer comprises up to three stems. In some cases, the aptamer comprises up to one terminal stem. In some cases, the aptamer comprises up to two internal stems. In some cases, the aptamer comprises up to two terminal loops. In some cases, the aptamer comprises up to three internal loops. In some cases, the aptamer comprises, in a 5' to 3' direction: (i) a first side of a first base paired stem (S1); (ii) optionally, a first loop (L1); (iii) a first side of a second base paired stem (S2); (iv) a second loop (L2); (v) a second side of the second base paired stem (S2'); (vi) a third loop (L3); (vii) a first side of a third base paired stem (S3); (vii) a fourth loop (L4); (viii) a second side of the third base paired stem (S3'); (ix) a fifth loop (L5); and (x) a second side of the first base paired stem (S1'). In some cases, the S1' forms at least one base pair with the S1. In some cases, the S1' forms from two to eight contiguous base pairs with the S1. In some cases, the S1' comprises from one to three nucleotides that are mismatched with the S1. In some cases, a 3' terminal nucleotide of the S1, and a 5' terminal nucleotide of the S1' form a base pair. In some cases, the base pair is C*G. In some cases, the base pair is separated from other base pairs in the S1 and the S1' by one or more mismatched nucleotides. In some cases, the S1 comprises a consensus nucleic acid sequence of 5'-HNBYHDCC-3', and the S1' comprises a consensus nucleic acid sequence of 5'-GKYNKVNW-3', where H is A, C, or U; N is A, C, G, or U; B is C, G, or U; Y is C or U; D is A, G, or U; K is G or U; V is A, C, or G; and W is A or U. In some cases, the S1 comprises a consensus nucleic acid sequence of 5'-HNBYHDNN-3', and the S1' comprises a consensus nucleic acid sequence of 5'-NNYNKVNW-3', where H is A, C, or U; N is A, C, G, or U; B is C, G, or U; Y is C or U; and D is A, G, or U. In some cases, the L1 comprises up to one nucleotide. In some cases, the L1 comprises a consensus nucleic acid sequence of 5'-N*-3', wherein N* is A, C, G, U, a 3-carbon non-nucleotidyl spacer, two 3 carbon non-nucleotidyl spacers, a 6-carbon non-nucleotidyl spacer, or a 9-carbon non-nucleotidyl spacer. In some cases, the 3-carbon non-nucleotidyl spacer is 1,3-propanediol. In some cases, the 6-carbon non-nucleotidyl spacer is 1,6-hexanediol. In some cases, the 9-carbon non-nucleotidyl spacer is triethyleneglycol. In some cases, the S2' forms at least one base pair with the S2. In some cases, the S2' forms up to two base pairs with the S2. In some cases, the S2 comprises a consensus nucleic acid sequence of 5'-CC-3', and the S2' comprises a consensus nucleic acid sequence of 5'-GG-3'. In some cases, the S2 comprises a consensus nucleic acid sequence of 5'-NN-3', and the S2' comprises a consensus nucleic acid sequence of 5'-NN-3', where N is A, C, G, or U. In some cases, the L2 comprises up to four nucleotides. In some cases, the L2 comprises a consensus nucleic acid sequence of 5'-GCGC-3'. In some cases, the L2 comprises a consensus nucleic acid sequence of 5'-KNGC-3', where K is G or U; and N is A, C, G or U. In some cases, the S3' forms at least one base pair with the S3. In some cases, the S3' forms from four to six base pairs with the S3. In some cases, the S3' forms six base pairs with the S3, and the S3 has one mismatch nucleotide at a 3' terminal nucleotide of the S3. In some cases, the S3' forms four base pairs with the S3, and the L4 has six or eight nucleotides. In some cases, the S3' forms five base pairs with the S3, and the L4 has four or six nucleotides. In some cases, the S3' forms six base pairs with the S3, and the L4 has four nucleotides. In some cases, the S3' forms six base pairs with S3, the S3 has one mismatch nucleotide at a 3' terminal nucleotide, and the L4 has three nucleotides. In some cases, the S3 comprises a consensus nucleic acid sequence of 5'-GRGRWN3', and the S3' comprises a consensus nucleic acid sequence of 5'-NHYCYC-3', where R is A or G; N is A, C, G, or U; W is A or U; and Y is C or U. In some cases, the S3 comprises a consensus nucleic acid sequence of 5'-GGGRUN3', and the S3' comprises a consensus nucleic acid sequence of 5'-NWYCCC-3', where R is A or G; N is A, C, G, or U; W is A or U; and Y is C or U. In some cases, the S3 comprises a consensus nucleic acid sequence of 5'-GGGRUN3', and the S3' comprises a consensus nucleic acid sequence of 5'-NAYCCC-3', where R is A or G; N is A, C, G, or U; and Y is C or U. In some cases, the S3 comprises a consensus nucleic acid sequence of 5'-GGGRUD-3', and the S3' comprises a consensus nucleic acid sequence of 5'-HWYCCC-3', wherein R is A or G; D is A, G, or U; H is A, C, or U; W is A or U; and Y is C or U. In some cases, the S3 comprises a consensus nucleic acid sequence of 5'-GKGN-3', and the S3' comprises a consensus nucleic acid sequence of 5'-NSMC-3', where K is G or U; N is A, C, G or or U and M is A or C. In some cases, the S3 comprises a consensus nucleic acid sequence of 5'-GGGG-3', and the S3' comprises a consensus nucleic acid sequence of 5'-CCCC-3'. In some cases, the S3 comprises a consensus nucleic acid sequence of 5'-GGGU-3', and the S3' comprises a consensus nucleic acid sequence of 5'-ACCC-3'. In some cases, the S3 comprises a consensus nucleic acid sequence of 5'-GGCU-3', and the S3' comprises a consensus nucleic acid sequence of 5'-AGCC-3'. In some cases, the S3 comprises a consensus nucleic acid sequence of 5'-GBBNY-3', and the S3' comprises a consensus nucleic acid sequence of 5'-RNBNC-3', where B is C, G or U; R is A or G; N is A, C, G or U and Y is C or U. In some cases, the S3 comprises a consensus nucleic acid sequence of 5'-GGGRU-3', and the S3' comprises a consensus nucleic acid sequence of 5'-AYCCC-3', where R is A or G; and Y is C or U. In some cases, the S3 comprises a consensus nucleic acid sequence of 5'-SVVVK-, and the S3' comprises a consensus nucleic acid sequence of 5'-MBBBS-3', where S is G or C; V is A, C, or G; K is G or U; M is A or C; and B is C, G, or U. In some cases, the S3 comprises a consensus nucleic acid sequence of 5'-GGGGUD-3', and the S3' comprises a consensus nucleic acid sequence of 5'-HAUCCC-3', where D is A, G, or U; and H is A, C, or U. In some cases, the S3 comprises a consensus nucleic acid sequence of 5'-GGGRUUR-3', and the S3' comprises a consensus nucleic acid sequence of 5'-UAUCCC-3', where the underlined U is the single mis-matched nucleotide, and R is A or G. In some cases, the L3 comprises up to one nucleotide. In some cases, the L3 comprises a consensus nucleic acid sequence of 5'-A-3'. In some cases, the L3 comprises a consensus nucleic acid sequence of 5'-W-3', where W is A or U. In some cases, the L4 has three, four, six, or eight nucleotides. In some cases, the L4 comprises a consensus nucleic acid sequence of 5'-MAU-3', where M is A or C. In some cases, the L4 comprises a consensus nucleic acid sequence of 5'-CUA-3'. In some cases, the L4 comprises a consensus nucleic acid sequence of 5'-DNAH-3', where D is A, G, or U; N is A, C, G, or U; and H is A, C, or U; or a consensus nucleic acid sequence of 5'-DNDH-3', where D is A, G, or U; N is A, C, G, or U; and H is A, C, or U; or a consensus nucleic acid sequence of 5'-DNDN-3', where D is A, G, or U; N is A, C, G, or U; and H is A, C, or U. In some cases, the L4 comprises a consensus nucleic acid sequence of 5'-UDNDHU-3', where D is A, G, or U; N is A, C, G, or U; and H is A, C, or U. In some cases, the L4 comprises a consensus nucleic acid sequence of 5'-UDRGBU-3', where D is A, G, or U; R is A or G, N is A, C, G, or U; and B is G, C, or U. In some cases, the L4 comprises a consensus nucleic acid sequence of 5'-KNNNNW-3', where K is U or G, N is A, C, G, or U; and W is A, or U. In some cases, the L4 comprises a consensus nucleic acid sequence of 5'-UDUHRKYU-3', where D is A D, or U; H is A, C or U; R is A or G; K is G or U and Y is C or U. In some cases, the L4 comprises a consensus nucleic acid sequence of 5'-UUUCAUUU-3'. In some cases, the L5 comprises up to four nucleotides. In some cases, the L5 comprises a consensus nucleic acid sequence of 5'-GYUU-3', where Y is C or U. In some cases, the L5 comprises a consensus nucleic acid sequence of GNNN-3', where N is A, C, G, or U. In some cases, the L5 comprises a consensus nucleic acid sequence of 5'-GNHW-3', where N is A, C, G, or U; H is A, C, or U; and W is A or U.

In another aspect, an aptamer is provided comprising a consensus nucleic acid sequence of 5'-HNBYHDC-CUCCGCGCGGAGG-GRUDDNDHHWYCCCGYUUGKYNKVNW-3' (SEQ ID NO: 1), where H is A, C, or U; N is A, C, G, or U; B is C, G, or U; Y is C or U; D is A, G, or U; R is A or G; W is A or U; K is G or U; and V is A, C, or G.

In yet another aspect, an aptamer is provided comprising a consensus nucleic acid sequence of 5'-HNBYHDC-CUCCGCGCGGAGGGRU-UDNDHUAYCCCGYUUGKYNKVNW-3' (SEQ ID NO: 2), where H is A, C, or U; N is A, C, G, or U; B is C, G, or U; Y is C or U; D is A, G, or U; R is A or G; K is G or U; V is A, C, or G; and W is A or U.

In yet another aspect, an aptamer is provided comprising a consensus nucleic acid sequence of 5'-WNKYHDC-CUCCGCGCGGAGGGGUDDNAHHAUCCCGUUUG-GYBKMHW-3' (SEQ ID NO: 3), where W is A or U; N is A, C, G, or U; K is G or U; Y is C or U; H is A, C, or U; D is A, G, or U; B is C, G, or U; and M is A or C.

In yet another aspect, an aptamer is provided comprising a consensus nucleic acid sequence of 5'-AUGCCGC-CUCCGCGCGGAGGGGUUU-CAUUUCCCCGUUUGGCUGCAU-3' (SEQ ID NO: 4).

In another aspect, an aptamer is provided comprising a consensus nucleic acid sequence of 5'-HNBYHDNNN*NNKNGCNNWGGGRUNDND-HNWYCCCGNNNNNYNKVNW-3' (SEQ ID NO: 5), where H is A, C, or U; N is A, C, G, or U; B is C, G, or U; Y is C or U; N* is A, C, G, U, deleted entirely, or a non-nucleotidyl spacer 3 modification, a 6 carbon alkyl linker (1,6-hexanediol), or a spacer 9 (triethyleneglycol) modification: D is A, G, or U; K is G or U; W is A or U; R is A or G; and V is A, C, or G.

In another aspect, an aptamer is provided comprising a consensus nucleic acid sequence of 5'-HNBYHDC-CUCCGCGCG-GAGDSBHDNNNNHNNBNCGYUUGKYNKVNW-3' (SEQ ID NO: 436), where H is A, C, or U; N is A, C, G, or U; B is C, G, or U; Y is C or U; D is A, G, or U; R is A or G; W is A or U; K is G or U; and V is A, C, or G.

In another aspect, an aptamer is provided comprising a consensus nucleic acid sequence of 5'-HNBYHDC-CUCCGCGCG-GAGKBHYDNNNKDBVCGYUUGKYNKVNW-3' (SEQ ID NO: 437), where H is A, C, or U; N is A, C, G, or U; B is C, G, or U; Y is C or U; D is A, G, or U; R is A or G; W is A or U; K is G or U; and V is A, C, or G.

In another aspect, an aptamer is provided comprising a consensus nucleic acid sequence of 5'-HNBYHDC-CUCCGCGCGGAGK-SHUDRGBUDSMCGYUUGKYNKVNW-3' (SEQ ID NO: 438), where H is A, C, or U; N is A, C, G, or U; B is C, G, or U; Y is C or U; D is A, G, or U; R is A or G; W is A or U; K is G or U; M is A or C; and V is A, C, or G.

In some cases, less than 50% of pyrimidines present in the nucleic acid sequence of any aptamer of the preceding comprise a C-5 modified pyrimidine. In some cases, less than 25% of pyrimidines present in the nucleic acid sequence of any aptamer of the preceding comprise a C-5 modified pyrimidine. In some cases, less than 10% of pyrimidines present in the nucleic acid sequence of any aptamer of the preceding comprise a C-5 modified pyrimidine. In some cases, the nucleic acid sequence of any aptamer of the preceding does not comprise any C-5 modified pyrimidines. In some cases, the C-5 modified pyrimidine comprises a C-5 modified cytosine or a C-5 modified uridine. In some cases, the C-5 modified pyrimidine comprises a C-5 hydrophobic modification. In some cases, less than 100% of uridines present in the nucleic acid sequence of any aptamer of the preceding comprise a C-5 modified uridine. In some cases, less than 50% of uridines present in the nucleic acid sequence of any aptamer of the preceding comprise a C-5 modified uridine. In some cases, less than 25% of uridines present in the nucleic acid sequence of any aptamer of the preceding comprise a C-5 modified uridine. In some cases, less than 10% of uridines present in the nucleic acid sequence of any aptamer of the preceding comprise a C-5 modified uridine. In some cases, no uridines present in the nucleic acid sequence of any aptamer of the preceding comprise a C-5 modified uridine. In some cases, the C-5 modified uridine comprises a C-5 hydrophobic modification. In some cases, the C-5 modified uridine is selected from the group consisting of: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-tyrosylcarboxyamide)-2'-deoxyuridine (TyrdU), 5-(N-3,4-methylenedioxybenzylcarboxyamide)-2'-deoxyuridine (MBndU), 5-(N-4-fluorobenzylcarboxyamide)-2'-deoxyuridine (FBndU), 5-(N-3-phenylpropylcarboxyamide)-2'-deoxyuridine (PPdU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine. In some cases, the C-5 modified uridine is 5-(N-naphthylmethylcarboxyamide)-2'-deoxyuridine (NapdU).

In some cases, any aptamer of the preceding selectively binds to a receptor binding face or receptor binding domain of VEGF-$A_{121}$ or VEGF-$A_{110}$. In some cases, the receptor binding domain comprises at least one of residues 1-109 of SEQ ID NO: 6-10. In some cases, the receptor binding domain comprises at least one of residues Phe17, Ile43, Ile46, Glu64, Gln79, Ile83, Lys84, Pro85, Arg82, His86, Asp63, and Glu67 of SEQ ID NO: 6-10. In some cases, any aptamer of the preceding inhibits VEGF-$A_{121}$, VEGF-$A_{110}$, or both, with an $IC_{50}$ of less than about 50 nM as measured by a VEGF-A:KDR competition binding assay, a KDR phosphorylation AlphaLISA® assay, or an in vitro model of VEGF-A-induced angiogenesis. In some cases, any aptamer of the preceding inhibits VEGF-$A_{121}$, VEGF-$A_{110}$, or both, with an $IC_{50}$ of less than about 25 nM as measured by a VEGF-A:KDR competition binding assay, a KDR phosphorylation AlphaLISA® assay, or an in vitro model of VEGF-A-induced angiogenesis. In some cases, any aptamer of the preceding inhibits VEGF-$A_{121}$, VEGF-$A_{110}$, or both, with an $IC_{50}$ of less than about 10 nM as measured by a VEGF-A:KDR competition binding assay, a KDR phosphorylation AlphaLISA® assay, or an in vitro model of VEGF-A-induced angiogenesis. In some cases, any aptamer of the preceding inhibits VEGF-$A_{121}$, VEGF-$A_{110}$, or both, with an $IC_{50}$ of less than about 5 nM as measured by a VEGF-A:KDR competition binding assay, a KDR phosphorylation AlphaLISA® assay, or an in vitro model of VEGF-A-induced angiogenesis. In some cases, any aptamer of the preceding inhibits VEGF-$A_{121}$, VEGF-$A_{110}$, or both, with an $IC_{50}$ of less than about 1 nM as measured by a VEGF-A:KDR competition binding assay, a KDR phosphorylation AlphaLISA® assay, or an in vitro model of VEGF-A-induced angiogenesis. In some cases, any aptamer of the preceding binds to VEGF-$A_{121}$, VEGF-$A_{110}$, or both, with a $K_d$ of less than about 50 nM as measured by surface plasmon resonance assay. In some cases, any aptamer of the preceding binds to VEGF-$A_{121}$, VEGF-$A_{110}$, or both, with a $K_d$ of less than about 25 nM as measured by surface plasmon resonance assay. In some cases, any aptamer of the preceding binds to VEGF-$A_{121}$, VEGF-$A_{110}$, or both, with a $K_d$ of less than about 10 nM as measured by surface plasmon resonance assay. In some cases, any aptamer of the preceding aptamer binds to VEGF-$A_{121}$, VEGF-$A_{110}$, or both, with a $K_d$ of less than about 5 nM as measured by surface plasmon resonance assay. In some cases, any aptamer of the preceding binds to VEGF-$A_{121}$, VEGF-$A_{110}$, or both, with a $K_d$ of less than about 1 nM as measured by surface plasmon resonance assay. In some cases, any aptamer of the preceding selectively binds to and inhibits at least one of VEGF-$A_{165}$, VEGF-$A_{189}$, and VEGF-$A_{206}$. In some cases, any aptamer of the preceding inhibits or reduces an interaction of VEGF-A with KDR. In some cases, any aptamer of the preceding inhibits or reduces VEGF-A-induced KDR phosphorylation.

In some cases, any aptamer of the preceding comprises RNA or sugar-modified RNA. In some cases, any aptamer of the preceding comprises DNA or sugar-modified DNA. In some cases, at least 50% of the nucleic acid sequence of any aptamer of the preceding comprises sugar-modified nucleotides. In some cases, 100% of the nucleic acid sequence of any aptamer of the preceding comprises sugar-modified nucleotides. In some cases, the sugar-modified nucleotides comprise a 2'F-modified nucleotide, a 2'OMe-modified nucleotide, or both. In some cases, the sugar-modified nucleotides are selected from the group consisting of: 2'F-G, 2'OMe-G, 2'OMe-U, 2'OMe-A, 2'OMe-C, and any combination thereof. In some cases, any aptamer of the preceding further comprises a 3' terminal inverted deoxythymidine. In some cases, any aptamer of the preceding comprises a nuclease-stabilized nucleic acid backbone. In some cases, the nucleic acid sequence of any aptamer of the preceding comprises from about 30 to about 90 nucleotides, wherein the nucleotides are unmodified nucleotides, modified nucleotides, or a combination of modified nucleotides and unmodified nucleotides. In some cases, any aptamer of the preceding is conjugated to a polyethylene glycol (PEG) molecule. In some cases, the PEG molecule has a molecular weight selected from the group consisting of: less than 5 kDa, less than 10 kDa, less than 20 kDa, less than 40 kDa, less than 60 kDa, and less than 80 kDa. In some cases, up to five nucleotides of any aptamer of the preceding comprise a phosphate-backbone modification. In some cases, the phosphate-backbone modification is a phosphorothioate substitution.

In another aspect, an aptamer is provided according to any aptamer described in Table 1 of the specification.

In another aspect, an aptamer is provided having at least 70% sequence identity with any aptamer described in Table 1 of the specification. In some cases, the aptamer has at least 70% modification identity with any aptamer described in Table 1 of the specification.

In some cases, any aptamer of the preceding is provided for use in treating an ocular disease or disorder in a subject in need thereof. In some cases, one or more symptoms of the ocular disease or disorder are treated.

In another aspect, a method is provided for treating an ocular disease or disorder in a subject in need thereof, comprising administering to the subject any aptamer of the preceding, thereby treating the ocular disease or disorder. In some cases, the ocular disease or disorder is selected from the group consisting of: diabetic retinopathy, retinopathy of prematurity, central retinal vein occlusion, macular edema, choroidal neovascularization, neovascular age-related macular degeneration, myopic choroidal neovascularization, punctate inner choroidopathy, ocular histoplasmosis syndrome, familial exudative vitreoretinopathy, and retinoblastoma. In some cases, the ocular disease or disorder exhibits elevated levels of VEGF-A.

In yet another aspect, any aptamer of the preceding is provided for use in a formulation of a medicament for treatment of an ocular disease or disorder.

In yet another aspect, any aptamer of the preceding is provided for use for treatment of an ocular disease or disorder.

In yet another aspect, a method is provided for modulating vascular endothelial growth factor-A (VEGF-A) in a biological system, the method comprising: administering to the biological system any aptamer of the preceding, thereby modulating VEGF-A in the biological system. In some cases, biological system comprises a biological tissue or biological cells. In some cases, the biological system is a subject. In some cases, the subject is a human. In some cases, the modulating comprises inhibiting a function associated with VEGF-A. In some cases, the modulating comprises preventing or reducing an association of VEGF-A with one or more of Flt-1, KDR, or Nrp-1.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A depicts a non-limiting example of an aptamer library suitable for screening for aptamers that target VEGF-A, according to embodiments of the disclosure.

FIG. 1B depicts a non-limiting example of a reverse oligonucleotide hybridized to a portion of the aptamer library sequence depicted in FIG. 1A, according to embodiments of the disclosure.

FIG. 1C depicts non-limiting examples of structures of modified nucleotides that may be used to generate an aptamer library suitable for the selection of anti-VEGF-A aptamers according to embodiments of the disclosure.

FIG. 6 depicts a representation of nucleotide conservation within the top 250 stacks of sequences from round 6 of the degenerate selection conducted on Aptamer 26 weighted by the total number of sequences represented according to embodiments of the disclosure.

DETAILED DESCRIPTION OF THE INVENTION

Figure 2A:
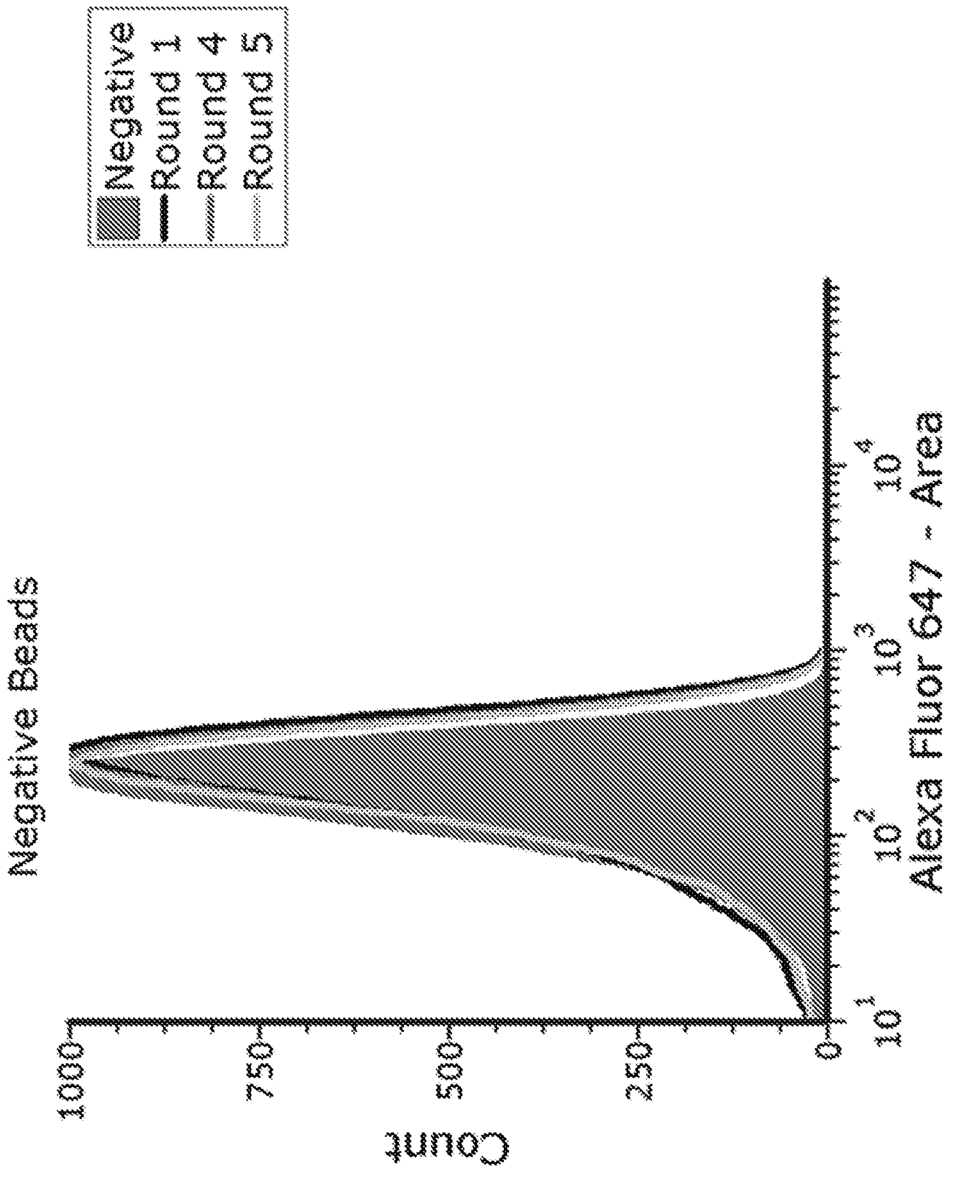
FIG. 2A and FIG. 2B depict non-limiting examples of flow cytometry data demonstrating the ability of various aptamer selection rounds to bind to bead-immobilized VEGF-$A_{121}$ according to embodiments of the disclosure.

The disclosure herein provides aptamer compositions that selectively bind to and inhibit vascular endothelial growth factor-A (VEGF-A) and methods of using said aptamer compositions. In various aspects, an aptamer composition of the disclosure may comprise an anti-VEGF-A aptamer that binds to one or more isoforms or variants of VEGF-A. In various aspects, an aptamer composition of the disclosure may comprise a pan-variant specific anti-VEGF-A aptamer that binds to each of VEGF-$A_{110}$, VEGF-$A_{121}$, VEGF-$A_{165}$, VEGF-$A_{189}$, and VEGF-$A_{206}$. In some cases, the anti-VEGF-A aptamers may bind to the receptor binding face of VEGF-A, or a portion thereof. In some cases, the anti-VEGF-A aptamers may bind to the receptor binding domain (RBD) of VEGF-A, or a portion thereof. In some cases, an aptamer of the disclosure does not bind to the heparin-binding domain (HBD) of VEGF-A. Without wishing to be bound by theory, anti-VEGF-A aptamers of the disclosure may prevent or reduce binding of VEGF-A to a VEGF receptor (VEGFR). For example, an anti-VEGF-A aptamer of the disclosure may prevent or reduce binding of VEGF-A to VEGFR1 (also known as Fms-related tyrosine kinase 1 (Flt1)), VEGFR2 (also known as Kinase insert domain receptor (KDR) or Flk-1), Neuropilin-1 (Nrp-1), or any combination thereof. In some cases, an anti-VEGF-A aptamer of the disclosure may inhibit a function associated with VEGF-A (e.g., engaging a VEGF receptor, a signaling pathway downstream of VEGF-A, or both).

The disclosure herein further provides aptamer compositions having unique stem-loop secondary structures that selectively bind to and inhibit a function associated with one or more isoforms or variants of VEGF-A and methods of using such aptamer compositions. In some cases, the aptamers of the disclosure may have, in a 5' to 3' direction, a first side of a first base paired stem (e.g., stem S1); optionally, a first loop (e.g., loop L1); a first side of a second base paired stem (e.g., stem S2); a second loop (e.g., loop L2); a second, complementary side of the second base paired stem (e.g., stem S2'); a third loop (e.g., loop L3); a first side of a third base paired stem (e.g., stem S3), a fourth loop (e.g., loop L4), a second, complementary side of the third base paired stem (e.g., stem S3'), a fifth loop (e.g., loop L5), and a second, complementary side of the first base paired stem (e.g., stem S1'). Put another way, an anti-VEGF-A aptamer of the disclosure may have the following stem and loop structure: 5'-S1-L1-S2-L2-S2'-L3-S3-L4-S3'-L5-S1'-3'. In some cases, an anti-VEGF-A aptamer of the disclosure may have the following stem and loop structure: 5'-S1-S2-L2-S2'-L3-S3-L4-S3'-L5-S1'-3'.

The aptamers disclosed herein may also include one or more further elements (e.g., additional stem(s) or loop(s)). In some cases, additional elements (e.g., additional stem(s), loop(s), one or more nucleotides, etc.) may be located before (e.g., 5' side) the first side of the first base paired stem, after (e.g., 3' side) the second, complementary side of the first base paired stem, or both. In some cases, additional elements may be located interspersed between other elements of the aptamer. Additional elements may include additional stem structures, loop structures, non-nucleotidyl linkers, or any number of overhanging, unpaired nucleotides.

In some embodiments, each element may be adjacent to each other. For example, the anti-VEGF-A aptamers of the disclosure may have, in a 5' to 3' direction, a first side of a first base paired stem. The 3' terminal end of the first side of the first base paired stem may be connected to the 5' terminal end of the first loop. The first loop may be connected at its 5' terminal end to the 3' terminal end of the first side of the first base paired stem, and the first loop may be connected at its 3' terminal end to the 5' terminal end of the first side of the second base paired stem. The first side of the second base paired stem may be connected at its 5' terminal end to the 3' terminal end of the first loop, and the first side of the second base paired stem may be connected at its 3' terminal end to the 5' terminal end of the second loop. The second loop may be connected at its 5' terminal end to the 3' terminal end of the first side of the second base paired stem, and the second loop may be connected at its 3' terminal end to the 5' terminal end of the second, complementary side of the second base paired stem. The second, complementary side of the second base paired stem may be connected at its 5' terminal end to the 3' terminal end of the second loop, and the second, complementary side of the second base paired stem may be connected at its 3' terminal end to the 5' terminal end of the third loop. The third loop may be connected at its 5' terminal end to the 3' terminal end of the second, complementary side of the second base paired stem, and the third loop may be connected at its 3' terminal end to the 5' terminal end of the first side of the third base paired stem. The first side of the third base paired stem may be connected at its 5' terminal end to the 3' terminal end of the third loop, and the first side of the third base paired stem may be connected at its 3' terminal end to the 5' terminal end of the fourth loop. The fourth loop may be connected at its 5' terminal end to the 3' terminal end of the first side of the third base paired stem, and the fourth loop may be connected at its 3' terminal end to the 5' terminal end of the second, complementary side of the third base paired stem. The second, complementary side of the third base paired stem may be connected at its 5' terminal end to the 3' terminal end of the fourth loop, and the second, complementary side of the third base paired stem may be connected at its 3' terminal end to the 5' terminal end of the fifth loop. The fifth loop may be connected at its 5' terminal end to the 3' terminal end of the second, complementary side of the third base paired stem, and the fifth loop may be connected at its 3' terminal end to the 5' terminal end of the second, complementary side of the first base paired stem. The second, complementary side of the first base paired stem may be connected at its 5' terminal end to the 3' terminal end of the fifth loop. In some cases, the anti-VEGF-A aptamers of the disclosure may comprise a terminal stem. In some cases, the terminal stem may be the first base paired stem (e.g., S1). In some cases, the anti-VEGF-A aptamers of the disclosure may comprise a plurality of terminal loops. In some cases, a terminal loop may include the second loop (e.g., L2), and/or the fourth loop (e.g., L4). In some cases, the anti-VEGF-A aptamers of the disclosure may comprise a plurality of internal stems. In some cases, an internal stem may include the second base paired stem (e.g., S2), and/or the third base paired stem (e.g., S3). In some cases, the anti-VEGF-A aptamers of the disclosure may comprise a plurality of internal loops. In some cases, an internal loop may include the first loop (e.g., L1), the third loop (e.g., L3), and/or the fifth loop (e.g., L5). Non-limiting examples of stem-loop aptamers that may be used to inhibit VEGF-A are described throughout.

As described above, in some cases, an anti-VEGF-A aptamer of the disclosure may have the following stem and loop structure: 5'-S1-L1-S2-L2-S2'-L3-S3-L4-S3'-L5-S1'-3'. In other cases, an anti-VEGF-A aptamer of the disclosure may have the following stem and loop structure: 5'-S1-S2-L2-S2'-L3-S3-L4-S3'-L5-S1'-3'. In some cases, S1/S1', S3/S3', L4, and/or L5 may comprise any combination of nucleotide sequences provided in Tables 10-13.

The disclosure further provides anti-VEGF-A aptamers comprising consensus nucleic acid sequences. In some cases, an anti-VEGF-A aptamer of the disclosure comprises a first side of a first base paired stem having a consensus nucleic acid sequence of 5'-HNBYHDCC-3', and a second, complementary side of the first base paired stem having a consensus nucleic acid sequence of 5'-GKYNKVNW-3', where H is A, C, or U; N is A, C, G, or U; B is C, G, or U; Y is C or U; D is A, G, or U; K is G or U; V is A, C, or G, and W is A or U. In some cases, an anti-VEGF-A aptamer of the disclosure comprises a first side of a first base paired stem having a consensus nucleic acid sequence of 5'-HNBYHDNN-3', and a second, complementary side of the first base paired stem having a consensus nucleic acid sequence of 5'-NNYNKVNW-3', where H is A, C, or U; N is A, C, G, or U; B is C, G, or U; Y is C or U; D is A, G, or U; K is G or U; V is A, C, or G, and W is A or U. In some cases, an anti-VEGF-A aptamer of the disclosure comprises a first loop having a nucleic acid sequence of 5'-U-3'. In some cases, an anti-VEGF-A aptamer of the disclosure comprises a nucleic acid sequence of 5'-N*-3', where N is A, C, G, or U, a non-nucleotidyl spacer 3 modification (Sp3), two non-nucleotidyl spacer 3 modifications (Sp3-Sp3), a 6 carbon alkyl linker (1,6-hexanediol), a spacer 9 (triethyleneglycol) modification, or may be deleted. In some cases, the first loop is optional. In such cases, the aptamer may have the following structure: 5'-S1-S2-L2-S2'-L3-S3-L4-S3'-L5-S1'-3'. In some cases, an anti-VEGF-A aptamer of the disclosure comprises a first side of a second base paired stem having a consensus nucleic acid sequence of 5'-CC-3', and a second, complementary side of a second base paired stem having a consensus nucleic acid sequence of 5'-GG-3'. In some cases, an anti-VEGF-A aptamer of the disclosure comprises a first side of a second base paired stem having a consensus nucleic acid sequence of 5'-NN-3', and a second, complementary side of a second base paired stem having a consensus nucleic acid sequence of 5'-NN-3', where N is A, C, G, or U. In some cases, an anti-VEGF-A aptamer of the disclosure comprises a second loop having a nucleic acid sequence of 5'-GCGC-3'. In some cases, an anti-VEGF-A aptamer of the disclosure comprises a second loop having a consensus nucleic acid sequence of 5'-GYGC-3', where Y is C or U. In some cases, an anti-VEGF-A aptamer of the disclosure comprises a second loop having a consensus nucleic acid sequence of 5'-KNGC-3', where K is G or U; and N is A, G, C, or U. In some cases, an anti-VEGF-A aptamer of the disclosure comprises a third loop having a nucleic acid sequence of 5'-A-3'. In some cases, an anti-VEGF-A aptamer of the disclosure comprises a third loop having a consensus nucleic acid sequence of 5'-W-3', where W is A or U.

In some cases, an anti-VEGF-A aptamer of the disclosure comprises a first side of a third base paired stem having a consensus nucleic acid sequence of 5'-GRGRWN-3', and a second, complementary side of a third base paired stem having a consensus nucleic acid sequence of 5'-NHYCYC-3', where R is A or G; D is A, G, or U; H is A, C, or U, W is A or U; and Y is C or U. In some cases, an anti-VEGF-A aptamer of the disclosure comprises a first side of a third base paired stem having a nucleic acid sequence of 5'-GKGN-3', and a second, complementary side of a third base paired stem having a nucleic acid sequence of 5'-NSMC-3' where K is G or U; N is A, C, G or U and M is A or C. In some cases, an anti-VEGF-A aptamer of the disclosure comprises a first side of a third base paired stem having a nucleic acid sequence of 5'-GBBNY-3' and a second, complementary side of a third base paired stem having a nucleic acid sequence of 5'-RNBNC-3', where B is C, G or U; R is A or G; N is A, C, G or U and Y is C or U. In some cases, an anti-VEGF-A aptamer of the disclosure comprises a first side of a third base paired stem having a consensus nucleic acid sequence of 5'-GGGRUD-3', and a second, complementary side of a third base paired stem having a consensus nucleic acid sequence of 5'-HWYCCC-3', where R is A or G; D is A, G, or U; H is A, C, or U; W is A or U; and Y is C or U. In some cases, an anti-VEGF-A aptamer of the disclosure comprises a first side of a third base paired stem having a nucleic acid sequence of 5'-GGGG-3', and a second, complementary side of a third base paired stem having a nucleic acid sequence of 5'-CCCC-3'. In some cases, an anti-VEGF-A aptamer of the disclosure comprises a first side of a third base paired stem having a nucleic acid sequence of 5'-GGGU-3', and a second, complementary side of a third base paired stem having a nucleic acid sequence of 5'-ACCC-3'. In some cases, an anti-VEGF-A aptamer of the disclosure comprises a first side of a third base paired stem having a nucleic acid sequence of 5'-GGCU-3', and a second, complementary side of a third base paired stem having a nucleic acid sequence of 5'-AGCC-3'. In some cases, an anti-VEGF-A aptamer of the disclosure comprises a first side of a third base paired stem having a nucleic acid sequence of 5'-GGGRU-3' and a second, complementary side of a third base paired stem having a nucleic acid sequence of 5'-AYCCC-3', where R is A or G; and Y is C or U. In some cases, an anti-VEGF-A aptamer of the disclosure comprises a first side of a third base paired stem having a nucleic acid sequence of 5'-GGGGUD-3', and a second, complementary side of a third base paired stem having a nucleic acid sequence of 5'-HAUCCC-3', where D is A, G, or U; and H is A, C, or U. In some cases, an anti-VEGF-A aptamer of the disclosure comprises a first side of a third base paired stem having a nucleic acid sequence of 5'-GGGRUUR-3', and a second, complementary side of a third base paired stem having a nucleic acid sequence of 5'-UAUCCC-3', where R is A or G. In some cases, an anti-VEGF-A aptamer of the disclosure comprises a first side of a third base paired stem having a consensus nucleic acid sequence of 5'-SVVVK-3', and a second, complementary side of a third base paired stem having a consensus nucleic acid sequence of 5'-MBBBS-3', where S is G or C; V is A, C, or G; K is G or U; M is A or C; and B is C, G, or U. In some cases, an anti-VEGF-A aptamer of the disclosure comprises a first side of a third base paired stem having a consensus nucleic acid sequence of 5'-GGGRUN'-3, and a second, complementary side of a third base paired stem having a consensus nucleic acid sequence of 5'-NWYCCC-3', where R is A or G; N is A, C, G, or U; W is A or U; and Y is C or U. In some cases, an anti-VEGF-A aptamer of the disclosure comprises a first side of a third base paired stem having a consensus nucleic acid sequence of 5'-GGGRUN'-3, and a second, complementary side of a third base paired stem having a consensus nucleic acid sequence of 5'-NAYCCC-3', where R is A or G; N is A, C, G, or U; W is A or U; and Y is C or U.

In some cases, an anti-VEGF-A aptamer of the disclosure comprises a fourth loop having a nucleic acid sequence of 5'-MAU-3', where M is A or C. In some cases, an anti-VEGF-A aptamer of the disclosure comprises a fourth loop having a nucleic acid sequence of 5'-DNAH-3', where D is A, G, or U; N is A, C, G, or U; and H is A, C, or U. In some cases, an anti-VEGF-A aptamer of the disclosure comprises a fourth loop having a nucleic acid sequence of 5'-DNDH-3', where D is A, G, or U; N is A, C, G, or U; and H is A, C, or U. In some cases, an anti-VEGF-A aptamer of the disclosure comprises a fourth loop having a nucleic acid sequence of 5'-UDNDHU-3', where D is A, G, or U; N is A, C, G, or U; and H is A, C, or U. In some cases, an anti-VEGF-A aptamer of the disclosure comprises a fourth loop having a nucleic acid sequence of 5'-UUUCAUUU-3'. In some cases, an anti-VEGF-A aptamer of the disclosure comprises a fifth loop having a nucleic acid sequence of 5'-GYUU-3', where Y is C or U. In some cases, an anti-VEGF-A aptamer of the disclosure comprises a fifth loop having a consensus nucleic acid sequence of 5'-GNNN-3', where N is A, C, G, or U. In some cases, an anti-VEGF-A aptamer of the disclosure comprises a fifth loop having a consensus nucleic acid sequence of 5'-GNHW-3', where N is A, C, G, or U; H is A, C, or U; and W is A or U. In some cases, an anti-VEGF-A aptamer of the disclosure comprises a consensus nucleic acid sequence of 5'-HNBYHDC-CUCCGCGCGGAGG-GRUDDNDHHWYCCCGYUUGKYNKVNW-3' (SEQ ID NO: 1), where H is A, C, or U; N is A, C, G, or U; B is C, G, or U; Y is C or U; D is A, G, or U; R is A or G; W is A or U; K is G or U; and V is A, C, or G. In some cases, an anti-VEGF-A aptamer of the disclosure comprises a consensus nucleic acid sequence of 5'-HNBYHDC-CUCCGCGCGGAGGGRU-UDNDHUAYCCCGYUUGKYNKVNW-3' (SEQ ID NO: 2), where H is A, C, or U; N is A, C, G, or U; B is C, G, or U; Y is C or U; D is A, G, or U; R is A or G; K is G or U; V is A, C, or G, and W is A or U. In some cases, an anti-VEGF-A aptamer of the disclosure comprises a consensus nucleic acid sequence of 5'-WNKYHDC-CUCCGCGCGGAGGGGUDDNAHHAUCCCGUUUG-GYBKMHW-3' (SEQ ID NO: 3), where W is A or U; N is A, C, G, or U; K is G or U; Y is C or U; H is A, C, or U, D is A, G, or U; B is C, G, or U; and M is A or C. In some cases, an anti-VEGF-A aptamer of the disclosure comprises a nucleic acid sequence of 5'-AUGCCGCCUCCGCGCG-GAGGGGUUUCAUUUCCCCGUUUGGCUGCAU-3' (SEQ ID NO: 4). In some cases, an anti-VEGF-A aptamer of the disclosure comprises a consensus nucleic acid sequence of 5'-HNBYHDNNN*NNKN-GCNNWGGGRUNDNDHNWYCCCGNNNN-NYNKVNW-3' (SEQ ID NO: 5), where H is A, C, or U; N is A, C, G, or U; B is C, G, or U; Y is C or U; N* is A, C, G, U, can be deleted entirely, or is a non-nucleotidyl spacer 3 modification, a 6 carbon alkyl linker (1,6-hexanediol), or a spacer 9 (triethyleneglycol) modification; D is A, G, or U; K is G or U; W is A or U; R is A or G; and V is A, C, or G. In some cases, an anti-VEGF-A aptamer of the disclosure comprises a consensus nucleic acid sequence of 5'-HNBYHDCCUCCGCGCGGAGDSBHDNNNNHNNBNCGYUUGKYNKVNW-3' (SEQ ID NO: 436), where H is A, C, or U; N is A, C, G, or U; B is C, G, or U; Y is C or U; D is A, G, or U; R is A or G; W is A or U; K is G or U; and V is A, C, or G.

In some cases, an anti-VEGF-A aptamer of the disclosure comprises a consensus nucleic acid sequence of 5'-HNBYHDCCUCCGCGCGGAGKBHYDNNNKDBVCGYUUGKYNKVNW-3' (SEQ ID NO: 437), where H is A, C, or U; N is A, C, G, or U; B is C, G, or U; Y is C or U; D is A, G, or U; R is A or G; W is A or U; K is G or U; and V is A, C, or G. In some cases, an anti-VEGF-A aptamer of the disclosure comprises a consensus nucleic acid sequence of 5'-HNBYHDCCUCCGCGCGGAGKSHUDRGBUDSMCGYUUGKYNKVNW-3' (SEQ ID NO: 438), where H is A, C, or U; N is A, C, G, or U; B is C, G, or U; Y is C or U; D is A, G, or U; R is A or G; W is A or U; K is G or U; M is A or C; and V is A, C, or G.

The disclosure herein further provides methods for inhibiting VEGF-A (and/or a downstream signaling pathway of VEGF-A). In some cases, the methods include administering an anti-VEGF-A aptamer (or a composition comprising said aptamer) to a biological system (e.g., biological cells, biological tissue, a subject, and the like). The disclosure further provides methods for treating ocular diseases or disorders including administering an anti-VEGF-A aptamer (or a pharmaceutical composition comprising said aptamer) to a subject having, suspected of having, or at risk of developing, an ocular disease or disorder. In some cases, the anti-VEGF-A aptamer is an aptamer having a stem-loop structure as described herein. In some cases, the ocular disease or disorder may be diabetic retinopathy. In some cases, the ocular disease or disorder may be retinopathy of prematurity. In some cases, the ocular disease or disorder may be central retinal vein occlusion. In some cases, the ocular disease or disorder may be macular edema. In some cases, the ocular disease or disorder may be choroidal neovascularization. In some cases, the ocular disease or disorder may be neovascular (or wet) age-related macular degeneration. In some cases, the ocular disease or disorder may be myopic choroidal neovascularization. In some cases, the ocular disease or disorder may be punctate inner choroidopathy. In some cases, the ocular disease or disorder may be presumed ocular histoplasmosis syndrome. In some cases, the ocular disease or disorder may be familial exudative vitreoretinopathy. In some cases, the ocular disease or disorder may be retinoblastoma. In some cases, a subject having, suspected of having, or at risk of developing, an ocular disease or disorder may exhibit elevated levels of one or more variants or isoforms of VEGF-A. For example, a subject having, suspected of having, or at risk of developing, an ocular disease or disorder may exhibit elevated levels of one or more of VEGF-$A_{206}$, VEGF-$A_{189}$, VEGF-$A_{165}$, VEGF-$A_{121}$, and VEGF-$A_{110}$.

In some aspects of the disclosure, the methods and compositions may involve the inhibition of a function associated with VEGF-A. In some cases, the methods and compositions may involve preventing or reducing VEGF-A binding to or interaction with one or more VEGF receptors. For example, the methods and compositions may involve preventing or reducing VEGF-A binding to or interaction with Flt-1, KDR, Nrp-1, or any combination thereof. In some cases, the methods and compositions may involve preventing or reducing downstream signaling associated with Flt-1, KDR, Nrp-1, or any combination thereof. In some cases, the methods and compositions may involve the inhibition of a function associated with VEGF-A for the treatment of ocular diseases or disorders. In some cases, the methods and compositions may involve the inhibition of a function associated with VEGF-A for the treatment of diabetic retinopathy. In some cases, the methods and compositions may involve the inhibition of a function associated with VEGF-A for the treatment of retinopathy of prematurity. In some cases, the methods and compositions may involve the inhibition of a function associated with VEGF-A for the treatment of central retinal vein occlusion. In some cases, the methods and compositions may involve the inhibition of a function associated with VEGF-A for the treatment of macular edema. In some cases, the methods and compositions may involve the inhibition of a function associated with VEGF-A for the treatment of choroidal neovascularization. In some cases, the methods and compositions may involve the inhibition of a function associated with VEGF-A for the treatment of neovascular (or wet) age-related macular degeneration. In some cases, the methods and compositions may involve the inhibition of a function associated with VEGF-A for the treatment of myopic choroidal neovascularization. In some cases, the methods and compositions may involve the inhibition of a function associated with VEGF-A for the treatment of punctate inner choroidopathy. In some cases, the methods and compositions may involve the inhibition of a function associated with VEGF-A for the treatment of presumed ocular histoplasmosis syndrome. In some cases, the methods and compositions may involve the inhibition of a function associated with VEGF-A for the treatment of familial exudative vitreoretinopathy. In some cases, the methods and compositions may involve the inhibition of a function associated with VEGF-A for the treatment of retinoblastoma. In some cases, the methods and compositions may involve the inhibition of a function associated with VEGF-A for the treatment of an ocular disease or disorder exhibiting elevated levels of one or more isoforms or variants of VEGF-A.

In various aspects, the compositions may include one or more aptamers that selectively bind to and inhibit a function associated with VEGF-A. In some cases, the compositions may include one or more aptamers that bind to the receptor binding face of VEGF-A. In some cases, the compositions may include one or more aptamers that bind to the receptor binding domain of VEGF-A. In some cases, the compositions may include one or more aptamers that bind to a region of VEGF-A other than the heparin binding domain of VEGF-A. Put another way, the compositions may include one or more aptamers that do not bind to the heparin binding domain of VEGF-A. In some cases, the compositions may include one or more aptamers that bind to one or more variants or isoforms of VEGF-A. For example, the compositions may include one or more aptamers that bind to one or more of VEGF-$A_{206}$, VEGF-$A_{189}$, VEGF-$A_{165}$, VEGF-$A_{121}$, and VEGF-$A_{110}$. In some cases, the compositions may include one or more pan-variant specific anti-VEGF-A aptamers. In particular cases, the compositions may include pan-variant specific aptamers that bind to each of VEGF-$A_{110}$, VEGF-$A_{121}$, VEGF-$A_{165}$, VEGF-$A_{189}$, and VEGF-$A_{206}$. Generally, a pan-variant specific aptamer disclosed herein may bind to a structural feature of VEGF-A which is shared amongst VEGF-$A_{110}$, VEGF-$A_{121}$, VEGF-$A_{165}$, VEGF-$A_{189}$, and VEGF-$A_{206}$. In some cases, the structural feature is the receptor binding face or the receptor binding domain. In some cases, the aptamers have a stem-loop secondary structure as described herein.

In some cases, the compositions may include one or more aptamers that prevent or reduce binding of VEGF-A to Flt-1, KDR, Nrp-1, or any combination thereof. In some cases, the compositions may include one or more aptamers that prevent or reduce downstream signaling pathways associated with Flt-1, KDR, Nrp-1, or any combination thereof. In some cases, the aptamers may be RNA aptamers, DNA aptamers, modified RNA aptamers, or modified DNA aptamers.

In some cases, the aptamers do not contain non-naturally occurring hydrophobic modifications. In some aspects, less than 100% of the pyrimidines (e.g., C, T, or U) present in a nucleic acid sequence of an aptamer herein comprise a C-5 modified pyrimidine. For example, less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the pyrimidines present in a nucleic acid sequence of an aptamer herein comprise a C-5 modified pyrimidine. In particular aspects, none of the pyrimidines present in a nucleic acid sequence of an aptamer herein comprise a C-5 modified pyrimidine. In another particular aspect, none of the bases in an aptamer sequence herein comprise a C-5 modification. In some aspects, less than 100% of the uridines present in a nucleic acid sequence of an aptamer herein comprise a C-5 modified uridine. For example, less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the uridines present in a nucleic acid sequence of an aptamer herein comprise a C-5 modified uridine. In particular aspects, none of the uridines present in a nucleic acid sequence of an aptamer herein comprise a C-5 modified uridine. In some cases, the C-5 modified pyrimidine or C-5 modified uridine is selected from the group consisting of: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-tyrosylcarboxyamide)-2'-deoxyuridine (TyrdU), 5-(N-3,4-methylenedioxybenzylcarboxyamide)-2'-deoxyuridine (MBndU), 5-(N-4-fluorobenzylcarboxyamide)-2'-deoxyuridine (FBndU), 5-(N-3-phenylpropylcarboxyamide)-2'-deoxyuridine (PPdU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-deoxyuridine (2NapdU), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-deoxyuridine (NEdU), 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-deoxyuridine (2NEdU), 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, and 5-(N-3-benzothiophenylethylcarboxyamide)-2'-fluorouridine. In particular aspects, none of the aptamers provided herein comprise NapdU. In other particular cases, the aptamers are not SOMAmers.

In general, "sequence identity" refers to an exact nucleotide-to-nucleotide or amino acid-to-amino acid correspondence of two polynucleotides or polypeptide sequences, respectively.

Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the longer sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, *Proc. Natl. Acad Sci. USA,* 87:2264-2268 (1990) and as discussed in Altschul, et al., *J. Mol. Biol.,* 215:403-410 (1990); Karlin And Altschul, *Proc. Natl. Acad. Sci. USA,* 90:5873-5877 (1993); and Altschul et al., *Nucleic Acids Res.,* 25:3389-3402 (1997). The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, *Computers and Chemistry* 17:149-163 (1993). Ranges of desired degrees of sequence identity are approximately 50% to 100% and integer values therebetween. In general, this disclosure encompasses sequences with at least 50%, at least 55%, at least 60%, at least 65%, at least 70%, at least 75%, at least 80%, at least 85%, at least 90%, at least 95%, or at least 98% sequence identity with any sequence provided herein.

In general, "modification identity" refers to two polynucleotides with identical patterns of modifications on a nucleotide-to-nucleotide level. Techniques for determining modification identity may include determining the modifications of a polynucleotide and comparing these modifications to modifications of a second polynucleotide. The percent modification identity of two sequences is the number of exact modification matches between two aligned sequences divided by the length of the longer sequence and multiplied by 100. Ranges of desired degrees of modification identity are generally approximately 50% to 100%, and integer values therebetween. In general, this disclosure encompasses sequences with at least 50%, at least 55%, at least 60%, at least 65%, at least 70%, at least 75%, at least 80%, at least 85%, at least 90%, at least 95%, or at least 98% modification identity with any sequence provided herein.

As used herein, "consensus sequence", when used in reference to a group or series of related nucleic acids, refers to a nucleotide sequence that reflects the most common choice of base at each position in the sequence where the series of related nucleic acids has been subjected to mathematical and/or sequence analysis. Unless otherwise indicated, nucleotide sequences provided herein are represented by standard nucleotide notation, as set forth by the International Union of Pure and Applied Chemistry (IUPAC). For example, the nucleotides typically found in DNA are represented by "A" "C", "G", "T"; and the nucleotides typically found in RNA are represented by "A", "C", "G", "U". Nucleotide sequences provided herein may include one or more degenerate bases. A "degenerate base" generally refers to a position on a nucleotide sequence that can have more than one possible alternative. Degenerate bases are generally represented by a Roman character as set forth by the International Union of Pure and Applied Chemistry (IUPAC). For example, the Roman character "D", when used in relation to a nucleotide sequence, represents a degenerate base of A, G, or U.

The term "aptamer" as used herein refers to an oligonucleotide and/or nucleic acid analogues that can bind to a specific target molecule. Aptamers can include RNA, DNA, modified RNA, modified DNA, any nucleic acid analogue, and/or combinations thereof. Aptamers can be single-stranded oligonucleotides. In some cases, aptamers may comprise more than one nucleic acid strand (e.g., two or more nucleic acid strands). Aptamers may bind to a target (e.g., a protein) with high affinity and specificity through non-Watson-Crick base pairing interactions. Generally, the aptamers described herein are non-naturally occurring oligonucleotides (e.g., synthetically produced) that are isolated and used for the treatment of a disorder or a disease. Aptamers can bind to essentially any target molecule including, without limitation, proteins, oligonucleotides, carbohydrates, lipids, small molecules, and even bacterial cells. Aptamers may be monomeric (composed of a single unit) or multimeric (composed of multiple units). Multimeric aptamers can be homomeric (composed of multiple identical units) or heteromeric (composed of multiple non-identical units). Aptamers herein may be described by their primary structures, meaning the linear nucleotide sequence of the aptamer. Aptamer sequences herein are generally described from the 5' end to the 3' end, unless otherwise stated. Additionally or alternatively, aptamers herein may be described by their secondary structures which may refer to the combination of single-stranded regions and base-pairing interactions within the aptamer. Whereas many naturally occurring oligonucleotides, such as mRNA, encode information in their linear base sequences, aptamers generally do not encode information in their linear base sequences. Further, aptamers can be distinguished from naturally occurring oligonucleotides in that binding of aptamers to target molecules is dependent upon secondary and tertiary structures of the aptamer. Aptamers may be suitable as therapeutic agents and may be preferable to other therapeutic agents because: 1) aptamers may be fast and economical to produce because aptamers can be developed entirely by in vitro processes; 2) aptamers may have low toxicity and may lack an immunogenic response; 3) aptamers may have high specificity and affinity for their targets; 4) aptamers may have good solubility; 5) aptamers may have tunable pharmacokinetic properties; 6) aptamers may be amenable to site-specific conjugation of PEG and other carriers; and 7) aptamers may be stable at ambient temperatures.

An aptamer may have a secondary structure having at least two complementary regions of the same nucleic acid strand that base-pair to form a double helix (referred to herein as a "stem"). Generally, these complementary regions are complementary when read in the opposite direction. The term "stem" as used herein may refer to either of the complementary nucleotide regions individually or may encompass a base-paired region containing both complementary regions, or a portion thereof. For example, the term "stem" may refer to the 5' side of the stem, that is, the stem sequence that is closer to the 5' end of the aptamer; additionally or alternatively, the term "stem" may refer to the 3' side of the stem, that is, the stem sequence that is closer to the 3' end of the aptamer. In some cases, the term "stem" may refer to the 5' side of the stem and the 3' side of the stem, collectively. The term "base-paired stem" is generally used herein to refer to both complementary stem regions collectively. A base-paired stem may be perfectly complementary meaning that 100% of its base pairs are Watson-Crick base pairs. A base-paired stem may also be "partially complementary." As used herein, the term "partially complementary stem" refers to a base-paired stem that is not entirely made up of Watson-Crick base pairs but does contain base pairs (either Watson-Crick base pairs or G-U/U-G wobble base pairs) at each terminus. In some cases, a partially complementary stem contains both Watson-Crick base-pairs and G-U/U-G wobble base pairs. In other cases, a partially complementary stem is exclusively made up of G-U/U-G wobble base pairs. A partially complementary stem may contain mis-matched base pairs and/or unpaired bases in the region between the base pairs at each terminus of the stem; but in such cases, the mis-matched base pairs and/or unpaired bases make up at most 50% of the positions between the base pairs at each terminus of the stem.

A stem as described herein may be referred to by the position, in a 5' to 3' direction on the aptamer, of the 5' side of the stem (e.g., the stem sequence closer to the 5' terminus of the aptamer), relative to the 5' side of additional stems present on the aptamer. For example, stem 1 (S1) may refer to the stem sequence that is closest to the 5' terminus of the aptamer, its complementary stem sequence, or both stem sequences collectively. Similarly, stem 2 (S2) may refer to the next stem sequence that is positioned 3' relative to S1, its complementary stem sequence, or both stem sequences collectively. Each additional stem may be referred to by its position, in a 5' to 3' direction, on the aptamer, as described above. For example, S3 may be positioned 3' relative to S2 on the aptamer, S4 may be positioned 3' relative to S3 on the aptamer, and so on. In some cases, the term "first stem" is used to refer to a stem in the aptamer, irrespective of its location. For example, a first stem may be S1, S2, S3, S4 or any other stem in the aptamer. A stem may be adjacent to an unpaired region. An unpaired region may be present at a terminus of the aptamer or at an internal region of the aptamer.

As used herein, the term "loop" generally refers to an internal unpaired region of an aptamer. The term "loop" generally refers to any unpaired region of an aptamer that is flanked on both the 5' end and the 3' end by a stem region. In some cases, a loop sequence may be adjacent to a single base-paired stem, such that the loop and stem structure together resemble a hairpin. In such cases, generally the primary sequence of the aptamer contains a first stem sequence adjacent to the 5' end of the loop sequence and a second stem sequence adjacent to the 3' end of the loop sequence; and the first and second stem sequences are complementary to each other. In some cases, each terminus of a loop is adjacent to first and second stem sequences that are not complementary. In such cases, the primary sequence of the aptamer may contain an additional loop sequence that is bordered at one or both ends by stem sequences that are complementary to the first and/or second stem sequences. In cases where the two loops have different number of nucleotides, the two loops are referred to jointly herein as an "asymmetric loop" or "asymmetric loop pair," terms that are used herein interchangeably. In cases where the two loops have the same number of nucleotides, they are referred to jointly as a "symmetric loop" or "symmetric loop pair," terms that are used interchangeably herein.

A loop as described herein may be referred to by its position, in a 5' to 3' direction, on the aptamer. For example, loop 1 (L1) may refer to a loop sequence that is positioned most 5' on the aptamer. Similarly, loop 2 (L2) may refer to a loop sequence that is positioned 3' relative to L1, and loop 3 (L3) may refer to a loop sequence that is positioned 3' relative to L2. Each additional loop may be referred to by its position, in a 5' to 3' direction, on the aptamer, as described above. For example, L4 may be positioned 3' relative to L3 on the aptamer, L5 may be positioned 3'relative to L4 on the aptamer, and so on. In some cases, the term "first loop" is used to refer to a loop in the aptamer, irrespective of its location. For example, a first loop may be L1, L2, L3, L4 or any other loop in the aptamer.

The term "stem-loop" as used herein generally refers to the secondary structure of an aptamer of the disclosure having at least one stem and at least one loop. In some cases, a stem-loop secondary structure may include a terminal stem and a terminal loop. In some cases, a stem-loop secondary structure includes structures having more than one stem, and more than one loop, which may include a terminal stem, at least one internal loop, at least one internal stem, and at least one terminal loop. A "terminal stem" as used herein generally refers to a stem that encompasses both the 5' and the 3' terminus of the aptamer. In some cases, a "terminal stem" is bordered at one or both termini by a "tail" comprising one or more unpaired nucleotides. For example, a terminal stem present in the aptamer may be bordered by a tail of one or more unpaired nucleotides (or other structures) at its 5' end. Similarly, a terminal stem present in the aptamer may be bordered by a tail of one or more unpaired nucleotides (or other structures) at its 3' end. In some cases, a terminal stem present in the aptamer may be bordered by a tail of one or more unpaired nucleotides (or other structures) at both its 5' end and its 3' end. A terminal stem may be adjacent to a loop; for example, the 5' side of a terminal stem (i.e., the terminal stem sequence closest to the 5' end of the molecule) may be bordered at its 3' terminus by the 5' terminus of a loop. Similarly, the 3' side of a terminal stem (i.e., the terminal stem sequence closest to the 3' end of the molecule) may be bordered at its 5' terminus by the 3' terminus of a loop. In some cases, the 5' side of a terminal stem (i.e., the terminal stem sequence closest to the 5' end of the molecule) may be bordered at its 3' terminus by the 5' terminus of a loop, and the 3' side of the terminal stem (i.e., the terminal stem sequence closest to the 3' end of the molecule) may be bordered at its 5' terminus by the 3' terminus of an internal stem. An "internal stem" as used herein may refer to a stem that is bordered at both termini by a loop sequence, or may refer to a stem that is bordered at one terminus by a loop sequence and bordered at the other terminus by a stem sequence. In some cases, a stem-loop secondary structure of the disclosure may include more than one internal stem. A "terminal loop" as used herein generally refers to a loop that is bordered by the same stem at both termini of the loop. For example, a terminal loop may be bordered at its 5' end by a stem sequence, and may be bordered at its 3' end by the complementary stem sequence. An "internal loop" as used herein generally refers to a loop that is bordered at both termini by different stems. For example, an internal loop may be bordered at its 5' end by a first stem sequence, and may be bordered at its 3' end by a second stem sequence that is not complementary to the first stem sequence. In some cases, a stem-loop secondary structure of the disclosure may include more than one internal loop. In some cases, a stem-loop secondary structure includes structures having more than two stems. Unless otherwise stated, when an aptamer includes more than one stem and/or more than one loop, the stems and loops are numbered consecutively in ascending order from the 5' end to the 3' end of the primary nucleotide sequence.

The term "VEGF-A", as used herein includes any variant or isoform of VEGF-A. Therefore, unless otherwise specified, "VEGF-A" may mean one or more of VEGF-$A_{110}$, VEGF-$A_{121}$, VEGF-$A_{165}$, VEGF-$A_{189}$, and VEGF-$A_{206}$.

The term "pan-variant specific aptamer" as used herein refers to an aptamer that selectively binds to at least VEGF-$A_{110}$, VEGF-Ain, VEGF-$A_{165}$, VEGF-$A_{189}$, and VEGF-$A_{206}$. A pan-variant specific aptamer may, but not necessarily, bind to one or more additional VEGF-A isoforms or variants. Generally, a pan-variant specific aptamer binds to a structural feature of VEGF-A which is common amongst VEGF-$A_{110}$, VEGF-$A_{121}$, VEGF-$A_{165}$, VEGF-$A_{189}$, and VEGF-$A_{206}$.

The terms "about" and "approximately" as used herein, generally refer to a range that is 15% greater than or less than a stated numerical value within the context of the particular usage. For example, "about 10" or "approximately 10" would include a range from 8.5 to 11.5.

As used herein, the term "or" is used nonexclusively to encompass "or" and "and." For example, "A or B" includes "A but not B," "B but not A," and "A and B", unless otherwise indicated.

"A", "an", and "the", as used herein, can include plural referents unless expressly and unequivocally limited to one referent Vascular Endothelial Growth Factor-A (VEGF-A)

This disclosure generally provides compositions that bind to vascular endothelial growth factor-A (VEGF-A), and methods of using such compositions to modulate VEGF-A signaling pathways. VEGF-A is thought to be the most significant regulator of angiogenesis in the VEGF family. VEGF-A promotes growth of vascular endothelial cells which leads to the formation of capillary-like structures and may be necessary for the survival of newly formed blood vessels. Vascular endothelial cells are thought to be major effectors of VEGF signaling. Retinal pigment epithelial (RPE) cells may also express VEGF receptors and have been shown to proliferate and migrate upon exposure to VEGF. In addition, VEGF is thought to play roles beyond the vascular system. For example, VEGF may play roles in normal physiological functions, including, but not limited to, bone formation, hematopoiesis, wound healing, and development. In various aspects, the compositions provided herein include aptamers that bind to VEGF-A, thereby inhibiting or reducing angiogenesis, e.g., by inhibiting or preventing growth of vascular endothelial cells, retinal pigment epithelial cells, or both. In some cases, the anti-VEGF-A aptamers provided herein may prevent or reduce binding or association of VEGF-A with a VEGF receptor (e.g., Flt-1, KDR, Nrp-1) expressed on vascular endothelial cells, retinal pigment epithelial cells, or both.

The VEGF family includes VEGF-A, VEGF-B, VEGF-C, VEGF-D, VEGF-E, VEGF-F, and placental growth factor (PIGF). The aptamers disclosed herein primarily bind to variants and isoforms of VEGF-A. In some cases, such aptamers may also bind to one or more of VEGF-B, VEGF-C, VEGF-D, VEGF-E, VEGF-F, and PIGF. Transcription of VEGF mRNA may be upregulated under hypoxic conditions. Furthermore, various growth factors and cytokines have been shown to upregulate VEGF mRNA expression, including, without limitation, epidermal growth factor (EGF), transforming growth factor-alpha (TGF-α), transforming growth factor-beta (TGF-β), keratinocyte growth factor (KGF), insulin-like growth factor-1 (IGF-1), fibroblast growth factor (FGF), platelet-derived growth factor (PDGF), interleukin 1-alpha (IL-1-α), interleukin-6 (IL-6), and interleukin-8 (IL8). VEGF-A is thought to play a role in various ocular diseases and disorders such as, but not limited to, diabetic retinopathy, retinopathy of prematurity, central retinal vein occlusion, macular edema, choroidal neovascularization, neovascular (or wet) age-related macular degeneration, myopic choroidal neovascularization, punctate inner choroidopathy, presumed ocular histoplasmosis syndrome, familial exudative vitreoretinopathy, and retinoblastoma.

In some cases, the aptamers provided herein may be used to treat an ocular disease or disorder involving one or more factors that upregulate VEGF-A expression and/or activity, including, but not limited to, hypoxic conditions; a growth factor such as EGF, TGF-α, TGF-β, KGF, IGF-1, FGF, or PDGF; and a cytokine such as IL-1-α, IL6, and IL8. In some cases, the aptamers provided herein may be used to treat an ocular disease or disorder selected from the group consisting of: diabetic retinopathy, retinopathy of prematurity, central retinal vein occlusion, macular edema, choroidal neovascularization, neovascular (or wet) age-related macular degeneration, myopic choroidal neovascularization, punctate inner choroidopathy, presumed ocular histoplasmosis syndrome, familial exudative vitreoretinopathy, and retinoblastoma.

The gene for human VEGF-A contains eight exons and encodes at least 16 isoforms. The most common isoforms generated by alternative splicing mechanisms are VEGF-$A_{121}$, VEGF-$A_{165}$, VEGF-$A_{189}$, and VEGF-$A_{206}$. Of these, VEGF-$A_{165}$, VEGF-$A_{189}$, and VEGF-$A_{206}$ each contain a C-terminal heparin binding domain (HBD). In contrast, VEGF-$A_{121}$ lacks a heparin-binding domain. Furthermore, plasmin activation may result in proteolytic cleavage of VEGF-$A_{165}$, VEGF-$A_{189}$, and VEGF-$A_{206}$, resulting in the release of the soluble VEGF-$A_{110}$ variant, which also lacks a heparin-binding domain.

In various aspects, the aptamers provided herein may bind to and inhibit a function associated with one or more VEGF-A isoforms or variants. For example, the aptamers provided herein may bind to and inhibit a function associated with one or more of VEGF-$A_{110}$, VEGF-$A_{121}$, VEGF-$A_{165}$, VEGF-$A_{189}$, and VEGF-$A_{206}$. In some cases, the aptamers provided herein may be pan-variant specific aptamers. In some cases, a pan-variant specific aptamer may bind to each of VEGF-$A_{110}$. VEGF-$A_{121}$, VEGF-$A_{165}$, VEGF-$A_{189}$, and VEGF-$A_{206}$. In some cases, the aptamers provided herein may bind to a structural feature that is common to each of VEGF-$A_{110}$, VEGF-$A_{121}$, VEGF-$A_{165}$, VEGF-$A_{189}$, and VEGF-$A_{206}$. For example, the aptamers provided herein may bind to the receptor binding face, or a portion thereof, of each of VEGF-$A_{110}$, VEGF-$A_{121}$, VEGF-$A_{165}$, VEGF-$A_{189}$, and VEGF-$A_{206}$. In another example, the aptamers provided herein may bind to the receptor binding domain, or a portion thereof, of each of VEGF-$A_{110}$, VEGF-$A_{121}$, VEGF-$A_{165}$, VEGF-$A_{189}$, and VEGF-$A_{206}$. In some cases, the aptamers provided herein may bind to a structural feature of VEGF-A other than the heparin binding domain found in VEGF-$A_{165}$, VEGF-$A_{189}$, and VEGF-$A_{206}$.

VEGF-A is known to interact with the receptor tyrosine kinases VEGFR1 (also known as Flt-1), VEGFR2 (also known as KDR or Flk-1), and Neuropilin-1 (Nrp-1). Nrp-1 is thought to be a co-receptor for KDR. VEGF receptors have been shown to be expressed by endothelial cells, macrophages, hematopoietic cells, and smooth muscle cells. KDR is a class IV receptor tyrosine kinase that binds 2:1 to VEGF-A dimers. Flt-1 is a receptor tyrosine kinase that binds to VEGF-A with a 3-10 fold higher affinity than KDR, and has also been shown to bind to VEGF-B and PlGF. Flt-1 expression may be upregulated by hypoxia, and its affinity for VEGF-A has been proposed as a negative regulator of signaling by KDR by acting as a decoy receptor. An alternative splicing variant of Flt-1 results in a soluble variant of the receptor (sFlt-1) which has been suggested to act as an anti-angiogenic sink for VEGF-A. Association of VEGF-$A_{165}$ with KDR may be enhanced by the interaction of the heparin binding domain with co-receptor Nrp-1, which may enhance downstream signaling of KDR. Nrp-1 also has strong affinity for Flt-1, which may prevent Nrp-1 association with VEGF-A165 and may be a secondary regulatory mechanism for VEGF-A induced angiogenesis.

In various aspects, aptamers provided herein may bind to one or more isoforms or variants of VEGF-A, and may prevent or reduce binding or association of VEGF-A with a VEGF receptor. For example, aptamers provided herein may prevent or reduce binding of one or more isoforms or variants of VEGF-A with Flt-1, KDR, Nrp-1, or any combination thereof. In some cases, aptamers provided herein may prevent or reduce binding of one or more of VEGF-$A_{110}$, VEGF-$A_{121}$, VEGF-$A_{165}$, VEGF-$A_{189}$, and VEGF-$A_{206}$ to one or more of Flt-1, KDR, and Nrp-1.

In particular cases, aptamers provided herein may prevent or reduce binding of one or more isoforms or variants of VEGF-A to KDR. In some aspects, the aptamers are pan-variant specific aptamers that bind to each of VEGF-$A_{110}$, VEGF-$A_{121}$, VEGF-$A_{165}$, VEGF-$A_{189}$, and VEGF-$A_{206}$, and reduce or prevent binding or association thereof with one or more of Fit-1, KDR, and Nrp-1.

In one instance, an amino acid sequence of human VEGF-$A_{206}$ may comprise the following sequence:

```
                                          (SEQ ID NO: 6)
APMAEGGGNHEEVVKFMDVYQRSYCHPIETLVDIFQEYPDEIEYIFKPSC

VPLMRCGGCCNDEGLECVPTEESNITMQIMRIKPHQGQHIGEMSFLQHNK

CECRPKKDRARQEKKSVRGKGKGQKRKRKKSRYKSWSVYVGARCCLMPWS

LPGPHPCGPCSERRKHLFVQDPQTCKCSCKNTDSRCKARQLELNERTCRC

DKPRR.
```

In one instance, an amino acid sequence of human VEGF-$A_{189}$ may comprise the following sequence:

```
                                          (SEQ ID NO: 7)
APMAEGGGQNHHEVVKFMDVYQRSYCHPIETLVDIFQEYPDEIEYIFKPS

CVPLMRCGGCCNDEGLECVPTEESNITMQIMRIKPHQGQHIGEMSFLQHN
```

-continued

KCECRPKKDRARQEKKSVRGKGKGQKRKRKKSRYKSWSVPCGPCSERRKH

LFVQDPQTCKVSCKNTDSRCKARQLELNERTCRVDKPRR

In one instance, an amino acid sequence of human VEGF-$A_{165}$ may comprise the following sequence:

(SEQ ID NO: 8)

APMAEGGGQNHHEVVKFMDVYQRSYCHPIETLVDIFQEYPDEIEYIFKPS

CVPLMRCGGCCNDEGLECVPTEESNITMQIMRIKPHQGQHIGEMSFLQHN

KCECRPKKDRARQENPCGPCSERRKHLFVQDPQTCKCSCKNTDSRCKARQ

LELNERTCRCDKPRR

In one instance, an amino acid sequence of human VEGF-$A_{121}$ may comprise the following sequence:

(SEQ ID NO: 9)

APMAEGGGQNHHEVVKFMDVYQRSYCHPIETLVDIFQEYPDEIEYIFKPS

CVPLMRCGGCCNDEGLECVPTEESNITMQIMRIKPHQGQHIGEMSFLQHN

KCECRPKKDRARQEKCDKPRR

In one instance, an amino acid sequence of human VEGF-$A_{110}$ may comprise the following sequence:

(SEQ ID NO: 10)

APMAEGGGQNHHEVVKFMDVYQRSYCHPEITLVDIFQEYPDEIEYIFKPS

CVPLMRCGGCCNDEGLECVPTEESNITMQIMRIKPHQGQHIGEMSFLQHN

KCECRPKKDR

Aptamers

In some cases, the methods and compositions described herein include the use of one or more aptamers for the treatment of an ocular disease or disorder. In some cases, the methods and compositions described herein use one or more aptamers having a secondary structure as described herein for the treatment of an ocular disease or disorder. In some cases, the methods and compositions described herein include the use of one or more aptamers for inhibiting an activity associated with VEGF-A. In some cases, the methods and compositions described herein include the use of one or more aptamers having a secondary structure as described herein for inhibiting an activity associated with VEGF-A.

Aptamers as described herein may include any number of modifications that can affect the function or affinity of the aptamer. For example, aptamers may be unmodified or they may contain modified nucleotides to improve stability, nuclease resistance or delivery characteristics.

Examples of such modifications may include chemical substitutions at the sugar and/or phosphate and/or base positions, for example, at the 2' position of ribose, the 5 position of pyrimidines, and the 8 position of purines, various 2'-modified pyrimidines and purines and modifications with 2'-amino (2'-$NH_2$), 2'-fluoro (2'-F), and/or 2'-O-methyl (2'-OMe) substituents. In some cases, aptamers described herein comprise a 2'-OMe and/or a 2'F modification to increase in vivo stability. In some cases, the aptamers described herein contain modified nucleotides to improve the affinity and specificity of the aptamers for a target. Examples of modified nucleotides include those modified with guanidine, indole, amine, phenol, hydroxymethyl, or boronic acid. In other cases, pyrimidine nucleotide triphosphate analogs or CE-phosphoramidites may be modified at the 5 position to generate, for example, 5-benzylaminocarbonyl-2'-deoxyuridine (BndU); 5-[N-(phenyl-3-propyl)carboxamide]-2'-deoxyuridine (PPdU); 5-(N-thiophenylmethylcarboxyamide)-2'-deoxyuridine (ThdU); 5-(N-4-fluorobenzylcarboxyamide)-2'-deoxyuridine (FBndU); 5-(N-(1-naphthylmethyl)carboxamide)-2'-deoxyuridine (NapdU); 5-(N-2-naphthylmethylcarboxyamide)-2'-deoxyuridine (2NapdU); 5-(N-1-naphthylethylcarboxyamide)-2'-deoxyuridine (NEdU); 5-(N-2-naphthylethylcarboxyamide)-2'-deoxyuridine (2NEdU); 5-(N-tryptaminocarboxyamide)-2'-deoxyuridine (TrpdU); 5-isobutylaminocarbonyl-2'-deoxyuridine (IbdU); 5-(N-tyrosylcarboxyamide)-2'-deoxyuridine (TyrdU); 5-(N-isobutylaminocarbonyl-2'-deoxyuridine (iBudU): 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-3,4-methylenedioxybenzylcarboxyamide)-2'-deoxyuridine (MBndU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, 5-(N-3-benzothiophenylethylcarboxyamide)-2'-fluorouridine; 5-[N-(1-morpholino-2-ethyl)carboxamide]-2'-deoxyuridine (MOEdu); R-tetrahydrofuranylmethyl-2'-deoxyuridine (RTMdU); 3-methoxybenzyl-2'-deoxyuridine (3MBndU); 4-methoxybenzyl-2'-deoxyuridine (4MBndU); 3,4-dimethoxybenzyl-2'-deoxyuridine (3,4DMBndU); S-tetrahydrofuranylmethyl-2'-deoxyuridine (STMdU); 3,4-methylenedioxyphenyl-2-ethyl-2'-deoxyuridine (MPEdU); 4-pyridinylmethyl-2'-deoxyuridine (PyrdU); or 1-benzimidazol-2-ethyl-2'-deoxyuridine (BidU); 5-(amino-1-propenyl)-2'-deoxyuridine; 5-(indole-3-acetamido-1-propenyl)-2'-deoxyuridine; or 5-(4-pivaloylbenzamido-1-propenyl)-2'-deoxyuridine.

Modifications of the aptamers contemplated in this disclosure include, without limitation, those which provide other chemical groups that incorporate additional charge, polarizability, hydrophobicity, hydrogen bonding, electrostatic interaction, and functionality to the nucleic acid aptamer bases or to the nucleic acid aptamer as a whole. Modifications to generate oligonucleotide populations that are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate, phosphorodithioate, or alkyl phosphate modifications, methylations, and unusual base-pairing combinations such as the isobases isocytidine and isoguanosine. Modifications can also include 3' and 5' modifications such as capping, e.g., addition of a 3'-3'-dT cap to increase exonuclease resistance, or conjugation of a PEG to the 5' or 3' end to increase exonuclease and endonuclease resistance.

Aptamers of the disclosure may generally comprise nucleotides having ribose in the β-D-ribofuranose configuration. In some cases, 100% of the nucleotides present in the aptamer have ribose in the β-D-ribofuranose configuration. In some cases, at least 50% of the nucleotides present in the aptamer have ribose in the β-D-ribofuranose configuration. In some cases, at least 10, at least 20%, at least 30%, at least 40%, at least 50%, at least 60%, at least 70%, at least 80%, at least 90%, or 100% of the nucleotides present in the aptamer have ribose in the β-D-ribofuranose configuration.

The length of the aptamer can be variable. In some cases, the length of the aptamer is less than 100 nucleotides. In some cases, the length of the aptamer is greater than 10 nucleotides. In some cases, the length of the aptamer is between 10 and 90 nucleotides. The aptamer can be, without limitation, about 10, about 15, about 20, about 25, about 30, about 35, about 40, about 45, about 50, about 55, about 60, about 65, about 70, about 75, about 80, about 85, or about 90 nucleotides in length.

In some instances, a polyethylene glycol (PEG) polymer chain is covalently bound to the aptamer, referred to herein as PEGylation. Without wishing to be bound by theory, PEGylation may increase the half-life and stability of the aptamer in physiological conditions. In some cases, the PEG polymer is covalently bound to the 5' end of the aptamer. In some cases, the PEG polymer is covalently bound to the 3' end of the aptamer. In some cases, the PEG polymer is covalently bound to both the 5' end and the 3 end of the aptamer. In some cases, the PEG polymer is covalently bound to a specific site on a nucleobase within the aptamer, including the 5-position of a pyrimidine or 8-position of a purine. In some cases, the PEG polymer is covalently bound to an abasic site within the aptamer.

In some cases, an aptamer described herein may be conjugated to a PEG having the general formula, $H—(O—CH_2—CH_2)_n—OH$. In some cases, an aptamer described herein may be conjugated to a methoxy-PEG (mPEG) of the general formula, $CH_3O—(CH_2—CH_2—O)_n—H$. In some cases, the aptamer is conjugated to a linear chain PEG or mPEG. The linear chain PEG or mPEG may have an average molecular weight of up to about 30 kD. Multiple linear chain PEGs or mPEGs can be linked to a common reactive group to form multi-arm or branched PEGs or mPEGs. For example, more than one PEG or mPEG can be linked together through an amino acid linker (e.g., lysine) or another linker, such as glycerine. In some cases, the aptamer is conjugated to a branched PEG or branched mPEG. Branched PEGs or mPEGs may be referred to by their total mass (e.g., two linked 20 kD mPEGs have a total molecular weight of 40 kD). Branched PEGs or mPEGs may have more than two arms. Multi-arm branched PEGs or mPEGs may be referred to by their total mass (e.g., four linked 10 kD mPEGs have a total molecular weight of 40 kD). In some cases, an aptamer of the present disclosure is conjugated to a PEG polymer having a total molecular weight from about 5 kD to about 200 kD, for example, about 5 kD, about 10 kD, about 20 kD, about 30 kD, about 40 kD, about 50 kD, about 60 kD, about 70 kD, about 80 kD, about 90 kD, about 100 kD, about 110 kD, about 120 kD, about 130 kD, about 140 kD, about 150 kD, about 160 kD, about 170 kD, about 180 kD, about 190 kD, or about 200 kD. In one non-limiting example, the aptamer is conjugated to a PEG having a total molecular weight of about 40 kD.

In some cases, the reagent that may be used to generate PEGylated aptamers is a branched PEG N-Hydroxysuccinimide (mPEG-NHS) having the general formula:

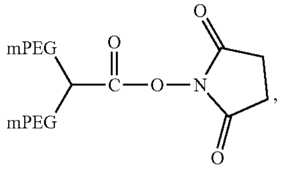

with a 20 kD, 40 kD or 60 kD total molecular weight (e.g., where each mPEG is about 10 kD, 20 kD or about 30 kD). As described above, the branched PEGs can be linked through any appropriate reagent, such as an amino acid (e.g., lysine or glycine residues).

In one non-limiting example, the reagent used to generate PEGylated aptamers is [$N^2$-(monomethoxy 20K polyethylene glycol carbamoyl)-$N^6$-(monomethoxy 20K polyethylene glycol carbamoyl)]-lysine N-hydroxysuccinimide having the formula:

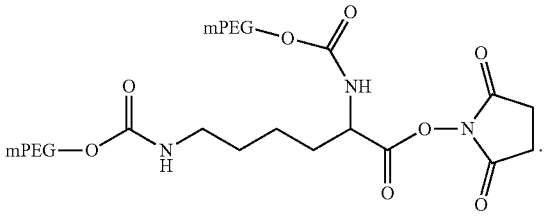

In yet another non-limiting example, the reagent used to generate PEGylated aptamers has the formula:

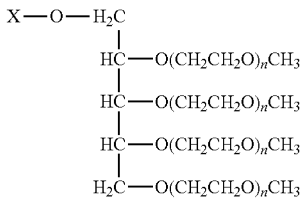

where X is N-hydroxysuccinimide and the PEG arms are of approximately equivalent molecular weight. Such PEG architecture may provide a compound with reduced viscosity compared to a similar aptamer conjugated to a two-armed or single-arm linear PEG.

In some examples, the reagent used to generate PEGylated aptamers has the formula:

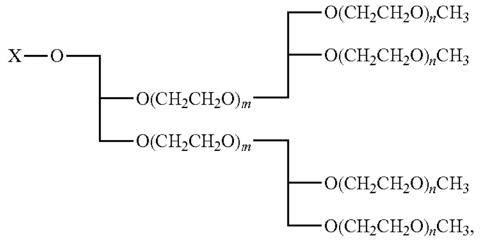

where X is N-hydroxysuccinimide and the PEG arms are of different molecular weights, for example, a 40 kD PEG of this architecture may be composed of 2 arms of 5 kD and 4 arms of 7.5 kD. Such PEG architecture may provide a compound with reduced viscosity compared to a similar aptamer conjugated to a two-armed PEG or a single-arm linear PEG.

In some cases, the reagent that may be used to generate PEGylated aptamers is a non-branched mPEG-Succinimidyl Propionate (mPEG-SPA), having the general formula:

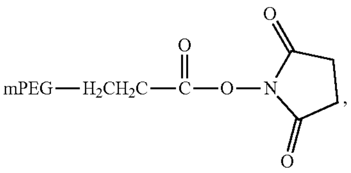, where mPEG is about 20 kD or about 30 kD. In one example, the reactive ester may be $-O-CH_2-CH_2-CO_2-NHS$.

In some instances, the reagent that may be used to generate PEGylated aptamers may include a branched PEG linked through glycerol, such as the SUNBRIGHT® series from NOF Corporation, Japan. Non-limiting examples of these reagents include:

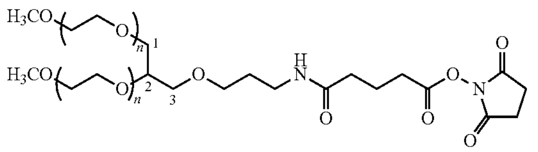

(SUNBRIGHT®GL2-400GS2) ;

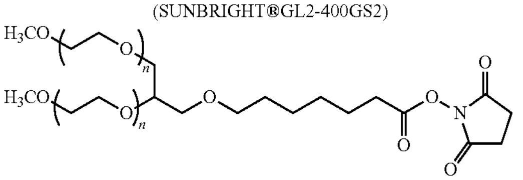

(SUNBRIGHT®GL2-400HS) ; and

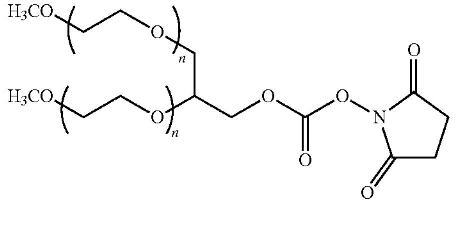

(SUNBRIGHT®GL2-400TS) .

In another example, the reagents may include a non-branched mPEG Succinimidyl alpha-methylbutanoate (mPEG-SMB) having the general formula:

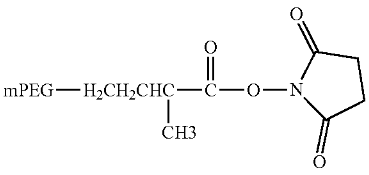, where mPEG is between 10 and 30 kD. In one example, the reactive ester may be $-O-CH_2.CH_2.CH(CH_3)-CO_2-NHS$.

In other instances, the PEG reagents may include nitrophenyl carbonate-linked PEGs, having the general formula:

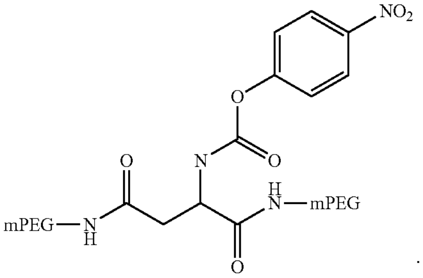.

Compounds including nitrophenyl carbonate can be conjugated to primary amine containing linkers.

In some cases, the reagents used to generate PEGylated aptamers may include PEG with thiol-reactive groups that can be used with a thiol-modified linker. One non-limiting example may include reagents having the following general structure:

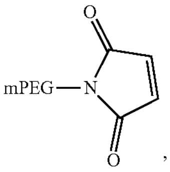, where mPEG is about 10 kD, about 20 kD or about 30 kD.

Another non-limiting example may include reagents having the following general structure:

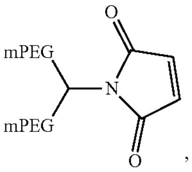, where each mPEG is about 10 kD, about 20 kD, or about 30 kD and the total molecular weight is about 20 kD, about 40 kD, or about 60 kD, respectively. Branched PEGs with thiol reactive groups that can be used with a thiol-modified linker, as described above, may include reagents in which the branched PEG has a total molecular weight of about 40 kD or about 60 kD (e.g., where each mPEG is about 20 kD or about 30 kD).

In some cases, the reagents used to generated PEGylated aptamers may include reagents having the following structure:

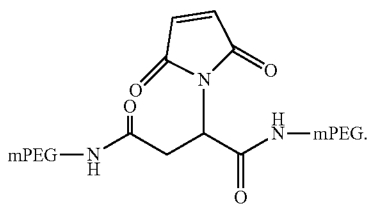

In some cases, the reaction to conjugate the PEG to the aptamer is carried out between about pH 6 and about pH 10, or between about pH 7 and pH 9 or about pH 8.

In some cases, the reagents used to generate PEGylated aptamers may include reagents having the following structure:

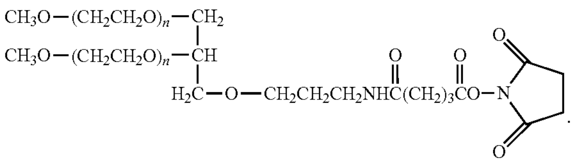

In some cases, the reagents used to generate PEGylated aptamers may include reagents having the following structure:

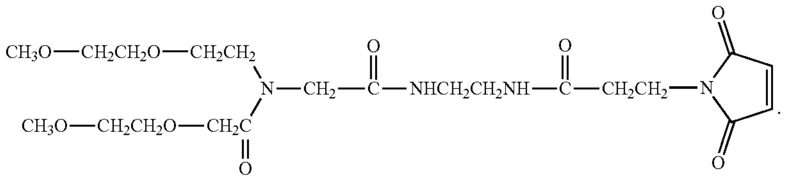

In some cases, the aptamer is associated with a single PEG molecule. In other cases, the aptamer is associated with two or more PEG molecules.

In some cases, the aptamers described herein may be bound or conjugated to one or more molecules having desired biological properties. Any number of molecules can be bound or conjugated to aptamers, non-limiting examples including antibodies, peptides, proteins, carbohydrates, enzymes, polymers, drugs, small molecules, gold nanoparticles, radiolabels, fluorescent labels, dyes, haptens (e.g., biotin), other aptamers, or nucleic acids (e.g., siRNA). In some cases, aptamers may be conjugated to molecules that increase the stability, the solubility or the bioavailability of the aptamer. Non-limiting examples include polyethylene glycol (PEG) polymers, carbohydrates and fatty acids. In some cases, molecules that improve the transport or delivery of the aptamer may be used, such as cell penetrating peptides. Non-limiting examples of cell penetrating peptides can include peptides derived from Tat, penetratin, polyarginine peptide $Arg_8$ sequence, Transportan, VP22 protein from Herpes Simplex Virus (HSV), antimicrobial peptides such as Buforin I and SynB, polyproline sweet arrow peptide molecules, Pep-1 and MPG. In some embodiments, the aptamer is conjugated to a lipophilic compound such as cholesterol, dialkyl glycerol, diacyl glycerol, or a non-immunogenic, high molecular weight compound or polymer such as polyethylene glycol (PEG) or other water-soluble pharmaceutically acceptable polymers including, but not limited to, polyaminoamines (PAMAM) and polysaccharides such as dextran, or polyoxazolines (POZ).

The molecule to be conjugated can be covalently bonded or can be associated through non-covalent interactions with the aptamer of interest. In one example, the molecule to be conjugated is covalently attached to the aptamer. The covalent attachment may occur at a variety of positions on the aptamer, for example, to the exocyclic amino group on the base, the 5-position of a pyrimidine nucleotide, the 8-position of a purine nucleotide, the hydroxyl group of the phosphate, or a hydroxyl group or other group at the 5' or 3' terminus. In one example, the covalent attachment is to the 5' or 3' hydroxyl group of the aptamer.

In some cases, the aptamer can be attached to another molecule directly or with the use of a spacer or linker. For example, a lipophilic compound or a non-immunogenic, high molecular weight compound can be attached to the aptamer using a linker or a spacer. Various linkers and attachment chemistries are known in the art. In a non-limiting example, 6-(trifluoroacetamido)hexanol (2-cyanoethyl-N,N-diisopropyl)phosphoramidite can be used to add a hexylamino linker to the 5' end of the synthesized aptamer. This linker, as with the other amino linkers provided herein, once the group protecting the amine has been removed, can be reacted with PEG-NHS esters to produce covalently linked PEG-aptamers. Other non-limiting examples of linker phosphoramidites may include: TFA-amino C4 CED phosphoramidite having the structure:

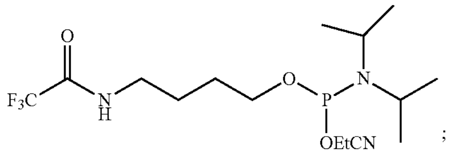

5'-amino modifier C3 TFA having the structure:

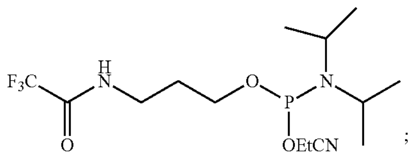

MMT amino modifier C6 CED phosphoramidite having the structure:

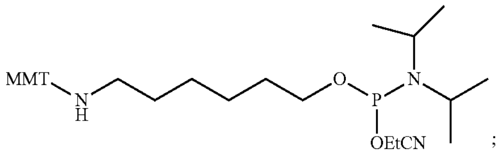

;

5'-amino modifier 5 having the structure:

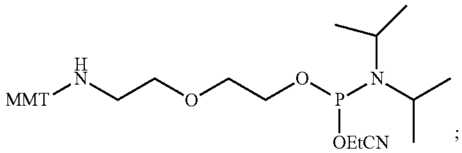

;

MMT: 4-Monomethoxytrityl

5'-amino modifier C12 having the structure:

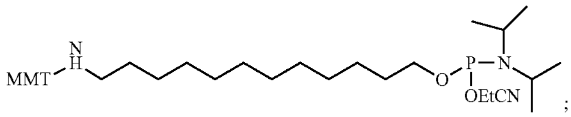

;

MMT: 4-Monomethoxytrityl

5' thiol-modifier C6 having the structure:

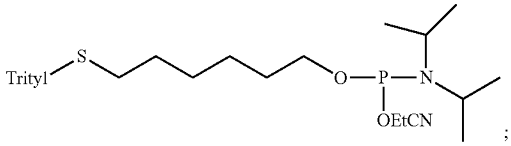

;

5' thiol-modifier C6 having the structure:

The 5'-thiol modified linker may be used, for example, with PEG-maleimides, PEG-vinylsulfone, PEG-iodoacetamide and PEG-orthopyridyl-disulfide. In one example, the aptamer may be bonded to the 5'-thiol through a maleimide or vinyl sulfone functionality.

In some cases, the aptamer formulated according to the present disclosure may also be modified by encapsulation within or displayed on the surface of a liposome. In other cases, the aptamer formulated according to the present disclosure may also be modified by encapsulation within or displayed on the surface of a micelle. Liposomes and micelles may be comprised of any lipids, and in some cases the lipids may be phospholipids, including phosphatidylcholine. Liposomes and micelles may also contain or be comprised in part or in total of other polymers and amphipathic molecules including PEG conjugates of poly lactic acid (PLA), poly DL-lactic-co-glycolic acid (PLGA), or poly caprolactone (PCL).

In some cases, the aptamers described herein may be designed to inhibit a function associated with VEGF-A. In some cases, the aptamers described herein may be designed to bind the receptor binding face of VEGF-A, or a portion thereof. In some cases, the aptamers described herein may be designed to bind the receptor binding domain of VEGF-A, or a portion thereof. The receptor binding domain of VEGF-A may include any one or more of residues 1-109 as described in SEQ ID NOs: 6-10. In some cases, the aptamers described herein may bind to a structural feature of VEGF-A other than the heparin binding domain of VEGF-A. The heparin binding domain of VEGF-A may include any one or more of residues 111-165 as described in SEQ ID NOs: 6-8. In some cases, the aptamers described herein may block or reduce binding of one or more isoforms or variants of VEGF-A to one or more of Flk-1, KDR, and Nip-1.

In some instances, an aptamer is isolated or purified. "Isolated" (used interchangeably with "substantially pure" or "purified") as used herein means an aptamer that is synthesized chemically, or has been separated from other aptamers.

In some cases, an aptamer of the disclosure may comprise one of the following sequences described in Table 1.

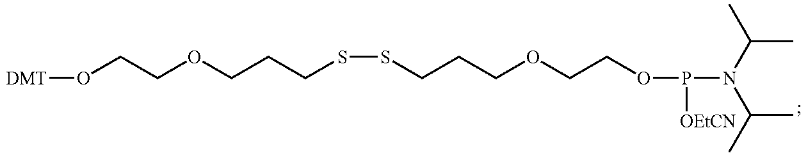

;

DMT: 4,4'-Dimethoxytrityl and 5' thiol-modifier C6 having the structure:

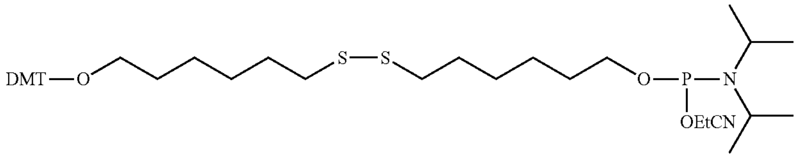

.

DMT: 4,4'-Dimethoxytrityl

TABLE 1

| VEGF-A Aptamer Sequences | | |
|---|---|---|
| Compound Name | Backbone | Sequence 5' to 3' |
| R6-1 truncated | RNA | AGGCCGCCUCCGCGCGGAGGGAUUUCAUUAUCCCGUUUGGCUGCUU (SEQ ID NO: 11), where G is 2'F; and A, C, & U are 2'OMe modified RNA. |
| R6-1 full | RNA | GGGAGUGUGUACGAGGCAUUAAGGCCGCCUCCGCGCGGAGGGAUUUCAUUAUCCCGUUUGGCUGCUUUGAUACUUGAUCGCCCUAGAAGC (SEQ ID NO: 12), where G is 2'F; and A, C, & U are 2'OMe modified RNA. |
| R6-2 truncated | RNA | AUGCCGCCUCCGCGCGGAGGGAUUUCAUUAUCCCGUUUGGCUGCUU (SEQ ID NO: 13), where G is 2'F; and A, C, & U are 2'OMe modified RNA. |
| R6-2 full | RNA | GGGAGUGUGUACGAGGCAUUAAUGCCGCCUCCGCGCGGAGGGAUUUCAUUAUCCCGUUUGGCUGCUUUGAUACUUGAUCGCCCUAGAAGC (SEQ ID NO: 14), where G is 2'F; and A, C, & U are 2'OMe modified RNA. |
| R6-3 truncated | RNA | AUGCCGCCUCCGCGCGGAGGGGUUUCAUUAUCCCGUUUGGCUGCAU (SEQ ID NO: 15), where G is 2'F; and A, C, & U are 2'OMe modified RNA. |
| R6-3 full | RNA | GGGAGUGUGUACGAGGCAUUAAUGCCGCCUCCGCGCGGAGGGGUUUCAUUAUCCCGUUUGGCUGCAUUGAUACUUGAUCGCCCUAGAAGC (SEQ ID NO: 16), where G is 2'F; and A, C, & U are 2'OMe modified RNA. |
| R6-4 truncated | RNA | AUGCCGCCUCCGCGCGGAGGGGUUUCAUUAUCCCGUUUGGCGGCUU (SEQ ID NO: 17), where G is 2'F; and A, C, & U are 2'OMe modified RNA. |
| R6-4 full | RNA | GGGAGUGUGUACGAGGCAUUAAUGCCGCCUCCGCGCGGAGGGGUUUCAUUAUCCCGUUUGGCGGCUUUGAUACUUGAUCGCCCUAGAAGC (SEQ ID NO: 18), where G is 2'F; and A, C, & U are 2'OMe modified RNA. |
| R6-5 truncated | RNA | AUGCCGCCUCCGCGCGGAGGGGUUUCAUAAUCCCGUUUGGCUGCAU (SEQ ID NO: 19), where G is 2'F; and A, C, & U are 2'OMe modified RNA. |
| R6-5 full | RNA | GGGAGUGUGUACGAGGCAUUAAUGCCGCCUCCGCGCGGAGGGGUUUCAUAAUCCCGUUUGGCUGCAUUGAUACUUGAUCGCCCUAGAAGC (SEQ ID NO: 20), where G is 2'F; and A, C, & U are 2'OMe modified RNA. |
| R6-6 truncated | RNA | AUGCCGCCUCCGCGCGGAGGGGUAUCAUUAUCCCGUUUGGCUGCAU (SEQ ID NO: 21), where G is 2'F; and A, C, & U are 2'OMe modified RNA. |
| R6-6 full | RNA | GGGAGUGUGUACGAGGCAUUAAUGCCGCCUCCGCGCGGAGGGGUAUCAUUAUCCCGUUUGGCUGCAUUGAUACUUGAUCGCCCUAGAAGC (SEQ ID NO: 22), where G is 2'F; and A, C, & U are 2'OMe modified RNA. |
| R6-7 truncated | RNA | AAGCCGCCUCCGCGCGGAGGGGUAUCAUUAUCCCGUUUGGCUGCUU (SEQ ID NO: 23), where G is 2'F; and A, C, & U are 2'OMe modified RNA. |
| R6-7 full | RNA | GGGAGUGUGUACGAGGCAUUAAAGCCGCCUCCGCGCGGAGGGGUAUCAUUAUCCCGUUUGGCUGCUUUGAUACUUGAUCGCCCUAGAAGC (SEQ ID NO: 24), where G is 2'F; and A, C, & U are 2'OMe modified RNA. |
| R6-8 truncated | RNA | AAGCUGCCUCCGCGCGGAGGGGUUUCAUUAUCCCGCUUGGCUGCUU (SEQ ID NO: 25), where G is 2'F; and A, C, & U are 2'OMe modified RNA. |
| R6-8 full | RNA | GGGAGUGUGUACGAGGCAUUAAAGCUGCCUCCGCGCGGAGGGGUUUCAUUAUCCCGUUUGGCUGCUUUGAUACUUGAUCGCCCUAGAAGC (SEQ ID NO: 26), where G is 2'F; and A, C, & U are 2'OMe modified RNA. |
| R6-9 truncated | RNA | AUGCCGCCUCCGCGCGGAGGGGUUACAUUAUCCCGUUUGGCUGCAU (SEQ ID NO: 27), where G is 2'F; and A, C, & U are 2'OMe modified RNA. |
| R6-9 full | RNA | GGGAGUGUGUACGAGGCAUUAAUGCCGCCUCCGCGCGGAGGGGUUACAUUAUCCCGUUUGGCUGCAUUGAUACUUGAUCGCCCUAGAAGC (SEQ ID NO: 28), where G is 2'F; and A, C, & U are 2'OMe modified RNA. |
| R6-12 truncated | RNA | AUGCCGCCUCCGCGCGGAGGGAUUUCAUUAUCCCGUUUGUCGGCUU (SEQ ID NO: 29), where G is 2'F; and A, C, & U are 2'OMe modified RNA. |
| R6-12 full | RNA | GGGAGUGUGUACGAGGCAUUAAUGCCGCCUCCGCGCGGAGGGAUUUCAUUAUCCCGUUUGUCGGCUUUGAUACUUGAUCGCCCUAGAAGC (SEQ ID NO: 30), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| R6-13 truncated | RNA | AUGCUGCCUCCGCGCGGAGGGGUUUCAUUAUCCCGUUUGGCUGCAU (SEQ ID NO: 31), where G is 2'F; and A, C, & U are 2'OMe modified RNA. |
| R6-13 full | RNA | GGGAGUGUGUACGAGGCAUUAAUGCUGCCUCCGCGCGGAGGGGUUUCAUUAUCCCGUUUGGCUGCAUUGAUACUUGAUCGCCCUAGAAGC (SEQ ID NO: 32), where G is 2'F; and A, C, & U are 2'OMe modified RNA. |
| R6-14 truncated | RNA | AAGCUGCCUCCGCGCGGAGGGGUUUCAUUAUCCCGUUUGGCCGCUU (SEQ ID NO: 33), where G is 2'F; and A, C, & U are 2'OMe modified RNA. |
| R6-14 full | RNA | GGGAGUGUGUACGAGGCAUUAAAGCUGCCUCCGCGCGGAGGGGUUUCAUUAUCCCGUUUGGCCGCUUUGAUACUUGAUCGCCCUAGAAGC (SEQ ID NO: 34), where G is 2'F; and A, C, & U are 2'OMe modified RNA. |
| R6-16 truncated | RNA | AAGCAUCCUCCGCGCGGAGGGGUUUCAUUAUCCCGUUUGGCUGCUU (SEQ ID NO: 35), where G is 2'F; and A, C, & U are 2'OMe modified RNA. |
| R6-16 full | RNA | GGGAGUGUGUACGAGGCAUUAAAGCAUCCUCCGCGCGGAGGGGUUUCAUUAUCCCGUUUGGCUGCUUUGAUACUUGAUCGCCCUAGAAGC (SEQ ID NO: 36), where G is 2'F; and A, C, & U are 2'OMe modified RNA. |
| R6-17 truncated | RNA | AUGCAGCCUCCGCGCGGAGGGGUUUCAUUAUCCCGUUUGGCUGCUU (SEQ ID NO: 37), where G is 2'F; and A, C, & U are 2'OMe modified RNA. |
| R6-17 full | RNA | GGGAGUGUGUACGAGGCAUUAAUGCAGCCUCCGCGCGGAGGGGUUUCAUUAUCCCGUUUGGCUGCUUUGAUACUUGAUCGCCCUAGAAGC (SEQ ID NO: 38), |
| R6-18 truncated | RNA | AUGCCGCCUCCGCGCGGAGGGGUUUCAUUAUCCCGUUUGGCGGCAU (SEQ ID NO: 39), where G is 2'F; and A, C, & U are 2'OMe modified RNA. |
| R6-18 full | RNA | GGGAGUGUGUACGAGGCAUUAAUGCCGCCUCCGCGCGGAGGGGUUUCAUUAUCCCGUUUGGCGGCAUUGAUACUUGAUCGCCCUAGAAGC (SEQ ID NO: 40), where G is 2'F; and A, C, & U are 2'OMe modified RNA. |
| R6-19 truncated | RNA | AUGUCGCCUCCGCGCGGAGGGGUUUCAUUAUCCCGUUUGGCGGCAU (SEQ ID NO: 41), where G is 2'F; and A, C, & U are 2'OMe modified RNA. |
| R6-19 full | RNA | GGGAGUGUGUACGAGGCAUUAAUGUCGCCUCCGCGCGGAGGGGUUUCAUUAUCCCGUUUGGCGGCAUUGAUACUUGAUCGCCCUAGAAGC (SEQ ID NO: 42), where G is 2'F; and A, C, & U are 2'OMe modified RNA. |
| R6-20 truncated | RNA | AGGCCGCCUCCGCGCGGAGGGAUUUCAUUAUCCCGUUUGGCUGCCU (SEQ ID NO: 43), where G is 2'F; and A, C, & U are 2'OMe modified RNA. |
| R6-20 full | RNA | GGGAGUGUGUACGAGGCAUUAAGGCCGCCUCCGCGCGGAGGGAUUUCAUUAUCCCGUUUGGCUGCCUUGAUACUUGAUCGCCCUAGAAGC (SEQ ID NO: 44), where G is 2'F; and A, C, & U are 2'OMe modified RNA. |
| R6-21 truncated | RNA | AGGCCGCCUCCGCGCGGAGGGAUUUCAUUAUCCCGUUUGUCGGCUU (SEQ ID NO: 45), where G is 2'F; and A, C, & U are 2'OMe modified RNA. |
| R6-21 full | RNA | GGGAGUGUGUACGAGGCAUUAAGGCCGCCUCCGCGCGGAGGGAUUUCAUUAUCCCGUUUGUCGGCUUUGAUACUUGAUCGCCCUAGAAGC (SEQ ID NO: 46), where G is 2'F; and A, C, & U are 2'OMe modified RNA. |
| R6-22 truncated | RNA | AUGCUGCCUCCGCGCGGAGGGGUUUCAUUAUCCCGUUUGGCGGCAU (SEQ ID NO: 47), where G is 2'F; and A, C, & U are 2'OMe modified RNA. |
| R6-22 full | RNA | GGGAGUGUGUACGAGGCAUUAAUGCUGCCUCCGCGCGGAGGGGUUUCAUUAUCCCGUUUGGCGGCAUUGAUACUUGAUCGCCCUAGAAGC (SEQ ID NO: 48), where G is 2'F; and A, C, & U are 2'OMe modified RNA. |
| R6-24 truncated | RNA | AUGCCGCCUCCGCGCGGAGGGGUUUCACAAUCCCGUUUGGCUGCAU (SEQ ID NO: 49), where G is 2'F; and A, C, & U are 2'OMe modified RNA. |
| R6-24 full | RNA | GGGAGUGUGUACGAGGCAUUAAUGCCGCCUCCGCGCGGAGGGGUUUCACAAUCCCGUUUGGCUGCAUUGAUACUUGAUCGCCCUAGAAGC (SEQ ID NO: 50), where G is 2'F; and A, C, & U are 2'OMe modified RNA. |
| R6-25 truncated | RNA | AUGCUGCCUCCGCGCGGAGGGGUUUCAUUAUCCCGUUUGGCCGCAU (SEQ ID NO: 51), where G is 2'F; and A, C, & U are 2'OMe modified RNA. |
| R6-25 full | RNA | GGGAGUGUGUACGAGGCAUUAAUGCUGCCUCCGCGCGGAGGGGUUUCAUUAUCCCGUUUGGCCGCAUUGAUACUUGAUCGCCCUAGAAGC (SEQ ID NO: 52), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| R6-27 truncated | RNA | AUGCCGCCUCCGCGCGGAGGGGUUACAUUAUCCCGUUUGGCGGCUU (SEQ ID NO: 53), where G is 2'F; and A, C, & U are 2'OMe modified RNA. |
| R6-27 full | RNA | GGGAGUGUGUACGAGGCAUUAAUGCCGCCUCCGCGCGGAGGGGUUACAUUAUCCCGUUUGGCGGCUUUGAUACUUGAUCGCCCUAGAAGC (SEQ ID NO: 54), where G is 2'F; and A, C, & U are 2'OMe modified RNA. |
| R6-29 truncated | RNA | AUGCCGCCUCCGCGCGGAGGGGUUACAUAAUCCCGUUUGGCUGCAU (SEQ ID NO: 55), where G is 2'F; and A, C, & U are 2'OMe modified RNA. |
| R6-29 full | RNA | GGGAGUGUGUACGAGGCAUUAAUGCCGCCUCCGCGCGGAGGGGUUACAUAAUCCCGUUUGGCUGCAUUGAUACUUGAUCGCCCUAGAAGC (SEQ ID NO: 56), where G is 2'F; and A, C, & U are 2'OMe modified RNA. |
| R6-31 truncated | RNA | AGGCAGCCUCCGCGCGGAGGGGUUUCAUUAUCCCGUUUGGCUGCUU (SEQ ID NO: 57), where G is 2'F; and A, C, & U are 2'OMe modified RNA. |
| R6-31 full | RNA | GGGAGUGUGUACGAGGCAUUAAGGCAGCCUCCGCGCGGAGGGGUUUCAUUAUCCCGUUUGGCUGCUUUGAUACUUGAUCGCCCUAGAAGC (SEQ ID NO: 58), where G is 2'F; and A, C, & U are 2'OMe modified RNA. |
| R6-33 truncated | RNA | AGGCCGCCUCCGCGCGGAGGGAUUACAUUAUCCCGUUUGGCUGCUU (SEQ ID NO: 59), where G is 2'F; and A, C, & U are 2'OMe modified RNA. |
| R6-33 full | RNA | GGGAGUGUGUACGAGGCAUUAAGGCCGCCUCCGCGCGGAGGGAUUACAUUAUCCCGUUUGGCUGCUUUGAUACUUGAUCGCCCUAGAAGC (SEQ ID NO: 60), where G is 2'F; and A, C, & U are 2'OMe modified RNA. |
| R6-34 truncated | RNA | AGGCUGCCUCCGCGCGGAGGGGUUUCAUUAUCCCGUUUGGCUGCUU (SEQ ID NO: 61), where G is 2'F; and A, C, & U are 2'OMe modified RNA. |
| R6-34 full | RNA | GGGAGUGUGUACGAGGCAUUAAGGCUGCCUCCGCGCGGAGGGGUUUCAUUAUCCCGUUUGGCUGCUUUGAUACUUGAUCGCCCUAGAAGC (SEQ ID NO: 62), where G is 2'F; and A, C, & U are 2'OMe modified RNA. |
| R6-36 truncated | RNA | AUGCCGCCUCCGCGCGGAGGGAUUUCAUUAUCCCGUUUGUCGGCAU (SEQ ID NO: 63), where G is 2'F; and A, C, & U are 2'OMe modified RNA. |
| R6-36 full | RNA | GGGAGUGUGUACGAGGCAUUAAUGCCGCCUCCGCGCGGAGGGAUUUCAUUAUCCCGUUUGUCGGCAUUGAUACUUGAUCGCCCUAGAAGC (SEQ ID NO: 64), where G is 2'F; and A, C, & U are 2'OMe modified RNA. |
| R6-39 truncated | RNA | AGGCAUCCUCCGCGCGGAGGGGUUUCAUUAUCCCGUUUGGCUGCCU (SEQ ID NO: 65), where G is 2'F; and A, C, & U are 2'OMe modified RNA. |
| R6-39 full | RNA | GGGAGUGUGUACGAGGCAUUAAGGCAUCCUCCGCGCGGAGGGGUUUCAUUAUCCCGUUUGGCUGCCUUGAUACUUGAUCGCCCUAGAAGC (SEQ ID NO: 66), where G is 2'F; and A, C, & U are 2'OMe modified RNA. |
| R6-42 truncated | RNA | AAGCUGCCUCCGCGCGGAGGGGUUUCAUUAUCCCGUUUGGCGGCUU (SEQ ID NO: 67), where G is 2'F; and A, C, & U are 2'OMe modified RNA. |
| R6-42 full | RNA | GGGAGUGUGUACGAGGCAUUAAAGCUGCCUCCGCGCGGAGGGGUUUCAUUAUCCCGUUUGGCGGCUUUGAUACUUGAUCGCCCUAGAAGC (SEQ ID NO: 68), where G is 2'F; and A, C, & U are 2'OMe modified RNA. |
| R6-43 truncated | RNA | AAGCUGCCUCCGCGCGGAGGGGUUGCAUUAUCCCGUUUGGCUGCUU (SEQ ID NO: 69), where G is 2'F; and A, C, & U are 2'OMe modified RNA. |
| R6-43 full | RNA | GGGAGUGUGUACGAGGCAUUAAAGCUGCCUCCGCGCGGAGGGGUUGCAUUAUCCCGUUUGGCUGCUUUGAUACUUGAUCGCCCUAGAAGC (SEQ ID NO: 70), where G is 2'F; and A, C, & U are 2'OMe modified RNA. |
| R6-45 truncated | RNA | AGUCAGCCUCCGCGCGGAGGGGUUUCAUUAUCCCGUUUGGCUGCCU (SEQ ID NO: 71), where G is 2'F; and A, C, & U are 2'OMe modified RNA. |
| R6-45 full | RNA | GGGAGUGUGUACGAGGCAUUAAGUCAGCCUCCGCGCGGAGGGGUUUCAUUAUCCCGUUUGGCUGCCUUGAUACUUGAUCGCCCUAGAAGC (SEQ ID NO: 72), where G is 2'F; and A, C, & U are 2'OMe modified RNA. |
| R6-48 truncated | RNA | AUGCCGCCUCCGCGCGGAGGGGUUUCAUUAUCCCGUUUGGUGGCAU (SEQ ID NO: 73), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| R6-48 full | RNA | GGGAGUGUGUACGAGGCAUUAAUGCCGCCUCCGCGCGGAGGGGUUUCAUUAUCCCGUUUGGUG GCAUUGAUACUUGAUCGCCCUAGAAGC (SEQ ID NO: 74), where G is 2'F; and A, C, & U are 2'OMe modified RNA. |
| R6-49 truncated | RNA | AUGCUGCCUCCGCGCGGAGGGGUUUCAUUAUCCCGUUUGGCGGCUU (SEQ ID NO: 75), where G is 2'F; and A, C, & U are 2'OMe modified RNA. |
| R6-49 full | RNA | GGGAGUGUGUACGAGGCAUUAAUGCUGCCUCCGCGCGGAGGGGUUUCAUUAUCCCGUUUGGCG GCUUUGAUACUUGAUCGCCCUAGAAGC (SEQ ID NO: 76), where G is 2'F; and A, C, & U are 2'OMe modified RNA. |
| R6-50 truncated | RNA | AUGCAUCCUCCGCGCGGAGGGGUUUCAUUAUCCCGUUUGGCUGCAU (SEQ ID NO: 77), where G is 2'F; and A, C, & U are 2'OMe modified RNA. |
| R6-50 full | RNA | GGGAGUGUGUACGAGGCAUUAAUGCAUCCUCCGCGCGGAGGGGUUUCAUUAUCCCGUUUGGCU GCAUUGAUACUUGAUCGCCCUAGAAGC (SEQ ID NO: 78), where G is 2'F; and A, C, & U are 2'OMe modified RNA. |
| R6-53 truncated | RNA | AGGCCACCUCCGCGCGGAGGGGUUUCAUUAUCCCGUUUGGUGGCUU (SEQ ID NO: 79), where G is 2'F; and A, C, & U are 2'OMe modified RNA. |
| R6-53 full | RNA | GGGAGUGUGUACGAGGCAUUAAGGCCACCUCCGCGCGGAGGGGUUUCAUUAUCCCGUUUGGUG GCUUUGAUACUUGAUCGCCCUAGAAGC (SEQ ID NO: 80), where G is 2'F; and A, C, & U are 2'OMe modified RNA. |
| R6-54 truncated | RNA | AGUCCGCCUCCGCGCGGAGGGGUUUCAUUAUCCCGUUUGGCGGCUA (SEQ ID NO: 81), where G is 2'F; and A, C, & U are 2'OMe modified RNA. |
| R6-54 full | RNA | GGGAGUGUGUACGAGGCAUUAAGUCCGCCUCCGCGCGGAGGGGUUUCAUUAUCCCGUUUGGCU AUGAUACUUGAUCGCCCUAGAAGC (SEQ ID NO: 82), where G is 2'F; and A, C, & U are 2'OMe modified RNA. |
| R6-57 truncated | RNA | AAGCAGCCUCCGCGCGGAGGGGUUUCAUUAUCCCGUUUGGCUGCUU (SEQ ID NO: 83), where G is 2'F; and A, C, & U are 2'OMe modified RNA. |
| R6-57 full | RNA | GGGAGUGUGUACGAGGCAUUAAAGCAGCCUCCGCGCGGAGGGGUUUCAUUAUCCCGUUUGGCU GCUUUGAUACUUGAUCGCCCUAGAAGC (SEQ ID NO: 84), where G is 2'F; and A, C, & U are 2'OMe modified RNA. |
| R6-58 truncated | RNA | AUGCAGCCUCCGCGCGGAGGGGUUUCAUUAUCCCGUUUGGCUGCAU (SEQ ID NO: 85), where G is 2'F; and A, C, & U are 2'OMe modified RNA. |
| R6-58 full | RNA | GGGAGUGUGUACGAGGCAUUAAUGCAGCCUCCGCGCGGAGGGGUUUCAUUAUCCCGUUUGGCU GCAUUGAUACUUGAUCGCCCUAGAAGC (SEQ ID NO: 86), where G is 2'F; and A, C, & U are 2'OMe modified RNA. |
| R6-61 truncated | RNA | AAGCAUCCUCCGCGCGGAGGGGUGUCAUCAUCCCGUUUGGCUGCUU (SEQ ID NO: 87), where G is 2'F; and A, C, & U are 2'OMe modified RNA. |
| R6-61 full | RNA | GGGAGUGUGUACGAGGCAUUAAAGCAUCCUCCGCGCGGAGGGGUGUCAUCAUCCCGUUUGGCU GCUUUGAUACUUGAUCGCCCUAGAAGC (SEQ ID NO: 88), where G is 2'F; and A, C, & U are 2'OMe modified RNA. |
| R6-62 truncated | RNA | AUGCCGCCUCCGCGCGGAGGGGUUUCAUUUCCCCGUUUGGCUGCAU (SEQ ID NO: 89), where G is 2'F; and A, C, & U are 2'OMe modified RNA. |
| R6-62 full | RNA | GGGAGUGUGUACGAGGCAUUAAUGCCGCCUCCGCGCGGAGGGGUUUCAUUUCCCCGUUUGGCU GCAUUGAUACUUGAUCGCCCUAGAAGC (SEQ ID NO: 90), where G is 2'F; and A, C, & U are 2'OMe modified RNA. |
| R6-65 truncated | RNA | AUGCCGCCUCCGCGCGGAGGGGUUUCAUUACCCCGUUUGGCUGCUU (SEQ ID NO: 91), where G is 2'F; and A, C, & U are 2'OMe modified RNA. |
| R6-65 full | RNA | GGGAGUGUGUACGAGGCAUUAAUGCCGCCUCCGCGCGGAGGGGUUUCAUUACCCCGUUUGGCU GCUUUGAUACUUGAUCGCCCUAGAAGC (SEQ ID NO: 92), where G is 2'F; and A, C, & U are 2'OMe modified RNA. |
| R6-67 truncated | RNA | AGGCCACCUCCGCGCGGAGGGGUUUCAUUAUCCCGUUUGGUGUCCU (SEQ ID NO: 93), where G is 2'F; and A, C, & U are 2'OMe modified RNA. |
| R6-67 full | RNA | GGGAGUGUGUACGAGGCAUUAAGGCCACCUCCGCGCGGAGGGGUUUCAUUAUCCCGUUUGGUG UCCUUGAUACUUGAUCGCCCUAGAAGC (SEQ ID NO: 94), where G is 2'F; and A, C, & U are 2'OMe modified RNA. |

TABLE 1-continued

VEGF-A Aptamer Sequences

| Compound Name | Backbone | Sequence 5' to 3' |
|---|---|---|
| R6-68 truncated | RNA | AUGCCGCCUCCGCGCGGAGGGAUUGCAUUAUCCCGUUUGGCUGCAU (SEQ ID NO: 95), where G is 2'F; and A, C, & U are 2'OMe modified RNA. |
| R6-68 full | RNA | GGGAGUGUGUACGAGGCAUUAAUGCCGCCUCCGCGCGGAGGGAUUGCAUUAUCCCGUUUGGCU GCAUUGAUACUUGAUCGCCCUAGAAGC (SEQ ID NO: 96), where G is 2'F; and A, C, & U are 2'OMe modified RNA. |
| R6-70 truncated | RNA | UUGCCGCCUCCGCGCGGAGGGAUUUCAUUAUCCCGUUUGGCUGCUU (SEQ ID NO: 97), where G is 2'F; and A, C, & U are 2'OMe modified RNA. |
| R6-70 full | RNA | GGGAGUGUGUACGAGGCAUUAUUGCCGCCUCCGCGCGGAGGGAUUUCAUUAUCCCGUUUGGCU GCUUUGAUACUUGAUCGCCCUAGAAGC (SEQ ID NO: 98), where G is 2'F; and A, C, & U are 2'OMe modified RNA. |
| R6-72 truncated | RNA | ACGCAGCCUCCGCGCGGAGGGGUUUCAUUAUCCCGUUUGGCUGCUU (SEQ ID NO: 99), where G is 2'F; and A, C, & U are 2'OMe modified RNA. |
| R6-72 full | RNA | GGGAGUGUGUACGAGGCAUUAACGCAGCCUCCGCGCGGAGGGGUUUCAUUAUCCCGUUUGGCU GCUUUGAUACUUGAUCGCCCUAGAAGC (SEQ ID NO: 100), where G is 2'F; and A, C, & U are 2'OMe modified RNA. |
| R6-75 truncated | RNA | AUGCCGCCUCCGCGCGGAGGGGUUUCACUAUCCCGUUUGGCGGCUU (SEQ ID NO: 101), where G is 2'F; and A, C, & U are 2'OMe modified RNA. |
| R6-75 full | RNA | GGGAGUGUGUACGAGGCAUUAAUGCCGCCUCCGCGCGGAGGGGUUUCACUAUCCCGUUUGGCG GCUUUGAUACUUGAUCGCCCUAGAAGC (SEQ ID NO: 102), where G is 2'F; and A, C, & U are 2'OMe modified RNA. |
| R6-76 truncated | RNA | UUGCUGCCUCCGCGCGGAGGGGUUUCAUUAUCCCGUUUGGCCGCAU (SEQ ID NO: 103), where G is 2'F; and A, C, & U are 2'OMe modified RNA. |
| R6-76 full | RNA | GGGAGUGUGUACGAGGCAUUAUUGCUGCCUCCGCGCGGAGGGGUUUCAUUAUCCCGUUUGGCC GCAUUGAUACUUGAUCGCCCUAGAAGC (SEQ ID NO: 104), where G is 2'F; and A, C, & U are 2'OMe modified RNA. |
| R6-79 truncated | RNA | AAGCCGCCUCCGCGCGGAGGGGUUUCAUUAUCCCGUUUGGCGGCUU (SEQ ID NO: 105), where G is 2'F; and A, C, & U are 2'OMe modified RNA. |
| R6-79 full | RNA | GGGAGUGUGUACGAGGCAUUAAAGCCGCCUCCGCGCGGAGGGGUUUCAUUAUCCCGUUUGGCG GCUUUGAUACUUGAUCGCCCUAGAAGC (SEQ ID NO: 106), where G is 2'F; and A, C, & U are 2'OMe modified RNA. |
| R6-80 truncated | RNA | AAUCAGCCUCCGCGCGGAGGGGUUUCAUUAUCCCGUUUGGCUGCUU (SEQ ID NO: 107), where G is 2'F; and A, C, & U are 2'OMe modified RNA. |
| R6-80 full | RNA | GGGAGUGUGUACGAGGCAUUAAAUCAGCCUCCGCGCGGAGGGGUUUCAUUAUCCCGUUUGGCU GCUUUGAUACUUGAUCGCCCUAGAAGC (SEQ ID NO: 108), where G is 2'F; and A, C, & U are 2'OMe modified RNA. |
| R6-83 truncated | RNA | UUGCCGCCUCCGCGCGGAGGGGUUUCAUUAUCCCGUUUGGCGGCUU (SEQ ID NO: 109), where G is 2'F; and A, C, & U are 2'OMe modified RNA. |
| R6-83 full | RNA | GGGAGUGUGUACGAGGCAUUAUUGCCGCCUCCGCGCGGAGGGGUUUCAUUAUCCCGUUUGGCG GCUUUGAUACUUGAUCGCCCUAGAAGC (SEQ ID NO: 110), where G is 2'F; and A, C, & U are 2'OMe modified RNA. |
| R6-85 truncated | RNA | CUGCCGCCUCCGCGCGGAGGGGUUUCAUUAUCCCGUUUGGCGGCUU (SEQ ID NO: 111), where G is 2'F; and A, C, & U are 2'OMe modified RNA. |
| R6-85 full | RNA | GGGAGUGUGUACGAGGCAUUACUGCCGCCUCCGCGCGGAGGGGUUUCAUUAUCCCGUUUGGCG GCUUUGAUACUUGAUCGCCCUAGAAGC (SEQ ID NO: 112), where G is 2'F; and A, C, & U are 2'OMe modified RNA. |
| R6-88 truncated | RNA | AUGCUGCCUCCGCGCGGAGGGGUUUCAUAAUCCCGUUUGGCUGCUU (SEQ ID NO: 113), where G is 2'F; and A, C, & U are 2'OMe modified RNA. |
| R6-88 full | RNA | GGGAGUGUGUACGAGGCAUUAAUGCUGCCUCCGCGCGGAGGGGUUUCAUAAUCCCGUUUGGCU GCUUUGAUACUUGAUCGCCCUAGAAGC (SEQ ID NO: 114), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| R6-92 truncated | RNA | ACGCAUCCUCCGCGCGGAGGGGUUUCAUUAUCCCGUUUGGCUGCGU (SEQ ID NO: 115), where G is 2'F; and A, C, & U are 2'OMe modified RNA. |
| R6-92 full | RNA | GGGAGUGUGUACGAGGCAUUAACGCAUCCUCCGCGCGGAGGGGUUUCAUUAUCCCGUUUGGCU GCGUUGAUACUUGAUCGCCCUAGAAGC (SEQ ID NO: 116), where G is 2'F; and A, C, & U are 2'OMe modified RNA. |
| R6-99 truncated | RNA | AUGCCGCCUCCGCGCGGAGGGGUUUAAUUAUCCCGUUUGGCGGCUU (SEQ ID NO: 117), where G is 2'F; and A, C, & U are 2'OMe modified RNA. |
| R6-99 full | RNA | GGGAGUGUGUACGAGGCAUUAAUGCCGCCUCCGCGCGGAGGGGUUUAAUUAUCCCGUUUGGCGG CUUUGAUACUUGAUCGCCCUAGAAGC (SEQ ID NO: 118), where G is 2'F; and A, C, & U are 2'OMe modified RNA. |
| R6-101 truncated | RNA | AAGCCGCCUCCGCGCGGAGGGAUUUCAUUAUCCCGUUUGUCGGCUU (SEQ ID NO: 119), where G is 2'F; and A, C, & U are 2'OMe modified RNA. |
| R6-101 full | RNA | GGGAGUGUGUACGAGGCAUUAAAGCCGCCUCCGCGCGGAGGGAUUUCAUUAUCCCGUUUGUCGG CUUUGAUACUUGAUCGCCCUAGAAGC (SEQ ID NO: 120), where G is 2'F; and A, C, & U are 2'OMe modified RNA. |
| R6-102 truncated | RNA | UUGCUGCCUCCGCGCGGAGGGGUUUCAUUAUCCCGUUUGGCUGCUU (SEQ ID NO: 121), where G is 2'F; and A, C, & U are 2'OMe modified RNA. |
| R6-102 full | RNA | GGGAGUGUGUACGAGGCAUUAUUGCUGCCUCCGCGCGGAGGGGUUUCAUUAUCCCGUUUGGCU GCUUUGAUACUUGAUCGCCCUAGAAGC (SEQ ID NO: 122), where G is 2'F; and A, C, & U are 2'OMe modified RNA. |
| R6-104 truncated | RNA | UGGCCGCCUCCGCGCGGAGGGAUUUCAUUAUCCCGUUUGGCUGCUU (SEQ ID NO: 123), where G is 2'F; and A, C, & U are 2'OMe modified RNA. |
| R6-104 full | RNA | GGGAGUGUGUACGAGGCAUUAUGGCCGCCUCCGCGCGGAGGGAUUUCAUUAUCCCGUUUGGCU GCUUUGAUACUUGAUCGCCCUAGAAGC (SEQ ID NO: 124), where G is 2'F; and A, C, & U are 2'OMe modified RNA. |
| R6-110 truncated | RNA | AUGCCGCCUCCGCGCGGAGGGGUUUUAUUAUCCCGUUUGGCUGCAU (SEQ ID NO: 125), where G is 2'F; and A, C, & U are 2'OMe modified RNA. |
| R6-110 full | RNA | GGGAGUGUGUACGAGGCAUUAAUGCCGCCUCCGCGCGGAGGGGUUUUAUUAUCCCGUUUGGCU GCAUUGAUACUUGAUCGCCCUAGAAGC (SEQ ID NO: 126), where G is 2'F; and A, C, & U are 2'OMe modified RNA. |
| R6-115 truncated | RNA | AGGCAUCCUCCGCGCGGAGGGAUUUCAUUAUCCCGUUUGGCUGCUU (SEQ ID NO: 127), where G is 2'F; and A, C, & U are 2'OMe modified RNA. |
| R6-115 full | RNA | GGGAGUGUGUACGAGGCAUUAAGGCAUCCUCCGCGCGGAGGGAUUUCAUUAUCCCGUUUGGCU GCUUUGAUACUUGAUCGCCCUAGAAGC (SEQ ID NO: 128), where G is 2'F; and A, C, & U are 2'OMe modified RNA. |
| R6-116 truncated | RNA | AGGCCGCCUCCGCGCGGAGGGAUUUCAUUAUCCCGUUUGUCGUCCU (SEQ ID NO: 129), where G is 2'F; and A, C, & U are 2'OMe modified RNA. |
| R6-116 full | RNA | GGGAGUGUGUACGAGGCAUUAAGGCCGCCUCCGCGCGGAGGGAUUUCAUUAUCCCGUUUGUCG UCCUUGAUACUUGAUCGCCCUAGAAGC (SEQ ID NO: 130), where G is 2'F; and A, C, & U are 2'OMe modified RNA. |
| R6-117 truncated | RNA | AUGCCGCCUCCGCGCGGAGGGGUUUGAUAAUCCCGUUUGGCUGCAU (SEQ ID NO: 131), where G is 2'F; and A, C, & U are 2'OMe modified RNA. |
| R6-117 full | RNA | GGGAGUGUGUACGAGGCAUUAAUGCCGCCUCCGCGCGGAGGGGUUUGAUAAUCCCGUUUGGCU GCAUUGAUACUUGAUCGCCCUAGAAGC (SEQ ID NO: 132), where G is 2'F; and A, C, & U are 2'OMe modified RNA. |
| R6-119 truncated | RNA | AGGCCGCCUCCGCGCGGAGGGAUUUCUUUAUCCCGUUUGGCUGCUU (SEQ ID NO: 133), where G is 2'F; and A, C, & U are 2'OMe modified RNA. |
| R6-119 full | RNA | GGGAGUGUGUACGAGGCAUUAAGGCCGCCUCCGCGCGGAGGGAUUUCUUUAUCCCGUUUGGCU GCUUUGAUACUUGAUCGCCCUAGAAGC (SEQ ID NO: 134), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| R6-123 truncated | RNA | AAUCCGCCUCCGCGCGGAGGGGUUUCAUUAUCCCGUUUGGCGGAUU (SEQ ID NO: 135), where G is 2'F; and A, C, & U are 2'OMe modified RNA. |
| R6-123 full | RNA | GGGAGUGUGUACGAGGCAUUAAAUCCGCCUCCGCGCGGAGGGGUUUCAUUAUCCCGUUUGGCG GAUUUGAUACUUGAUCGCCCUAGAAGC (SEQ ID NO: 136), where G is 2'F; and A, C, & U are 2'OMe modified RNA. |
| R6-124 truncated | RNA | AGGCUGCCUCCGCGCGGAGGGGUUUCAUUAUCCCGUUUGGCUGCCU (SEQ ID NO: 137), where G is 2'F; and A, C, & U are 2'OMe modified RNA. |
| R6-124 full | RNA | GGGAGUGUGUACGAGGCAUUAAGGCUGCCUCCGCGCGGAGGGGUUUCAUUAUCCCGUUUGGCU GCCUUGAUACUUGAUCGCCCUAGAAGC (SEQ ID NO: 138), where G is 2'F; and A, C, & U are 2'OMe modified RNA. |
| R6-130 truncated | RNA | AAUCCGCCUCCGCGCGGAGGGGUAUCAUUAUCCCGUUUGGCGGCUU (SEQ ID NO: 139), where G is 2'F; and A, C, & U are 2'OMe modified RNA. |
| R6-130 full | RNA | GGGAGUGUGUACGAGGCAUUAAAUCCGCCUCCGCGCGGAGGGGUAUCAUUAUCCCGUUUGGCG GCUUUGAUACUUGAUCGCCCUAGAAGC (SEQ ID NO: 140), where G is 2'F; and A, C, & U are 2'OMe modified RNA. |
| R6-131 truncated | RNA | AUGCCGCCUCCGCGCGGAGGGGUUUCAAUAUCCCGUUUGGCUGCAU (SEQ ID NO: 141), where G is 2'F; and A, C, & U are 2'OMe modified RNA. |
| R6-131 full | RNA | GGGAGUGUGUACGAGGCAUUAAUGCCGCCUCCGCGCGGAGGGGUUUCAAUAUCCCGUUUGGCU GCAUUGAUACUUGAUCGCCCUAGAAGC (SEQ ID NO: 142), where G is 2'F; and A, C, & U are 2'OMe modified RNA. |
| R6-134 truncated | RNA | AUGCUGCCUCCGCGCGGAGGGGUUUCAUUAUCCCGUUUGGCAGCUU (SEQ ID NO: 143), where G is 2'F; and A, C, & U are 2'OMe modified RNA. |
| R6-134 full | RNA | GGGAGUGUGUACGAGGCAUUAAUGCUGCCUCCGCGCGGAGGGGUUUCAUUAUCCCGUUUGGCA GCUUUGAUACUUGAUCGCCCUAGAAGC (SEQ ID NO: 144), where G is 2'F; and A, C, & U are 2'OMe modified RNA. |
| R6-135 truncated | RNA | AGGCUGCCUCCGCGCGGAGGGGUUUCAUUAUCCCGUUUGGCGGCUU (SEQ ID NO: 145), where G is 2'F; and A, C, & U are 2'OMe modified RNA. |
| R6-135 full | RNA | GGGAGUGUGUACGAGGCAUUAAGGCUGCCUCCGCGCGGAGGGGUUUCAUUAUCCCGUUUGGCG GCUUUGAUACUUGAUCGCCCUAGAAGC (SEQ ID NO: 146), where G is 2'F; and A, C, & U are 2'OMe modified RNA. |
| R6-138 truncated | RNA | AUGCUGCCUCCGCGCGGAGGGGUUUCAUUAUCCCGUUUGGCAGCAU (SEQ ID NO: 147), where G is 2'F; and A, C, & U are 2'OMe modified RNA. |
| R6-138 full | RNA | GGGAGUGUGUACGAGGCAUUAAUGCUGCCUCCGCGCGGAGGGGUUUCAUUAUCCCGUUUGGC AGCAUUGAUACUUGAUCGCCCUAGAAGC (SEQ ID NO: 148), where G is 2'F; and A, C, & U are 2'OMe modified RNA. |
| R6-139 truncated | RNA | AGGCCGCCUCCGCGCGGAGGGAUUUCAUUAUCCCGCUUGGCUGCUU (SEQ ID NO: 149), where G is 2'F; and A, C, & U are 2'OMe modified RNA. |
| R6-139 full | RNA | GGGAGUGUGUACGAGGCAUUAAGGCCGCCUCCGCGCGGAGGGAUUUCAUUAUCCCGCUUGGC UGCUUUGAUACUUGAUCGCCCUAGAAGC (SEQ ID NO: 150), where G is 2'F; and A, C, & U are 2'OMe modified RNA. |
| R6-142 truncated | RNA | AUGCCGCCUCCGCGCGGAGGGGUUUGAUUAUCCCGUUUGGCUGCAU (SEQ ID NO: 151), where G is 2'F; and A, C, & U are 2'OMe modified RNA. |
| R6-142 full | RNA | GGGAGUGUGUACGAGGCAUUAAUGCCGCCUCCGCGCGGAGGGGUUUGAUUAUCCCGUUUGGC UGCAUUGAUACUUGAUCGCCCUAGAAGC (SEQ ID NO: 152), where G is 2'F; and A, C, & U are 2'OMe modified RNA. |
| R6-145 truncated | RNA | UUGCUGCCUCCGCGCGGAGGGGUUUCAUUAUCCCGUUUGGCGGCUU (SEQ ID NO: 153), where G is 2'F; and A, C, & U are 2'OMe modified RNA. |
| R6-145 full | RNA | GGGAGUGUGUACGAGGCAUUAUUGCUGCCUCCGCGCGGAGGGGUUUCAUUAUCCCGUUUGGC GGCUUUGAUACUUGAUCGCCCUAGAAGC (SEQ ID NO: 154), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| R6-152 truncated | RNA | CUGCCGCCUCCGCGCGGAGGGGUUUCAUUAUCCCGUUUGGCGGCAU (SEQ ID NO: 155), where G is 2'F; and A, C, & U are 2'OMe modified RNA. |
| R6-152 full | RNA | GGGAGUGUGUACGAGGCAUUACUGCCGCCUCCGCGCGGAGGGGUUUCAUUAUCCCGUUUGGC GGCAUUGAUACUUGAUCGCCCUAGAAGC (SEQ ID NO: 156), where G is 2'F; and A, C, & U are 2'OMe modified RNA. |
| R6-153 truncated | RNA | AUUCAGCCUCCGCGCGGAGGGGUUUCAUUAUCCCGUUUGGCUGCAU (SEQ ID NO: 157), where G is 2'F; and A, C, & U are 2'OMe modified RNA. |
| R6-153 full | RNA | GGGAGUGUGUACGAGGCAUUAAUUCAGCCUCCGCGCGGAGGGGUUUCAUUAUCCCGUUUGGC UGCAUUGAUACUUGAUCGCCCUAGAAGC (SEQ ID NO: 158), where G is 2'F; and A, C, & U are 2'OMe modified RNA. |
| R6-157 truncated | RNA | AAGCAGCCUCCGCGCGGAGGGGUUUCAUUAUCCCGUUUGGCGGCUU (SEQ ID NO: 159), where G is 2'F; and A, C, & U are 2'OMe modified RNA. |
| R6-157 full | RNA | GGGAGUGUGUACGAGGCAUUAAAGCAGCCUCCGCGCGGAGGGGUUUCAUUAUCCCGUUUGGC GGCUUUGAUACUUGAUCGCCCUAGAAGC (SEQ ID NO: 160), where G is 2'F; and A, C, & U are 2'OMe modified RNA. |
| R6-162 truncated | RNA | AUGCCGCCUCCGCGCGGAGGGAUUUCAUUAUCCCGUUUGUCGGCCU (SEQ ID NO: 161), where G is 2'F; and A, C, & U are 2'OMe modified RNA. |
| R6-162 full | RNA | GGGAGUGUGUACGAGGCAUUAAUGCCGCCUCCGCGCGGAGGGAUUUCAUUAUCCCGUUUGUC GGCCUUGAUACUUGAUCGCCCUAGAAGC (SEQ ID NO: 162), where G is 2'F; and A, C, & U are 2'OMe modified RNA. |
| R6-166 truncated | RNA | AGUCCGCCUCCGCGCGGAGGGGUUUCAUUAUCCCGUUUGGCUGACU (SEQ ID NO: 163), where G is 2'F; and A, C, & U are 2'OMe modified RNA. |
| R6-166 full | RNA | GGGAGUGUGUACGAGGCAUUAAGUCCGCCUCCGCGCGGAGGGGUUUCAUUAUCCCGUUUGGC UGACUUGAUACUUGAUCGCCCUAGAAGC (SEQ ID NO: 164), where G is 2'F; and A, C, & U are 2'OMe modified RNA. |
| R6-169 truncated | RNA | AGUCCGCCUCCGCGCGGAGGGGUUUCAUUAUCCCGUUUGGCGGAUU (SEQ ID NO: 165), where G is 2'F; and A, C, & U are 2'OMe modified RNA. |
| R6-169 full | RNA | GGGAGUGUGUACGAGGCAUUAAGUCCGCCUCCGCGCGGAGGGGUUUCAUUUAUCCCGUUUGG CGGAUUUGAUACUUGAUCGCCCUAGAAGC (SEQ ID NO: 166), where G is 2'F; and A, C, & U are 2'OMe modified RNA. |
| R6-170 truncated | RNA | CUGCUGCCUCCGCGCGGAGGGGUUUCAUUAUCCCGUUUGGCGGCAU (SEQ ID NO: 167), where G is 2'F; and A, C, & U are 2'OMe modified RNA. |
| R6-170 full | RNA | GGGAGUGUGUACGAGGCAUUACUGCUGCCUCCGCGCGGAGGGGUUUCAUUAUCCCGUUUGGC GGCAUUGAUACUUGAUCGCCCUAGAAGC (SEQ ID NO: 168), where G is 2'F; and A, C, & U are 2'OMe modified RNA. |
| R6-171 truncated | RNA | ACUCAGCCUCCGCGCGGAGGGGUUUCAUUAUCCCGUUUGGCUGCGU (SEQ ID NO: 169), where G is 2'F; and A, C, & U are 2'OMe modified RNA. |
| R6-171 full | RNA | GGGAGUGUGUACGAGGCAUUAACUCAGCCUCCGCGCGGAGGGGUUUCAUUAUCCCGUUUGGC UGCGUUGAUACUUGAUCGCCCUAGAAGC (SEQ ID NO: 170), where G is 2'F; and A, C, & U are 2'OMe modified RNA. |
| R6-172 truncated | RNA | AGGCUGCCUCCGCGCGGAGGGGUUUCAUUAUCCCGUUUGGCAUCCU (SEQ ID NO: 171), where G is 2'F; and A, C, & U are 2'OMe modified RNA. |
| R6-172 full | RNA | GGGAGUGUGUACGAGGCAUUAAGGCUGCCUCCGCGCGGAGGGGUUUCAUUAUCCCGUUUGGC AUCCUUGAUACUUGAUCGCCCUAGAAGC (SEQ ID NO: 172), where G is 2'F; and A, C, & U are 2'OMe modified RNA. |
| R6-173 truncated | RNA | UUGCUGCCUCCGCGCGGAGGGGUUUCAUUAUCCCGUUUGGCUGCAU (SEQ ID NO: 173), where G is 2'F; and A, C, & U are 2'OMe modified RNA. |
| R6-173 full | RNA | GGGAGUGUGUACGAGGCAUUAUUGCUGCCUCCGCGCGGAGGGGUUUCAUUAUCCCGUUUGGC UGCAUUGAUACUUGAUCGCCCUAGAAGC (SEQ ID NO: 174), where G is 2'F; and A, C, & U are 2'OMe modified RNA. |

TABLE 1-continued

VEGF-A Aptamer Sequences

| Compound Name | Backbone | Sequence 5' to 3' |
|---|---|---|
| R6-177 truncated | RNA | UGUCCGCCUCCGCGCGGAGGGGUUUCAUUAUCCCGUUUGGCGGCUU (SEQ ID NO: 175), where G is 2'F; and A, C, & U are 2'OMe modified RNA. |
| R6-177 full | RNA | GGGAGUGUGUACGAGGCAUUAUGUCCGCCUCCGCGCGGAGGGGUUUCAUUAUCCCGUUUGGC GGCUUUGAUACUUGAUCGCCCUAGAAGC (SEQ ID NO: 176), where G is 2'F; and A, C, & U are 2'OMe modified RNA. |
| R6-178 truncated | RNA | CUGCAGCCUCCGCGCGGAGGGGUUUCAUUAUCCCGUUUGGCUGCUU (SEQ ID NO: 177), where G is 2'F; and A, C, & U are 2'OMe modified RNA. |
| R6-178 full | RNA | GGGAGUGUGUACGAGGCAUUACUGCAGCCUCCGCGCGGAGGGGUUUCAUUAUCCCGUUUGGC UGCUUUGAUACUUGAUCGCCCUAGAAGC (SEQ ID NO: 178) where G is 2'F; and A, C, & U are 2'OMe modified RNA. |
| R6-179 truncated | RNA | AGUCCGCCUCCGCGCGGAGGGGUAUCAUUAUCCCGUUUGGCGUACU (SEQ ID NO: 179), where G is 2'F; and A, C, & U are 2'OMe modified RNA. |
| R6-179 full | RNA | GGGAGUGUGUACGAGGCAUUAAGUCCGCCUCCGCGCGGAGGGGUAUCAUUAUCCCGUUUGGC GUACUUGAUACUUGAUCGCCCUAGAAGC (SEQ ID NO: 180), where G is 2'F; and A, C, & U are 2'OMe modified RNA. |
| R6-181 truncated | RNA | AGCCCGCCUCCGCGCGGAGGGGUUUCAUUAUCCCGUUUGGCGUGCU (SEQ ID NO: 181), where G is 2'F; and A, C, & U are 2'OMe modified RNA. |
| R6-181 full | RNA | GGGAGUGUGUACGAGGCAUUAAGCCCGCCUCCGCGCGGAGGGGUUUCAUUAUCCCGUUUGGC GUGCUUGAUACUUGAUCGCCCUAGAAGC (SEQ ID NO: 182), where G is 2'F; and A, C, & U are 2'OMe modified RNA. |
| R6-182 truncated | RNA | AGUCCACCUCCGCGCGGAGGGGUUUCAUAAUCCCGUUUGGUGGCUA (SEQ ID NO: 183), where G is 2'F; and A, C, & U are 2'OMe modified RNA. |
| R6-182 full | RNA | GGGAGUGUGUACGAGGCAUUAAGUCCACCUCCGCGCGGAGGGGUUUCAUAAUCCCGUUUGGU GGCUAUGAUACUUGAUCGCCCUAGAAGC (SEQ ID NO: 184), where G is 2'F; and A, C, & U are 2'OMe modified RNA. |
| R6-186 truncated | RNA | AUGCCGCCUCCGCGCGGAGGGAUUUCGUUAUCCCGUUUGGCUGCUU (SEQ ID NO: 185), where G is 2'F; and A, C, & U are 2'OMe modified RNA. |
| R6-186 full | RNA | GGGAGUGUGUACGAGGCAUUAAUGCCGCCUCCGCGCGGAGGGAUUUCGUUAUCCCGUUUGGC UGCUUUGAUACUUGAUCGCCCUAGAAGC (SEQ ID NO: 186), where G is 2'F; and A, C, & U are 2'OMe modified RNA. |
| R6-197 truncated | RNA | AUGCAGCCUCCGCGCGGAGGGGUUUCAUUAUCCCGUUUGGCUGCCU (SEQ ID NO: 187), where G is 2'F; and A, C, & U are 2'OMe modified RNA. |
| R6-197 full | RNA | GGGAGUGUGUACGAGGCAUUAAUGCAGCCUCCGCGCGGAGGGGUUUCAUUAUCCCGUUUGGC UGCCUUGAUACUUGAUCGCCCUAGAAGC (SEQ ID NO: 188), where G is 2'F; and A, C, & U are 2'OMe modified RNA. |
| R6-198 truncated | RNA | AGGCCGCCUCCGCGCGGAGGGAUUUCAUUAUCCCGUUUGGCUGCAU (SEQ ID NO: 189), where G is 2'F; and A, C, & U are 2'OMe modified RNA. |
| R6-198 full | RNA | GGGAGUGUGUACGAGGCAUUAAGGCCGCCUCCGCGCGGAGGGAUUUCAUUAUCCCGUUUGGC UGCAUUGAUACUUGAUCGCCCUAGAAGC (SEQ ID NO: 190), where G is 2'F; and A, C, & U are 2'OMe modified RNA. |
| R6-200 truncated | RNA | AUGCCGCCUCCGCGCGGAGGGGUAUUAUUAUCCCGUUUGGCUGCAU (SEQ ID NO: 191), where G is 2'F; and A, C, & U are 2'OMe modified RNA. |
| R6-200 full | RNA | GGGAGUGUGUACGAGGCAUUAAUGCCGCCUCCGCGCGGAGGGGUAUUAUUAUCCCGUUUGGC UGCAUUGAUACUUGAUCGCCCUAGAAGC (SEQ ID NO: 192), where G is 2'F; and A, C, & U are 2'OMe modified RNA. |
| R6-201 truncated | RNA | AUUCAGCCUCCGCGCGGAGGGGUUUCAUUAUCCCGUUUGGCUGCUU (SEQ ID NO: 193), where G is 2'F; and A, C, & U are 2'OMe modified RNA. |
| R6-201 full | RNA | GGGAGUGUGUACGAGGCAUUAAUUCAGCCUCCGCGCGGAGGGGUUUCAUUAUCCCGUUUGGC UGCUUUGAUACUUGAUCGCCCUAGAAGC (SEQ ID NO: 194), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| R6-203 truncated | RNA | AUGCCGCCUCCGCGCGGAGGGAUUUCAUUAUCCCGUUUGGCUGCGU (SEQ ID NO: 195), where G is 2'F; and A, C, & U are 2'OMe modified RNA. |
| R6-203 full | RNA | GGGAGUGUGUACGAGGCAUUAAUGCCGCCUCCGCGCGGAGGGAUUUCAUUAUCCCGUUUGGC UGCGUUGAUACUUGAUCGCCCUAGAAGC (SEQ ID NO: 196), where G is 2'F; and A, C, & U are 2'OMe modified RNA. |
| R6-204 truncated | RNA | AUUCCGCCUCCGCGCGGAGGGGUAUCAUUAUCCCGUUUGGCGGCAU (SEQ ID NO: 197), where G is 2'F; and A, C, & U are 2'OMe modified RNA. |
| R6-204 full | RNA | GGGAGUGUGUACGAGGCAUUAAUUCCGCCUCCGCGCGGAGGGGUAUCAUUAUCCCGUUUGGC GGCAUUGAUACUUGAUCGCCCUAGAAGC (SEQ ID NO: 198) where G is 2'F; and A, C, & U are 2'OMe modified RNA. |
| R6-205 truncated | RNA | AUGUCGCCUCCGCGCGGAGGGGUUUCAUUAUCCCGUUUGGCGGCUU (SEQ ID NO: 199), where G is 2'F; and A, C, & U are 2'OMe modified RNA. |
| R6-205 full | RNA | GGGAGUGUGUACGAGGCAUUAAUGUCGCCUCCGCGCGGAGGGGUUUCAUUAUCCCGUUUGGC GGCUUUGAUACUUGAUCGCCCUAGAAGC (SEQ ID NO: 200), where G is 2'F; and A, C, & U are 2'OMe modified RNA. |
| R6-208 truncated | RNA | ACUCAGCCUCCGCGCGGAGGGGUUUCAUUAUCCCGUUUGGCUGAUU (SEQ ID NO: 201), where G is 2'F; and A, C, & U are 2'OMe modified RNA. |
| R6-208 full | RNA | GGGAGUGUGUACGAGGCAUUAACUCAGCCUCCGCGCGGAGGGGUUUCAUUAUCCCGUUUGGC UGAUUUGAUACUUGAUCDGCCCUAGAAGC (SEQ ID NO: 202), where G is 2'F; and A, C, & U are 2'OMe modified RNA. |
| R6-210 truncated | RNA | AAGCCACCUCCGCGCGGAGGGGUUUCAUUAUCCCGUUUGGUGGCUU (SEQ ID NO: 203), where G is 2'F; and A, C, & U are 2'OMe modified RNA. |
| R6-210 full | RNA | GGGAGUGUGUACGAGGCAUUAAAGCCACCUCCGCGCGGAGGGGUUUCAUUAUCCCGUUUGGU GGCUUUGAUACUUGAUCGCCCUAGAAGC (SEQ ID NO: 204), where G is 2'F; and A, C, & U are 2'OMe modified RNA. |
| R6-211 truncated | RNA | AUGCCGCCUCCGCGCGGAGGGGUUGAAUUAUCCCGUUUGGCUGCAU (SEQ ID NO: 205), where G is 2'F; and A, C, & U are 2'OMe modified RNA. |
| R6-211 full | RNA | GGGAGUGUGUACGAGGCAUUAAUGCCGCCUCCGCGCGGAGGGGUUGAAUUAUCCCGUUUGG CUGCAUUGAUACUUGAUCGCCCUAGAAGC (SEQ ID NO: 206), where G is 2'F; and A, C, & U are 2'OMe modified RNA. |
| R6-214 truncated | RNA | AGGCCGCCUCCGCGCGGAGGGGUUUCAUUAUCCCGUUUGGCGUCCU (SEQ ID NO: 207), where G is 2'F; and A, C, & U are 2'OMe modified RNA. |
| R6-214 full | RNA | GGGAGUGUGUACGAGGCAUUAAGGCCGCCUCCGCGCGGAGGGGUUUCAUUAUCCCGUUUGGC GUCCUUGAUACUUGAUCGCCCUAGAAGC (SEQ ID NO: 208), where G is 2'F; and A, C, & U are 2'OMe modified RNA. |
| R6-221 truncated | RNA | AGUCCACCUCCGCGCGGAGGGGUUUCAUUAUCCCGUUUGGUGGCCU (SEQ ID NO: 209), where G is 2'F; and A, C, & U are 2'OMe modified RNA. |
| R6-221 full | RNA | GGGAGUGUGUACGAGGCAUUAAGUCCACCUCCGCGCGGAGGGGUUUCAUUAUCCCGUUUGGU GGCCUUGAUACUUGAUCGCCUAGAAGC (SEQ ID NO: 210), where G is 2'F; and A, C, & U are 2'OMe modified RNA. |
| R6-227 truncated | RNA | CUGCUGCCUCCGCGCGGAGGGGUUUCAUUAUCCCGUUUGGCUGCAU (SEQ ID NO: 211), where G is 2'F; and A, C, & U are 2'OMe modified RNA. |
| R6-227 full | RNA | GGGAGUGUGUACGAGGCAUUACUGCUGCCUCCGCGCGGAGGGGUUUCAUUAUCCCGUUUGGC UGCAUUGAUACUUGAUCGCCCUAGAAGC (SEQ ID NO: 212), where G is 2'F; and A, C, & U are 2'OMe modified RNA. |
| R6-228 truncated | RNA | AUGCCGCCUCCGCGCGGAGGGGUAGCAAUAUCCCGUUUGGCUGCUU (SEQ ID NO: 213), where G is 2'F; and A, C, & U are 2'OMe modified RNA. |
| R6-228 full | RNA | GGGAGUGUGUACGAGGCAUUAAUGCCGCCUCCGCGCGGAGGGGUAGCAAUAUCCCGUUUGGC UGCUUUGAUACUUGAUCGCCCUAGAAGC (SEQ ID NO: 214) where G is 2'F; and A, C, & U are 2'OMe modified RNA. |

TABLE 1-continued

VEGF-A Aptamer Sequences

| Compound Name | Backbone | Sequence 5' to 3' |
|---|---|---|
| R6-229 truncated | RNA | AAGCCGCCUCCGCGCGGAGGGGUAUAAUUAUCCCGUUUGGCUGCUU (SEQ ID NO: 215), where G is 2'F; and A, C, & U are 2'OMe modified RNA. |
| R6-229 full | RNA | GGGAGUGUGUACGAGGCAUUAAAGCCGCCUCCGCGCGGAGGGGUAUAAUUAUCCCGUUUGGC UGCUUUGAUACUUGAUCGCCCUAGAAGC (SEQ ID NO: 216), where G is 2'F; and A, C, & U are 2'OMe modified RNA. |
| R6-241 truncated | RNA | AGGCUGCCUCCGCGCGGAGGGGUUUCAUUAUCCCGUUUGGCAGCUU (SEQ ID NO: 217), where G is 2'F; and A, C, & U are 2'OMe modified RNA. |
| R6-241 full | RNA | GGGAGUGUGUACGAGGCAUUAAGGCUGCCUCCGCGCGGAGGGGUUUCAUUAUCCCGUUUGGC AGCUUUGAUACUUGAUCGCCCUAGAAGC (SEQ ID NO: 218), where G is 2'F; and A, C, & U are 2'OMe modified RNA. |
| Aptamer 4.2 | RNA | C6SS- AGGCCGCCUCCGCGCGGAGGGGUUUCAUUAUCCCGUUUGGCGGCUU-idT (SEQ ID NO: 219), where G is 2'F; A, C, & U are 2'OMe modified RNA; C6SS is a disulfide linker; and idT is an inverted deoxythymidine residue. |
| Aptamer 26 | RNA | $C6NH_2$- UAGGCCGCCUCCGCGCGGAGGGGUUUCAUUAUCCCGUUUGGCGGCUUU-idT (SEQ ID NO: 220), where G is 2'F; A, C, & U are 2'OMe modified RNA; $C6NH_2$ is is a hexylamine linker; and idT is an inverted deoxythymidine residue. |
| Aptamer 27 | RNA | $C6NH_2$- UAGGCCGCCUCCGCGCGGGGGGGUUUCAUUAUCCCGUUUGGCGGCUUU-idT (SEQ ID NO: 221), where G is 2'F; A, C, & U are 2'OMe modified RNA; $C6NH_2$ is a hexylamini linker; and idT is an inverted deoxythymidine residue. |
| Aptamer 28 | RNA | $C6NH_2$- UAGGCCGCCUCCGCGCGGUGGGGUUUCAUUAUCCCGUUUGGCGGCUUU-idT (SEQ ID NO: 222), where G is 2'F; A, C, & U are 2'OMe modified RNA; $C6NH_2$ is a hexylamine linker; and idT is an inverted deoxythymidine residue. |
| Aptamer 29 | RNA | $C6NH_2$- UAGUCCGCCUCCGCGCGGAGGGGUUUCAUUAUCCCGUUUGGCGGCUUU-idT (SEQ ID NO: 223), where G is 2'F; A, C, & U are 2'OMe modified RNA; $C6NH_2$ is a hexylamine linker; and idT is an inverted deoxythymidine residue. |
| Aptamer 30 | RNA | $C6NH_2$- UAGGCCGCCUCCGCGCGGAGGGGUUUCAUUUAUCCCGUUUGGCGGCUUU-idT (SEQ ID NO: 224), where G is 2'F; A, C, & U are 2'OMe modified RNA; $C6NH_2$ is a hexylamine linker; and idT is an inverted deoxythymidine residue. |
| Aptamer 31 | RNA | $C6NH_2$- UAGACCGCCUCCGCGCGGAGGGGUUUCAUUAUCCCGUUUGGCGGCUUU-idT (SEQ ID NO: 225), where G is 2'F; A, C, & U are 2'OMe modified RNA; $C6NH_2$ is a hexylamine linker; and idT is an inverted deoxythymidine residue. |
| Aptamer 32 | RNA | $C6NH_2$- UAGGCCGCCUCCGCGCGGAGGGGUUUCAUUAUCCCGUUUGGCGGCCUU-idT (SEQ ID NO: 226), where G is 2'F; A, C, & U are 2'OMe modified RNA; $C6NH_2$ is a hexylamine linker; and idT is an inverted deoxythymidine residue. |
| Aptamer 47 | RNA | $C6NH_2$-AGGCCGCC-Sp3- CCGCGCGGAGGGGUUUCAUUAUCCCGUUUGGCGGCUU-idT (SEQ ID NO: 227), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |

TABLE 1-continued

VEGF-A Aptamer Sequences

| Compound Name | Backbone | Sequence 5' to 3' |
| --- | --- | --- |
| Aptamer 48 | RNA | $C6NH_2$-AGGCCGCC-Sp3-CGCGCGGAGGGGUUUCAUUAUCCCGUUUGGCGGCUU-idT (SEQ ID NO: 228), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 49 | RNA | $C6NH_2$-AGGCCGCCUC (SEQ ID NO: 229)-Sp3-GCGCGGAGGGGUUUCAUUAUCCCGUUUGGCGGCUU-idT (SEQ ID NO: 230), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 50 | RNA | $C6NH_2$-AGGCCGCCUCC (SEQ ID NO: 231)-Sp3-CGCGGAGGGGUUUCAUUAUCCCGUUUGGCGGCUU-idT (SEQ ID NO: 232), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 51 | RNA | $C6NH_2$-AGGCCGCCUCCG (SEQ ID NO: 233)-Sp3-GCGGAGGGGUUUCAUUAUCCCGUUUGGCGGCUU (SEQ ID NO: 234), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 52 | RNA | $C6NH_2$-AGGCCGCCUCCGC (SEQ ID NO: 235)-Sp3-CGGAGGGGUUUCAUUAUCCCGUUUGGCGGCUU-idT-(SEQ ID NO: 236), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 53 | RNA | $C6NH_2$-AGGCCGCCUCCGCG (SEQ ID NO: 237)-Sp3-GGAGGGGUUUCAUUAUCCCGUUUGGCGGCUU-idT (SEQ ID NO: 238), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 54 | RNA | $C6NH_2$-AGGCCGCCUCCGCGC (SEQ ID NO: 239)-Sp3-GAGGGGUUUCAUUAUCCCGUUUGGCGGCUU-idT (SEQ ID NO: 240), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 55 | RNA | $C6NH_2$-AGGCCGCCUCCGCGCG (SEQ ID NO: 241)-Sp3-AGGGGUUUCAUUAUCCCGUUUGGCGGCUU-idT (SEQ ID NO: 242), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 56 | RNA | $C6NH_2$-AGGCCGCCUCCGCGCGG (SEQ ID NO: 243)-Sp3-GGGGUUUCAUUAUCCCGUUUGGCGGCUU-idT (SEQ ID NO: 244), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 57 | RNA | $C6NH_2$-AGGCCGCCUCCGCGCGGA (SEQ ID NO: 245)-Sp3-GGGUUUCAUUAUCCCGUUUGGCGGCUU-idT (SEQ ID NO: 246), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 58 | RNA | $C6NH_2$-AGGCCGCCUCCGCGCGGAG (SEQ ID NO: 247)-Sp3-GGUUUCAUUAUCCCGUUUGGCGGCUU-idT (SEQ ID NO: 248), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 59 | RNA | $C6NH_2$-AGGCCGCCUCCGCGCGGAGG (SEQ ID NO: 249)-Sp3-GUUUCAUUAUCCCGUUUGGCGGCUU-idT (SEQ ID NO: 250), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 60 | RNA | $C6NH_2$-AGGCCGCCUCCGCGCGGAGGG (SEQ ID NO: 251)-Sp3-UUUCAUUAUCCCGUUUGGCGGCUU-idT (SEQ ID NO: 252), |

TABLE 1-continued

| VEGF-A Aptamer Sequences | | |
|---|---|---|
| Compound Name | Backbone | Sequence 5' to 3' |
| | | where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 61 | RNA | $C6NH_2$-AGGCCGCCUCCGCGCGGAGGGG (SEQ ID NO: 253)-Sp3-UUCAUUAUCCCGUUUGGCGGCUU-idT (SEQ ID NO: 254), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 62 | RNA | $C6NH_2$-AGGCCGCCUCCGCGCGGAGGGGU (SEQ ID NO: 255)-Sp3-UCAUUAUCCCGUUUGGCGGCUU-idT (SEQ ID NO: 256), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 63 | RNA | $C6NH_2$-AGGCCGCCUCCGCGCGGAGGGGUU (SEQ ID NO: 257)-Sp3-CAUUAUCCCGUUUGGCGGCUU-idT (SEQ ID NO: 258), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 64 | RNA | $C6NH_2$-AGGCCGCCUCCGCGCGGAGGGGUUU (SEQ ID NO: 259)-Sp3-AUUAUCCCGUUUGGCGGCUU-idT (SEQ ID NO: 260), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 65 | RNA | $C6NH_2$-AGGCCGCCUCCGCGCGGAGGGGUUUC (SEQ ID NO: 261)-Sp3-UUAUCCCGUUUGGCGGCUU-idT (SEQ ID NO: 262), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 66 | RNA | $C6NH_2$-AGGCCGCCUCCGCGCGGAGGGGUUUCA (SEQ ID NO: 263)-Sp3-UAUCCCGUUUGGCGGCUU-idT (SEQ ID NO: 264) where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 67 | RNA | $C6NH_2$-AGGCCGCCUCCGCGCGGAGGGGUUUCAU (SEQ ID NO: 265)-Sp3-AUCCCGUUUGGCGGCUU-idT (SEQ ID NO: 266), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 68 | RNA | $C6NH_2$-AGGCCGCCUCCGCGCGGAGGGGUUUCAUU (SEQ ID NO: 267)-Sp3-UCCCGUUUGGCGGCUU-idT (SEQ ID NO: 268), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 69 | RNA | $C6NH_2$-AGGCCGCCUCCGCGCGGAGGGGUUUCAUUA (SEQ ID NO: 269)-Sp3-CCCGUUUGGCGGCUU-idT (SEQ ID NO: 270), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 70 | RNA | $C6NH_2$-AGGCCGCCUCCGCGCGGAGGGGUUUCAUUAU (SEQ ID NO: 271)-Sp3-CCGUUUGGCGGCUU-idT (SEQ ID NO: 272), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 71 | RNA | $C6NH_2$-AGGCCGCCUCCGCGCGGAGGGGUUUCAUUAUC (SEQ ID NO: 273)-Sp3-CGUUUGGCGGCUU-idT (SEQ ID NO: 274), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 72 | RNA | $C6NH_2$-AGGCCGCCUCCGCGCGGAGGGGUUUCAUUAUCC (SEQ ID NO: 275)-Sp3-GUUUGGCGGCUU-idT (SEQ ID NO: 276) where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |

TABLE 1-continued

| VEGF-A Aptamer Sequences | | |
|---|---|---|
| Compound Name | Backbone | Sequence 5' to 3' |
| Aptamer 73 | RNA | $C6NH_2$-AGGCCGCCUCCGCGCGGAGGGGUUUCAUUAUCCC (SEQ ID NO: 277)-Sp3-UUUGGCGGCUU-idT (SEQ ID NO: 278), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 74 | RNA | $C6NH_2$-AGGCCGCCUCCGCGCGGAGGGGUUUCAUUAUCCCG (SEQ ID NO: 279)-Sp3-UUGGCGGCUU-idT (SEQ ID NO: 280), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 75 | RNA | $C6NH_2$-AGGCCGCCUCCGCGCGGAGGGGUUUCAUUAUCCCGU (SEQ ID NO: 281)-Sp3-UGGCGGCUU-idT (SEQ ID NO: 282) where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 76 | RNA | $C6NH_2$-AGGCCGCCUCCGCGCGGAGGGGUUUCAUUAUCCCGUU (SEQ ID NO: 283)-Sp3-GGCGGCUU-idT, where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 79 | RNA | $C6NH_2$-AGGCCGCCCCGCGCGGAGGGGUUUCAUUAUCCCGUUUGGCGGCUU-idT (SEQ ID NO: 284), where G is 2'F; and A, C, and U are 2'OMe modified RNA; $C6NH_2$ is a hexylamine linker; and idT is an inverted deoxythymidine residue. |
| Aptamer 108 | RNA | $C6NH_2$-AGGCCGCCUCCGCGCGGAGGGGUUCAUUUCCCGUUUGGCGGCUU-idT (SEQ ID NO: 285), where G is 2'F; and A, C, and U are 2'OMe modified RNA; $C6NH_2$ is a hexylamine linker; and idT is an inverted deoxythymidine residue. |
| Aptamer 109 | RNA | $C6NH_2$-AGGCCGCCUCCGCGCGGAGGGUUUCAUUACCCGUUUGGCGGCUU-idT (SEQ ID NO: 286), where G is 2'F; and A, C, and U are 2'OMe modified RNA; $C6NH_2$ is a hexylamine linker; and idT is an inverted deoxythymidine residue. |
| Aptamer 112 | RNA | $C6NH_2$-AGGCCGCCUCCGCGCGGAAGGGUUUCAUUAUCCUGUUUGGCGGCUU-idT (SEQ ID NO: 287), where G is 2'F; and A, C, and U are 2'OMe modified RNA; $C6NH_2$ is a hexylamine linker; and idT is an inverted deoxythymidine residue. |
| Aptamer 113 | RNA | $C6NH_2$-AGGCCGCCUCCGCGCGGAUGGGUUUCAUUAUCCAGUUUGGCGGCUU-idT (SEQ ID NO: 288), where G is 2'F; and A, C, and U are 2'OMe modified RNA; $C6NH_2$ is a hexylamine linker; and idT is an inverted deoxythymidine residue. |
| Aptamer 114 | RNA | $C6NH_2$-AGGCCGCCUCCGCGCGGACGGGUUUCAUUAUCCGGUUUGGCGGCUU-idT (SEQ ID NO: 289), where G is 2'F; and A, C, and U are 2'OMe modified RNA; $C6NH_2$ is a hexylamine linker; and idT is an inverted deoxythymidine residue. |
| Aptamer 115 | RNA | $C6NH_2$-AGGCCGCCUCCGCGCGGAGAGGUUUCAUUAUCUCGUUUGGCGGCUU-idT (SEQ ID NO: 290), where G is 2'F; and A, C, and U are 2'OMe modified RNA; $C6NH_2$ is a hexylamine linker; and idT is an inverted deoxythymidine residue. |
| Aptamer 116 | RNA | $C6NH_2$-AGGCCGCCUCCGCGCGGAGUGGUUUCAUUAUCACGUUUGGCGGCUU-idT (SEQ ID NO: 291), where G is 2'F; and A, C, and U are 2'OMe modified RNA; $C6NH_2$ is a hexylamine linker; and idT is an inverted deoxythymidine residue. |

TABLE 1-continued

| VEGF-A Aptamer Sequences | | |
| --- | --- | --- |
| Compound Name | Backbone | Sequence 5' to 3' |
| Aptamer 117 | RNA | $C6NH_2$-AGGCCGCCUCCGCGCGGAGCGGUUUCAUUAUCGCGUUUGGCGGCUU-idT (SEQ ID NO: 292), where G is 2'F; and A, C, and U are 2'OMe modified RNA; $C6NH_2$ is a hexylamine linker; and idT is an inverted deoxythymidine residue. |
| Aptamer 119 | RNA | $C6NH_2$-AGGCCGCCUCCGCGCGGACCGGUUUCAUUACCGGGUUUGGCGGCUU-idT (SEQ ID NO: 293), where G is 2'F; and A, C, and U are 2'OMe modified RNA; $C6NH_2$ is a hexylamine linker; and idT is an inverted deoxythymidine residue. |
| Aptamer 120 | RNA | $C6NH_2$-AGGCCGCCUCCGCGCGGAGAGGGUUCAUUCCCUCGUUUGGCGGCUU-idT (SEQ ID NO: 294), where G is 2'F; and A, C, and U are 2'OMe modified RNA; $C6NH_2$ is a hexylamine linker; and idT is an inverted deoxythymidine residue. |
| Aptamer 121 | RNA | $C6NH_2$-AGGCCGCGUCCGCGCGGAGGGGUUUCAUUAUCCCGUUUCGCGGCUU-idT (SEQ ID NO: 295), where G is 2'F; and A, C, and U are 2'OMe modified RNA; $C6NH_2$ is a hexylamine linker; and idT is an inverted deoxythymidine residue. |
| Aptamer 122 | RNA | $C6NH_2$-AGGCCGCAUCCGCGCGGAGGGGUUUCAUUAUCCCGUUUUGCGGCUU-idT (SEQ ID NO: 296), where G is 2'F; and A, C, and U are 2'OMe modified RNA; $C6NH_2$ is a hexylamine linker; and idT is an inverted deoxythymidine residue. |
| Aptamer 123 | RNA | $C6NH_2$-AGGCCGCUUCCGCGCGGAGGGGUUUCAUUAUCCCGUUUAGCGGCUU-idT (SEQ ID NO: 297), where G is 2'F; and A, C, and U are 2'OMe modified RNA; $C6NH_2$ is a hexylamine linker; and idT is an inverted deoxythymidine residue. |
| Aptamer 124 | RNA | $C6NH_2$-AGGCCGGCUCCGCGCGGAGGGGUUUCAUUAUCCCGUUUGCCGGCUU-idT (SEQ ID NO: 298), where G is 2'F; and A, C, and U are 2'OMe modified RNA; $C6NH_2$ is a hexylamine linker; and idT is an inverted deoxythymidine residue. |
| Aptamer 125 | RNA | $C6NH_2$-AGGCCGACUCCGCGCGGAGGGGUUUCAUUAUCCCGUUUGUCGGCUU-idT (SEQ ID NO: 299), where G is 2'F; and A, C, and U are 2'OMe modified RNA; $C6NH_2$ is a hexylamine linker; and idT is an inverted deoxythymidine residue. |
| Aptamer 126 | RNA | $C6NH_2$-AGGCCGUCUCCGCGCGGAGGGGUUUCAUUAUCCCGUUUGACGGCUU-idT (SEQ ID NO: 300), where G is 2'F; and A, C, and U are 2'OMe modified RNA; $C6NH_2$ is a hexylamine linker; and idT is an inverted deoxythymidine residue. |
| Aptamer 127 | RNA | $C6NH_2$-AGGCCGCCUCCGCGCGGAGGGCUUUCAUUAGCCCGUUUGGCGGCUU-idT (SEQ ID NO: 301), where G is 2'F; and A, C, and U are 2'OMe modified RNA; $C6NH_2$ is a hexylamine linker; and idT is an inverted deoxythymidine residue. |
| Aptamer 128 | RNA | $C6NH_2$-AGGCCGCCUCCGCGCGGAGGACUUUCAUUAGUCCGUUUGGCGGCUU-idT (SEQ ID NO: 302), where G is 2'F; and A, C, and U are 2'OMe modified RNA; $C6NH_2$ is a hexylamine linker; and idT is an inverted deoxythymidine residue. |
| Aptamer 129 | RNA | $C6NH_2$-AGGCCGCCUCCGCGCGGAGGUCUUUCAUUAGACCGUUUGGCGGCUU-idT (SEQ ID NO: 303), where G is 2'F; and A, C, and U are 2'OMe modified RNA; $C6NH_2$ is a hexylamine linker; and idT is an inverted deoxythymidine residue. |

TABLE 1-continued

| VEGF-A Aptamer Sequences | | |
|---|---|---|
| Compound Name | Backbone | Sequence 5' to 3' |
| Aptamer 130 | RNA | $C6NH_2$-AGGCCGCCUCCGCGCGGAGGUGUUUCAUUACACCGUUUGGCGGCUU-idT (SEQ ID NO: 304), where G is 2'F; and A, C, and U are 2'OMe modified RNA; $C6NH_2$ is a hexylamine linker; and idT is an inverted deoxythymidine residue. |
| Aptamer 131 | RNA | $C6NH_2$-AGGCCGCCUCCGCGCGGAGGAGUUUCAUUACUCCGUUUGGCGGCUU-idT (SEQ ID NO: 305), where G is 2'F; and A, C, and U are 2'OMe modified RNA; $C6NH_2$ is a hexylamine linker; and idT is an inverted deoxythymidine residue. |
| Aptamer 132 | RNA | $C6NH_2$-AGGCCGCCUCCGCGCGGAGGCGUUUCAUUACGCCGUUUGGCGGCUU-idT (SEQ ID NO: 306), where G is 2'F; and A, C, and U are 2'OMe modified RNA; $C6NH_2$ is a hexylamine linker; and idT is an inverted deoxythymidine residue. |
| Aptamer 133 | RNA | $C6NH_2$-AGGCCGAAUCCGCGCGGAGGGGUUUCAUUAUCCCGUUUUUCGGCUU-idT (SEQ ID NO: 307), where G is 2'F; and A, C, and U are 2'OMe modified RNA; $C6NH_2$ is a hexylamine linker; and idT is an inverted deoxythymidine residue. |
| Aptamer 134 | RNA | $C6NH_2$-AGGCCGAUUCCGCGCGGAGGGGUUUCAUUAUCCCGUUUAUCGGCUU-idT (SEQ ID NO: 308), where G is 2'F; and A, C, and U are 2'OMe modified RNA; $C6NH_2$ is a hexylamine linker; and idT is an inverted deoxythymidine residue. |
| Aptamer 135 | RNA | $C6NH_2$-AGGCCGUAUCCGCGCGGAGGGGUUUCAUUAUCCCGUUUUACGGCUU-idT (SEQ ID NO: 309), where G is 2'F; and A, C, and U are 2'OMe modified RNA; $C6NH_2$ is a hexylamine linker; and idT is an inverted deoxythymidine residue. |
| Aptamer 136 | RNA | $C6NH_2$-AGGCCGUUUCCGCGCGGAGGGGUUUCAUUAUCCCGUUUAACGGCUU-idT (SEQ ID NO: 310), where G is 2'F; and A, C, and U are 2'OMe modified RNA; $C6NH_2$ is a hexylamine linker; and idT is an inverted deoxythymidine residue. |
| Aptamer 137 | RNA | $C6NH_2$-AGGCCGAA-Sp3-CCGCGCGGAGGGGUUUCAUUAUCCCGUUUUUCGGCUU-idT (SEQ ID NO: 311), where G is 2'F; and A, C, and U are 2'OMe modified RNA; $C6NH_2$ is a hexylamine linker; and idT is an inverted deoxythymidine residue; and Sp3 is the SP3 spacer (1,3-propanediol). |
| Aptamer 138 | RNA | $C6NH_2$-AGGCCGAU-Sp3-CCGCGCGGAGGGGUUUCAUUAUCCCGUUUAUCGGCUU-idT (SEQ ID NO: 312), where G is 2'F; and A, C, and U are 2'OMe modified RNA; $C6NH_2$ is a hexylamine linker; and idT is an inverted deoxythymidine residue; and Sp3 is the SP3 spacer (1,3-propanediol). |
| Aptamer 139 | RNA | $C6NH_2$-AGGCCGUA-Sp3-CCGCGCGGAGGGGUUUCAUUAUCCCGUUUUACGGCUU-idT (SEQ ID NO: 313), where G is 2'F; and A, C, and U are 2'OMe modified RNA; $C6NH_2$ is a hexylamine linker; and idT is an inverted deoxythymidine residue; and Sp3 is the SP3 spacer (1,3-propanediol). |
| Aptamer 140 | RNA | $C6NH_2$-AGGCCGUU-Sp3-CCGCGCGGAGGGGUUUCAUCAUCCCGUUUAACGGCUU-idT (SEQ ID NO: 314), where G is 2'F; and A, C, and U are 2'OMe modified RNA; $C6NH_2$ is a hexylamine linker; and idT is an inverted deoxythymidine residue; and Sp3 is the SP3 spacer (1,3-propanediol). |
| Aptamer 141 | RNA | $C6NH_2$-AGGCCGAC-Sp3-CCGCGCGGAGGGGUUUCAUUAUCCCGUUUGUCGGCUU-idT (SEQ ID NO: 315), where G is 2'F; and A, C, and U are 2'OMe modified RNA; $C6NH_2$ is a hexylamine linker; and idT is an inverted deoxythymidine residue; and Sp3 is the SP3 spacer (1,3-propanediol). |

TABLE 1-continued

VEGF-A Aptamer Sequences

| Compound Name | Backbone | Sequence 5' to 3' |
|---|---|---|
| Aptamer 142 | RNA | $C6NH_2$-AGGCCGUC-Sp3-CCGCGCGGAGGGGUUUCAUUAUCCCGUUUGACGGCUU-idT (SEQ ID NO: 316), where G is 2'F; and A, C, and U are 2'OMe modified RNA; $C6NH_2$ is a hexylamine linker; and idT is an inverted deoxythymidine residue; and Sp3 is the SP3 spacer (1,3-propanediol). |
| Aptamer 143 | RNA | $C6NH_2$-AGGCCGCA-Sp3-CCGCGCGGAGGGGUUUCAUUAUCCCGUUUUGCGGCUU-idT (SEQ ID NO: 317), where G is 2'F; and A, C, and U are 2'OMe modified RNA; $C6NH_2$ is a hexylamine linker; and idT is an inverted deoxythymidine residue; and Sp3 is the SP3 spacer (1,3-propanediol). |
| Aptamer 144 | RNA | $C6NH_2$-AGGCCGCU-Sp3-CCGCGCGGAGGGGUUUCAUUAUCCCGUUUAGCGGCUU-idT (SEQ ID NO: 318), where G is 2'F; and A, C, and U are 2'OMe modified RNA; $C6NH_2$ is a hexylamine linker; and idT is an inverted deoxythymidine residue; and Sp3 is the SP3 spacer (1,3-propanediol). |
| Aptamer 145 | RNA | $C6NH_2$-AGGCCGCCUCCGCGCGGAGGGGUUCAUAUCCCGUUUGGCGGCUU-idT (SEQ ID NO: 319), where G is 2'F; and A, C, and U are 2'OMe modified RNA; $C6NH_2$ is a hexylamine linker; and idT is an inverted deoxythymidine residue. |
| Aptamer 146 | RNA | $C6NH_2$-AGGCCGCCACCGCGCGGAGGGGUUUCAUUAUCCCGUUUGGCGGCUU-idT (SEQ ID NO: 320), where G is 2'F; and A, C, and U are 2'OMe modified RNA; $C6NH_2$ is a hexylamine linker; and idT is an inverted deoxythymidine residue. |
| Aptamer 147 | RNA | $C6NH_2$-AGGCCGCCCCCGCGCGGAGGGGUUUCAUUAUCCCGUUUGGCGGCUU-idT (SEQ ID NO: 321), where G is 2'F; and A, C, and U are 2'OMe modified RNA; $C6NH_2$ is a hexylamine linker; and idT is an inverted deoxythymidine residue. |
| Aptamer 148 | RNA | $C6NH_2$-AGGCCGCCGCCGCGCGGAGGGGUUUCAUUAUCCCGUUUGGCGGCUU-idT (SEQ ID NO: 322), where G is 2'F; and A, C, and U are 2'OMe modified RNA; $C6NH_2$ is a hexylamine linker; and idT is an inverted deoxythymidine residue. |
| Aptamer 149 | RNA | $C6NH_2$-AGGCCGCCUCCACGCGGAGGGGUUUCAUUAUCCCGUUUGGCGGCUU-idT (SEQ ID NO: 323), where G is 2'F; and A, C, and U are 2'OMe modified RNA; $C6NH_2$ is a hexylamine linker; and idT is an inverted deoxythymidine residue. |
| Aptamer 150 | RNA | $C6NH_2$-AGGCCGCCUCCCCGCGGAGGGGUUUCAUUAUCCCGUUUGGCGGCUU-idT (SEQ ID NO: 324), where G is 2'F; and A, C, and U are 2'OMe modified RNA; $C6NH_2$ is a hexylamine linker; and idT is an inverted deoxythymidine residue. |
| Aptamer 151 | RNA | $C6NH_2$-AGGCCGCCUCCUCGCGGAGGGGUUUCAUUAUCCCGUUUGGCGGCUU-idT (SEQ ID NO: 325), where G is 2'F; and A, C, and U are 2'OMe modified RNA; $C6NH_2$ is a hexylamine linker; and idT is an inverted deoxythymidine residue. |
| Aptamer 152 | RNA | $C6NH_2$-AGGCCGCCUCCGAGCGGAGGGGUUUCAUUAUCCCGUUUGGCGGCUU-idT (SEQ ID NO: 326), where G is 2'F; and A, C, and U are 2'OMe modified RNA; $C6NH_2$ is a hexylamine linker; and idT is an inverted deoxythymidine residue. |
| Aptamer 153 | RNA | $C6NH_2$-AGGCCGCCUCCGGGCGGAGGGGUUUCAUUAUCCCGUUUGGCGGCUU-idT (SEQ ID NO: 327), where G is 2'F; and A, C, and U are 2'OMe modified RNA; $C6NH_2$ is a hexylamine linker; and idT is an inverted deoxythymidine residue. |

TABLE 1-continued

| VEGF-A Aptamer Sequences | | |
|---|---|---|
| Compound Name | Backbone | Sequence 5' to 3' |
| Aptamer 154 | RNA | $C6NH_2$-AGGCCGCCUCCGUGCGGAGGGGUUUCAUUAUCCCGUUUGGCGGCUU-idT (SEQ ID NO: 328), where G is 2'F; and A, C, and U are 2'OMe modified RNA; $C6NH_2$ is a hexylamine linker; and idT is an inverted deoxythymidine residue. |
| Aptamer 155 | RNA | $C6NH_2$-AGGCCGCCUCCGCACGGAGGGGUUUCAUUAUCCCGUUUGGCGGCUU-idT (SEQ ID NO: 329), where G is 2'F; and A, C, and U are 2'OMe modified RNA; $C6NH_2$ is a hexylamine linker; and idT is an inverted deoxythymidine residue. |
| Aptamer 156 | RNA | $C6NH_2$-AGGCCGCCUCCGCCCGGAGGGGUUUCAUUAUCCCGUUUGGCGGCUU-idT (SEQ ID NO: 330), where G is 2'F; and A, C, and U are 2'OMe modified RNA; $C6NH_2$ is a hexylamine linker; and idT is an inverted deoxythymidine residue. |
| Aptamer 157 | RNA | $C6NH_2$-AGGCCGCCUCCGCUCGGAGGGGUUUCAUUAUCCCGUUUGGCGGCUU-idT (SEQ ID NO: 331), where G is 2'F; and A, C, and U are 2'OMe modified RNA; $C6NH_2$ is a hexylamine linker; and idT is an inverted deoxythymidine residue. |
| Aptamer 158 | RNA | $C6NH_2$-AGGCCGCCUCCGCGAGGAGGGGUUUCAUUAUCCCGUUUGGCGGCUU-idT (SEQ ID NO: 332), where G is 2'F; and A, C, and U are 2'OMe modified RNA; $C6NH_2$ is a hexylamine linker; and idT is an inverted deoxythymidine residue. |
| Aptamer 159 | RNA | $C6NH_2$-AGGCCGCCUCCGCGGGGAGGGGUUUCAUUAUCCCGUUUGGCGGCUU-idT (SEQ ID NO: 333), where G is 2'F; and A, C, and U are 2'OMe modified RNA; $C6NH_2$ is a hexylamine linker; and idT is an inverted deoxythymidine residue. |
| Aptamer 160 | RNA | $C6NH_2$-AGGCCGCCUCCGCGUGGAGGGGUUUCAUUAUCCCGUUUGGCGGCUU-idT (SEQ ID NO: 334), where G is 2'F; and A, C, and U are 2'OMe modified RNA; $C6NH_2$ is a hexylamine linker; and idT is an inverted deoxythymidine residue. |
| Aptamer 161 | RNA | $C6NH_2$-AGGCCGCCUCCGCGCGGCGGGGUUUCAUUAUCCCGUUUGGCGGCUU-idT (SEQ ID NO: 335), where G is 2'F; and A, C, and U are 2'OMe modified RNA; $C6NH_2$ is a hexylamine linker; and idT is an inverted deoxythymidine residue. |
| Aptamer 162 | RNA | $C6NH_2$-AGGCCGCCUCCGCGCGGAGGGGUUUCAUUAUCCCAUUUGGCGGCUU-idT (SEQ ID NO: 336), where G is 2'F; and A, C, and U are 2'OMe modified RNA; $C6NH_2$ is a hexylamine linker; and idT is an inverted deoxythymidine residue. |
| Aptamer 163 | RNA | $C6NH_2$-AGGCCGCCUCCGCGCGGAGGGGUUUCAUUAUCCCCUUUGGCGGCUU-idT (SEQ ID NO: 337), where G is 2'F; and A, C, and U are 2'OMe modified RNA; $C6NH_2$ is a hexylamine linker; and idT is an inverted deoxythymidine residue. |
| Aptamer 164 | RNA | $C6NH_2$-AGGCCGCCUCCGCGCGGAGGGGUUUCAUUAUCCCUUUUGGCGGCUU-idT (SEQ ID NO: 338), where G is 2'F; and A, C, and U are 2'OMe modified RNA; $C6NH_2$ is a hexylamine linker; and idT is an inverted deoxythymidine residue. |
| Aptamer 165 | RNA | $C6NH_2$-AGGCCGCCUCCGCGCGGAGGGGUUUCAUUAUCCCGAJUUGGCGGCUU-idT (SEQ ID NO: 339), where G is 2'F; and A, C, and U are 2'OMe modified RNA; $C6NH_2$ is a hexylamine linker; and idT is an inverted deoxythymidine residue. |

TABLE 1-continued

| VEGF-A Aptamer Sequences | | |
|---|---|---|
| Compound Name | Backbone | Sequence 5' to 3' |
| Aptamer 166 | RNA | $C6NH_2$-AGGCCGCCUCCGCGCGGAGGGGUUUCAUUAUCCCGCUUGGCGGCUU-idT (SEQ ID NO: 340), where G is 2'F; and A, C, and U are 2'OMe modified RNA; $C6NH_2$ is a hexylamine linker; and idT is an inverted deoxythymidine residue. |
| Aptamer 167 | RNA | $C6NH_2$-AGGCCGCCUCCGCGCGGAGGGGUUUCAUUAUCCCGGUUGGCGGCUU-idT (SEQ ID NO: 341), where G is 2'F; and A, C, and U are 2'OMe modified RNA; $C6NH_2$ is a hexylamine linker; and idT is an inverted deoxythymidine residue. |
| Aptamer 168 | RNA | $C6NH_2$-AGGCCGCCUCCGCGCGGAGGGGUUUCAUUAUCCCGUAUGGCGGCUU-idT (SEQ ID NO: 342), where G is 2'F; and A, C, and U are 2'OMe modified RNA; $C6NH_2$ is a hexylamine linker; and idT is an inverted deoxythymidine residue. |
| Aptamer 169 | RNA | $C6NH_2$-AGGCCGCCUCCGCGCGGAGGGGUUUCAUUAUCCCGUCUGGCGGCUU-idT (SEQ ID NO: 343), where G is 2'F; and A, C, and U are 2'OMe modified RNA; $C6NH_2$ is a hexylamine linker; and idT is an inverted deoxythymidine residue. |
| Aptamer 170 | RNA | $C6NH_2$-AGGCCGCCUCCGCGCGGAGGGGUUUCAUUAUCCCGUGUGGCGGCUU-idT (SEQ ID NO: 344), where G is 2'F; and A, C, and U are 2'OMe modified RNA; $C6NH_2$ is a hexylamine linker; and idT is an inverted deoxythymidine residue. |
| Aptamer 171 | RNA | $C6NH_2$-AGGCCGCCUCCGCGCGGAGGGGUUUCAUUAUCCCGUUAGGCGGCUU-idT (SEQ ID NO: 345), where G is 2'F; and A, C, and U are 2'OMe modified RNA; $C6NH_2$ is a hexylamine linker; and idT is an inverted deoxythymidine residue. |
| Aptamer 172 | RNA | $C6NH_2$-AGGCCGCCUCCGCGCGGAGGGGUUUCAUUAUCCCGUUCGGCGGCUU-idT (SEQ ID NO: 346), where G is 2'F; and A, C, and U are 2'OMe modified RNA; $C6NH_2$ is a hexylamine linker; and idT is an inverted deoxythymidine residue. |
| Aptamer 173 | RNA | $C6NH_2$-AGGCCGCCUCCGCGCGGAGGGGUUUCAUUAUCCCGUUGGGCGGCUU-idT (SEQ ID NO: 347), where G is 2'F; and A, C, and U are 2'OMe modified RNA; $C6NH_2$ is a hexylamine linker; and idT is an inverted deoxythymidine residue. |
| Aptamer 174 | RNA | $C6NH_2$-AGGCCGCCUGCGCGCGCAGGGGUUUCAUUAUCCCGUUUGGCGGCUU-idT (SEQ ID NO: 348), where G is 2'F; and A, C, and U are 2'OMe modified RNA; $C6NH_2$ is a hexylamine linker; and idT is an inverted deoxythymidine residue. |
| Aptamer 175 | RNA | $C6NH_2$-AGGCCGCCUACGCGCGUAGGGGUUUCAUUAUCCCGUUUGGCGGCUU-idT (SEQ ID NO: 349), where G is 2'F; and A, C, and U are 2'OMe modified RNA; $C6NH_2$ is a hexylamine linker; and idT is an inverted deoxythymidine residue. |
| Aptamer 176 | RNA | $C6NH_2$-AGGCCGCCUUCGCGCGAAGGGGUUUCAUUAUCCCGUUUGGCGGCUU-idT (SEQ ID NO: 350), where G is 2'F; and A, C, and U are 2'OMe modified RNA; $C6NH_2$ is a hexylamine linker; and idT is an inverted deoxythymidine residue. |
| Aptamer 177 | RNA | $C6NH_2$-aggccgccucggcgccgaggggguuucauuaucccguuuggcggcuu-idT (SEQ ID NO: 351), where G is 2'F; and A, C, and U are 2'OMe modified RNA; $C6NH_2$ is a hexylamine linker; and idT is an inverted deoxythymidine residue. |

TABLE 1-continued

VEGF-A Aptamer Sequences

| Compound Name | Backbone | Sequence 5' to 3' |
|---|---|---|
| Aptamer 178 | RNA | $C6NH_2$-AGGC CGCCUCAGCGCUGAGGGGUUUCAUUAUCCCGUUUGGCGCCU-idT (SEQ ID NO: 352), where G is 2'F; and A, C, and U are 2'OMe modified RNA; $C6NH_2$ is a hexylamine linker; and idT is an inverted deoxythymidine residue. |
| Aptamer 179 | RNA | $C6NH_2$-AGGCCGCCUCUGCGCAGAGGGGUUUCAUUAUCCCGUUUGGCGGCU-idT (SEQ ID NO: 353), where G is 2'F; and A, C, and U are 2'OMe modified RNA; $C6NH_2$ is a hexylamine linker; and idT is an inverted deoxythymidine residue. |
| Aptamer 180 | RNA | $C6NH_2$-AGGCCGCAUCCGCGCGGAGGGGUUUCAUUAUCCCGUUUAACCGCUU-idT (SEQ ID NO: 354), where G is 2'F; and A, C, and U are 2'OMe modified RNA; $C6NH_2$ is a hexylamine linker; and idT is an inverted deoxythymidine residue. |
| Aptamer 181 | RNA | $C6NH_2$-AGGCCGCAUCCGCGCGGAGGGGUUUCAUUAUCCCGUUUAACCGAUU-idT (SEQ ID NO: 355), where G is 2'F; and A, C, and U are 2'OMe modified RNA; $C6NH_2$ is a hexylamine linker; and idT is an inverted deoxythymidine residue. |
| Aptamer 182 | RNA | $C6NH_2$-AGGCCGCCUUUGCGCUUAGGGGUUUCAUUAUCCCGUUUGGCGGCUU-idT (SEQ ID NO: 356), where G is 2'F; and A, C, and U are 2'OMe modified RNA; $C6NH_2$ is a hexylamine linker; and idT is an inverted deoxythymidine residue. |
| Aptamer 183 | RNA | $C6NH_2$-AGGCCGCCUCCGCGCCCAGGGGUUUCAUUAUCCCGUUUGGCGGCUU-idT (SEQ ID NO: 357), where G is 2'F; and A, C, and U are 2'OMe modified RNA; $C6NH_2$ is a hexylamine linker; and idT is an inverted deoxythymidine residue. |
| Aptamer 184 | RNA | $C6NH_2$-AGGCCGCCUCCGCGCGGAGCCGUUUCAUUAUCCCGUUUGGCGGCUU-idT (SEQ ID NO: 358), where G is 2'F; and A, C, and U are 2'OMe modified RNA; $C6NH_2$ is a hexylamine linker; and idT is an inverted deoxythymidine residue. |
| Aptamer 185 | RNA | $C6NH_2$-AGGCCGCCUCCGCGCGGAGGGGUUUCAUUAUAACGUUUGGCGGCUU-idT (SEQ ID NO: 359), where G is 2'F; and A, C, and U are 2'OMe modified RNA; $C6NH_2$ is a hexylamine linker; and idT is an inverted deoxythymidine residue. |
| Aptamer 187 | RNA | $C6NH_2$-AGGCCGAC-Sp3-CCGCGCGGAGGGGUUUCAUUACCCCGUUUGUCGGCUU-idT (SEQ ID NO: 360), where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 188 | RNA | $C6NH_2$-AGGCCXAC-Sp3-CCGCGCGGAGGGGUUUCAUUAUCCCGUUUGUCGGCUU-idT (SEQ ID NO: 361), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 189 | RNA | $C6NH_2$-AGGCCGAC-Sp3-CCXCGCGGAGGGGUUUCAUUAUCCCGUUUGUCGGCUU-idT (SEQ ID NO: 362), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 190 | RNA | $C6NH_2$-AGGCCGAC-Sp3-CCGCXCGGAGGGGUUUCAUUAUCCCGUUUGUCGGCUU-idT (SEQ ID NO: 363), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |

TABLE 1-continued

| Compound Name | Backbone | Sequence 5' to 3' |
|---|---|---|
| VEGF-A Aptamer Sequences | | |
| Aptamer 191 | RNA | $C6NH_2$-AGGCCGAC-Sp3-CCGCGCXGAGGGGUUUCAUUAUCCCGUUUGUCGGCUU-idT where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 192 | RNA | $C6NH_2$-AGGCCGAC-Sp3-CCGCGCGXAGGGGUUUCAUUAUCCCGUUUGUCGGCUU-idT (SEQ ID NO: 365), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 193 | RNA | $C6NH_2$-AGGCCGAC-Sp3-CCGCGCGGAXGGGUUUCAUUAUCCCGUUUGUCGGCUU-idT (SEQ ID NO: 366), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 194 | RNA | $C6NH_2$-AGGCCGAC-Sp3-CCGCGCGGAGXGGUUUCAUUAUCCCGUUUGUCGGCUU-idT (SEQ ID NO: 367), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 195 | RNA | $C6NH_2$-AGGCCGAC-Sp3-CCGCGCGGAGGXGUUUCAUUAUCCCGUUUGUCGGCUU-idT (SEQ ID NO: 368), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 196 | RNA | $C6NH_2$-AGGCCGAC-Sp3-CCGCGCGGAGGGXUUUCAUUAUCCCGUUUGUCGGCUU-idT (SEQ ID NO: 369), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 197 | RNA | $C6NH_2$-AGGCCGAC-Sp3-CCGCGCGGAGGGGUUUCAUUAUCCCXUUUGUCGGCUU-idT (SEQ ID NO: 370), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 198 | RNA | $C6NH_2$-AGGCCGAC-Sp3-CCGCGCGGAGGGGUUUCAUUAUCCCGUUUXUCGGCUU-idT (SEQ ID NO: 371), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 199 | RNA | $C6NH_2$-GCCGAC-Sp3-CCGCGCGGAGGGGUUUCAUUAUCCCGUUUGUCGGC-idT where G is 2'F; and A, C, and U are 2'OMe modified RNA; $C6NH_2$ is a hexylamine linker; idT is an inverted deoxythymidine residue; and Sp3 is the SP3 spacer (1,3-propanediol). |
| Aptamer 201 | RNA | $C6NH_2$-AGGCCXAC-Sp3-CCGCGCGGAGGGXUUUCAUUACCCCGUUUXUCGGCUU-idT (SEQ ID NO: 373), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 213 | RNA | $C6NH_2$-XCCGAC-Sp3-CCGCGCGGAGGGGUUUCAUUAUCCCGUUUGUCXXC-idT (SEQ ID NO: 374), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |

TABLE 1-continued

| VEGF-A Aptamer Sequences | | |
|---|---|---|
| Compound Name | Backbone | Sequence 5' to 3' |
| Aptamer 214 | RNA | $C6NH_2$-XCCXAC-Sp3-CCGCGCGGAGGGGUUUCAUUAUCCCGUUUGUCXXC-idT (SEQ ID NO: 375), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 215 | RNA | $C6NH_2$-XCCGAC-Sp3-CCGCGCGGAGGGXUUUCAUUAUCCCGUUUGUCXXC-idT (SEQ ID NO: 376), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 216 | RNA | $C6NH_2$-XCCGAC-Sp3-CCGCGCGGAGGGGUUUCAUUAUCCCGUUUXUCXXC-idT (SEQ ID NO: 377), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 217 | RNA | $C6NH_2$-XCCXAC-Sp3-CCGCGCGGAGGGXUUUCAUUAUCCCGUUUGUCXXC-idT (SEQ ID NO: 378), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 218 | RNA | $C6NH_2$-XCCXAC-Sp3-CCGCGCGGAGGGGUUUCAUUAUCCCGUUUXUCXXC-idT (SEQ ID NO: 379), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 219 | RNA | $C6NH_2$-XCCGAC-Sp3-CCGCGCGGAGGGXUUUCAUUAUCCCGUUUXUCXXU-idT (SEQ ID NO: 380), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 220 | RNA | $C6NH_2$-XCCXAC-Sp3-CCGCGCGGAGGGXUUUCAUUAUCCCGUUUXUCXX-idT (SEQ ID NO: 381), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 221 | RNA | $C6NH_2$-CCXAC-Sp3-CCGCGCGGAGGGGUUUCAUUAUCCCGUUUGUCXX-idT (SEQ ID NO: 382), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 222 | RNA | $C6NH_2$-CCGAC-Sp3-CCGCGCGGAGGGXUUUCAUUAUCCCGUUUGUCXX-idT (SEQ ID NO: 383), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 223 | RNA | $C6NH_2$-CCGAC-Sp3-CCGCGCGGAGGGGUUUCAUUAUCCCGUUUXUCXX-idT (SEQ ID NO: 384), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 224 | RNA | $C6NH_2$-CCXAC-Sp3-CCGCGCGGAGGGXUUUCAUUAUCCCGUUUGUCXX-idT (SEQ ID NO: 385), where G is 2'F; and A, C, and U are 2'OMe modified RNA; X is 2'OMe G modified RNA; $C6NH_2$ is a hexylamine linker; idT |

TABLE 1-continued

| VEGF-A Aptamer Sequences | | |
|---|---|---|
| Compound Name | Backbone | Sequence 5' to 3' |
| | | is an inverted deoxythymidine residue; and Sp3 is the SP3 spacer (1,3-propanediol). |
| Aptamer 225 | RNA | $C6NH_2$-CCXAC-Sp3-CCGCGCGGAGGGGUUUCAUUAUCCCGUUUXUCXX-idT (SEQ ID NO: 386), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 226 | RNA | $C6NH_2$-CCGAC-Sp3-CCGCGCGGAGGGXUUUCAUUAUCCCGUUUXUCXX-idT (SEQ ID NO: 387), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 227 | RNA | $C6NH_2$-CCXAC-Sp3-CCGCGCGGAGGGXUUUCAUUAUCCCGUUUXUCXX-idT (SEQ ID NO: 388), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 228 | RNA | $C6NH_2$-CXAC-Sp3-CCGCGCGGAGGGGUUUCAUUAUCCCGUUUGUXC-idT (SEQ ID NO: 389), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 229 | RNA | $C6NH_2$-CGAC-Sp3-CCGCGCGGAGGGXUUUCAUUAUCCCGUUUGUCX-idT (SEQ ID NO: 390), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 230 | RNA | $C6NH_2$-CGAC-Sp3-CCGCGCGGAGGGGUUUCAUUAUCCCGUUUXUCX-idT (SEQ ID NO: 391), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 231 | RNA | $C6NH_2$-CXAC-Sp3-CCGCGCGGAGGGXUUUCAUUAUCCCGUUUGUCX-idT (SEQ ID NO: 392), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 232 | RNA | $C6NH_2$-CXAC-Sp3-CCGCGCGGAGGGGUUUCAUUAUCCCGUUUXUCX-idT (SEQ ID NO: 393), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 233 | RNA | $C6NH_2$-CGAC-Sp3-CCGCGCGGAGGGXUUUCAUUAUCCCGUUUXUCX-idT (SEQ ID NO: 394), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 234 | RNA | $C6NH_2$-CXAC-Sp3-CCGCGCGGAGGGXUUUCAUUAUCCCGUUUXUCX-idT (SEQ ID NO: 395), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |

TABLE 1-continued

| VEGF-A Aptamer Sequences | | |
|---|---|---|
| Compound Name | Backbone | Sequence 5' to 3' |
| Aptamer 235 | RNA | $C6NH_2$-XAC-Sp3-CCGCGCGGAGGGGUUUCAUUAUCCCGUUUGUC-idT (SEQ ID NO: 396), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 236 | RNA | $C6NH_2$-GAC-Sp3-CCGCGCGGAGGGXUUUCAUUAUCCCGUUUGUC-idT (SEQ ID NO: 397), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 237 | RNA | $C6NH_2$-GAC-Sp3-CCGCGCGGAGGGGUUUCAUUAUCCCGUUUXUC-idT (SEQ ID NO: 398), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 238 | RNA | $C6NH_2$-XAC-Sp3-CCGCGCGGAGGGXUUUCAUUAUCCCGUUUGUC-idT (SEQ ID NO: 399), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 239 | RNA | $C6NH_2$-XAC-Sp3-CCGCGCGGAGGGGUUUCAUUAUCCCGUUUXUC-idT (SEQ ID NO: 400), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 240 | RNA | $C6NH_2$-GAC-Sp3-CCGCGCGGAGGGXUUUCAUUAUCCCGUUUXUC-idT (SEQ ID NO: 401), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 241 | RNA | $C6NH_2$-XAC-Sp3-CCGCGCGGAGGGXUUUCAUUAUCCCGUUUXUC-idT (SEQ ID NO: 402), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 276 | RNA | $C6NH_2$-AC-Sp3-CCGCGCGAGGGXUUUCAUUAUCCCGUUUGU-idT (SEQ ID NO: 403), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 277 | RNA | $C6NH_2$-AC-Sp3-CCGCGCGGAGGGGUUUCAUUAUCCCGUUUXU-idT (SEQ ID NO: 404), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 278 | RNA | $C6NH_2$-AC-Sp3-CCGCGCGGAGGGXUUUCAUUAUCCCGUUUXU-idT (SEQ ID NO: 405), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |

TABLE 1-continued

| VEGF-A Aptamer Sequences | | |
|---|---|---|
| Compound Name | Backbone | Sequence 5' to 3' |
| Aptamer 279 | RNA | $C6NH_2$-C-Sp3-CCGCGCGGAGGGXUUUCAUUAUCCCGUUUG-idT (SEQ ID NO: 406), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 280 | RNA | $C6NH_2$-C-Sp3-CCGCGCGGAGGGGUUUCAUUAUCCCGUUUX-idT (SEQ ID NO: 407), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 281 | RNA | $C6NH_2$-C-Sp3-CCGCGCGGAGGGXUUUCAUUAUCCCGUUUX-idT (SEQ ID NO: 408), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 282 | RNA | $C6NH_2$-CXAC-Sp3-CCGCGCGGAGGGAUUUCAUUAUCCCGUUUXUCX-idT (SEQ ID NO: 409), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 283 | RNA | $C6NH_2$-CXAC-Sp3-CCGCGCGAGGGXUAUCAUUAUCCCGUUUXUCX-idT (SEQ ID NO: 410), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 284 | RNA | $C6NH_2$-CXAC-Sp3-CCGCGCGGAGGGXUUACAUUAUCCCGUUUXUCX-idT (SEQ ID NO: 411), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 285 | RNA | $C6NH_2$-CXAC-Sp3-CCGCGCGGAGGGXUUUCAUAAUCCCGUUUXUCX-idT (SEQ ID NO: 412), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 286 | RNA | $C6NH_2$-CXAC-Sp3-CCGCGCGGAGGGXUUUCAUUACCCCGUUUXUCX-idT (SEQ ID NO: 413), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 287 | RNA | $C6NH_2$-CXAC-Sp3-CCGCGCGGAGGGAUAUCAUUAUCCCGUUUXUCX-idT (SEQ ID NO: 414), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 288 | RNA | $C6NH_2$-CXAC-Sp3-CCGCGCGGAGGGAUUACAUUAUCCCGUUUXUCX-idT (SEQ ID NO: 415), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |

TABLE 1-continued

VEGF-A Aptamer Sequences

| Compound Name | Backbone | Sequence 5' to 3' |
|---|---|---|
| Aptamer 289 | RNA | $C6NH_2$-CXAC-Sp3-CCGCGCGGAGGGAUUUCAUAAUCCCGUUUXUCX-idT (SEQ ID NO: 416), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 290 | RNA | $C6NH_2$-CXAC-Sp3-CCGCGCGGAGGGXUAUCAUUACCCCGUUUXUCX-idT (SEQ ID NO: 417), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 291 | RNA | $C6NH_2$-CXAC-Sp3-CCGCGCGGAGGGXUUUCAUAACCCCGUUUXUCX-idT (SEQ ID NO: 418), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 292 | RNA | $C6NH_2$-CXAX-Sp3-CCGCGCGGAGGGXUUACAUAAUCCCGUUUXUCX-idT (SEQ ID NO: 419), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 293 | RNA | $C6NH_2$-CXAC-Sp3-CAGCGCUGAGGGXUUUCAUUAUCCCGUUUXUCX-idT (SEQ ID NO: 420), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 294 | RNA | $C6NH_2$-CXAC-Sp3-CCXCGCGGAGGGXUUUCAUUAUCCCGUUUXUCX-idT (SEQ ID NO: 421), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 295 | RNA | $C6NH_2$-CXAC-Sp3-CAXCGCUGAGGGXUUUCAUUAUCCCGUUUXUCX-idT (SEQ ID NO: 422), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 296 | RNA | $C6NH_2$-CXAX-Sp3-CCGCGCGGAGGGAUXUCAUCAUCCCGUUUXUCX-idT (SEQ ID NO: 423), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 297 | RNA | $C6NH_2$-CXAC-Sp3-CCGCGCGGAGGGAUCUCAUXAUCCCGUUUXUCS-idT (SEQ ID NO: 424), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 298 | RNA | $C6NH_2$-CXAC-Sp3-Sp3-CCGCGCGGAGGGXUUUCAUUAUCCCGUUUXUCX-idT (SEQ ID NO: 425), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |

TABLE 1-continued

VEGF-A Aptamer Sequences

| Compound Name | Backbone | Sequence 5' to 3' |
|---|---|---|
| Aptamer 299 | RNA | $C6NH_2$-CXAC-Sp6-CCGCGCGGAGGGXUUUCAUUAUCCCGUUUXUCX-idT (SEQ ID NO: 426), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 300 | RNA | $C6NH_2$-CXAC-Sp9-CCGCGCGGAGGGXUUUCAUUAUCCCGUUUXUCX-idT (SEQ ID NO: 427), where G is 2'F; and A, C, and U are 2'OMe modified RNA; X is 2'OMe G modified RNA; $C6NH_2$ is a hexylamine linker; idT is an inverted deoxythymidine residue; and Sp3 is the SP3 spacer (1,3-propanediol). |
| Aptamer 301 | RNA | CGACUCCGCGCGGAGGUUGGAGGUUACCCGUUUGUCG (SEQ ID NO: 439), where G is 2'F; and A, C, & U are 2'OMe modified RNA. |
| Aptamer 302 | RNA | GGGAGAGUCGGUAGCCUCAACGACUCCGCGCGGAGGGUUGGAGGUUACCCGUUUGUCGCUAUGUGGAAAUGGCGCUGU (SEQ ID NO: 440), where G is 2'F; and A, C, & U are 2'OMe modified RNA. |
| Aptamer 303 | RNA | CGACUCCGCGCGGAGUCCCUAAUUUGGGGCGUUUGUCG (SEQ ID NO: 441), where G is 2'F; and A, C, & U are 2'OMe modified RNA. |
| Aptamer 304 | RNA | GGGAGAGUCGGUAGCCUCAACGACUCCGCGCGGAGUCCCUAAUUUGGGGCGUUUGUCGCUAUGUGGAAAUGGCGCUGU (SEQ ID NO: 442), where G is 2'F; and A, C, & U are 2'OMe modified RNA. |
| Aptamer 305 | RNA | CGACUCCGCGCGGAGUCCCUUCAUUGGGGCGUUUGUCG (SEQ ID NO: 443), where G is 2'F; and A, C, & U are 2'OMe modified RNA. |
| Aptamer 306 | RNA | GGGAGAGUCGGUAGCCUCAACGACUCCGCGCGGAGUCCCUUCAUUGGGGCGUUUGUCGCUAUGUGGAAAUGGCGCUGU (SEQ ID NO: 444), where G is 2'F; and A, C, & U are 2'OMe modified RNA. |
| Aptamer 307 | RNA | CGACUCCGCGCGGAGGGUUAAUGGCUACCCGUUUGUCG (SEQ ID NO: 445), where G is 2'F; and A, C, & U are 2'OMe modified RNA. |
| Aptamer 308 | RNA | GGGAGAGUCGGUAGCCUCAACGACUCCGCGCGGAGGGUUAAUGGCUACCCGUUUGUCGCUAUGUGGAAAUGGCGCUGU (SEQ ID NO: 446), where G is 2'F; and A, C, & U are 2'OMe modified RNA. |
| Aptamer 309 | RNA | CGACUCCGCGCGGAGUCCCUGUAAUGGGGCGUUUGUCG (SEQ ID NO: 447), where G is 2'F; and A, C, & U are 2'OMe modified RNA. |
| Aptamer 310 | RNA | GGGAGAGUCGGUAGCCUCAACGACUCCGCGCGGAGUCCCUGUAAUGGGGCGUUUGUCGCUAUGUGGAAAUGGCGCUGU (SEQ ID NO: 448), where G is 2'F; and A, C, & U are 2'OMe modified RNA. |
| Aptamer 311 | RNA | CGACUCCGCGCGGAGUCCCUAUUUUGGGGCGUUUGUCG (SEQ ID NO: 449), where G is 2'F; and A, C, & U are 2'OMe modified RNA. |
| Aptamer 312 | RNA | GGGAGAGUCGGUAGCCUCAACGACUCCGCGCGGAGUCCCUAUUUUGGGGCGUUUGUCGCUAUGUGGAAAUGGCGCUGU (SEQ ID NO: 450), where G is 2'F; and A, C, & U are 2'OMe modified RNA. |
| Aptamer 313 | RNA | CGACUCCGCGCGGAGAGGAGGUUACCCCUCGUUUGUCG (SEQ ID NO: 451), where G is 2'F; and A, C, & U are 2'OMe modified RNA. |
| Aptamer 314 | RNA | GGGAGAGUCGGUAGCCUCAACGACUCCGCGCGGAGAGGAGGUUACCCCUCGUUUGUCGCUAUGUGGAAAUGGCGCUGU (SEQ ID NO: 452), where G is 2'F; and A, C, & U are 2'OMe modified RNA. |
| Aptamer 315 | RNA | CGACUCCGCGCGGAGUCCCUUGAUUGGGGCGUUUGUCG (SEQ ID NO: 453), where G is 2'F; and A, C, & U are 2'OMe modified RNA. |
| Aptamer 316 | RNA | GGGAGAGUCGGUAGCCUCAACGACUCCGCGCGGAGUCCCUUGAUUGGGGCGUUUGUCGCUAUGUGGAAAUGGCGCUGU (SEQ ID NO: 454), where G is 2'F; and A, C, & U are 2'OMe modified RNA. |
| Aptamer 317 | RNA | CGACUCCGCGCGGAGGGUUACUGGCUACCCGUUUGUCG (SEQ ID NO: 455), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| Aptamer 318 | RNA | GGGAGAGUCGGUAGCCUCAACGACUCCGCGCGGAGGGUUACUGGCUACCCGUUUGUCGCUAUGUGGAAAUGGCGCUGU (SEQ ID NO: 456), where G is 2'F; and A, C, & U are 2'OMe modified RNA. |
| Aptamer 319 | RNA | CGACUCCGCGCGGAGUCCCUAACAUGGGGCGUUUGUCG (SEQ ID NO: 457), where G is 2'F; and A, C, & U are 2'OMe modified RNA. |
| Aptamer 320 | RNA | GGGAGAGUCGGUAGCCUCAACGACUCCGCGCGGAGUCCCUAACAUGGGGCGUUUGUCGCUAUGUGGAAAUGGCGCUGU (SEQ ID NO: 458), where G is 2'F; and A, C, & U are 2'OMe modified RNA. |
| Aptamer 321 | RNA | CGACUCCGCGCGGAGGGGAGGCAACUUCCCGUUUGUCG (SEQ ID NO: 459), where G is 2'F; and A, C, & U are 2'OMe modified RNA. |
| Aptamer 322 | RNA | GGGAGAGUCGGUAGCCUCAACGACUCCGCGCGGAGGGGAGGCAACUUCCCGUUUGUCGCUAUGUGGAAAUGGCGCUGU (SEQ ID NO: 460), where G is 2'F; and A, C, & U are 2'OMe modified RNA. |
| Aptamer 323 | RNA | CGACUCCGCGCGGAGUCCCUUUAUUGGGGCGUUUGUCG (SEQ ID NO: 461), where G is 2'F; and A, C, & U are 2'OMe modified RNA. |
| Aptamer 324 | RNA | GGGAGAGUCGGUAGCCUCAACGACUCCGCGCGGAGUCCCUUUAUUGGGGCGUUUGUCGCUAUGUGGAAAUGGCGCUGU (SEQ ID NO: 462), where G is 2'F; and A, C, & U are 2'OMe modified RNA. |
| Aptamer 325 | RNA | CGACUCCGCGCGGAGUCCCUACAAUGGGGCGUUUGUCG (SEQ ID NO: 463), where G is 2'F; and A, C, & U are 2'OMe modified RNA. |
| Aptamer 326 | RNA | GGGAGAGUCGGUAGCCUCAACGACUCCGCGCGGAGUCCCUACAAUGGGGCGUUUGUCGCUAUGUGGAAAUGGCGCUGU (SEQ ID NO: 464), where G is 2'F; and A, C, & U are 2'OMe modified RNA. |
| Aptamer 327 | RNA | CGACUCCGCGCGGAGUGCCGUUUGAGGUACGUUUGUCG (SEQ ID NO: 465), where G is 2'F; and A, C, & U are 2'OMe modified RNA. |
| Aptamer 328 | RNA | GGGAGAGUCGGUAGCCUCAACGACUCCGCGCGGAGUGCCGUUUGAGGUACGUUUGUCGCUAUGUGGAAAUGGCGCUGU (SEQ ID NO: 466), where G is 2'F; and A, C, & U are 2'OMe modified RNA. |
| Aptamer 329 | RNA | CGACUCCGCGCGGAGGGCUGAGGCAAUGCCCGUUUGUC (SEQ ID NO: 467), where G is 2'F; and A, C, & U are 2'OMe modified RNA. |
| Aptamer 330 | RNA | GGGAGAGUCGGUAGCCUCAACGACUCCGCGCGGAGGGCUGAGGCAAUGCCCGUUUGUCCUAUGUGGAAAUGGCGCUGU (SEQ ID NO: 468), where G is 2'F; and A, C, & U are 2'OMe modified RNA. |
| Aptamer 331 | RNA | CGACUCCGCGCGGAGUCCCUACUUUGGGGCGUUUGUCG (SEQ ID NO: 469), where G is 2'F; and A, C, & U are 2'OMe modified RNA. |
| Aptamer 332 | RNA | GGGAGAGUCGGUAGCCUCAACGACUCCGCGCGGAGUCCCUACUUUGGGGCGUUUGUCGCUAUGUGGAAAUGGCGCUGU (SEQ ID NO: 470), where G is 2'F; and A, C, & U are 2'OMe modified RNA. |
| Aptamer 333 | RNA | CGACUCCGCGCGGAGUCCCUCACAUGGGGCGUUUGUCG (SEQ ID NO: 471), where G is 2'F; and A, C, & U are 2'OMe modified RNA. |
| Aptamer 334 | RNA | GGGAGAGUCGGUAGCCUCAACGACUCCGCGCGGAGUCCCUCACAUGGGGCGUUUGUCGCUAUGUGGAAAUGGCGCUGU (SEQ ID NO: 472), where G is 2'F; and A, C, & U are 2'OMe modified RNA. |
| Aptamer 335 | RNA | CGACUCCGCGCGGAGGGUUACAGGCUACCCGUUUGUCG (SEQ ID NO: 473), where G is 2'F; and A, C, & U are 2'OMe modified RNA. |
| Aptamer 336 | RNA | GGGAGAGUCGGUAGCCUCAACGACUCCGCGCGGAGGGUUACAGGCUACCCGUUUGUCGCUAUGUGGAAAUGGCGCUGU (SEQ ID NO: 474), where G is 2'F; and A, C, & U are 2'OMe modified RNA. |
| Aptamer 337 | RNA | CGACUCCGCGCGGAGUCCCUUUGUUGGGGCGUUUGUCG (SEQ ID NO: 475), where G is 2'F; and A, C, & U are 2'OMe modified RNA. |
| Aptamer 338 | RNA | GGGAGAGUCGGUAGCCUCAACGACUCCGCGCGGAGUCCCUUUGUUGGGGCGUUUGUCGCUAUGUGGAAAUGGCGCUGU (SEQ ID NO: 476), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| Aptamer 339 | RNA | CGACUCCGCGCGGAGUCCCUAAAAUGGGGCGUUUGUCG (SEQ ID NO: 477), where G is 2'F; and A, C, & U are 2'OMe modified RNA. |
| Aptamer 340 | RNA | GGGAGAGUCGGUAGCCUCAACGACUCCGCGCGGAGUCCCUAAAAUGGGGCGUUUGUCGCUAUGUGGAAAUGGCGCUGU (SEQ ID NO: 478), where G is 2'F; and A, C, & U are 2'OMe modified RNA. |
| Aptamer 341 | RNA | CGACUCCGCGCGGAGGGUUUGGCUACCCGUUUGUCG (SEQ ID NO: 479), where G is 2'F; and A, C, & U are 2'OMe modified RNA. |
| Aptamer 342 | RNA | GGGAGAGUCGGUAGCCUCAACGACUCCGCGCGGAGGGUUUGGCUACCCGUUUGUCGCUAUGUGGAAAUGGCGCUGU (SEQ ID NO: 480), where G is 2'F; and A, C, & U are 2'OMe modified RNA. |
| Aptamer 343 | RNA | CGACUCCGCGCGGAGGCUUGAGGUAGCCGUUUGUCG (SEQ ID NO: 481), where G is 2'F; and A, C, & U are 2'OMe modified RNA. |
| Aptamer 344 | RNA | GGGAGAGUCGGUAGCCUCAACGACUCCGCGCGGAGGCUUGAGGUAGCCGUUUGUCGCUAUGUGGAAAUGGCGCUGU (SEQ ID NO: 482), where G is 2'F; and A, C, & U are 2'OMe modified RNA. |
| Aptamer 345 | RNA | CGACUCCGCGCGGAGUCCCACAUGGGGCGUUUGUCG (SEQ ID NO: 483), where G is 2'F; and A, C, & U are 2'OMe modified RNA. |
| Aptamer 346 | RNA | GGGAGAGUCGGUAGCCUCAACGACUCCGCGCGGAGUCCCACAUGGGGCGUUUGUCGCUAUGUGGAAAUGGCGCUGU (SEQ ID NO: 484), where G is 2'F; and A, C, & U are 2'OMe modified RNA. |
| Aptamer 347 | RNA | CGACUCCGCGCGGAGGGAUGAGGUUCCCGUUUGUCG (SEQ ID NO: 485), where G is 2'F; and A, C, & U are 2'OMe modified RNA. |
| Aptamer 348 | RNA | GGGAGAGUCGGUAGCCUCAACGACUCCGCGCGGAGGGAUGAGGUUCCCGUUUGUCGCUAUGUGGAAAUGGCGCUGU (SEQ ID NO: 486), where G is 2'F; and A, C, & U are 2'OMe modified RNA. |
| Aptamer 349 | RNA | CGACUCCGCGCGGAGGCAUGAGGUUGCCGUUUGUCG (SEQ ID NO: 487), where G is 2'F; and A, C, & U are 2'OMe modified RNA. |
| Aptamer 350 | RNA | GGGAGAGUCGGUAGCCUCAACGACUCCGCGCGGAGGCAUGAGGUUGCCGUUUGUCGCUAUGUGGAAAUGGCGCUGU (SEQ ID NO: 488), where G is 2'F; and A, C, & U are 2'OMe modified RNA. |
| Aptamer 351 | RNA | CGACUCCGCGCGGAGUGCUGAGGUGCACGUUUGUCG (SEQ ID NO: 489), where G is 2'F; and A, C, & U are 2'OMe modified RNA. |
| Aptamer 352 | RNA | GGGAGAGUCGGUAGCCUCAACGACUCCGCGCGGAGUGCUGAGGUGCACGUUUGUCGCUAUGUGGAAAUGGCGCUGU (SEQ ID NO: 490), where G is 2'F; and A, C, & U are 2'OMe modified RNA. |
| Aptamer 353 | RNA | CGACUCCGCGCGGAGUCCCUAUUGGGGCGUUUGUCG (SEQ ID NO: 491), where G is 2'F; and A, C, & U are 2'OMe modified RNA. |
| Aptamer 354 | RNA | GGGAGAGUCGGUAGCCUCAACGACUCCGCGCGGAGUCCCUAUUGGGGCGUUUGUCGCUAUGUGGAAAUGGCGCUGU (SEQ ID NO: 492), where G is 2'F; and A, C, & U are 2'OMe modified RNA. |
| Aptamer 355 | RNA | CGACUCCGCGCGGAGGGUUAGGCUACCCGUUUGUCG (SEQ ID NO: 493), where G is 2'F; and A, C, & U are 2'OMe modified RNA. |
| Aptamer 356 | RNA | GGGAGAGUCGGUAGCCUCAACGACUCCGCGCGGAGGGUUAGGCUACCCGUUUGUCGCUAUGUGGAAAUGGCGCUGU (SEQ ID NO: 494), where G is 2'F; and A, C, & U are 2'OMe modified RNA. |
| Aptamer 357 | RNA | CGACUCCGCGCGGAGCUUCGGAUGAGGCGUUUGUCG (SEQ ID NO: 495), where G is 2'F; and A, C, & U are 2'OMe modified RNA. |
| Aptamer 358 | RNA | GGGAGAGUCGGUAGCCUCAACGACUCCGCGCGGAGCUUCGGAUGAGGCGUUUGUCGCUAUGUGGAAAUGGCGCUGU (SEQ ID NO: 496), where G is 2'F; and A, C, & U are 2'OMe modified RNA. |
| Aptamer 359 | RNA | CGACUCCGCGCGGAGUCCCUCAUGGGGCGUUUGUCG (SEQ ID NO: 497), where G is 2'F; and A, C, & U are 2'OMe modified RNA. |

TABLE 1-continued

| VEGF-A Aptamer Sequences | | |
|---|---|---|
| Compound Name | Backbone | Sequence 5' to 3' |
| Aptamer 360 | RNA | GGGAGAGUCGGUAGCCUCAACGACUCCGCGCGGAGUCCCUCAUGGGGCGUUUGUCGCUAUGU GGAAAUGGCGCUGU (SEQ ID NO: 498), where G is 2'F; and A, C, & U are 2'OMe modified RNA. |
| Aptamer 361 | RNA | CGACUCCGCGCGGAGUCCCGUAUGGGGCGUUUGUCG (SEQ ID NO: 499), where G is 2'F; and A, C, & U are 2'OMe modified RNA. |
| Aptamer 362 | RNA | GGGAGAGUCGGUAGCCUCAACGACUCCGCGCGGAGUCCCGUAUGGGGCGUUUGUCGCUAUGU GGAAAUGGCGCUGU (SEQ ID NO: 500), where G is 2'F; and A, C, & U are 2'OMe modified RNA. |
| Aptamer 363 | RNA | CGACUCCGCGCGGAGUCCCAAUUGGGGCGUUUGUCG (SEQ ID NO: 501), where G is 2'F; and A, C, & U are 2'OMe modified RNA. |
| Aptamer 364 | RNA | GGGAGAGUCGGUAGCCUCAACGACUCCGCGCGGAGUCCCAAUUGGGGCGUUUGUCGCUAUGU GGAAAUGGCGCUGU (SEQ ID NO: 502), where G is 2'F; and A, C, & U are 2'OMe modified RNA. |
| Aptamer 365 | RNA | CGACUCCGCGCGGAGGGUUUGGUUACCCGUUUGUCG (SEQ ID NO: 503), where G is 2'F; and A, C, & U are 2'OMe modified RNA. |
| Aptamer 366 | RNA | GGGAGAGUCGGUAGCCUCAACGACUCCGCGCGGAGGGUUUGGUUACCCGUUUGUCGCUAUGU GGAAAUGGCGCUGU (SEQ ID NO: 504), where G is 2'F; and A, C, & U are 2'OMe modified RNA. |
| Aptamer 367 | RNA | CGACUCCGCGCGGAGUCCCAUUUGGGGCGUUUGUCG (SEQ ID NO: 505), where G is 2'F; and A, C, & U are 2'OMe modified RNA. |
| Aptamer 368 | RNA | GGGAGAGUCGGUAGCCUCAACGACUCCGCGCGGAGUCCCAUUUGGGGCGUUUGUCGCUAUGU GGAAAUGGCGCUGU (SEQ ID NO: 506), where G is 2'F; and A, C, & U are 2'OMe modified RNA. |
| Aptamer 369 | RNA | CGACUCCGCGCGGAGUCCCACAAGGGGCGUUUGUCG (SEQ ID NO: 507), where G is 2'F; and A, C, & U are 2'OMe modified RNA. |
| Aptamer 370 | RNA | GGGAGAGUCGGUAGCCUCAACGACUCCGCGCGGAGUCCCACAAGGGGCGUUUGUCGCUAUGU GGAAAUGGCGCUGU (SEQ ID NO: 508), where G is 2'F; and A, C, & U are 2'OMe modified RNA. |
| Aptamer 371 | RNA | CGACUCCGCGCGGAGCUUCGGAAGAGGCGUUUGUCG (SEQ ID NO: 509), where G is 2'F; and A, C, & U are 2'OMe modified RNA. |
| Aptamer 372 | RNA | GGGAGAGUCGGUAGCCUCAACGACUCCGCGCGGAGCUUCGGAAGAGGCGUUUGUCGCUAUGU GGAAAUGGCGCUGU (SEQ ID NO: 510), where G is 2'F; and A, C, & U are 2'OMe modified RNA. |
| Aptamer 373 | RNA | CGACUCCGCGCGGAGUCCCAUUAGGGGCGUUUGUCG (SEQ ID NO: 511), where G is 2'F; and A, C, & U are 2'OMe modified RNA. |
| Aptamer 374 | RNA | GGGAGAGUCGGUAGCCUCAACGACUCCGCGCGGAGUCCCAUUAGGGGCGUUUGUCGCUAUGU GGAAAUGGCGCUGU (SEQ ID NO: 512), where G is 2'F; and A, C, & U are 2'OMe modified RNA. |
| Aptamer 375 | RNA | CGACUCCGCGCGGAGUGCCAACUGGUACGUUUGUCG (SEQ ID NO: 513), where G is 2'F; and A, C, & U are 2'OMe modified RNA. |
| Aptamer 376 | RNA | GGGAGAGUCGGUAGCCUCAACGACUCCGCGCGGAGUGCCAACUGGUACGUUUGUCGCUAUGU GGAAAUGGCGCUGU (SEQ ID NO: 514), where G is 2'F; and A, C, & U are 2'OMe modified RNA. |
| Aptamer 377 | RNA | CGACUCCGCGCGGAGUCCCUAUAGGGGCGUUUGUCG (SEQ ID NO: 515), where G is 2'F; and A, C, & U are 2'OMe modified RNA. |
| Aptamer 378 | RNA | GGGAGAGUCGGUAGCCUCAACGACUCCGCGCGGAGUCCCUAUAGGGGCGUUUGUCGCUAUGU GGAAAUGGCGCUGU (SEQ ID NO: 516), where G is 2'F; and A, C, & U are 2'OMe modified RNA. |
| Aptamer 379 | RNA | CGACUCCGCGCGGAGUCCCUAAUGGGGCGUUUGUCG (SEQ ID NO: 517), where G is 2'F; and A, C, & U are 2'OMe modified RNA. |
| Aptamer 380 | RNA | GGGAGAGUCGGUAGCCUCAACGACUCCGCGCGGAGUCCCUAAUGGGGCGUUUGUCGCUAUGU GGAAAUGGCGCUGU (SEQ ID NO: 518), where G is 2'F; and A, C, & U are 2'OMe modified RNA. |

In some aspects, an aptamer of the disclosure may have a primary nucleic acid sequence according to any one of the aptamer sequences described in Table 1, or may have a primary nucleic acid sequence that shares at least 500% sequence identity to any one of the aptamer sequences described in Table 1. In some aspects, an aptamer of the disclosure may have a primary nucleic acid sequence consisting of any one of the aptamer sequences described in Table 1, or may have a nucleic acid sequence that shares at least 50% sequence identity to a primary nucleic acid sequence that consists of any one of the aptamer sequences described in Table 1. In some cases, the nucleic acid sequence may comprise one or more modified nucleotides. In some cases, at least 50%, of said nucleic acid sequence may comprise the one or more modified nucleotides. In some cases, the one or more modified nucleotides may comprise a 2'F-modified nucleotide, a 2'OMe-modified nucleotide, or a combination thereof. In some cases, the one or more modified nucleotides may be selected from the group consisting of; 2'F-G, 2'OMe-G, 2'OMe-U, 2'OMe-A, 2'OMe-C, an inverted deoxythymidine at the 3' terminus, and any combination thereof. In some cases, the aptamer may comprise a nucleic acid sequence comprising modified nucleotides as described in Table 1. In some cases, the aptamer is any aptamer described in Table 1. For example, the aptamer may be any one of Aptamers 4.2, 26-32, 47-76, 108, 109, 112-117, 119-185, 187-199, 201, 213-241, and 276-300. In some cases, the aptamer may be conjugated to a polyethylene glycol (PEG) molecule. In some cases, the PEG molecule may have a molecular weight of 80 kDa or less (e.g., 40 kDa).

In some cases, an aptamer of the disclosure may have at least 50%, 55%, 600%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described herein. For example, an anti-VEGF-A aptamer of the disclosure may have at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described in Table 1.

In some cases, an anti-VEGF-A aptamer of the disclosure may have at least 50% sequence identity with any one of the aptamer sequences described in Table 1. In some cases, an anti-VEGF-A aptamer of the disclosure may have at least 55% sequence identity with any one of the aptamer sequences described in Table 1. In some cases, an anti-VEGF-A aptamer of the disclosure may have at least 60% sequence identity with any one of the aptamer sequences described in Table 1. In some cases, an anti-VEGF-A aptamer of the disclosure may have at least 65% sequence identity with any one of the aptamer sequences described in Table 1. In some cases, an anti-VEGF-A aptamer of the disclosure may have at least 70% sequence identity with any one of the aptamer sequences described in Table 1. In some cases, an anti-VEGF-A aptamer of the disclosure may have at least 75% sequence identity with any one of the aptamer sequences described in Table 1. In some cases, an anti-VEGF-A aptamer of the disclosure may have at least 80% sequence identity with any one of the aptamer sequences described in Table 1.

In some cases, an anti-VEGF-A aptamer of the disclosure may have at least 85% sequence identity with any one of the aptamer sequences described in Table 1. In some cases, an anti-VEGF-A aptamer of the disclosure may have at least 90% sequence identity with any one of the aptamer sequences described in Table 1. In some cases, an anti-VEGF-A aptamer of the disclosure may have at least 95% sequence identity with any one of the aptamer sequences described in Table 1.

In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides with a nucleotide sequence described in Table 1.

In such cases where specific nucleotide modifications have been recited, it should be understood that any number and type of nucleotide modifications may be substituted. For example, 2'OMe-G may be substituted for 2'F-G. Non-limiting examples of nucleotide modifications have been provided herein. In some instances, all of the nucleotides of an aptamer are modified. In some instances, at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% of the nucleotides of an aptamer of the disclosure may be modified. In some aspects, an aptamer of the disclosure has the modified nucleotide sequence of any aptamer sequence described in Table 1.

In some cases, an aptamer of the disclosure may have a modified nucleotide sequence. In some cases, an aptamer of the disclosure may have a modified nucleotide sequence as described in Table 1. In some cases, an aptamer of the disclosure may have a primary nucleotide sequence according to any aptamer described in Table 1, and a modified nucleotide sequence that is different than that described in Table 1. In such cases, an aptamer of the disclosure may have a modified nucleotide sequence that shares at least 10% modification identity with any modified nucleotide sequence described in Table 1. For example, an aptamer of the disclosure may have a modified nucleotide sequence that shares at least 10%, at least 15%, at least 20%, at least 25%, at least 300%, at least 35%, at least 40%, at least 45%, at least 50%, at least 55%, at least 60%, at least 65%, at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% modification identity with any modified nucleotide sequence described in Table 1.

In some cases, an aptamer of the disclosure may have a primary nucleotide sequence of any aptamer sequence described in Table 1, and a modified nucleotide sequence in which at least 10% of the C nucleotides are modified (e.g., 2'OMe-C). For example, an aptamer of the disclosure may have a modified nucleotide sequence in which at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% of the C nucleotides are modified (e.g., 2'OMe-C). In some cases, an aptamer of the disclosure may have a modified nucleotide sequence wherein at least 10%, at least 15%, at least 20%, at least 25%, at least 300%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% of the C nucleotides (C) are modified according to Table 1.

In some cases, an aptamer of the disclosure may have a primary nucleotide sequence of any aptamer sequence described in Table 1, and a modified nucleotide sequence in which at least 10% of the A nucleotides are modified (e.g., 2'OMe-A). For example, an aptamer of the disclosure may have a modified nucleotide sequence in which at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% of the A nucleotides are modified (e.g., 2'OMe-A). In some cases, an aptamer of the disclosure may have a modified nucleotide sequence wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% of the A nucleotides are modified according to Table 1.

In some cases, an aptamer of the disclosure may have a primary nucleotide sequence of any aptamer sequence described in Table 1, and a modified nucleotide sequence in which at least 10% of the U nucleotides are modified (e.g., 2'OMe-U). For example, an aptamer of the disclosure may have a modified nucleotide sequence in which at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% of the U nucleotides are modified (e.g., 2'OMe-U). In some cases, an aptamer of the disclosure may have a modified nucleotide sequence wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% of the U nucleotides are modified according to Table 1.

In some cases, an aptamer of the disclosure may have a primary nucleotide sequence of any aptamer sequence described in Table 1, and a modified nucleotide sequence in which at least 10% of the G nucleotides are modified (e.g., 2'F-G, 2'OMe-G). For example, an aptamer of the disclosure may have a modified nucleotide sequence in which at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90° %, at least 95%, at least 99%, or 100% of the G nucleotides are modified (e.g., 2'F-G, 2'OMe-G). In some cases, an aptamer of the disclosure may have a modified nucleotide sequence wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 900%, at least 95%, at least 99%, or 100% of the G nucleotides are modified according to Table 1.

In some cases, an anti-VEGF-A aptamer of the disclosure may comprise a stem-loop secondary structure. In some cases, the aptamers of the disclosure may comprise, in a 5' to 3' direction, a first side of a first base paired stem; optionally, a first loop; a first side of a second base paired stem; a second loop; a second, complementary side of the second base paired stem; a third loop; a first side of a third base paired stem; a fourth loop; a second, complementary side of the third base paired stem; a fifth loop; and a second, complementary side of the first base paired stem.

In some embodiments, each element may be adjacent to each other. For example, the anti-VEGF-A aptamers of the disclosure may comprise, in a 5' to 3' direction, a first side of a first base paired stem. The 3' terminal end of the first side of the first base paired stem may be connected to the 5' terminal end of the first loop. The first loop may be connected at its 5' terminal end to the 3' terminal end of the first side of the first base paired stem, and the first loop may be connected at its 3' terminal end to the 5' terminal end of the first side of the second base paired stem. The first side of the second base paired stem may be connected at its 5' terminal end to the 3' terminal end of the first loop, and the first side of the second base paired stem may be connected at its 3' terminal end to the 5' terminal end of the second loop. The second loop may be connected at its 5' terminal end to the 3' terminal end of the first side of the second base paired stem, and the second loop may be connected at its 3' terminal end to the 5' terminal end of a second, complementary side of the second base paired stem. The second, complementary side of the second base paired stem may be connected at its 5' terminal end to the 3' terminal end of the second loop, and the second, complementary side of the second base paired stem may be connected at its 3' terminal end to the 5' terminal end of a third loop. The third loop may be connected at its 5' terminal end to the 3' terminal end of the second, complementary side of the second base paired stem, and the third loop may be connected at its 3' terminal end to the 5' terminal end of a first side of a third base paired stem. The first side of the third base paired stem may be connected at its 5' terminal end to the 3' terminal end of the third loop, and the first side of the third base paired stem may be connected at its 3' terminal end to the 5' terminal end of the fourth loop. The fourth loop may be connected at its 5' terminal end to the 3' terminal end of the first side of the third base paired stem, and the fourth loop may be connected at its 3' terminal end to the 5' terminal end of the second, complementary side of the third base paired stem. The second, complementary side of the third base paired stem may be connected at its 5' terminal end to the 3' terminal end of the fourth loop, and the second, complementary side of the third based paired stem may be connected at its 3' terminal end to the 5' terminal end of a fifth loop. The fifth loop may be connected at its 5' terminal end to the 3' terminal end of the second, complementary side of the third base paired stem, and the fifth loop may be connected at its 3' terminal end to the 5' terminal end of a second, complementary side of the first base paired stem. The second, complementary side of the first base paired stem may be connected at its 5' terminal end to the 3' terminal end of the fifth loop. In some cases, the anti-VEGF-A aptamers of the disclosure may comprise a terminal stem. In some cases, the terminal stem may be the first base paired stem (e.g., S1/S1'). In some cases, the anti-VEGF-A aptamers of the disclosure may comprise a plurality of terminal loops. In some cases, the terminal loops may include the second loop (e.g., L2) and/or the fourth loop (e.g., L4). In some cases, the anti-VEGF-A aptamers of the disclosure may comprise a plurality of internal stems. In some cases, the internal stems may include the second stem (e.g., S2/S2'), and/or the third stem (e.g., S3/S3'). In some cases, the anti-VEGF-A aptamers of the disclosure may comprise a plurality of internal loops. In some cases, the internal loops may include the first loop (e.g., L1), the third loop (e.g., L3), and/or the fifth loop (e.g., L5).

In a particular aspect, an anti-VEGF-A aptamer of the disclosure may have a stem-loop secondary structure comprising: (i) a first side of Stem 1 (S1); (ii) optionally, Loop 1 (L1) connected to the 3' terminal end of S1 and the 5' terminal end of a first side of Stem 2 (S2); (iii) S2 connected to the 3' terminal end of L1 (or, when L1 is absent, the 3' terminal end of S1) and the 5' terminal end of Loop 2 (L2); (iv) L2 connected to the 3' terminal end of S2 and the 5' terminal end of a second, complementary side of Stem 2 (S2'); (v) S2' connected to the 3' terminal end of L2 and the 5' terminal end of Loop 3 (L3); (vi) L3 connected to the 3' terminal end of S2' and the 5' terminal end of a first side of Stem 3 (S3); (vii) S3 connected to the 3' terminal end of L3 and the 5' terminal end of Loop 4 (L4); (vi) L4 connected to the 3' terminal end of S3 and the 5' terminal end of a second, complementary side of Stem 3 (S3'); (vii) S3' connected to the 3' terminal end of L4 and the 5' terminal end of Loop 5 (L5); (viii) L5 connected to the 3' terminal end of S3' and the 5' terminal end of a second, complementary side of Stem 1 (S1'); and (ix) S1' connected to the 3' terminal end of L5. In particular aspects, an anti-VEGF-A aptamer of the disclosure may have the following stem-loop secondary structure: 5'-S1-L1-S2-L2-S2'-L3-S3-L4-S3'-L5-S1'. In other particular aspects, an anti-VEGF-A aptamer of the disclosure may have the following stem-loop secondary structure: 5'-S1-S2-L2-S2'-L3-S3-L4-S3'-L5-S1'.

In some cases, Stem 1 (S1) may comprise from two to eight contiguous base pairs. For example, S1 may comprise two, three, four, five, six, seven, or eight contiguous base pairs. In some cases, S1 may comprise one or more mismatched nucleotides. For example, S1 may comprise one, two, or three mismatched nucleotides. In some cases, the mismatched nucleotides may be adjacent to each other. In other cases, the mismatched nucleotides may be separated by one, two, or three base pairs. In some cases, the 3' terminal nucleotide of the first side of S1 (e.g., nucleotide position 8), and the 5' terminal nucleotide of the second, complementary side of S1, may form a base pair (e.g., nucleotide position 39). In some cases, this base pair may be C*G. In some cases, the base pair between the 3' terminal nucleotide of the first side of S1, and the 5' terminal nucleotide of the second, complementary side of S1 may be separated from other S1 base pairs by mismatched nucleotides (e.g., at positions 7 and 40). In some cases, S1 may comprise a mismatch at nucleotide positions 5 and 42. In some cases, S1 may be truncated. In some cases, the first side of S1 may comprise a consensus nucleic acid sequence of 5'-HNBYHDCC-3', and the second, complementary side of S1 may comprise a consensus nucleic acid sequence of 5'-GKYNKVNW-3', where H is A, C, or U; N is A, C, G, or U; B is C, G, or U; Y is C or U; D is A, G, or U; K is G or U; V is A, C, or G; and W is A or U. In some cases, the first side of S1 may comprise a consensus nucleic acid sequence of 5'-HNBYHDNN-3', and the second, complementary side of S1 may comprise a consensus nucleic acid sequence of 5'-NNYNKVNW-3', where H is A, C, or U; N is A, C, G, or U; B is C, G, or U; Y is C or U; and D is A, G, or U.

In some cases, L1 may be optional. In cases in which L1 is present, L1 may comprise one nucleotide. In some cases, when L1 is present, L1 has a nucleic acid sequence of 5'-U-3'. In some cases, when L1 is present, L1 has a nucleic acid sequence of 5'-A-3'. In some cases, when L1 is present, L1 has a nucleic acid sequence of 5'-C-3'. In some cases, when L1 is present, L1 has a nucleic acid sequence of 5'-G-3'. In some cases, L1 may comprise a single non-nucleotidyl spacer 3 modification (e.g., 1,3-propanediol). In some cases, L1 may comprise two non-nucleotidyl spacer 3 modifications. In some cases, L1 may comprise a 6-carbon spacer (e.g., 1,6-hexanediol). In some cases, L1 may comprise a 9-carbon spacer (e.g., triethyleneglycol).

In some cases, S2 may comprise two base pairs. In some cases, S2 may comprise more than one base pair. In some cases, S2 may comprise less than three base pairs. In some cases, a first side of S2 may comprise a consensus nucleic acid sequence of 5'-CC-3', and a second, complementary side of S2 may comprise a consensus nucleic acid sequence of 5'-GG-3'. In some cases, the first side of S2 may comprise a consensus nucleic acid sequence of 5'-NN-3', and the second, complementary side of S2 may comprise a consensus nucleic acid sequence of 5'-NN-3', where N is A, C, G, or U.

In some cases, L2 may comprise four nucleotides. In some cases, L2 may have more than three nucleotides. In some cases, L2 may have less than five nucleotides. In some cases, L2 may comprise a consensus nucleic acid sequence of 5'-GCGC-3'. In some cases, L2 may comprise a consensus nucleic acid sequence of 5'-GYGC-3', where Y is C or U. In some cases, L2 may comprise a consensus nucleic acid sequence of 5'-KNGC-3', where K is G or U; and N is A, C, G, or U.

In some cases, S3 may comprise from four to six base pairs. For example, S3 may comprise four base pairs, five base pairs, or six base pairs. In some cases, S3 may comprise less than seven base pairs. In some cases, S3 may comprise more than three base pairs. In some cases, when S3 comprises six base pairs, a first side of S3 may be seven nucleotides in length. In such cases, the 3' terminal nucleotide of the first side of S3 may form a single mismatch. In some cases, the length of S3 may be directly related to the length of L4. In some cases, when S3 is four base pairs in length, L4 is eight nucleotides in length. In some cases, when S3 is four base pairs in length, L4 is six nucleotides in length. In some cases, when S3 is five base pairs in length, L4 is six nucleotides in length. In some cases, when S3 is five base pairs in length, L4 is four nucleotides in length. In some cases, when S3 is six base pairs in length, L4 is four nucleotides in length. In some cases, when S3 comprises six base pairs and a single mismatched nucleotide, L4 is three nucleotides in length. In some cases, a first side of S3 may comprise a consensus nucleic acid sequence of 5'-GRGRWN-3', and the second, complementary side of S3 may comprise a consensus nucleic acid sequence of 5'-NHYCYC-3', where R is A or G; N is A, C, G, or U; W is A or U; and Y is C or U. In some cases, a first side of S3 may comprise a consensus nucleic acid sequence of 5'-GGGRUN3', and the second, complementary side of S3 may comprise a consensus nucleic acid sequence of 5'-NWYCCC-3', where R is A or G; N is A, C, G, or U; W is A or U; and Y is C or U. In some cases, a first side of S3 may comprise a consensus nucleic acid sequence of 5'-GGGRUN3', and the second, complementary side of S3 may comprise a consensus nucleic acid sequence of 5'-NAYCCC-3', where R is A or G; N is A, C, G, or U; and Y is C or U. In some cases, a first side of S3 comprises a consensus nucleic acid sequence of 5'-GGGRUD-3', and a second, complementary side of S3 comprises a consensus nucleic acid sequence of 5'-HWYCCC-3', wherein R is A or G; D is A, G, or U; H is A, C, or U; W is A or U; and Y is C or U. In some cases, when S3 is four base pairs in length, the first side of S3 may comprise a consensus nucleic acid sequence of 5'-GKGN-3', and the second, complementary side of S3 may comprise a consensus nucleic acid sequence of 5'-NSMC-3', where K is G or U; N is A, C, G or U and M is A or C. In some cases, when S3 is four base pairs in length, the first side of S3 may comprise a consensus nucleic acid sequence of 5'-GGGG-3', and the second, complementary side of S3 may comprise a consensus nucleic acid sequence of 5'-CCCC-3'. In some cases, when S3 is four base pairs in length, the first side of S3 may comprise a consensus nucleic acid sequence of 5'-GGGU-3', and the second, complementary side of S3 may comprise a consensus nucleic acid sequence of 5'-ACCC-3'. In some cases, when S3 is four base pairs in length, the first side of S3 may comprise a consensus nucleic acid sequence of 5'-GGCU-3', and the second, complementary side of S3 may comprise a consensus nucleic acid sequence of 5'-AGCC-3'. In some cases, when S3 is five base pairs in length, the first side of S3 may comprise a consensus nucleic acid sequence of 5'-GBBNY-3', and the second, complementary side of S3 may comprise a consensus nucleic acid sequence of 5'-RNBNC-3', where R is A or G; and Y is C or U. In some cases, when S3 is five base pairs in length, the first side of S3 may comprise a consensus nucleic acid sequence of 5'-GGGRU-3', and the second, complementary side of S3 may comprise a consensus nucleic acid sequence of 5'-AYCCC-3', where R is A or G; and Y is C or U. In some cases, when S3 is five base pairs in length, the first side of S3 may comprise a consensus nucleic acid sequence of 5'-SVVVK-, and the second, complementary side of S3 may comprise a consensus nucleic acid sequence of 5'-MBBBS-3', where S is G or C; V is A, C, or G: K is G or U; M is A or C; and B is C, G, or U. In some cases, when S3 is six base pairs in length, the first side of S3 may comprise a consensus nucleic acid sequence of 5'-GGGGUD-3', and the second, complementary side of S3 may comprise a consensus nucleic acid sequence of 5'-HAUCCC-3', where D is A, G, or U; and H is A, C, or U. In some cases, when S3 comprises six base pairs and a single mis-matched nucleotide, the first side of S3 may comprise a consensus nucleic acid sequence of 5'-GGGRUUR-3', and the second, complementary side of S3 may comprise a consensus nucleic acid sequence of 5'-UAUCCC-3', where the underlined U is the single mis-matched nucleotide, and R is A or G.

In some cases, L3 may comprise one nucleotide. In some cases, L3 may comprise less than two nucleotides. In some cases, L3 may comprise a consensus nucleic acid sequence of 5'-A-3'. In some cases, L3 may comprise a consensus nucleic acid sequence of 5'-W-3', where W is A or U.

In some cases, L4 may comprise eight, six, four, or three nucleotides. In some cases, the variation between the number of nucleotides in loop L4 may directly relate to the variation in the length of S3 (e.g., as described above). In some cases, when L4 is three nucleotides in length, L4 may comprise a consensus nucleic acid sequence of 5'-MAU-3', where M is A or C. In some cases, when L4 is three nucleotides in length, L4 may comprise a consensus nucleic acid sequence of 5'-CUA-3'. In some cases, when L4 is four nucleotides in length, L4 may comprise a consensus nucleic acid sequence of 5'-DNAH-3', where D is A, G, or U; N is A, C, G, or U; and H is A, C, or U. In some cases, when L4 is four nucleotides in length, L4 may comprise a consensus nucleic acid sequence of 5'-DNDH-3', where D is A, G, or U; N is A, C, G, or U; and H is A, C, or U. In some cases, when L4 is four nucleotides in length, L4 may comprise a consensus nucleic acid sequence of 5'-DNDN-3', where D is A, G, or U; N is A, C, G, or U; and N is A, C, G or U. In some cases, when L4 is six nucleotides in length, L4 may comprise a consensus nucleic acid sequence of 5'-UDNDHU-3', where D is A, G, or U; N is A, C, G, or U; and H is A, C, or U. In some cases, the L4 comprises a consensus nucleic acid sequence of 5'-UDRGBU-3', where D is A, G, or U; R is A or G, N is A, C, G, or U; and B is G, C, or U. In some cases, the L4 comprises a consensus nucleic acid sequence of 5'-KNNNNW-3', where K is U or G, N is A, C, G, or U; and W is A, or U. In some cases, the L4 comprises a consensus nucleic acid sequence of 5'-UDUHRKYU-3', where D is A D, or U; H is A, C or U; R is A or G; K is G or U and Y is C or U. In some cases, when L4 is eight nucleotides in length, L4 may comprise a consensus nucleic acid sequence of 5'-UUUCAUUU-3'.

In some cases, L5 may comprise four nucleotides. In some cases, L5 may comprise less than five nucleotides. In some cases, L5 may comprise more than three nucleotides. In some cases, L5 may comprise a consensus nucleic acid sequence of 5'-GYUU-3', where Y is C or U.

In some cases, L5 may comprise a consensus nucleic acid sequence of GNNN-3', where N is A, C, G, or U. In some cases, L5 may comprise a consensus nucleic acid sequence of 5'-GNHW-3', where N is A, C, G, or U; H is A, C, or U; and W is A or U.

In some cases, an anti-VEGF-A aptamer of the disclosure may comprise a consensus nucleic acid sequence of 5'-HNBYHDCCUCCGCGCGGAGG-GRUDDNDHHWYCCCGYUUGKYNKVNW-3' (SEQ ID NO: 1), where H is A, C, or U; N is A, C, G, or U; B is C, G, or U; Y is C or U; D is A, G, or U; R is A or G; W is A or U; K is G or U; and V is A, C, or G. In some cases, when S3 is five base pairs in length and L4 is six nucleotides in length, an anti-VEGF-A aptamer of the disclosure may comprise a consensus nucleic acid sequence of 5'-HNBYHDCCUCCGCGCGGAGGGRU-UDNDHUAYCCCGYUUGKYNKVNW-3' (SEQ ID NO: 2), where H is A, C, or U; N is A, C, G, or U; B is C, G, or U; Y is C or U; D is A, G, or U; R is A or G; K is G or U; V is A, C, or G; and W is A or U. In some cases, when S3 is six base pairs in length and L4 is 4 nucleotides in length, an anti-VEGF-A aptamer of the disclosure may comprise a consensus nucleic acid sequence of 5'-WNKYHDC-CUCCGCGCGGAGGGGUDDNAHHAUCCCGUUUG-GYBKMHW-3' (SEQ ID NO: 3), where W is A or U; N is A, C, G, or U; K is G or U; Y is C or U; H is A, C, or U; D is A, G, or U; B is C, G, or U; and M is A or C. In some cases, when S3 is four base pairs in length and L4 is eight nucleotides in length, an anti-VEGF-A aptamer of the disclosure may comprise a consensus nucleic acid sequence of 5'-AUGCCGCCUCCGCGCGGAGGGGUUU-CAUUUCCCCGUUUGGCUGCAU-3' (SEQ ID NO: 4). In some cases, an anti-VEGF-A aptamer of the disclosure comprises a consensus nucleic acid sequence of 5'-HNBYHDCCUCCGCGCG-GAGDSBHDNNNNHNNBNCGYUUGKYNKVNW-3' (SEQ ID NO: 436), where H is A, C, or U; N is A, C, G, or U; B is C, G, or U; Y is C or U; D is A, G, or U; R is A or G; W is A or U; K is G or U; and V is A, C, or G.

In some cases, an anti-VEGF-A aptamer of the disclosure comprises a consensus nucleic acid sequence of 5'-HNBYHDCCUCCGCGCG-GAGKBHYDNNNKDBVCGYUUGKYNKVNW-3' (SEQ ID NO: 437), where H is A, C, or U; N is A, C, G, or U; B is C, G, or U; Y is C or U; D is A, G, or U; R is A or G; W is A or U; K is G or U; and V is A, C, or G. In some cases, an anti-VEGF-A aptamer of the disclosure comprises a consensus nucleic acid sequence of 5'-HNBYHDC-CUCCGCGCGGAGK-SHUDRGBUDSMCGYUUGKYNKVNW-3' (SEQ ID NO: 438), where H is A, C, or U; N is A, C, G, or U; B is C, G, or U; Y is C or U; D is A, G, or U; R is A or G; W is A or U; K is G or U; M is A or C; and V is A, C, or G.

In some cases, an anti-VEGF-A aptamer of the disclosure may comprise a consensus nucleic acid sequence of 5'-HNBYHDNNN*NNKNGCNNWGGGRUNDNDH-NWYCCCGNNNNNYNKVNW-3' (SEQ ID NO: 5), where H is A, C, or U; N is A, C, G, or U; B is C, G, or U; Y is C or U; N* is A, C, G, U, can be deleted entirely, or is a non-nucleotidyl spacer 3 modification, a 6 carbon alkyl linker (1,6-hexanediol), or a spacer 9 (triethyleneglycol) modification; D is A, G, or U; K is G or U; W is A or U; R is A or G; and V is A, C, or G Anti-VEGF-A Compositions In some aspects, the disclosure provides anti-VEGF-A compositions that inhibit a function associated with VEGF-A. The anti-VEGF-A compositions may include one or more anti-VEGF-A aptamers that bind to specific regions of VEGF-A with high specificity and high affinity. In some cases, the anti-VEGF-A compositions may include one or more anti-VEGF-A aptamers that bind to a region of VEGF-A that includes the receptor binding face of VEGF-A.

In some cases, the anti-VEGF-A compositions may include one or more anti-VEGF-A aptamers that bind to a region of VEGF-A which includes the receptor binding domain of VEGF-A, or a portion thereof. The receptor binding domain of VEGF-A may include any one or more of residues 1-109 as described in SEQ ID NOs: 6-10. In some cases, the anti-VEGF-A compositions may include one or more anti-VEGF-A aptamers that prevent or reduce binding of one or more isoforms or variants of VEGF-A with Flt-1, KDR, Nrp-1, or any combination thereof.

Anti-VEGF-A Aptamers

In some aspects, anti-VEGF-A aptamers of the disclosure may block or reduce the interaction of VEGF-A with Flt-1, may block or reduce the interaction of VEGF-A with KDR, may block or reduce the interaction of VEGF-A with Nrp-1, or any combination thereof.

In some aspects, anti-VEGF-A aptamers of the disclosure bind to structural features that are common to VEGF-$A_{110}$, VEGF-$A_{121}$, VEGF-$A_{165}$, VEGF-$A_{189}$, and VEGF-$A_{206}$. In some cases, anti-VEGF-A aptamers of the disclosure bind to regions of VEGF-A other than the heparin binding domain present in VEGF-$A_{165}$, VEGF-$A_{189}$, and VEGF-$A_{206}$. The heparin binding domain may include residues 111-165 as described by SEQ ID NOs: 6-8. Without wishing to be bound by theory, the cationic heparin binding domain of VEGF-A is thought to be the dominant epitope for aptamer recognition due to the anionic nature of the oligonucleotide sugar phosphate backbone. Therefore, selection of aptamers to regions of VEGF-A other than the heparin binding domain have proven difficult. For example, pegaptanib (brand name Macugen®) is an oligonucleotide inhibitor of VEGF-A which binds to the heparin binding domain. Because VEGF-$A_{121}$ and VEGF-$A_{110}$ lack the heparin binding domain, pegaptanib does not bind to or inhibit VEGF-$A_{121}$ and VEGF-$A_{110}$, thereby providing inferior VEGF-A suppression as compared to an inhibitor that binds to the receptor binding domain of VEGF-A.

Similarly, additional aptamer inhibitors of VEGF-A have been described which bind to the heparin binding domain of VEGF-A. For example, a DNA aptamer specific for VEGF-$A_{165}$, but not VEGF-$A_{121}$ has been described (Hasegawa, Hijiri, Koji Sode, and Kazunori Ikebukuro. "Selection of DNA aptamers against VEGF165 using a protein competitor and the aptamer blotting method." Biotechnology letters 30.5 (2008): 829-834; Kaur, Harleen, and Lin-Yue Lanry Yung. "Probing high affinity sequences of DNA aptamer against VEGF165." PLoS One 7.2 (2012): e31196.). Additionally, a 2'-O-Methyl aptamer has been described that binds to VEGF-$A_{165}$, but not VEGF-$A_{121}$ (Burmeister, Paula E., et al. "Direct in vitro selection of a 2'-O-methyl aptamer to VEGF." Chemistry & biology 12.1 (2005): 25-33.). Similarly, DNA aptamers with an expanded 6-base nucleotide alphabet have been described that recognize VEGF-$A_{165}$, but not VEGF-$A_{121}$ (Kimoto, Michiko, et al. "Generation of high-affinity DNA aptamers using an expanded genetic alphabet." Nature biotechnology 31.5 (2013): 453.). Furthermore, aptamer selections against other proteins that contain heparin binding domains tend to generate aptamers to those epitopes. For example, RNA aptamers that bind to the heparin binding domain have been described for thrombin (Jeter, Martha L., et al. "RNA aptamer to thrombin binds anion□ binding exosite□2 and alters protease inhibition by heparin□binding serpins." FEBS letters 568.1-3 (2004): 10-14; Long, Stephen B., et al. "Crystal structure of an RNA aptamer bound to thrombin." RNA (2008)), basic fibroblast growth factor (Jellinek, D., et al. "High-affinity RNA ligands to basic fibroblast growth factor inhibit receptor binding." Proceedings of the National Academy of Sciences 90.23 (1993): 11227-11231.), interleukin-8 (Sung, Ho Jin, et al. "Inhibition of human neutrophil activity by an RNA aptamer bound to interleukin-8." Biomaterials 35.1 (2014): 578-589.), and *Plasmodium falciparum* erythrocyte membrane protein 1 (Barfod, Anders, Tina Persson, and Johan Lindh. "In vitro selection of RNA aptamers against a conserved region of the *Plasmodium falciparum* erythrocyte membrane protein 1." Parasitology research 105.6 (2009): 1557-1566.).

In some cases, anti-VEGF-A aptamers of the disclosure may bind to a region of VEGF-A that includes the receptor-binding face of any isoform or variant of VEGF-A, or portions thereof. The receptor-binding face of VEGF-A may include strands β2, β5, and β6, and loops β1 to β2 of one monomer, and the N-terminal a helix and loop β3 to β4 of a second monomer. The receptor-binding face of VEGF-A may be as described by Muller et al. "The crystal structure of vascular endothelial growth factor (VEGF) refined to 1.93 Å resolution: multiple copy flexibility and receptor binding." Structure 5.10 (1997): 1325-1338. In some cases, anti-VEGF-A aptamers of the disclosure may bind to one or more amino acid residues of any isoform or variant of VEGF-A, including, without limitation, Phe17, Ile43, Ile46, Glu64, Gln79, Ile83, Lys84, Pro85, Arg82, His86, Asp63, and Glu67 as described by SEQ ID NOs: 6-10. In some cases, anti-VEGF-A aptamers that bind to the receptor-binding face of VEGF-A, or a portion thereof, may prevent or reduce the association of VEGF-A with one or more of Flt-1, KDR, or Nrp-1. In some cases, anti-VEGF-A aptamers that bind to the receptor-binding face of VEGF-A, or a portion thereof, may interact with recombinant bead-bound VEGF-$A_{165}$, VEGF-$A_{121}$, or VEGF-$A_{110}$ as measured by flow cytometry or may interact with recombinant surface-bound VEGF-$A_{165}$, VEGF-$A_{121}$, or VEGF-$A_{110}$ as measured by surface plasmon resonance (see Examples 1 and 2, respectively). In some cases, anti-VEGF-A aptamers that bind to the receptor-binding face of VEGF-A, or a portion thereof, may inhibit or reduce the interaction of VEGF-$A_{165}$, VEGF-$A_{121}$, or VEGF-$A_{110}$ with KDR as measured by a reduction in FRET signal (see Example 3). In some cases, anti-VEGF-A aptamers that bind to the receptor-binding face of VEGF-A, or a portion thereof, may inhibit or reduce VEGF-$A_{165}$, VEGF-$A_{121}$, or VEGF-$A_{110}$ induced trans autophosphorylation of the intracellular domain of KDR as measured by phospho-KDR AlphaLISA® (see Example 4). In some cases, anti-VEGF-A aptamers that bind to the receptor-binding face of VEGF-A, or a portion thereof, may inhibit or reduce VEGF-$A_{165}$, VEGF-$A_{121}$, or VEGF-$A_{110}$ induced gene expression of tissue factor in HUVEC cells as measured by qPCR. In some cases, anti-VEGF-A aptamers that bind to the receptor-binding face of VEGF-A, or a portion thereof, may inhibit or reduce VEGF-$A_{165}$, VEGF-$A_{121}$, or VEGF-$A_{110}$ induced tube formation of GFP-HU- VECs in co-culture with human dermal fibroblasts cells as measured by change in network length or network area (see Example 5). In some cases, anti-VEGF-A aptamers that bind to the receptor-binding face of VEGF-A, or a portion thereof, may inhibit or reduce vascular leakage in a mouse, rat, rabbit, or primate eye following exogenous VEGF-$A_{165}$, VEGF-$A_{121}$, or VEGF-$A_{110}$ challenge as measured by fluorescein angiography and Evans-blue albumin staining.

In some cases, anti-VEGF-A aptamers of the disclosure may bind to a region of VEGF-A that includes the receptor binding domain of any isoform or variant of VEGF-A, or portions thereof. The receptor binding domain of VEGF-A may include one or more of residues 1-109, as described in SEQ ID NOs: 6-10. In some cases, anti-VEGF-A aptamers of the disclosure may bind to one or more amino acid residues of any isoform or variant of VEGF-A, including, without limitation, Phe17, Tyr21, Tyr25, Ile43, Ile46, Ile83, Asp63, Glu64, Pro85, and His86, as described by SEQ ID NOs: 6-10. In some cases, anti-VEGF-A aptamers of the disclosure may bind to a region within the receptor binding domain of VEGF-A which results in global conformational changes in VEGF-A such that it no longer binds to and activates signaling via KDR. In some cases, anti-VEGF-A aptamers that bind to the receptor binding domain of VEGF-A, or a portion thereof, may prevent or reduce the association of VEGF-A with one or more of Flt-1, KDR, and Nrp-1. In some cases, anti-VEGF-A aptamers that bind to the receptor binding domain of VEGF-A, or a portion thereof, may interact with recombinant bead-bound VEGF-$A_{165}$, VEGF-$A_{121}$, or VEGF-$A_{110}$ as measured by flow cytometry or may interact with recombinant surface-bound VEGF-$A_{165}$, VEGF-$A_{121}$, or VEGF-$A_{110}$ as measured by surface plasmon resonance (see Examples 1 and 2, respectively). In some cases, anti-VEGF-A aptamers that bind to the receptor-binding domain of VEGF-A, or a portion thereof, may inhibit or reduce the interaction of VEGF-$A_{165}$, VEGF-$A_{121}$, or VEGF-$A_{110}$ with KDR as measured by a reduction in FRET signal (see Example 3). In some cases, anti-VEGF-A aptamers that bind to the receptor-binding domain of VEGF-A, or a portion thereof, may inhibit or reduce VEGF-$A_{165}$, VEGF-$A_{121}$, or VEGF-$A_{110}$ induced trans autophosphorylation of the intracellular domain of KDR as measured by phospho-KDR AlphaLISA® (see Example 4). In some cases, anti-VEGF-A aptamers that bind to the receptor binding domain of VEGF-A, or a portion thereof, may inhibit or reduce VEGF-$A_{165}$, VEGF-$A_{121}$, or VEGF-$A_{110}$ induced gene expression of tissue factor in HUVEC cells as measured by qPCR. In some cases, anti-VEGF-A aptamers that bind to the receptor binding domain of VEGF-A, or a portion thereof, may inhibit or reduce VEGF-$A_{165}$, VEGF-$A_{121}$, or VEGF-$A_{110}$ induced tube formation of GFP-HUVECs in co-culture with human dermal fibroblasts cells as measured by change in network length or network area (see Example 5). In some cases, anti-VEGF-A aptamers that bind to the receptor binding domain of VEGF-A, or a portion thereof, may inhibit or reduce vascular leakage in a mouse, rat, rabbit, or primate eye following exogenous VEGF-$A_{165}$, VEGF-$A_{121}$, or VEGF-$A_{110}$ challenge as measured by fluorescein angiography and Evans-blue albumin staining.

Binding Affinity

The dissociation constant ($K_d$) can be used to describe the affinity of an aptamer for a target (or to describe how tightly the aptamer binds to the target) or to describe the affinity of an aptamer for a specific epitope of a target. The dissociation constant may be defined as the molar concentration at which half of the binding sites of a target are occupied by the aptamer. Thus, the smaller the $K_d$, the tighter the binding of the aptamer to its target. In some cases, an anti-VEGF-A aptamer of the disclosure may have a $K_d$ for one or more isoforms or variants of VEGF-A of less than about 1000 nM, for example, less than about 500 nM, less than about 100 nM, less than about 50 nM, less than about 10 nM, less than about 5 nM, less than about 1 nM, less than about 0.5 nM, or less than about 0.1 nM, as measured by a surface plasmon resonance assay (see Example 2). In some cases, an anti-VEGF-A aptamer may have a dissociation constant ($K_d$) for one or more isoforms or variants of VEGF-A of less than about 50 nM, as measured by a surface plasmon resonance assay (see Example 2). In some cases, an anti-VEGF-A aptamer may have a dissociation constant ($K_d$) for one or more isoforms or variants of VEGF-A of less than about 25 nM, as measured by a surface plasmon resonance assay (see Example 2). In some cases, an anti-VEGF-A aptamer may have a dissociation constant ($K_d$) for one or more isoforms or variants VEGF-A of less than about 10 nM, as measured by a surface plasmon resonance assay (see Example 2). In some cases, an anti-VEGF-A aptamer may have a dissociation constant ($K_d$) for one or more isoforms or variants of VEGF-A of less than about 5 nM, as measured by a surface plasmon resonance assay (see Example 2). In some cases, an anti-VEGF-A aptamer may have a dissociation constant ($K_d$) for one or more isoforms or variants of VEGF-A of less than about 1 nM, as measured by a surface plasmon resonance assay (see Example 2). In some cases, an anti-VEGF-A aptamer may have a dissociation constant ($K_d$) for one or more isoforms or variants of VEGF-A of less than about 0.5 nM, as measured by a surface plasmon resonance assay (see Example 2). In some cases, an anti-VEGF-A aptamer may have a dissociation constant ($K_d$) for one or more isoforms or variants of VEGF-A of less than about 0.1 nM, as measured by a surface plasmon resonance assay (see Example 2). In some cases, the aptamer may be a pan-variant specific aptamer that binds to each of VEGF-$A_{110}$, VEGF-$A_{121}$, VEGF-$A_{165}$, VEGF-A is, and VEGF-$A_{206}$ with a $K_d$ of less than about 1000 nM, for example, less than about 500 nM, less than about 100 nM, less than about 50 nM, less than about 25 nM, less than about 10 nM, less than about 5 nM, less than about 1 nM, less than about 0.5 nM, or less than about 0.1 nM, as measured by a surface plasmon resonance assay (see Example 2). In some cases, the aptamer may bind to any region of VEGF-A described herein, or a portion thereof, with a $K_d$ of less than about 1000 nM, for example, less than about 500 nM, less than about 100 nM, less than about 50 nM, less than about 25 nM, less than about 10 nM, less than about 5 nM, less than about 1 nM, less than about 0.5 nM, or less than about 0.1 nM, as measured by a surface plasmon resonance assay (see Example 2). In some cases, the aptamer may bind to the receptor-binding face or the receptor binding domain of VEGF-A, or portions thereof, with a $K_d$ of less than about 1000 nM, for example, less than about 500 nM, less than about 100 nM, less than about 50 nM, less than about 25 nM, less than about 10 nM, less than about 5 nM, less than about 1 nM, less than about 0.5 nM, or less than about 0.1 nM, as measured by a surface plasmon assay (see Example 2). In some cases, the anti-VEGF-A aptamer may bind to the receptor-binding face or the receptor binding domain of VEGF-A, or portions thereof, with a $K_d$ from about 0.5 nM to about 25 nM, as measured by a surface plasmon resonance assay (see Example 2).

In some cases, the aptamers disclosed herein may bind to a region of VEGF-A, such as the receptor-binding face of VEGF-A, or the receptor binding domain of VEGF-A, or portions thereof, with a $K_d$ of less than about 50 nM as measured by a surface plasmon assay (see Example 2), and may have an $IC_{50}$ of less than about 50 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 50 nM as measured by a surface plasmon resonance assay (see Example 2), and may have an $IC_{50}$ of less than about 10 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 50 nM as measured by a surface plasmon resonance assay (see Example 2), and may have an $IC_{50}$ of less than about 5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 50 nM as measured by a surface plasmon resonance assay (see Example 2), and may have an $IC_{50}$ of less than about 1 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 50 nM as measured by a surface plasmon resonance assay (see Example 2), and may have an $IC_{50}$ of less than about 0.5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 50 nM as measured by a surface plasmon resonance assay (see Example 2), and may have an $IC_{50}$ of less than about 0.1 nM as measured by a VEGF-A:KDR competition binding assay (see Example 3), a KDR phosphorylation AlphaLISA® assay (see Example 4), or an in vitro model of VEGF-A-induced angiogenesis (see Example 5).

In some cases, the aptamers disclosed herein may bind to a region of VEGF-A, such as the receptor binding face of VEGF-A, or the receptor binding domain of VEGF-A, or portions thereof, with a $K_d$ of less than about 10 nM as measured by a surface plasmon resonance assay (see Example 2), and may have an $IC_{50}$ of less than about 50 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 10 nM as measured by a surface plasmon resonance assay (see Example 2), and may have an $IC_{50}$ of less than about 10 nM as measured by a VEGF-A:KDR competition binding assay (see Example 3), a KDR phosphorylation AlphaLISA® assay (see Example 4), or an in vitro model of VEGF-A-induced angiogenesis (see, Example 5). In some cases, the aptamers disclosed herein may bind to a region of VEGF-A, such as the receptor binding face of VEGF-A, or the receptor binding domain of VEGF-A, or portions thereof, with a $K_d$ of less than about 10 nM as measured by a surface plasmon resonance assay (see Example 2), and may have an $IC_{50}$ of less than about 5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 10 nM as measured by a surface plasmon resonance assay (see Example 2), and may have an $IC_{50}$ of less than about 1 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 10 nM as measured by a surface plasmon resonance assay (see Example 2), and may have an $IC_{50}$ of less than about 0.5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a K of less than about 10 nM as measured by a surface plasmon resonance assay (see Example 2), and may have an $IC_{50}$ of less than about 0.1 nM as measured by a VEGF-A:KDR competition binding assay (see Example 3), a KDR phosphorylation AlphaLISA® assay (see Example 4), or an in vitro model of VEGF-A-induced angiogenesis (see Example 5).

In some cases, the aptamers disclosed herein may bind to a region of VEGF-A, such as the receptor binding face of VEGF-A, or the receptor binding domain of VEGF-A, or portions thereof, with a $K_d$ of less than about 5 nM as measured by a surface plasmon resonance assay (see Example 2), and may have an $IC_{50}$ of less than about 50 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 5 nM as measured by a surface plasmon resonance assay (see Example 2), and may have an $IC_{50}$ of less than about 10 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 5 nM as measured by a surface plasmon resonance assay (see Example 2), and may have an $IC_{50}$ of less than about 5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 5 nM as measured by a surface plasmon resonance assay (see Example 2), and may have an $IC_{50}$ of less than about 1 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 5 nM as measured by a surface plasmon resonance assay (see Example 2), and may have an $IC_{50}$ of less than about 0.5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 5 nM as measured by a surface plasmon resonance assay (see Example 2), and may have an $IC_{50}$ of less than about 0.1 nM as measured by a VEGF-A:KDR competition binding assay (see Example 3), a KDR phosphorylation AlphaLISA® assay (see Example 4), or an in vitro model of VEGF-A-induced angiogenesis (see Example 5).

In some cases, the aptamers disclosed herein may bind to a region of VEGF-A, such as the receptor binding face of VEGF-A, or the receptor binding domain of VEGF-A, or portions thereof, with a $K_d$ of less than about 1 nM as measured by a surface plasmon resonance assay (see Example 2), and may have an $IC_{50}$ of less than about 50 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 1 nM as measured by a surface plasmon resonance assay (see Example 2), and may have an $IC_{50}$ of less than about 10 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 1 nM as measured by a surface plasmon resonance assay (see Example 2), and may have an $IC_{50}$ of less than about 5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 1 nM as measured by a surface plasmon resonance assay (see Example 2), and may have an $IC_{50}$ of less than about 1 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 1 nM as measured by a surface plasmon resonance assay (see Example 2), and may have an $IC_{50}$ of less than about 0.5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 1 nM as measured by a surface plasmon resonance assay (see Example 2), and may have an $IC_{50}$ of less than about 0.1 nM as measured by a VEGF-A:KDR competition binding assay (see Example 3), a KDR phosphorylation AlphaLISA® assay (see Example 4), or an in vitro model of VEGF-A-induced angiogenesis (see Example 5).

In some cases, the aptamers disclosed herein may bind to a region of VEGF-A, such as the receptor binding face of VEGF-A, or the receptor binding domain of VEGF-A, or portions thereof, with a $K_d$ of less than about 0.5 nM as measured by a surface plasmon resonance assay (see Example 2), and may have an $IC_{50}$ of less than about 50 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.5 nM as measured by a surface plasmon resonance assay (see Example 2), and may have an $IC_{50}$ of less than about 10 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.5 nM as measured by a surface plasmon resonance assay (see Example 2), and may have an $IC_{50}$ of less than about 5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.5 nM as measured by a surface plasmon resonance assay (see Example 2), and may have an $IC_{50}$ of less than about 1 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as receptor binding face of VEGF-A, or the receptor binding domain of VEGF-A, or portions thereof, with a $K_d$ of less than about 0.5 nM as measured by a surface plasmon resonance assay (see Example 2), and may have an $IC_{50}$ of less than about 0.5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.5 nM as measured by a surface plasmon resonance assay (see Example 2), and may have an $IC_{50}$ of less than about 0.1 nM as measured by a VEGF-A:KDR competition binding assay (see Example 3), a KDR phosphorylation AlphaLISA® assay (see Example 4), or an in vitro model of VEGF-A-induced angiogenesis (see Example 5).

In some cases, the aptamers disclosed herein may bind to a region of VEGF-A, such as the receptor binding face of VEGF-A, or the receptor binding domain of VEGF-A, or portions thereof, with a $K_d$ of less than about 0.1 nM as measured by a surface plasmon resonance assay (see Example 2), and may have an $IC_{50}$ of less than about 50 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.1 nM as measured by a surface plasmon resonance assay (see Example 2), and may have an $IC_{50}$ of less than about 10 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.1 nM as measured by a surface plasmon resonance assay (see Example 2), and may have an $IC_{50}$ of less than about 5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.1 nM as measured by a surface plasmon resonance assay (see Example 2), and may have an $IC_{50}$ of less than about 1 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.1 nM as measured by a surface plasmon resonance assay (see Example 2), and may have an $IC_{50}$ of less than about 0.5 nM as measured by a VEGF-A:KDR competition binding assay (see Example 3), a KDR phosphorylation AlphaLISA® assay (see Example 4), or an in vitro model of VEGF-A-induced angiogenesis (see Example 5). In some cases, the aptamers disclosed herein may bind to a region of VEGF-A, such as the receptor binding face of VEGF-A, or the receptor binding domain of VEGF-A, or portions thereof, with a $K_d$ of less than about 0.1 nM as measured by a surface plasmon resonance assay (see Example 2), and may have an $IC_{50}$ of less than about 0.1 nM as measured by a VEGF-A:KDR competition binding assay (see Example 3), a KDR phosphorylation AlphaLISA® assay (see Example 4), or an in vitro model of VEGF-A-induced angiogenesis (see Example 5).

In some aspects, the aptamers disclosed herein may have an improved half-life as compared to other therapeutics, including antibodies. In some cases, the aptamers may have an improved half-life in a biological fluid or solution as compared to an antibody. In some cases, the aptamers may have an improved half-life in vivo as compared to an antibody. In one example, the aptamers may have an improved half-life when injected into the eye (intraocular half-life) as compared to an antibody. In some cases, the aptamers may have an improved intraocular half-life when injected into the eye of a human. In some cases, the aptamers may demonstrate improved stability over antibodies under physiological conditions.

In some cases, the aptamers described herein may have an intraocular half-life of at least 7 days in a human. In some cases, the aptamers described herein may have an intraocular half-life of at least 8 days, at least 9 days, at least 10 days, at least 11 days, at least 12 days, at least 13 days, at least 14 days, at least 15 days, at least 20 days or greater in a human.

In some cases, the aptamers described herein may have an intraocular half-life of at least 1 day in a non-human animal (e.g., rodent/rabbit/monkey/chimpanzee/pig). In some cases, the aptamers described herein may have an intraocular half-life of at least 1 day, at least 2 days, at least 3 days, at least 4 days, at least 5 days, at least 6 days, at least 7 days, at least 8 days, at least 9 days, at least 10 days or greater in a non-human animal such as a rodent, rabbit or monkey.

In some aspects, the aptamers described herein may have a shorter half-life as compared to other therapeutics. For example, an unmodified or unconjugated aptamer may have a lower half-life as compared to a modified or conjugated aptamer, however, the low molecular weight of the unmodified or unconjugated forms may allow for orders of magnitude greater initial concentrations, thereby achieving greater duration/efficacy. In some examples, the aptamer may have an intraocular half-life of less than about 7 days in a human. In some examples, the aptamers described herein may have an intraocular half-life of less than about 6 days, less than about 5 days or even less than about 4 days in a human.

The aptamers disclosed herein may demonstrate high specificity for VEGF-A versus other members of the VEGF family, including VEGF-B, VEGF-C, VEGF-D, VEGF-E, VEGF-F, and PIGF. In some cases, the aptamer may be selected such that the aptamer has high affinity for VEGF-A, but with little to no affinity for VEGF-B, VEGF-C, VEGF-D, VEGF-E, VEGF-F, or PIGF. In some cases, the aptamers of the disclosure may bind to VEGF-A with a specificity of at least 5-fold, at least 10-fold, at least 15-fold, at least 20-fold, at least 50-fold, at least 100-fold, at least 250-fold, at least 500-fold, at least 1,000-fold, at least 5,000-fold, at least 10,000-fold, at least 50,000-fold, or at least 100,000-fold, or greater than 100,000-fold than the aptamers bind to VEGF-B, VEGF-C, VEGF-D, VEGF-E, VEGF-F, or PIGF at relative serum concentrations.

The activity of a therapeutic agent can be characterized by the half maximal inhibitory concentration ($IC_{50}$). The $IC_{50}$ may be calculated as the concentration of therapeutic agent in nM at which half of the maximum inhibitory effect of the therapeutic agent is achieved. The $IC_{50}$ may be dependent upon the assay utilized to calculate the value. In some examples, the $IC_{50}$ of an aptamer described herein may be less than 100 nM, less than 50 nM, less than 25 nM, less than 10 nM, less than 5 nM, less than 1 nM, less than 0.5 nM, less than 0.1 nM or less than 0.01 nM as measured by a VEGF-A:KDR competition binding assay (see Example 3). In some examples, the $IC_{50}$ of an aptamer described herein may be less than 100 nM, less than 50 nM, less than 25 nM, less than 10 nM, less than 5 nM, less than 1 nM, less than 0.5 nM, less than 0.1 nM or less than 0.01 nM as measured by a KDR phosphorylation AlphaLISA® assay (see Example 4). In some examples, the $IC_{50}$ of an aptamer described herein may be less than 100 nM, less than 50 nM, less than 25 nM, less than 10 nM, less than 5 nM, less than 1 nM, less than 0.5 nM, less than 0.1 nM or less than 0.01 nM as measured by an in vitro model of VEGF-A-induced angiogenesis (see Example 5).

Aptamers generally have high stability at ambient temperatures for extended periods of time. The aptamers described herein may demonstrate greater than 70%, greater than 75%, greater than 80%, greater than 85%, greater 90%, greater than 91%, greater than 92%, greater than 93%, greater than 94%, greater than 95%, greater than 96%, greater than 97%, greater than 98%, greater than 99%, greater than 99.5%, or greater than 99.9% activity in solution under physiological conditions at 30 days or later.

In some cases, a composition of the disclosure comprises anti-VEGF-A aptamers, wherein essentially 100% of the anti-VEGF-A aptamers comprise nucleotides having ribose in the β-D-ribofuranose configuration. In other examples, a composition of the disclosure may comprise anti-VEGF-A aptamers, wherein at least 50%, at least 60%, at least 70%, at least 80%, at least 90%, or greater than 90% of the anti-VEGF-A aptamers have ribose in the β-D-ribofuranose configuration.

Indications

In some aspects, the methods and compositions provided herein may be suitable for the treatment of ocular diseases or disorders. In some aspects, the methods and compositions provided herein may be suitable for the prevention of ocular diseases or disorders. In some aspects, the methods and compositions provided herein may be suitable to slow or halt the progression of ocular diseases or disorders. In some cases, the ocular disease or disorder is diabetic retinopathy. In some cases, the ocular disease or disorder is retinopathy of prematurity. In some cases, the ocular disease or disorder is central retinal vein occlusion. In some cases, the ocular disease or disorder is macular edema. In some cases, the ocular disease or disorder is choroidal neovascularization. In some cases, the ocular disease or disorder is neovascular (or wet) age-related macular degeneration. In some cases, the ocular disease or disorder is myopic choroidal neovascularization. In some cases, the ocular disease or disorder is punctate inner choroidopathy. In some cases, the ocular disease or disorder is presumed ocular histoplasmosis syndrome. In some cases, the ocular disease or disorder is familial exudative vitreoretinopathy. In some cases, the ocular disease or disorder is retinoblastoma.

Additional examples of ocular diseases or disorders that may be amendable to treatment by the methods and compositions provided herein may include, without limitation, pterygium, inflammatory conjunctivitis, including allergic and giant papillary conjunctivitis, infectious conjunctivitis, vernal keratoconjunctivitis, Stevens-Johnson disease, corneal herpetic keratitis, rhegmatogenous retinal detachment, pseudo-exfoliation syndrome, endophthalmitis, scleritis, corneal ulcers, dry eye syndrome, glaucoma, ischemic retinal disease, corneal transplant rejection, complications related to intraocular surgery such intraocular lens implantation and inflammation associated with cataract surgery, Behcet's disease, Stargardt disease, immune complex vasculitis, Fuch's disease, Vogt-Koyanagi-Harada disease, subretinal fibrosis, keratitis, vitreo-retinal inflammation, ocular parasitic infestation/migration, retinitis pigmentosa, cytomegalovirus retinitis and choroidal inflammation, ectropion, lagophthalmos, blepharochalasis, ptosis, xanthelasma of the eyelid, parasitic infestation of the eyelid, dermatitis of the eyelid, dacryoadenitis, epiphora, dysthyroid exophthalmos, conjunctivitis, scleritis, adenovirus keratitis, corneal ulcer, corneal abrasion, snow blindness, arc eye, Thygeson's superficial punctate keratopathy, corneal neovascularization, Fuchs' dystrophy, keratoconus, keratoconjunctivitis sicca, iritis, sympathetic ophthalmia, cataracts, chorioretinal inflammation, focal chorioretinal inflammation, focal chorioretinitis, focal choroiditis, focal retinitis, focal retinochoroiditis, disseminated chorioretinal inflammation, disseminated chorioretinitis, disseminated choroiditis, disseminated retinitis, disseminated retinochoroiditis, exudative retinopathy, posterior cyclitis, pars planitis, Harada's disease, chorioretinal scars, macula scars of posterior pole, solar retinopathy, choroidal degeneration, choroidal atrophy, choroidal sclerosis, angioid streaks, hereditary choroidal dystrophy, choroideremia, choroidal dystrophy (central arealor), gyrate atrophy (choroid), ornithinaemia, choroidal haemorrhage and rupture, choroidal haemorrhage (not otherwise specified), choroidal haemorrhage (expulsive), choroidal detachment, retinoschisis, retinal artery occlusion, retinal vein occlusion, hypertensive retinopathy, diabetic retinopathy, retinopathy, retinopathy of prematurity, macular degeneration, Bull's Eye maculopathy, epiretinal membrane, peripheral retinal degeneration, hereditary retinal dystrophy, retinitis pigmentosa, retinal haemorrhage, separation of retinal layers, central serous retinopathy, retinal detachment, macular edema, glaucoma-optic neuropathy, glaucoma suspect-ocular hypertension, primary open-angle glaucoma, primary angle-closure glaucoma, floaters, Leber's hereditary optic neuropathy, optic disc drusen, strabismus, ophthalmoparesis, progressive external ophthaloplegia, esotropia, exotropia, disorders of refraction and accommodation, hypermetropia, myopia, astigmastism, anisometropia, presbyopia, internal ophthalmoplegia, amblyopia, Leber's congenital amaurosis, scotoma, anopsia, color blindness, achromatopsia, maskun, nyctalopia, blindness, River blindness, micropthalmia, coloboma, red eye, Argyll Robertson pupil, keratomycosis, xerophthalmia, aniridia, sickle cell retinopathy, ocular neovascularization, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy-2 and lensectomy, vascular diseases, retinal ischemia, choroidal vascular insufficiency, choroidal thrombosis, neovascularization of the optic nerve, diabetic macular edema, cystoid macular edema, proliferative vitreoretinopathy, and neovascularization due to penetration of the eye or ocular injury.

In some aspects, the methods and compositions provided herein are suitable for the treatment of diseases that cause one or more ocular symptoms. Non-limiting examples of symptoms which may be amenable to treatment with the methods disclosed herein include, but are not limited to choroidal or vitreal neovascularization, vascular leakage, reduced reading speed, reduced color vision, macular edema, increased retinal thickening, increase in central retinal volume and/or, macular sensitivity, loss of retinal cells, increase in area of retinal atrophy, reduced best corrected visual acuity such as measured by Snellen or ETDRS scales, reduced Best Corrected Visual Acuity under low luminance conditions, impaired night vision, impaired light sensitivity, impaired dark adaptation, impaired contrast sensitivity, worsened patient reported outcomes, and any combination thereof.

In some cases, the methods and compositions provided herein may alleviate or reduce a symptom of a disease. In some cases, treatment with an aptamer provided herein may result in a reduction in the severity of any of the symptoms described herein. In some cases, treatment with an aptamer described herein may slow, halt or reverse the progression of any of the symptoms described herein. In some cases, treatment with an aptamer described herein may prevent the development of any of the symptoms described herein. In some cases, treatment with an aptamer described herein may slow, halt or reverse the progression of a disease, as measured by the number and severity of symptoms experienced. Examples of symptoms and relevant endpoints where the aptamer may have a therapeutic effect include choroidal or retinal neovascularization, vascular leakage, reduced reading speed, reduced color vision, macular edema, increased retinal thickening, increase in central retinal volume and/or, macular sensitivity, loss of retinal cells, increase in area of retinal atrophy, reduced best corrected visual acuity such as measured by Snellen or ETDRS scales, reduced Best Corrected Visual Acuity under low luminance conditions, impaired night vision, impaired light sensitivity, impaired dark adaptation, impaired contrast sensitivity, and worsening patient reported outcomes. In some instances, treatment with an aptamer described herein may have beneficial effects as measured by clinical endpoints including reading speed, choroidal or retinal neovascularization or vascular leakage as measured by fluorescein angiography, retinal thickness as measured by Optical Coherence Tomography or other techniques, central retinal volume, number and density of retinal cells, area of retinal atrophy as measured by Fundus Photography or Fundus Autofluorescence or other techniques, best corrected visual acuity such as measured by Snellen or ETDRS scales, Best Corrected Visual Acuity under low luminance conditions, light sensitivity, dark adaptation, contrast sensitivity, and patient reported outcomes as measured by such tools as the National Eye Institute Visual Function Questionnaire and Health Related Quality of Life Questionnaires.

In some cases, the methods and compositions provided herein may alleviate or reduce a symptom of a neovascular eye disease. In some cases, treatment with an aptamer provided herein may result in a reduction in the severity of any symptoms associated with a neovascular eye disease. In some cases, treatment with an aptamer described herein may slow, halt or reverse the progression of any symptom associated with a neovascular eye disease. In some cases, treatment with an aptamer described herein may prevent the development of any symptom associated with a neovascular eye disease. In some cases, treatment with an aptamer described herein may slow, halt or reverse the progression of a neovascular eye disease, as measured by the number and severity of symptoms experienced. Non-limiting examples of symptoms associated with neovascular eye diseases where the aptamer may have a therapeutic effect include choroidal or retinal neovascularization, vascular leakage within the eye, macular edema, central retinal thickness and visual acuity.

Subjects

The terms "subject" and "patient" are used interchangeably herein to refer to a vertebrate, preferably a mammal, and more preferably a human. Mammals include, but are not limited to, rodents (e.g., mice, rats, rabbits, etc.) simians, humans, research animals (e.g., beagles, etc.), farm animals (e.g., pigs, horses, cows, llamas, alpacas, etc.), sport animals, and pets. In some cases, the methods described herein may be used on tissues or cells derived from a subject and the progeny of such tissues or cells. For example, aptamers described herein may be used to affect some function in tissues or cells of a subject. The tissues or cells may be obtained from a subject in vivo. In some cases, the tissues or cells are cultured in vitro and contacted with a composition provided herein (e.g., an aptamer).

In some aspects, the methods and compositions provided herein are used to treat a subject in need thereof. In some cases, the subject has, is suspected of having, or is at risk of developing, an ocular disease or disorder. In some cases, the subject is a human. In some cases, the human is a patient at a hospital or a clinic. In some cases, the subject is a non-human animal, for example, a non-human primate, a livestock animal, a domestic pet, or a laboratory animal. For example, a non-human animal can be an ape (e.g., a chimpanzee, a baboon, a gorilla, or an orangutan), an old world monkey (e.g., a rhesus monkey), a new world monkey, a dog, a cat, a bison, a camel, a cow, a deer, a pig, a donkey, a horse, a mule, a lama, a sheep, a goat, a buffalo, a reindeer, a yak, a mouse, a rat, a rabbit, or any other non-human animal.

In cases where the subject is a human, the subject may be of any age. In some cases, the subject has an age-related ocular disease or disorder (e.g., age-related macular degeneration). In some cases, the subject is about 50 years or older. In some cases, the subject is about 55 years or older. In some cases, the subject is about 60 years or older. In some cases, the subject is about 65 years or older. In some cases, the subject is about 70 years or older. In some cases, the subject is about 75 years or older. In some cases, the subject is about 80 years or older. In some cases, the subject is about 85 years or older. In some cases, the subject is about 90 years or older. In some cases, the subject is about 95 years or older. In some cases, the subject is about 100 years or older. In some cases, the subject is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater than 100 years old. In some cases, the subject is about 1, 2, 3, 4, 5, 6, 7, 8, 9, 10, 11, 12, 13, 14, 15, 16, 17, 18, 19, 20 or greater than 20 years old.

In some aspects, the methods and compositions provided herein may be used to treat a subject having, suspected of having, or at risk of developing ocular symptoms as described herein. In some aspects, the methods and compositions provided herein may be used to treat a subject having, suspected of having, or at risk of developing an ocular disease as provided herein. In some cases, the methods and compositions provided herein may be used to treat a subject having, suspected of having, or at risk of developing an ocular disease or disorder. In some cases, the ocular disease or disorder is diabetic retinopathy. In some cases, the ocular disease or disorder is retinopathy of prematurity. In some cases, the ocular disease or disorder is central retinal vein occlusion. In some cases, the ocular disease or disorder is macular edema. In some cases, the ocular disease or disorder is choroidal neovascularization. In some cases, the ocular disease or disorder is neovascular (or wet) age-related macular degeneration. In some cases, the ocular disease or disorder is myopic choroidal neovascularization. In some cases, the ocular disease or disorder is punctate inner choroidopathy. In some cases, the ocular disease or disorder is presumed ocular histoplasmosis syndrome. In some cases, the ocular disease or disorder is familial exudative vitreoretinopathy. In some cases, the ocular disease or disorder is retinoblastoma. In some cases, the methods and compositions provided herein may be used to treat a subject having, suspected of having, or at risk of developing an ocular disease or disorder exhibiting elevated levels of one or more isoforms or variants of VEGF-A.

Pharmaceutical Compositions or Medicaments

Disclosed herein are pharmaceutical compositions or medicaments, used interchangeably, for use in a method of therapy, or for use in a method of medical treatment. Such use may be for the treatment of ocular diseases or disorders. In some cases, the pharmaceutical compositions can be used for the treatment of an ocular disease or disorder. In some cases, the pharmaceutical compositions comprise one or more anti-VEGF-A aptamers for the treatment of an ocular disease or disorder. In some cases, the ocular disease or disorder is diabetic retinopathy. In some cases, the ocular disease or disorder is retinopathy of prematurity. In some cases, the ocular disease or disorder is central retinal vein occlusion. In some cases, the ocular disease or disorder is macular edema. In some cases, the ocular disease or disorder is choroidal neovascularization. In some cases, the ocular disease or disorder is neovascular (or wet) age-related macular degeneration. In some cases, the ocular disease or disorder is myopic choroidal neovascularization. In some cases, the ocular disease or disorder is punctate inner choroidopathy. In some cases, the ocular disease or disorder is presumed ocular histoplasmosis syndrome. In some cases, the ocular disease or disorder is familial exudative vitreoretinopathy. In some cases, the ocular disease or disorder is retinoblastoma. In some cases, the pharmaceutical compositions can be used for the treatment of an ocular disease or disorder that exhibits elevated levels of one or more isoforms or variants of VEGF-A.

In some cases, the one or more anti-VEGF-A aptamers may bind to one or more isoforms or variants of VEGF-A. In some cases, the one or more anti-VEGF-A aptamers are pan-variant specific aptamers that bind to each of VEGF-$A_{110}$, VEGF-$A_{121}$, VEGF-$A_{165}$, VEGF-$A_{189}$, and VEGF-$A_{206}$. In some cases, the one or more anti-VEGF-A aptamers may bind to the receptor binding face of VEGF-A, or a portion thereof. The receptor binding face of VEGF-A may include strands β2, β5, and β6 and loop β1 and β2 of a first monomer, and the N-terminal a helix and loop β3 to β4 of the second monomer (see Muller, Yves A., et al. "The crystal structure of vascular endothelial growth factor (VEGF) refined to 1.93 Å resolution: multiple copy flexibility and receptor binding." Structure 5.10 (1997): 1325-1338.). In some cases, anti-VEGF-A aptamers that bind to the receptor binding face of VEGF-A may bind to one or more of residues Phe17, Ile43, Ile46, Glu64, Gln79, Ile83, Lys84, Pro85, Arg82, His86, Asp63, Glu67, as described in SEQ ID NOs: 6-10. In some cases, the one or more anti-VEGF-A aptamers may bind to the receptor binding domain of VEGF-A, or a portion thereof. The receptor binding domain of VEGF-A may include any one or more of residues 1-109, as described in SEQ ID NOs: 6-10. In some cases, the one or more anti-VEGF-A aptamers may prevent or reduce the binding of one or more isoforms or variants of VEGF-A with Flt-1, KDR, or Nrp-1. In some cases, the compositions may include, e.g., an effective amount of the aptamer, alone or in combination, with one or more vehicles (e.g., pharmaceutically acceptable compositions or e.g., pharmaceutically acceptable carriers).

Formulations

Compositions as described herein may comprise a liquid formulation, a solid formulation or a combination thereof. Non-limiting examples of formulations may include a tablet, a capsule, a gel, a paste, a liquid solution and a cream. The compositions of the present disclosure may further comprise any number of excipients. Excipients may include any and all solvents, coatings, flavorings, colorings, lubricants, disintegrants, preservatives, sweeteners, binders, diluents, and vehicles (or carriers). Generally, the excipient is compatible with the therapeutic compositions of the present disclosure. The pharmaceutical composition may also contain minor amounts of non-toxic auxiliary substances such as wetting or emulsifying agents, pH buffering agents, and other substances such as, for example, sodium acetate, and triethanolamine oleate.

Dosage and Routes of Administration

Therapeutic doses of formulations of the disclosure can be administered to a subject in need thereof. In some cases, a formulation is administered to the eye of a subject for the treatment of an ocular disease as described herein. Administration to the eye can be; a) local ocular delivery; or b) systemic. A topical formulation can be applied directly to the eye (e.g., eye drops, contact lens loaded with the formulation) or to the eyelid (e.g., cream, lotion, gel). In some cases, topical administration can be to a site remote from the eye, for example, to the skin of an extremity. This form of administration may be suitable for targets that are not produced directly by the eye. In some cases, a formulation of the disclosure is administered by local ocular delivery. Non-limiting examples of local ocular delivery include intravitreal (IVT), intracamarel, subconjunctival, subtenon, retrobulbar, posterior juxtascleral, and peribulbar. In some cases, a formulation of the disclosure is delivered by intravitreal administration (IVT). Local ocular delivery may generally involve injection of a liquid formulation. In other cases, a formulation of the disclosure is administered systemically. Systemic administration can involve oral administration. In some cases, systemic administration can be intravenous administration, subcutaneous administration, infusion, implantation, and the like.

Other formulations suitable for delivery of the pharmaceutical compositions described herein may include a sustained release gel or polymer formulations by surgical implantation of a biodegradable microsize polymer system, e.g., microdevice, microparticle, or sponge, or other slow release transscleral devices, implanted during the treatment of an ophthalmic disease, or by an ocular delivery device, e.g., polymer contact lens sustained delivery device. In some cases, the formulation is a polymer gel, a self-assembling gel, a durable implant, an eluting implant, a biodegradable matrix or biodegradable polymers. In some cases, the formulation may be administered by iontophoresis using electric current to drive the composition from the surface to the posterior of the eye. In some cases, the formulation may be administered by a surgically implanted port with an intravitreal reservoir, an extra-vitreal reservoir or a combination thereof. Examples of implantable ocular devices can include, without limitation, the Durasert™ technology developed by Bausch & Lomb, the ODTx device developed by On Demand Therapeutics, the Port Delivery System developed by ForSight VISION4 and the Replenish MicroPump™ System developed by Replenish, Inc. In some cases, nanotechnologies can be used to deliver the pharmaceutical compositions including nanospheres, nanoparticles, nanocapsules, liposomes, nanomicelles and dendrimers.

A composition of the disclosure can be administered once or more than once each day. In some cases, the composition is administered as a single dose (i.e., one-time use). In this example, the single dose may be curative. In other cases, the composition may be administered serially (e.g., taken every day without a break for the duration of the treatment regimen). In some cases, the treatment regime can be less than a week, a week, two weeks, three weeks, a month, or greater than a month. In some cases, the composition is administered over a period of at least 12 weeks, at least 16 weeks, at least 20 weeks, or at least 24 weeks. In other cases, the composition is administered for a day, at least two consecutive days, at least three consecutive days, at least four consecutive days, at least five consecutive days, at least six consecutive days, at least seven consecutive days, at least eight consecutive days, at least nine consecutive days, at least ten consecutive days, or at least greater than ten consecutive days. In some cases, a therapeutically effective amount can be administered one time per week, two times per week, three times per week, four times per week, five times per week, six times per week, seven times per week, eight times per week, nine times per week, 10 times per week, 11 times per week, 12 times per week, 13 times per week, 14 times per week, 15 times per week, 16 times per week, 17 times per week, 18 times per week, 19 times per week, 20 times per week, 25 times per week, 30 times per week, 35 times per week, 40 times per week, or greater than 40 times per week. In some cases, a therapeutically effective amount can be administered one time per day, two times per day, three times per day, four times per day, five times per day, six times per day, seven times per day, eight times per day, nine times per day, 10 times per day, or greater than 10 times per day. In some cases, the composition is administered at least twice a day. In further cases, the composition is administered at least every hour, at least every two hours, at least every three hours, at least every four hours, at least every five hours, at least every six hours, at least every seven hours, at least every eight hours, at least every nine hours, at least every 10 hours, at least every 11 hours, at least every 12 hours, at least every 13 hours, at least every 14 hours, at least every 15 hours, at least every 16 hours, at least every 17 hours, at least every 18 hours, at least every 19 hours, at least every 20 hours, at least every 21 hours, at least every 22 hours, at least every 23 hours, or at least every day.

Aptamers as described herein may be particularly advantageous over antibodies as they may sustain therapeutic intravitreal concentrations of drug for longer periods of time, thus requiring less frequent administration. The aptamers described herein may have a longer intraocular half-life, and/or sustain therapeutic intravitreal concentrations of drug for longer periods of time than an anti-VEGF-A antibody therapy and can be dosed less frequently. In some cases, the aptamers of the disclosure are dosed at least once every 4 weeks (q4w), once every 5 weeks (q5w), once every 6 weeks (q6w), once every 7 weeks (q7w), once every 8 weeks (q8w), once every 9 weeks (q9w), once every 10 weeks (q10w), once every 11 weeks (q11w) once every 12 weeks (q12w), once every 13 weeks (q13w), once every 14 weeks (q14w), once every 15 weeks (q15w), once every 16 weeks (q16w), once every 17 weeks (q17w), once every 18 weeks (q18w), once every 19 weeks (q19w), once every 20 weeks (q20w), once every 21 weeks (q21w), once every 22 weeks (q22w), once every 23 weeks (q23w), once every 24 weeks (q24w), or greater than once every 24 weeks.

In some aspects, a therapeutically effective amount of the aptamer may be administered. A "therapeutically effective amount" or "therapeutically effective dose" are used interchangeably herein and refer to an amount of a therapeutic agent (e.g., an aptamer) that provokes a therapeutic or desired response in a subject. The therapeutically effective amount of the composition may be dependent on the route of administration. In the case of systemic administration, a therapeutically effective amount may be about 10 mg/kg to about 100 mg/kg. In some cases, a therapeutically effective amount may be about 10 μg/kg to about 1000 μg/kg for systemic administration. For intravitreal administration, a therapeutically effective amount can be about 0.01 mg to about 150 mg in about 25 μl to about 100 μl volume per eye.

Methods of Treatment

Disclosed herein are methods for the treatment of ocular diseases or disorders. In some cases, the ocular disease or disorder may be diabetic retinopathy. In some cases, the ocular disease or disorder may be retinopathy of prematurity. In some cases, the ocular disease or disorder may be central retinal vein occlusion. In some cases, the ocular disease or disorder may be macular edema. In some cases, the ocular disease or disorder may be choroidal neovascularization. In some cases, the ocular disease or disorder may be neovascular (or wet) age-related macular degeneration. In some cases, the ocular disease or disorder may be myopic choroidal neovascularization. In some cases, the ocular disease or disorder may be punctate inner choroidopathy. In some cases, the ocular disease or disorder may be presumed ocular histoplasmosis syndrome. In some cases, the ocular disease or disorder may be familial exudative vitreoretinopathy. In some cases, the ocular disease or disorder may be retinoblastoma. In some cases, the ocular disease or disorder may exhibit elevated levels of one or more isoforms or variants of VEGF-A.

In some cases, the method involves administering a therapeutically effective amount of a composition to a subject to treat an ocular disease. In some cases, the composition includes one or more aptamers as described herein. The aptamers may bind to and inhibit a function associated with one or more isoforms or variants of VEGF-A as described herein. The methods can be performed at a hospital or a clinic, for example, the pharmaceutical compositions can be administered by a health-care professional. In other cases, the pharmaceutical compositions can be self-administered by the subject. Treatment may commence with the diagnosis of a subject with an ocular disease. In the event that further treatments are necessary, follow-up appointments may be scheduled for the administration of subsequent doses of the composition, for example, administration every 8, 12, 16, 20, or 24 weeks.

Further disclosed herein are methods of using an anti-VEGF-A composition of the disclosure to inhibit a function associated with VEGF-A. For example, the methods may involve administering a composition of the disclosure, including one or more anti-VEGF-A aptamers, to a biological system (e.g., biological cells, biological tissue, a subject) to inhibit a function associated with VEGF-A. In some cases, the anti-VEGF-A aptamers may bind to the receptor binding face of VEGF-A, or portions thereof. In some cases, the anti-VEGF-A aptamers may bind to the receptor binding domain of VEGF-A. In some cases, the methods may be used to prevent or reduce binding of VEGF-A to Flt-1, KDR, Nrp-1, or any combination thereof. In some cases, the methods may be used to inhibit downstream signaling pathways associated with VEGF-A.

Methods of Generating Aptamers

The SELEX™ Method

The aptamers described herein can be generated by any method suitable for generating aptamers. In some cases, the aptamers described herein are generated by a process known as Systematic Evolution of Ligands by Exponential Enrichment" ("SELEX™"). The SELEX™ process is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see, also WO 91/19813) entitled "Nucleic Acid Ligands", each of which are herein incorporated by reference. By performing iterative cycles of selection and amplification, SELEX™ may be used to obtain aptamers with any desired level of target binding affinity.

The SELEX™ method generally relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs, hybridization sites for PCR primers, promoter sequences for RNA polymerases (e.g., T3, T4, T7, and SP6), sequences to form stems to present the randomized region of the library within a defined terminal stem structure, restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool can include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in some cases, random oligonucleotides comprise entirely random sequences; however, in other cases, random oligonucleotides can comprise stretches of nonrandom or partially random sequences. Partially random sequences can be created by adding the four nucleotides in different molar ratios at each addition step.

The starting library of oligonucleotides may be RNA, DNA, substituted RNA or DNA or combinations thereof. In those instances where an RNA library is to be used as the starting library it is typically generated by synthesizing a DNA library, optionally PCR amplifying, then transcribing the DNA library in vitro using phage RNA polymerase or modified phage RNA polymerases, and purifying the transcribed library. The nucleic acid library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. Those which have the higher affinity (lower dissociation constants) for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested as ligands or aptamers for 1) target binding affinity; and 2) ability to effect target function.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 3 to 20 cycle procedure.

In some cases, the aptamers of the disclosure are generated using the SELEX™ method as described above. In other cases, the aptamers of the disclosure are generated using any modification or variant of the SELEX™ method.

Methods of Generating Pan-Variant Specific Anti-VEGF-A Aptamers

Further provided herein are methods for generating and screening pan-variant specific anti-VEGF-A aptamers. In some cases, the pan-variant specific aptamers bind to the receptor binding face of VEGF-A, or the receptor binding domain of VEGF-A. Generally, the methods provided herein bias the selection process towards aptamers that selectively bind to the receptor binding face or receptor binding domain of VEGF-A. In some cases, such aptamers do not bind to the heparin binding domain of VEGF-A. In various aspects, the methods may involve incubating an aptamer library with an isoform or variant of VEGF-A which contains a receptor binding domain but does not contain a heparin binding domain. In some cases, the isoform or variant of VEGF-A is VEGF-$A_{121}$ or VEGF-$A_{110}$. In various aspects, the methods involve immobilizing the VEGF-A variant on a solid support in a manner that does not preclude access of the library to the receptor binding face or receptor binding domain of VEGF-A. In various aspects, the methods involve performing the selection in the absence of $Ca^{++}$ In various aspects, methods for screening pan-variant specific anti-VEGF-A aptamers are provided. In some cases, the methods may involve measuring the interaction of a candidate aptamers with recombinant bead-bound VEGF-$A_{165}$, VEGF-$A_{121}$, or VEGF-$A_{110}$ by flow cytometry (see Example 1). In such cases, interaction with each isoform or variant would indicate binding to the receptor binding domain, while only binding to VEGF-$A_{165}$ would indicate recognition of the heparin binding domain. In some cases, the methods may involve measuring the ability of the candidate aptamer to inhibit or reduce the interaction of VEGF-$A_{165}$, VEGF-$A_{121}$, or VEGF-$A_{110}$ with KDR by a reduction in FRET signal (see Example 3). In such cases, efficacy against each variant would indicate binding to the receptor binding domain, while only inhibiting VEGF-$A_{165}$ would indicate binding to the heparin binding domain. In some cases, the methods may involve measuring the ability of the candidate aptamer to inhibit or reduce VEGF-$A_{165}$, VEGF-$A_{121}$, or VEGF-$A_{110}$ induced trans autophosphorylation of the intracellular domain of KDR by phospho-KDR AlphaLISA® (see Example 4). In such cases, efficacy against each variant would indicate binding to the receptor binding domain, while only inhibiting VEGF165 would indicate binding to the heparin binding domain. In some cases, the methods may involve measuring the ability of the candidate aptamer to inhibit or reduce VEGF-$A_{165}$, VEGF-$A_{121}$, or VEGF-$A_{110}$ induced gene expression of tissue factor in HUVEC cells as measured by qPCR. In such cases, efficacy against each variant would indicate binding to the receptor binding domain, while only inhibiting $VEGF_{165}$ would indicate binding to the heparin binding domain. In some cases, the methods may involve measuring the ability of the candidate aptamer to inhibit or reduce VEGF-$A_{165}$, VEGF-$A_{121}$, or VEGF-$A_{110}$ induced tube formation of GFP-HUVECs in co-culture with human dermal fibroblasts cells by change in network length or network area (see Example 5). In such cases, efficacy against each variant would indicate binding to the receptor binding domain, while only inhibiting VEGF-$A_{165}$ would indicate binding to the heparin binding domain. In some cases, the methods may involve measuring the ability of the candidate aptamer to inhibit or reduce vascular leakage in a mouse, rat, rabbit, or primate eye following exogenous VEGF-$A_{165}$, VEGF-$A_{121}$, or VEGF-$A_{110}$ challenge by fluorescein angiography and Evans-blue albumin staining. In such cases, efficacy against each VEGF isoform or variant would indicate binding to the receptor binding domain, while only inhibiting VEGF-$A_{165}$ would indicate binding to the heparin binding domain.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1A. Selection of Anti-VEGF-A Aptamers

Anti-VEGF-A (VEGF) aptamers targeting the receptor binding domain (RBD) were identified using an N30 library (N30S) comprised of a 30-nucleotide random region flanked by constant regions containing a built-in stem region as depicted in FIG. 1A. The sequence in italics represents the forward and reverse primer binding sites. The built-in stem region is underlined and shown in bold. FIG. 1B depicts a representation of the N30S library with the reverse primer hybridized. For nuclease stability, the library was composed of 2'-fluoro-G (2'F GTP) and 2'-O-methyl (2'OMe) A/C/U. FIG. 1C depicts structures of modified nucleotides used to generate the N30S library for selection against target VEGF-A. For simplicity, the nucleosides, and not the nucleotide triphosphates are shown.

The library sequence (underlined sequences represent the built-in stem) and the sequence of oligos used to amplify the library are described in Table 2.

TABLE 2

Library sequence and sequence of oligos used to amplify the library

| SEQ ID NO. | | Sequence (5' to 3') |
|---|---|---|
| SEQ ID NO: 428 | Library sequence (Total library length: 89 bases) | GGGAGTGTGTACGAGGCATTAGGCCGCC-N30-GGCGGCTTTGATACTTGATCGCCCTAGAAGC |
| SEQ ID NO: 429 | N30S.F | P-GGGAGTGTGTACGAGGCATTA |
| SEQ ID NO: 430 | N30S.R | GCTTCTAGGGCGATCAAGTATCA |

where G, A, T and C are deoxyribonucleotides and P-denotes a phage polymerase promoter.

The starting library was transcribed from a pool of ~$10^{14}$ double-stranded DNA (dsDNA) molecules. The dsDNA library was generated by primer extension using Klenow exo(−) DNA polymerase, the pool forward primer (N30S.F; SEQ ID NO: 429) and synthetic single-stranded DNA (ssDNA) molecules encoding the reverse complement of the library. The dsDNA was subsequently converted to 100% backbone modified RNA via transcription using a mixture of 2'F GTP, 2'OMe ATP/CTP/UTP and a modified phage polymerase in buffer optimized to facilitate efficient transcription. Following transcription, RNAs were treated with DNAse to remove the template dsDNA and purified.

In order to isolate pan-specific aptamer inhibitors of VEGF-A that bind to the RBD and inhibit VEGF-A via directly blocking its interaction with its receptor, KDR (also known as VEGFR-2), and avoid the identification of anti-VEGF-A aptamers that bound exclusively to the heparin binding domain (HBD) of the protein, aptamer selections were performed using a combination of the 121 and 110 variants of VEGF-A (VEGF-$A_{121}$ or VEGF-$A_{110}$). Both of these variants lack the HBD but possess the RBD and therefore maintain high affinity for the target receptor, KDR.

Aptamer selection was facilitated by the use of biotin-tagged recombinant human VEGF-$A_{121}$ or VEGF-$A_{110}$. To ensure the biotin tag did not interfere with the availability of desired epitopes within the RBD during the selection, biotin was chemically conjugated to the terminal sugars on the glycan. These VEGF-A monomers bear a single N-linked glycosylation site on Asn74, which is located in the center of the RBD, distal to the receptor binding face, making this an ideal site for target immobilization. In brief, VEGF-A glycans were oxidized with 100 μM sodium periodate for 30 minutes, and excess periodate was quenched with 1 mM glycerol. 1 mM biotin-$PEG_{12}$-alkoxyamine and 10 mM anthranilic acid final were added to the reaction and allowed to incubate for another 2 hours. Reactions were cleaned up by membrane filtration using a 10 kDa cutoff filter.

Biotinylated VEGF-A variants were immobilized on magnetic streptavidin capture beads (Dynal, Strepavidin MyOne™) at a constant ratio of 1 μL beads per 1 μg protein. Briefly, beads were washed three times with binding buffer SB1T(−) (40 mM HEPES, pH 7.5, 125 mM NaCl, 5 mM KCl, 1 mM $MgCl_2$, 0.05% Tween-20) and were resuspended in 50 μL of recombinant VEGF-A in SB1T(−) and incubated at room temperature for 30 minutes. The beads were subsequently blocked with excess biotin for 10 minutes. The amount of target protein varied with each round (Table 3). The beads were washed three times with SB1T(−) buffer to remove any unbound protein.

For the first round of selection, ~1 nanomole of the Round 0 RNA pool, ~3× coverage for $2\times10^4$ sequences, was used. Prior to each round, the library was thermally equilibrated by heating at 90° C. for 3 minutes and cooled at room temperature for 15 minutes in the presence of a 1.5-fold molar excess of reverse primer (N30S.R; SEQ ID NO: 430) to allow the library to refold. Following renaturation, the final volume of the reaction was adjusted to 50 μL in SB1T(−) supplemented with 1 μg/ml ssDNA and 0.1% BSA.

For the first round, the library was added to VEGF-$A_{110}$ immobilized on beads and incubated at 37° C. for 30 minutes on a tube rotary. After 30 minutes, the beads were washed three times using 0.5 mL SB1T(−) buffer to remove unbound aptamers. After washing, VEGF-$A_{110}$-bound aptamers were eluted using 200 μL elution buffer (2M Guanidine-HCl in SB1T(−) buffer) two times (total volume 400 μL). The eluted aptamers, in 400 μL of elution buffer, were ethanol precipitated. The recovered library was converted to DNA by reverse transcription using Super Script IV reverse transcriptase, and the ssDNA was subsequently amplified by PCR. The resulting dsDNA library was subsequently converted back into modified RNA via transcription as described above. DNased, purified RNA was used for subsequent rounds.

Following the first round, a negative selection step was included in all the subsequent rounds. For the negative selection, the pool was prepared as described before and first incubated with biotin saturated beads (in the absence of target protein) for 30 minutes at 37° C. in SB1T(−) buffer. The beads were pelleted and the supernatant, containing molecules that did not bind to the beads, was incubated with VEGF-A-labeled beads for an additional 30 minutes at 37° C. For rounds 2-4, the input RNA was kept fixed at 25 picomoles, and the protein target was fixed at 0.5 μg.

For rounds 5-7, the target was varied between VEGF-$A_{121}$ and VEGF-$A_{110}$ and a solution capture method was implemented. Negative selections were implemented as described above, and positive selection involved incubation with biotinylated target without the presence of beads for 30 minutes at 37° C. For capture, 2 μL of streptavidin beads were washed with 0.5 mL of SB1T(−) and the positive selection was used to re-suspend the bead pellet. After a 5 minute incubation, the beads were washed according to Table 3 prior to elution and precipitation as described above.

TABLE 3

Selection Details

| Round | Input library (moles/conc.) | Target protein | Target dimer (pMoles/conc.) | 1 μg/ml ssDNA & 0.1% BSA | Solution capture | Washes | # cycles |
|---|---|---|---|---|---|---|---|
| 1 | 1 nm/19.5 μM | VEGF-$A_{110}$ | 80 pm/1.5 μM | NO | NO | 3 × 0 min. | 24 |
| 2 | 25 pm/0.5 nM | VEGF-$A_{110}$ | 20 pm/400 nM | YES | NO | 3 × 0 min. | 33 |
| 3 | 25 pm/0.5 nM | VEGF-$A_{110}$ | 20 pm/400 nM | YES | NO | 3 × 0 min. | 22 |
| 4 | 25 pm/0.5 nM | VEGF-$A_{110}$ | 20 pm/400 nM | YES | NO | 3 × 5 min. | 22 |
| 5 | 25 pm/0.5 nM | VEGF-$A_{121}$ | 5 pm/100 nM | YES | YES | 3 × 5 min. | 27 |
| 6 | 25 pm/0.5 nM | VEGF-$A_{121}$ | 5 pm/100 nM | YES | YES | 0, 5, 15 min. | 25 |
| 7 | 25 pm/0.5 nM | VEGF-$A_{110}$ | 1 pm/20 nM | YES | YES | 0, 5, 15 min. | 28 |

Example 1B. Assessing the Progress of Selection

Figure 2B:
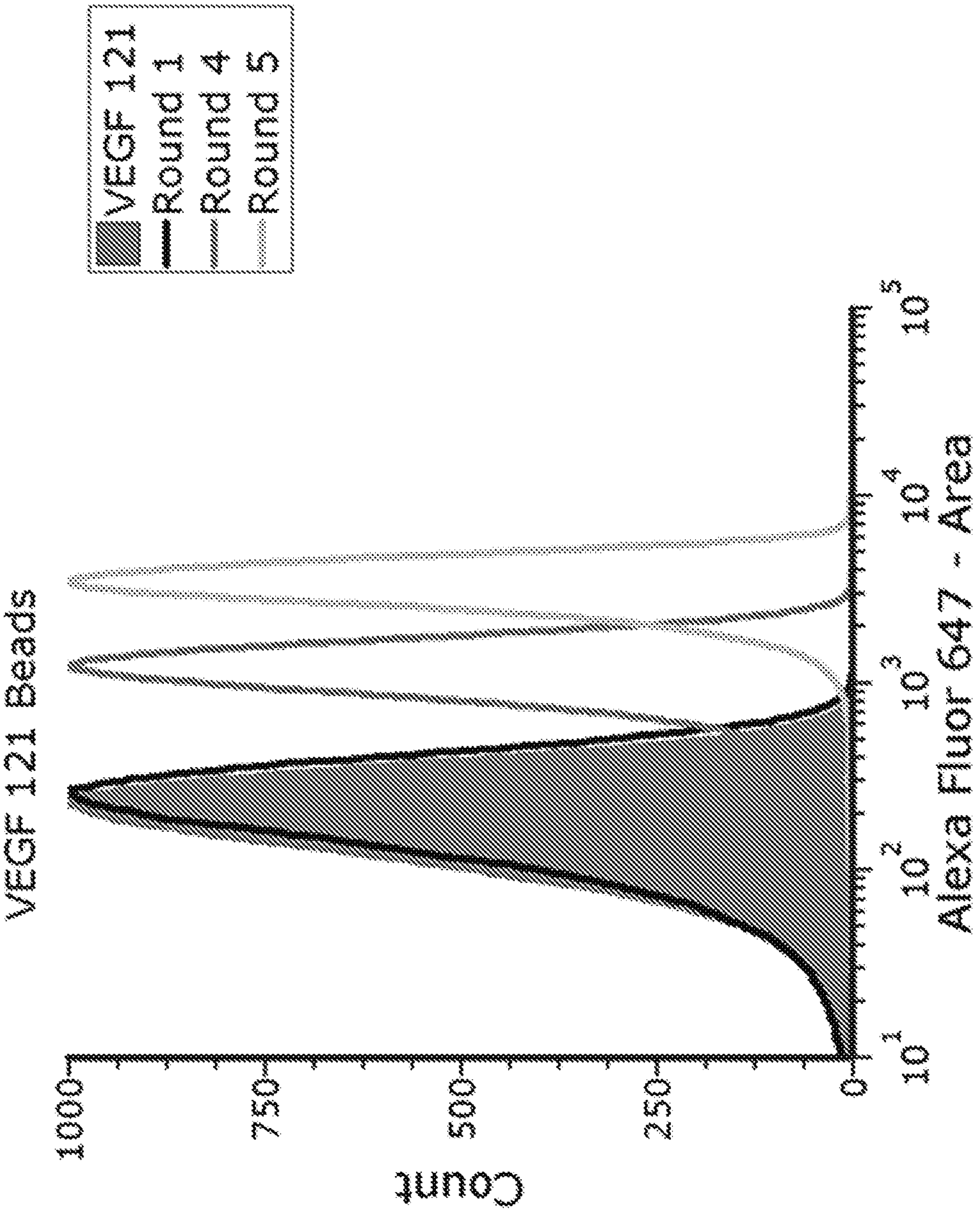
Figure 2C:
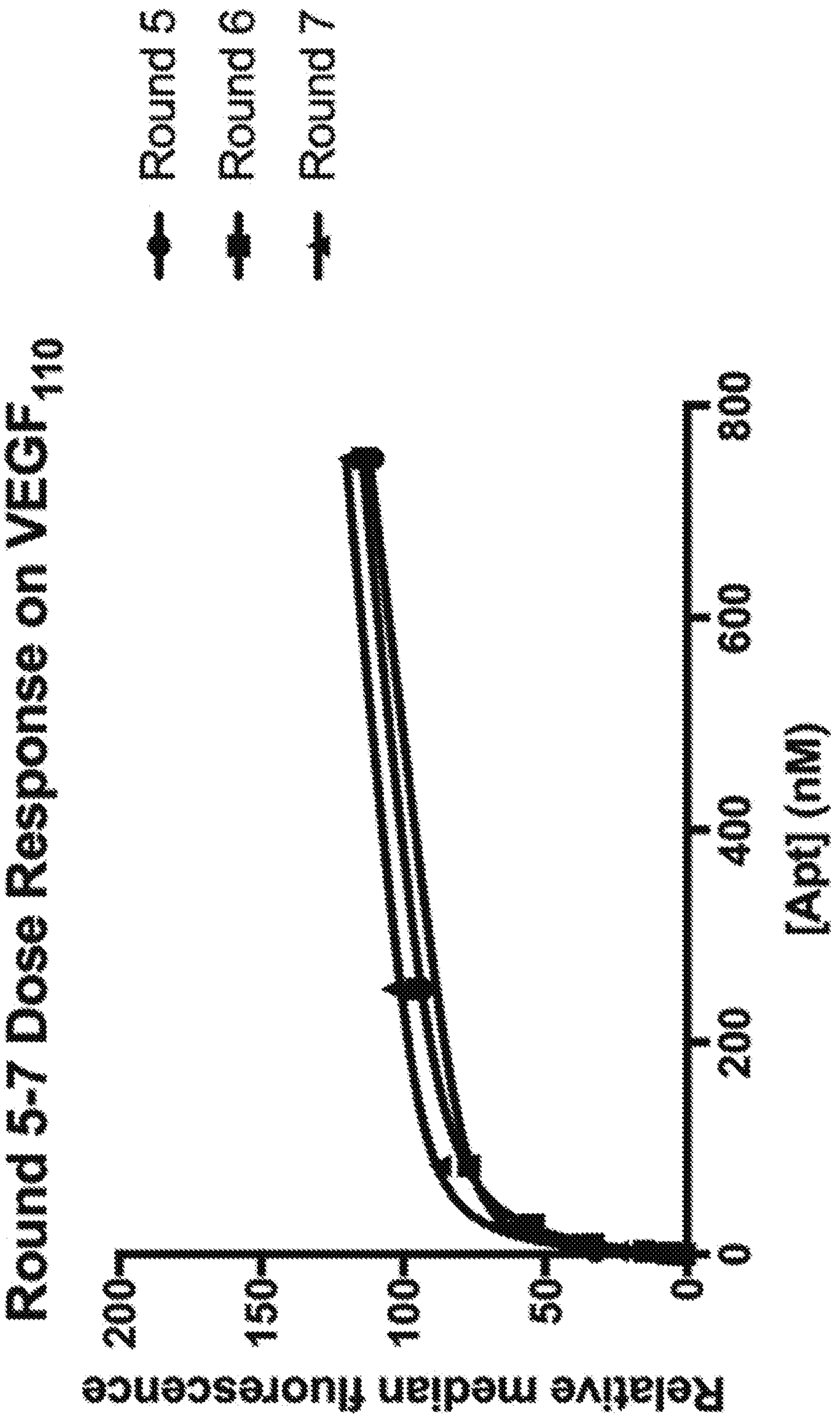
FIG. 2C depicts non-limiting examples of flow cytometry data demonstrating the ability of various aptamer selection rounds fluorescently labeled by hybridization to a fluorescently labeled primer to bind to bead-immobilized VEGF-$A_{110}$ in a dose-dependent fashion according to embodiments of the disclosure.
Figure 2D:
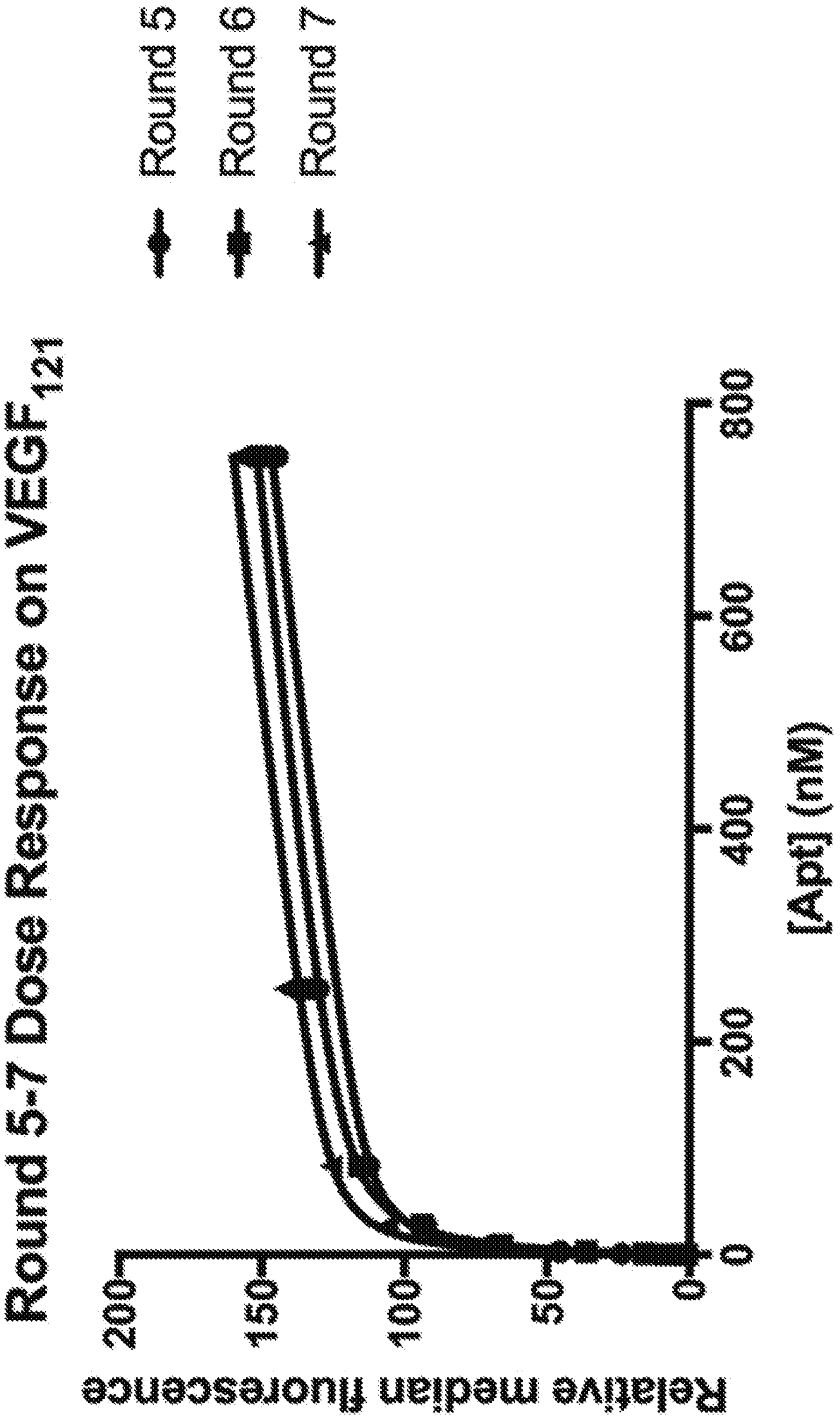
FIG. 2D depicts non-limiting examples of flow cytometry data demonstrating the ability of various aptamer selection rounds fluorescently labeled by hybridization to a fluorescently labeled primer to bind to bead-immobilized VEGF-$A_{121}$ in a dose-dependent fashion according to embodiments of the disclosure.
Figure 2E:
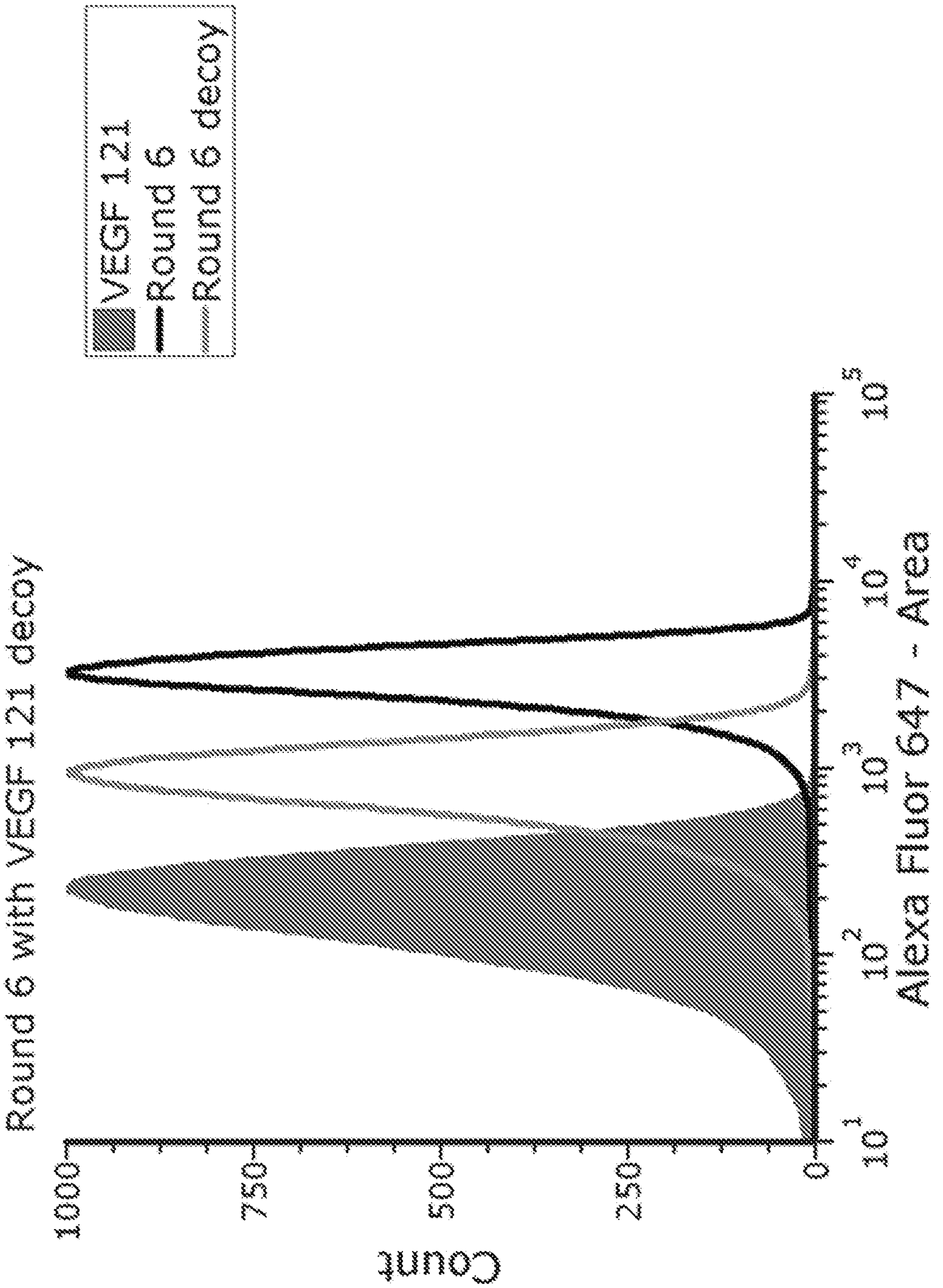
FIG. 2E depicts non-limiting examples of flow cytometry data demonstrating the ability of various aptamers from round 6 of the aptamer selection to bind to bead-immobilized VEGF-$A_{121}$ in the presence of soluble VEGF-$A_{121}$ according to embodiments of the disclosure.

Flow cytometry was used to assess the progress of the selection. For these assays, RNA from each round was first hybridized with reverse complement oligonucleotide composed of 2'OMe RNA labeled with Dylight® 650 (Dy650-N30S.R.OMe, sequence identical to N30S.R). Briefly, the library was combined with a 1.5-fold molar excess of Dy650-N30S.R.OMe, heated at 90° C. for 3 minutes and allowed to cool at room temperature for 15 minutes, after which it was incubated with unlabeled "Negative" beads or beads labelled with VEGF-$A_{121}$ in SB1T(−) buffer supplemented with 0.1% BSA and 1 mg/mL ssDNA final. Following incubation for 30 minutes at 37° C., the beads were washed 3 times with SB1T(−), re-suspended in SB1T(−) buffer, and analyzed by flow cytometry. As shown in FIG. 2A and FIG. 2B, an improvement in fluorescent signal was observed by Round 4. After Round 5, there was little change in the binding signal through Round 7. "Negative" and "VEGF 121" refers to the signal of unlabeled and VEGF-$A_{121}$-labeled beads, respectively, in the absence of fluorescently labeled RNA. Titrations of Rounds 5-7 prepared as described above also showed dose-dependent responses in median fluorescence for the bead populations functionalized with VEGF-$A_{121}$ and VEGF-$A_{110}$, which indicated that the selection strategy was successful in enriching for aptamers that bind to the RBD of VEGF-A (FIG. 2C and FIG. 2D). Importantly, similar binding experiments performed in the presence of 1 μM non-biotinylated VEGF-$A_{121}$ demonstrated a significant loss in binding signal (FIG. 2E; "Round 6 decoy"). Thus, the iterative rounds of selection resulted in the enrichment of an aptamer population capable of specifically binding the RBD of VEGF-A when both immobilized on beads and, more importantly, in solution.

Example 1C. Selection, Purification and Characterization of Clones

Figure 3:
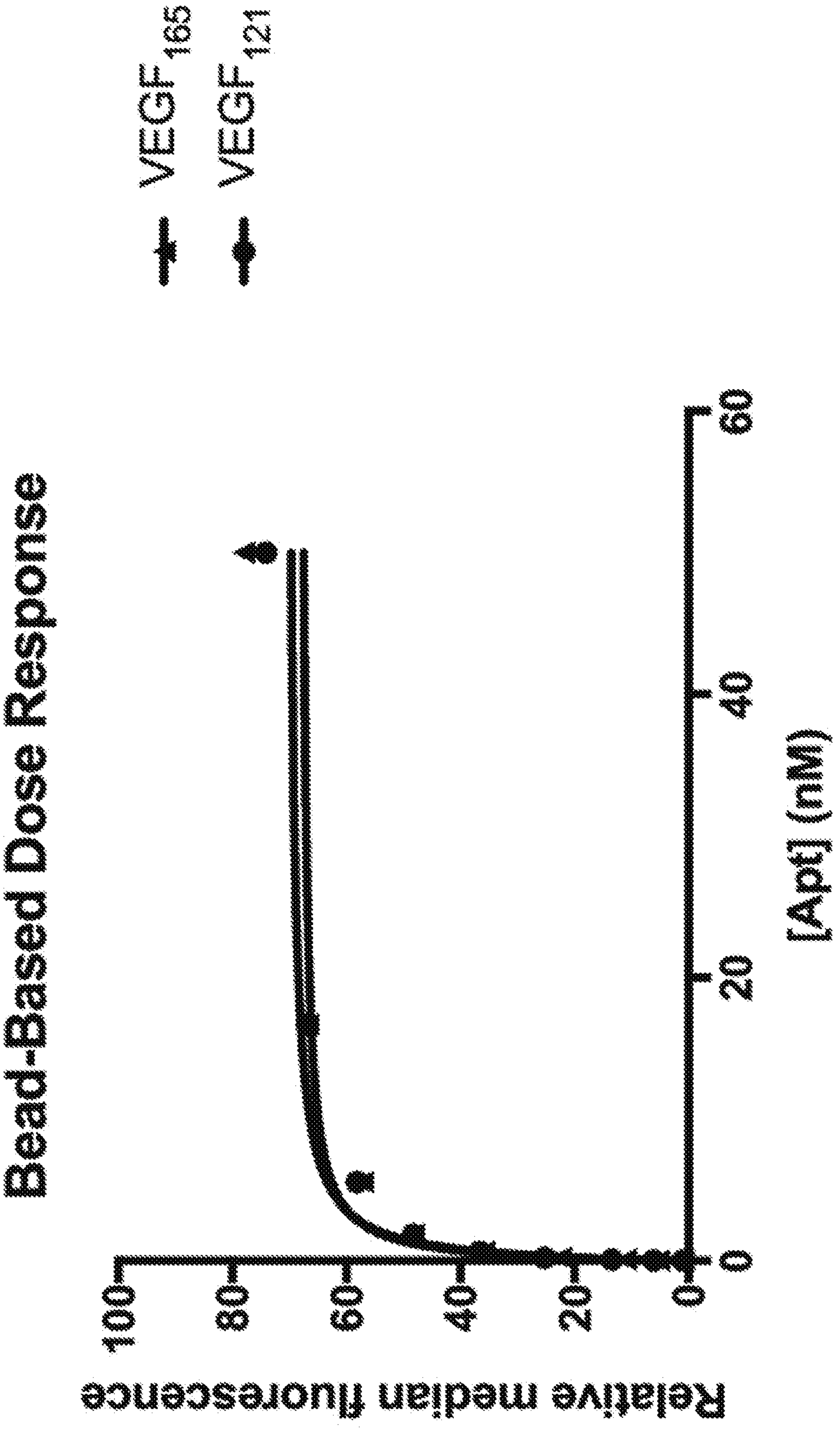
FIG. 3 depicts non-limiting examples of flow cytometry analysis of Aptamer 4.2 fluorescently labeled by chemical conjugation interacting with VEGF-$A_{165}$- and VEGF-$A_{121}$-functionalized beads in a dose-dependent fashion according to embodiments of the disclosure.

The enriched aptamer population from Round 7 was cloned into a TOPO TA vector, transformed into competent cells, and sequenced by Sanger sequencing. All in silico analyses were performed using Geneious software (Biomatters Inc., Newark N.J., USA). Of the 45 sequences identified, 10 were unique and all fell into a single family with one sequence representing 32 identical reads. The dominant sequence, Aptamer 4.2 (r7-01) was chemically synthesized with 2'-fluoro-G and 2'-O-methyl (2'OMe) A/C/U modified phosphoramidites along with a 3' inverted deoxythymidine and a 5' C6 disulfide linker, which was conjugated to Dylight® 650 maleimide (Table 4). The aptamer was purified by reversed phase high-performance liquid chromatography (HPLC) and assayed for activity in the flow cytometry assay described above. A dose response against beads bearing VEGF-$A_{121}$ or VEGF-$A_{165}$ demonstrated that Aptamer 4.2 was capable of binding to both isoforms (FIG. 3). Therefore, Aptamer 4.2 bound to a common epitope on multiple isoforms of VEGF-A, with VEGF-A recognition independent of the HBD. In combination with the bead binding results above for VEGF-$A_{110}$, the surface plasmon resonance binding data shown below in Example 2, and the receptor competition shown below in Example 3, these data support the notion that aptamers in this family of molecules bind to the VEGF-A RBD.

TABLE 4

Chemical synthesis and testing of Round 7 sequence

| SEQ ID NO | Aptamer Number | Back-bone | Sequence 5' to 3' | Binding 165 | Binding 121 |
|---|---|---|---|---|---|
| SEQ ID NO: 219 | Aptamer 4.2 | RNA | C6SS-AGGCCGCCUCCGCGCGGAGGGGUUUCAUUAUCCCGUUUGGCGGCUU-idT | + | + |

where G is 2'F; A, C, & U are 2'OMe modified RNA; C6SS is a disulfide linker; and idT is an inverted deoxythymidine residue.
+ indicates dose-dependent binding of the target

Example 1D. Deep Sequencing, Chemical Synthesis, and Assessment of VEGF-A Inhibition In order to gain deeper insight to the progression of the selection, the enriched libraries from Rounds 3-6 were sequenced using next-generation sequencing (NGS) to identify individual functional clones. Data from greater than 100,000 individual sequences per round were processed by trimming the flanking constant regions from the library. Aptamers with identical sequences were de-duplicated into stacks and annotated with frequency. Stacks were ranked by frequency within the libraries and organized into families by clustering aptamers with similar sequence relatedness using the MAFFT alignment algorithm. To a first approximation, the number of times a sequence occurs in a stack directly correlates with its molecular function; more functional molecules typically occur more times. Thus, the rank order of each stack can be thought of as a proxy for fitness. From an analysis of Rounds 5 and 6, clones related to r7-01 were selected for testing, chemically synthesized with 2'-fluoro-G and 2'-O-methyl (2'OMe) A/C/U modified phosphoramidites, purified by reversed phase HPLC, and desalted into nuclease-free $H_2O$ via buffer exchange before further analysis (Table 5).

Aptamer function was determined by assessing the ability to inhibit VEGF-$A_{165}$ and VEGF-$A_{121}$ induced KDR phosphorylation using a cell-based assay described in detail in Example 3. Of the 7 compounds assayed, 5 were able to inhibit KDR phosphorylation by both VEGF-$A_{165}$ and VEGF-$A_{121}$ (Table 5).

TABLE 5

A summary of the clones tested capable of inhibiting VEGF-A induced receptor phosphorylation

| SEQ ID NO | Aptamer Number | Back-bone | Sequence (5' to 3') | pKDR 165 | pKDR 121 |
|---|---|---|---|---|---|
| SEQ ID NO: 220 | Aptamer 26 | RNA | $C6NH_2$-UAGGCCGCCUCCGCGCGGAGGGGUUUCAUUAUCCCGUUUGGCGGCUUU-idT | ++ | + |
| SEQ ID NO: 221 | Aptamer 27 | RNA | $C6NH_2$-UAGGCCGCCUCCGCGCGGGGGGGUUUCAUUAUCCCGUUUGGCGGCUUU-idT | - | - |
| SEQ ID NO: 222 | Aptamer 28 | RNA | $C6NH_2$-UAGGCCGCCUCCGCGCGGUGGGGUUUCAUUAUCCCGUUUGGCGGCUUU-idT | ++ | - |
| SEQ ID NO: 223 | Aptamer 29 | RNA | $C6NH_2$-UAGUCCGCCUCCGCGCGGAGGGGUUUCAUUAUCCCGUUUGGCGGCUUU-idT | ++ | + |
| SEQ ID NO: 224 | Aptamer 30 | RNA | $C6NH_2$-UAGGCCGCCUCCGCGCGGAGGGGUUUCAUUUAUCCCGUUUGGCGGCUUU-idT | ++ | + |
| SEQ ID NO: 225 | Aptamer 31 | RNA | $C6NH_2$-UAGACCGCCUCCGCGCGGAGGGGUUUCAUUAUCCCGUUUGGCGGCUUU-idT | ++ | + |
| SEQ ID NO: 226 | Aptamer 32 | RNA | $C6NH_2$-UAGGCCGCCUCCGCGCGGAGGGGUUUCAUUAUCCCGUUUGGCGGCCUU-idT | ++ | + |

where G is 2'F; A, C, & U are 2'OMe modified RNA; $C6NH_2$ is a hexylainine linker; and idT is an inverted deoxythymidine residue.
++ indicates >50% inhibition at 10 nM; + indicates >50% inhibition at 100 nM, - indicates no inhibition at 100 nM Example 2. Binding Affinity and Confirmation of Pan-Specificity with Surface Plasmon Resonance To measure binding affinity of the identified aptamer and confirm its pan-specific binding to VEGF-A variants described in Example 1, SPR experiments were conducted against VEGF-$A_{165}$, VEGF-$A_{121}$, and VEGF-$A_{110}$ with Aptamer 26 (Table 5) as compared to a previously described HBD binding aptamer, Aptamer 7 (Table 6) (Ruckman, 1998). Aptamer 26 was identical in sequence to Aptamer 4.2 but contained a hexylamine linker in place of the C6 disulfide linker at the 5' terminus. Aptamer 7 has been demonstrated to bind directly to the HBD of VEGF-A at an epitope overlapping the binding site of the VEGF-$A_{165}$ co-receptor neuropilin-1 (Ruckman et al. 1998). Briefly, in the SPR studies, 1.0-2.5 μg/mL of glycan biotinylated VEGF-$A_{165}$, VEGF-$A_{121}$, and VEGF-$A_{110}$ were diluted in HEPES running buffer (10 mM HEPES, 137.5 mM NaCl, 5.7 mM KCl, 1 mM $MgCl_2$, 1 mM $CaCl_2$, and 0.05% Tween20; pH 7.4) and immobilized to a streptavidin dextran chip (GE Healthcare Life Sciences) for 1-2 minutes. The chip was then blocked with 0.2 mg/mL biotin in running buffer, followed by 3 cycles of buffer blanks and regenerated with 50 mM NaOH to equilibrate the chip. This resulted in 200-3000 RIU immobilized. After coating and blocking, samples were screened at 100 nM in duplicate injections at a flow rate of 25 μL/min, with an association time of 3 minutes 20 seconds and a dissociation time of 10 minutes. Regeneration conditions of chips were optimized based on the protein immobilized and effected with either 50 mM NaOH for 30 seconds or 2M guanidine HCl for 2×40 seconds. To determine binding affinities, aptamers were subsequently run in an 11-point, 2-fold dose response with Aptamer 26 starting at a top concentration of 1.0 μM, and Aptamer 7 starting at 500 nM.

TABLE 6

An anti-VEGF-A HBD aptamer

| SEQ ID NO | Aptamer Number | Back-bone | Sequence (5' to 3') |
|---|---|---|---|
| SEQ ID NO: 431 | Aptamer 7 | RNA | $C6NH_2$-fCmGmGAAgUfCmAmGfUmGmAmAfUmGfCfUfUmAfUmAfCmAfUfCfCmG-idT |

where mG and mA are 2'OMe modified RNA; fC and fU are 2'F modified RNA; $C6NH_2$ is a hexylamine linker; and idT is an inverted deoxythymidine residue Data was fit to a 1:1 kinetic binding model. Binding affinities were calculated based on these fits and are shown in Table 7. Results of the assay demonstrate that Aptamer 26 bound to all three variants of VEGF-A tested, whereas, consistent with the literature, Aptamer 7 only bound to VEGF-$A_{165}$. The affinity for Aptamer 7 to VEGF-$A_{165}$ as determined here was consistent with the literature reported value (Ruckman et al. 1998). This result provided further evidence that the selection effectively identified pan-specific anti-VEGF-A aptamers, which recognized an epitope of VEGF-A contained within the RBD. This differentiated the aptamers identified in the selection described herein from previously described aptamers to VEGF-A, such as Aptamer 7, which recognize an epitope of VEGF-A contained within the HBD, and thus do not bind the non-HBD bearing variants VEGF-$A_{110}$ and VEGF-$A_{121}$.

TABLE 7

Binding affinity (nM) of aptamers to VEGF-A variants as determined by SPR

| Aptamer | VEGF-$A_{165}$ | VEGF-$A_{121}$ | VEGF-$A_{110}$ |
|---|---|---|---|
| Aptamer 26 | 0.5 ± 0.2 | 4.6 ± 1.7 | 9.9 ± 3.5 |
| Aptamer 7 | 0.6 | no binding | no binding |

"No binding" means no change in signal observed at the highest concentration tested

Example 3. Characterization of Mechanisms of Interaction by VEGF-A:KDR Competition Binding The SPR data in Example 2 demonstrated that Aptamer 26 bound to the RBD of VEGF-A. To further define the epitope within the RBD of VEGF-A recognized by Aptamer 26, the mechanism of action of Aptamer 26 was interrogated by testing the ability of Aptamer 26 to directly inhibit KDR binding to either VEGF-$A_{165}$ or VEGF-$A_{121}$ as compared to a clone of an anti-VEGF-A antibody (Ferrara 2004 b) known to bind an epitope contained in the RBD that defines the receptor binding face of VEGF-A (SEQ ID NO: 432 and SEQ ID NO: 433, shown in Table 8), and as compared to Aptamer 7.

Briefly, the aptamers were heated at 90° C. for 3 minutes and allowed to cool to room temperature for a minimum of 10 minutes. Aptamers and anti-VEGF-A antibody were serial diluted in a polypropylene plate and 5 µL was transferred to a white low volume 384 well Optiplate (Perkin Elmer). A solution of VEGF-$A_{165}$ (Acro BioSystems) or VEGF-$A_{121}$ (Acro BioSystems) that was glycan biotinylated was prepared and added to the assay plate containing aptamers or anti-VEGF-A antibody to yield a final assay concentration of 2 nM. A mixture of human recombinant his-tagged KDR, (Sino Biological), AlphaLISA® nickel chelate acceptor beads (Perkin Elmer), and AlphaScreen® streptavidin donor beads (Perkin Elmer) was then prepared and 10 µL was added to the assay plate. The final concentrations of KDR and beads were 5 nM and 5 ug/mL, respectively. The assay plate was sealed and incubated in the dark for approximately 2 hours, after which it was read on a Biotek CYTATION™ 5 plate reader using the Alpha 384 well optical cube. The low signal control was determined using excess anti-VEGF-A inhibitor and the high signal control was determined by buffer only.

Percent inhibition for each sample was calculated by the following formula:

% inhibition=1−(sample−low control)/(high control−low control)*100

The values were fit by using a four-parameter non-linear fit in GraphPad Prism Version 7.0.

The results (FIG. 4A and FIG. 4B) demonstrate that Aptamer 26 and the anti-VEGF-A mAb directly block the interaction of VEGF-A (VEGF-$A_{165}$ or VEGF-$A_{121}$) with KDR. In contrast, despite its high affinity for VEGF-$A_{165}$ as provided in Example 2, Aptamer 7 shows no activity in this assay against VEGF-$A_{165}$, demonstrating that it does not directly inhibit the interaction between VEGF-A and its receptor. As expected, given the lack of interaction between Aptamer 7 and VEGF-$A_{121}$. Aptamer 7 also showed no inhibition of the interaction between this variant of VEGF-A and KDR. Aptamer 26 blocked the interaction of VEGF-$A_{165}$ with KDR with an $IC_{50}$ of 3.7±2.4 nM and the interaction of VEGF-$A_{121}$ with KDR with an $IC_{50}$ of 19±19 nM, consistent with the affinity of Aptamer 26 for the respective VEGF-A variants. Similarly, the anti-VEGF mAb also inhibited the interaction of VEGF-$A_{165}$ and VEGF-$A_{121}$ with an $IC_{50}$ of 0.71±0.48 nM and 0.63±0.22 nM, respectively, consistent with its affinity for these VEGF-A variants.

Figure 4A:
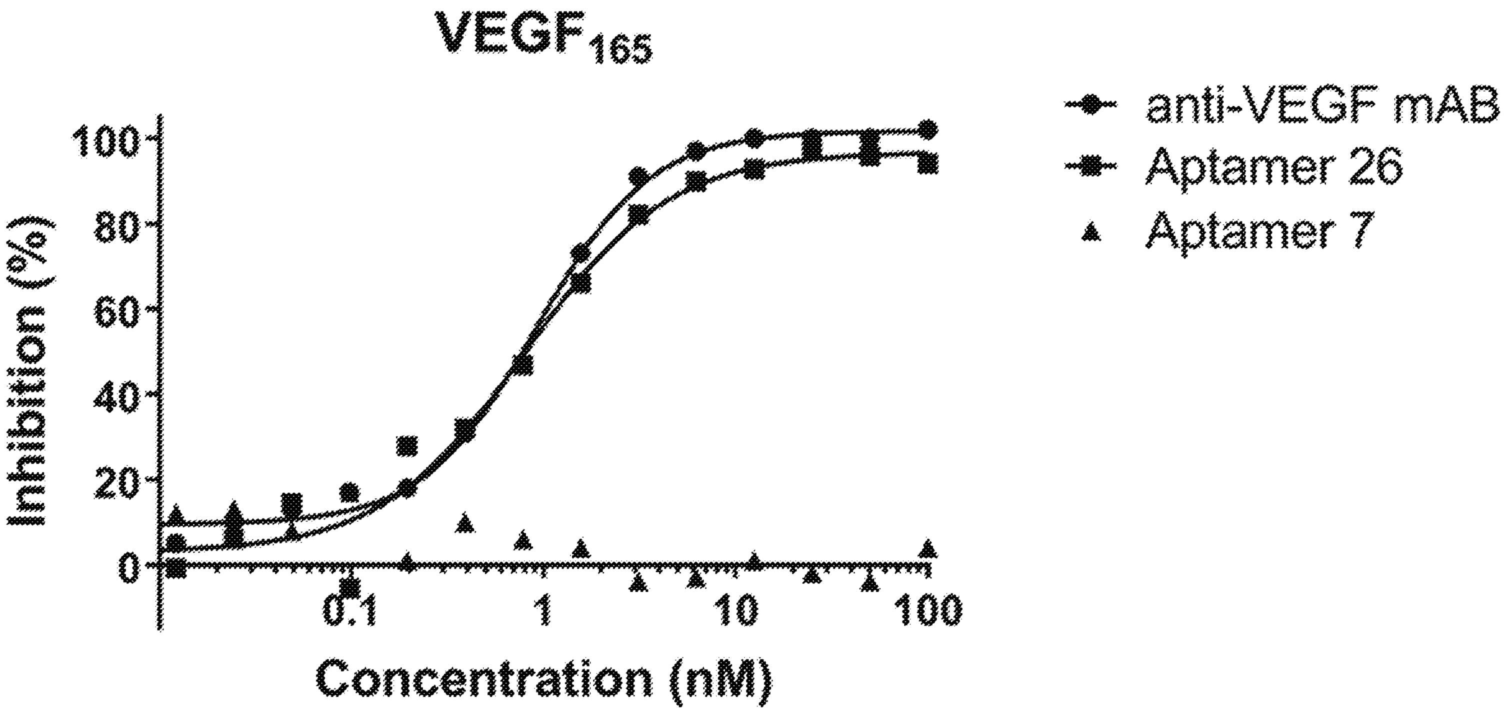
FIG. 4A depicts non-limiting examples of inhibition of VEGF-$A_{165}$ binding to KDR by Aptamer 26, compared to Aptamer 7 or an anti-VEGF-A mAb. Compounds were tested in a dose-dependent fashion to determine an $IC_{50}$ against each isoform according to embodiments of the disclosure.
Figure 4B:
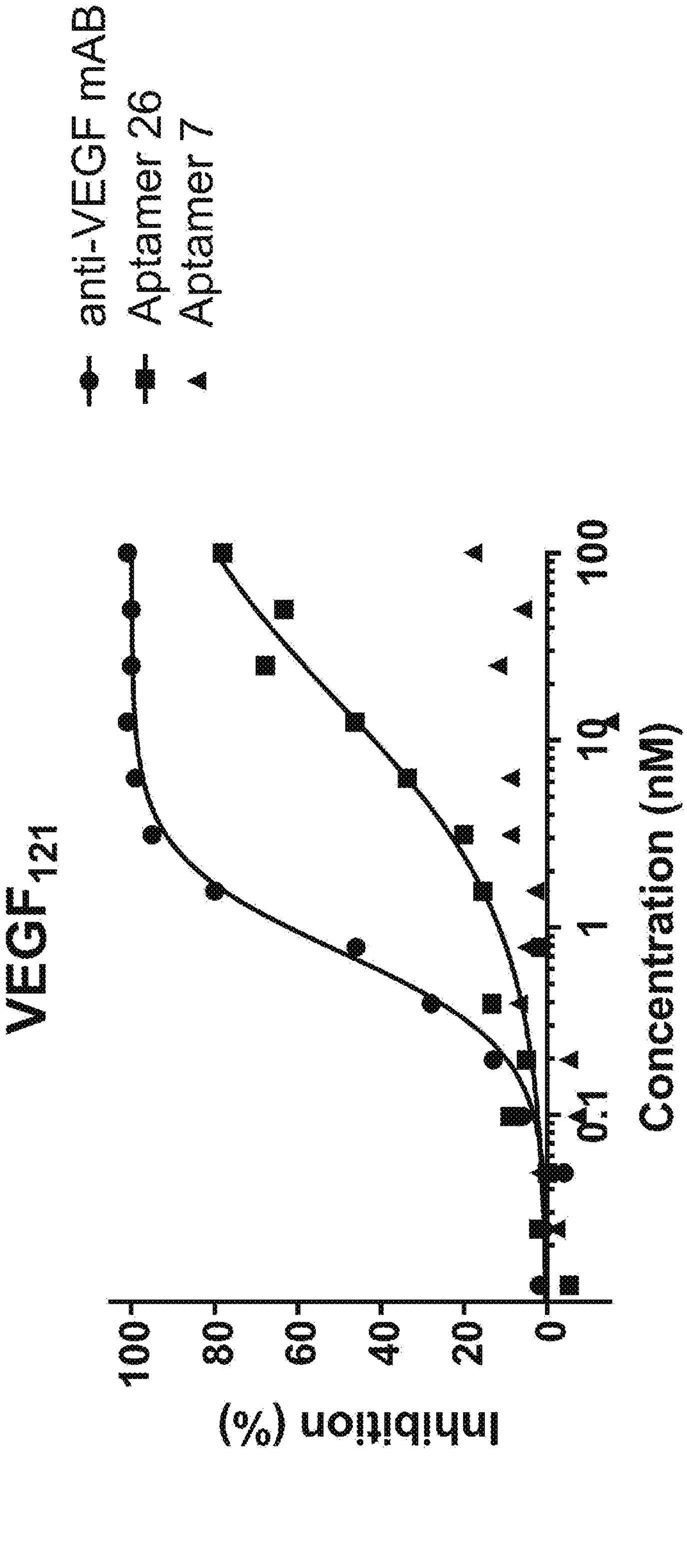
FIG. 4B depicts non-limiting examples of inhibition of VEGF-$A_{121}$ binding to KDR by Aptamer 26, compared to Aptamer 7 or an anti-VEGF-A mAb. Compounds were tested in a dose-dependent fashion to determine an $IC_{50}$ against each isoform according to embodiments of the disclosure.

The data presented in FIG. 4A and FIG. 4B demonstrated that Aptamer 26 bound to an epitope consisting of, or overlapping with, the receptor binding face contained within the RBD of VEGF-A, and thus directly blocked the interaction of VEGF-A with its cognate receptor. The absence of inhibition of the interaction of VEGF-$A_{165}$ with KDR by Aptamer 7 is consistent with the literature, which demonstrates that this aptamer engages VEGF-A by binding to an epitope within the HBD and does not directly block binding of VEGF-A to its receptor, KDR (Ruckman, 1998; Lee 2005; Ng, 2006). The lack of inhibition of VEGF-$A_{121}$ activity by Aptamer 7 is consistent with the SPR binding data described in Example 2 and the published literature (Ruckman, 1998).

TABLE 8

Anti-VEGF-A mAb

| SEQ ID NO | Name | Type | Sequence (N to C terminus) |
|---|---|---|---|
| SEQ ID NO: 432 | Light Chain | Protein | DIQMTQSPSSLSASBGDRVTITCSASQDISNYLNWYQQKPGK APKVLIYFTSSLHSGVPSRFSGSGSGTDFTLTISSLQPEDFATY YCQQYSTVPWTFGQGTKVEIKRTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRG EC |
| SEQ ID NO: 433 | Heavy Chain | Protein | EVQLVESGGGLVQPGGSLRLSCAASGYTFTNYGMNWVRQAP GKGLEWVGWINTYTGEPTYAADFKRRFTFSLDTSKSTAYLQ MNSLRAEDTAVYYCAKYPHYYGSSHWYFDVWGQGTLVTVS |

TABLE 8-continued

| Anti-VEGF-A mAb | | | |
|---|---|---|---|
| SEQ ID NO | Name | Type | Sequence (N to C terminus) |
| | | | SASTKGPSVFPLAPSSKSTSGGTAALGCLVKDYFPEPVTVSWN SGALTSKVHTFPAVLQSSGLYSLSSVVTVPSSSLGTQTYICNV NHKPSNTKVDKKVEPKSCDKTHTCPPCPAPELLGGPSVFLFPP KPKDTLMISRTPEVTCVVVDVSHEDPEVKFNWYVDGVEVHN AKTKPREEQYNSTYRVVSVLTVLHQDWLNGKEYKCKVSNK ALPAPIEKTISKAKGQPREPQVYTLPPSREEMTKNQVSLTCLV KGFYPSDIAVEWESNGQPENNYKTTPPVLDSDGSFFLYSKLT VDKSRWQQGNVFSCSVMHEALHNHYTQKSLSLSPGK |

Example 4. Characterization of Inhibition of VEGF-A Signal Transduction by KDR Phosphorylation AlphaLisa®

When the RBD of VEGF-A binds to KDR, the receptor dimerizes leading to trans-autophosphorylation and activation of VEGF-A signaling. To determine if Aptamer 26 binding to the RBD of VEGF-A resulted in inhibition of VEGF-A activity, Aptamer 26 was tested for its ability to inhibit KDR phosphorylation induced by either VEGF-$A_{165}$ or VEGF-$A_{121}$ as compared to a clone of an anti-VEGF-A antibody (Ferrara 2004 b) (SEQ ID NO: 432 and SEQ ID NO: 433, shown in Table 8), and as compared to Aptamer 7 for inhibition of VEGF-$A_{165}$-induced KDR phosphorylation.

Briefly, HEK293 cells engineered to stably overexpress KDR were plated overnight in collagen coated 96 well plates at 50 k cells/well. Aptamers in SB1+ (40 mM HEPES, pH 7.5, 125 mM NaCl, 5 mM KCl, 1 mM $MgCl_2$) were heated to 90° C. for 3 minutes and allowed to cool to room temperature for a minimum of 10 minutes. VEGF-$A_{121}$ (Biolegend) and VEGF-$A_{165}$ (R&D Systems) were prepared at 12.5 nM in DMEM+0.8% FBS, a 20× stock for the reaction. 15 μL of VEGF-A was added to 15 μL titrated aptamer in a polypropylene plate and diluted to 300 μL with TS buffer (10 mM Tris pH 7.5; 100 mM NaCl; 5.7 mM KCl; 1 mM $MgCl_2$; 1 mM $CaCl_2$). The aptamer/VEGF-A mixture was incubated at 37° C. for 30 minutes, after which 100 μL was added to the cells for 5 minutes at 37° C. in 5% $CO_2$. Treatments were aspirated from cells, and cells were lysed with 100 μL cold lysis buffer [20 mM Tris-HCl, pH 7.5, 150 mM NaCl, 1 mM EDTA, 1% Triton X-100, 0.5 mM sodium orthovanadate (freshly prepared), 1 mM PMSF (freshly prepared), lx protease inhibitor cocktail (freshly prepared)] on ice for 10 minutes. Plates were centrifuged at 4000×g for 10 minutes before transferring the cell lysis to the AlphaLISA® assay plate.

To perform the AlphaLISA® assay, 10 μL of cell lysis was transferred to a white low volume 384 well Optiplate (Perkin Elmer). A mixture of the following components was made in order of which they are listed: 1.25 nM anti-hVEGFR2 polyclonal goat IgG antibody (R&D Systems), 10 μg/ml AlphaLISA® anti-goat IgG acceptor beads (Perkin Elmer), 1.25 nM P-tyrosine biotinylated mouse mAb (Cell Signaling Technology), and 10 μg/ml AlphaScreen® streptavidin donor beads (Perkin Elmer). 10 μL of this reagent mixture was added to the assay plate that contained 10 μL of cell lysate. The assay plate was sealed and incubated in the dark for approximately 2 hours, then was read on a Biotek CYTATION™ 5 plate reader using the Alpha 384 well optical cube. Percent inhibition was calculated by subtracting TS buffer background from each value and normalizing to VEGF-A only controls. The values were fit by using a four-parameter non-linear fit in GraphPad Prism Version 7.0.

Figure 5A:
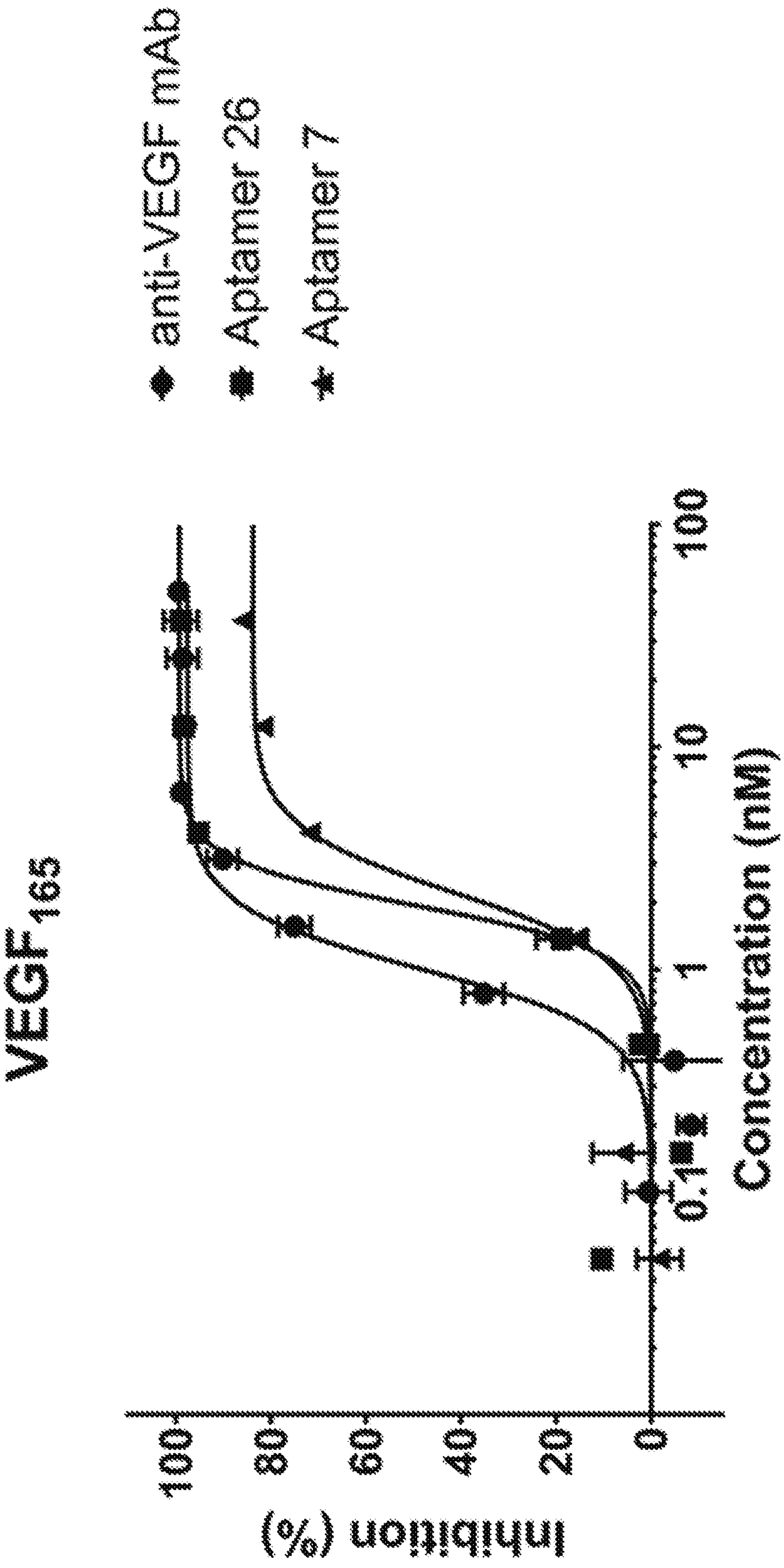
FIG. 5A depicts non-limiting examples of inhibition of VEGF-$A_{165}$-stimulated KDR phosphorylation by Aptamers 26, compared to Aptamer 7 or an anti-VEGF-A mAb. Compounds were tested in a dose-dependent fashion to determine an $IC_{50}$ against each isoform according to embodiments of the disclosure.
Figure 5B:
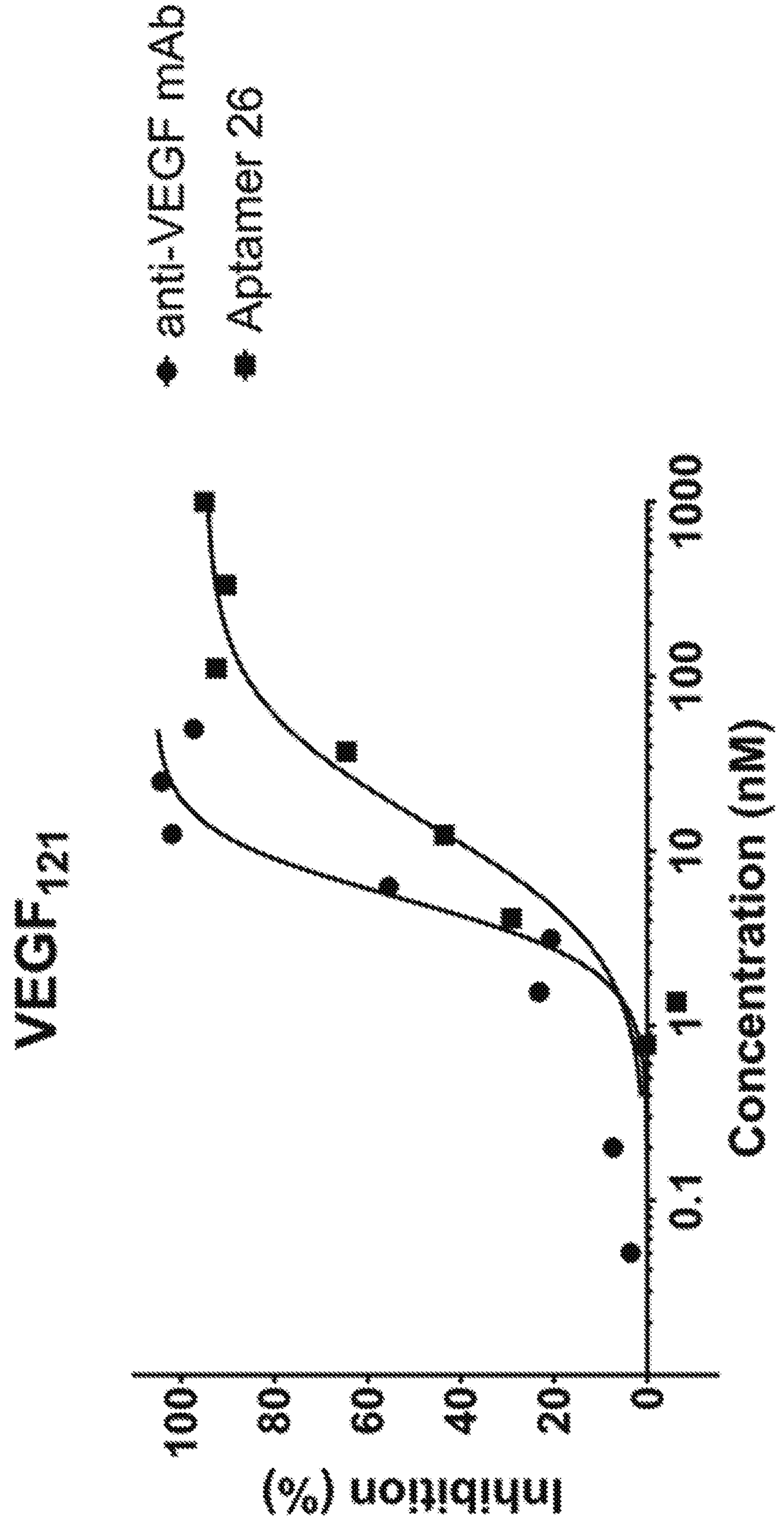
FIG. 5B depicts non-limiting examples of inhibition of VEGF-$A_{121}$-stimulated KDR phosphorylation by Aptamer 26, compared an anti-VEGF-A mAb. Compounds were tested in a dose-dependent fashion to determine an $IC_{50}$ against each isoform according to embodiments of the disclosure.

The results demonstrated that Aptamer 26 and the anti-VEGF-A mAb achieved full inhibition of the phosphorylation of KDR by inhibiting its interaction with VEGF-$A_{165}$ or VEGF-$A_{121}$ (FIG. 5A and FIG. 5B). Consistent with their measured affinities for VEGF-$A_{165}$ and VEGF-$A_{121}$, calculated $IC_{50}$ values for Aptamer 26 were 1.5±0.6 nM and 20±5.2 nM, and for the anti-VEGF-A mAb 1.1±0.20 nM and 2.8±1.7 nM, respectively, for inhibition of phosphorylation of KDR by VEGF-$A_{165}$ or VEGF-$A_{121}$. Conversely, Aptamer 7 only partially inhibited phosphorylation of KDR by VEGF-$A_{165}$ (maximum inhibition of ~80%), with an $IC_{50}$ of 2.2 nM (FIG. 5A and FIG. 5B).

The potency and complete inhibition of VEGF-$A_{165}$ or VEGF-$A_{121}$ induced phosphorylation of KDR by Aptamer 26, and its comparable activity profile to an anti-VEGF-A mAb, was consistent with the ability of Aptamer 26 to bind to the receptor binding face present within the RBD of VEGF-A and directly block the interaction between VEGF-A and KDR. The partial inhibition of VEGF-$A_{165}$-induced phosphorylation of KDR by Aptamer 7 was consistent with indirect inhibition of KDR phosphorylation via blocking the interaction of neuropilin-1 with VEGF-$A_{165}$ (Soker, 1998). This result supported the conclusion that binding of Aptamer 26 to the receptor binding face within the RBD of VEGF-A variants confers inhibition of VEGF-A signaling. Further, these results differentiated the mechanism of action of Aptamer 26 from previously described HBD binding aptamers such as Aptamer 7.

Example 5. Secondary Selection of a VEGF-A Inhibiting Aptamer

To further define the secondary structure of the active aptamer, as well as to potentially identify VEGF-A aptamers with increased potency, secondary selections were performed utilizing a partially randomized library based on Aptamer 26 (85% of the parental sequence+5% of the other three nucleotides at each position within the aptamer). The library sequence and the sequence of oligos used to amplify the library are described in Table 9.

TABLE 9

Library sequence and sequence of oligos used to amplify the degenerate library

| SEQ ID NO. | Sequence (5' to 3') |
|---|---|
| SEQ ID NO: 434 Doped library sequence (Total library length: 89 bases) | GGGAGAGTCGGTAGCATACT-**AGGCCGCCTCCGCGCGGAGGGGTTTCATTATCCCGTTTGGCGGCTT**-TGATACTTGATCGCCCTAGAAGC |
| SEQ ID NO: 435 Dope.F24 | P-GGGAGAGTCGGTAGCATACT |
| SEQ ID NO: 430 N30S.R | GCTTCTAGGGCGATCAAGTATCA |

where A, C, G and T are deoxyribonucleondes and P-denotes a phage polymerase promoter.
Bold denotes doped positions where the indicated parent nucleotide comprises 85% of the phosphoramidite mix and each of the other 3 nucleotides account for 5%.

Six rounds of selection were conducted against VEGF-$A_{110}$. The progress of the selection was monitored by flow cytometry to ensure the enrichment for function (data not shown).

Library DNA from Round 1 through Round 6 were barcoded, pooled, and sequenced on a MiniSeq high throughput sequencer (Illumina), which yielded approximately 400,000 sequences per round. Sequences were trimmed to remove constant regions from the 5' and 3' ends, leaving the core 30 nucleotide region from the library and the terminal 8 base pair stem.

Identical sequences were de-duplicated to form stacks of identical sequences. The resultant stacks were then rank ordered based on the total number of sequences within each stack. To a first approximation, the number of times a sequence occurs in a stack directly correlates with molecular function: more functional molecules typically occur more times. Thus, the rank order of each stack can be thought of as a proxy for fitness.

Alignment of the top 250 stacks for Aptamer 26, which represented ~185,000 de-duplicated sequences and corresponded to the top performing ~40% of the selected population from Round 6 of the secondary selection, revealed a significant level of conservation in the identity of each nucleotide within the aptamer family. Most positions displayed conservation levels >90% (FIG. 6), with half of the positions proving to be invariant (conservation=100%). Close examination of these stacks strongly supported the predicted stem loop secondary structure (FIG. 7).

Example 6. Sequence Analysis for Degenerate Selection of Aptamer 26

Figure 7:
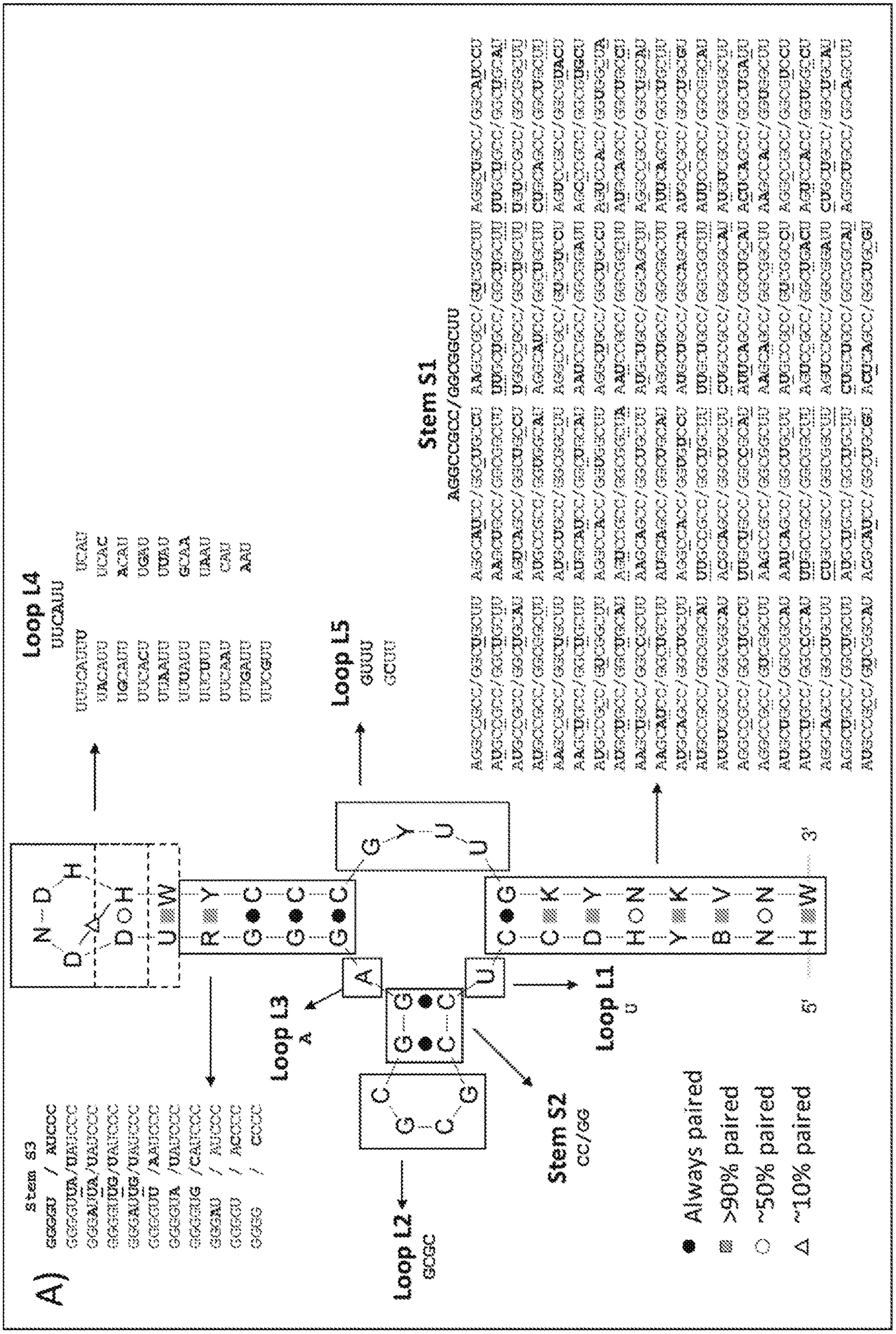
FIG. 7 depicts an exemplary secondary structure and consensus sequence for the top 250 stacks of sequences from the degenerate selection along with sequence variations observed within each domain of the aptamer. Dashed boxes indicate the variable lengths of stem S3 and loop L4. The statistics for the frequency of observed base pairing at each position are as indicated.

Comparison of the top 250 stacks revealed that the enriched sequences readily adopted a stem loop structure consistent with the secondary structure shown in FIG. 7. Such a structure may comprise a terminal stem S1 that may be connected to the 5' terminal end of loop L1. Loop L1 may be connected to the 3' terminal end of stem S1 and the 5' terminal end of stem S2. Stem S2 may be connected to the 3' terminal end of loop L1 and the 5' terminal end of loop L2. Loop L2 may be connected to the 3' terminal end of stem S2 and the 5' terminal end of the complementary region of stem S2. The complementary region of stem S2 may be connected to the 3' terminal end of loop L2 and the 5' terminal end of loop L3. Loop L3 may be connected to the 3' terminal end of the complementary region of stem S2 and the 5' end of stem S3. Stem S3 may be connected to the 3' terminal end of loop L3 and the 5' terminal end of loop L4. Loop L4 may be connected to the 3' terminal end of stem S3 and the 5' terminal end of the complementary region of stem S3. The complementary region of stem S3 may be connected to the 3' end of loop L4 and the 5' end of loop L5. Loop L5 may be connected to the 3' terminal end of the complementary region of stem S3 and the 5' terminal end of the complementary region of stem S1. The complementary region of stem S1 may be connected to the 3' terminal end of loop L5.

A comparison of sequences observed in stem S1 are shown in Table 10. These data provide additional support of the formation of Stem 1, as indicated by the sequence covariation in this region. In some cases, stem S1 contained one, two or three mismatched nucleotides. In some cases, the mismatched nucleotides were adjacent to each other. In some cases, the mismatched nucleotides were separated by one, two, or three base pairs. In some cases, stem S1 was composed of two to eight contiguous base pairs that ended in a base pair at positions 8 and 39. As depicted in FIG. 6, positions 8 and 39 were 100% conserved and formed a C:G pair that closed stem S1 adjacent to loop L1 and loop L5. In some cases, the base pair between positions 8 and 39 (8/39) was separated from other contiguous base pairs in stem S1 by mismatched nucleotides at positions 7 and 40 (7/40). In some cases, the preferred length of the contiguous run within stem S1 that ends in a base pair at positions 8 and 39 was three base pairs.

In some cases, stem S1 contained a mismatch at positions 5 and 42, demonstrated by a preference for conversion from G in the parent sequence to a U in approximately 69% of the sequences represented in the top 250 stacks (FIG. 6). The introduction of the mispairing in the middle of stem S1 suggested the possibility that truncation may be favorable. Together, these data suggested that the consensus sequence was 5'-HNBYHDCC-3' for the 5' side of the stem. The consensus sequence for the 3' complementary side of stem S1 was 5'-GKYNKVNW-3', where Y is C or U; W is A or U; K is G or U; B is C, G or U; D is A, G or U; H is A, C, or U; V is A, C, or G; and N is A, C, G, or U.

TABLE 10

Doped selection sequence variation observed in stem S1 (S1) (Full sequences and truncated sequences are described in Table 1).

| | Sequence (5' to 3') | | Sequence (5' to 3') |
|---|---|---|---|
| Aptamer 26 | AGGCCGCC/GGCGGCUU | R6-92 | ACGCAUCC/GGCUGCGU |
| R6-1 | AGGCCGCC/GGCUGCUU | R6-101 | AAGCCGCC/GUCGGCUU |
| R6-2 | AUGCCGCC/GGCUGCUU | R6-102 | UUGCUGCC/GGCUGCUU |
| R6-3 | AUGCCGCC/GGCUGCAU | R6-104 | UGGCCGCC/GGCUGCUU |
| R6-4 | AUGCCGCC/GGCGGCUU | R6-115 | AGGCAUCC/GGCUGCUU |
| R6-7 | AAGCCGCC/GGCUGCUU | R6-116 | AGGCCGCC/GUCGUCCU |
| R6-8 | AAGCUGCC/GGCUGCUU | R6-123 | AAUCCGCC/GGCGGAUU |
| R6-12 | AUGCCGCC/GUCGGCUU | R6-124 | AGGCUGCC/GGCUGCCU |
| R6-13 | AUGCUGCC/GGCUGCAU | R6-130 | AAUCCGCC/GGCGGCUU |
| R6-14 | AAGCUGCC/GGCCGCUU | R6-134 | AUGCUGCC/GGCAGCUU |
| R6-16 | AAGCAUCC/GGCUGCUU | R6-135 | AGGCUGCC/GGCGGCUU |
| R6-17 | AUGCAGCC/GGCUGCUU | R6-138 | AUGCUGCC/GGCAGCAU |
| R6-18 | AUGCCGCC/GGCGGCAU | R6-145 | UUGCUGCC/GGCGGCUU |
| R6-19 | AUGUCGCC/GGCGGCAU | R6-152 | CUGCCGCC/GGCGGCAU |
| R6-20 | AGGCCGCC/GGCUGCCU | R6-153 | AUUCAGCC/GGCUGCAU |
| R6-21 | AGGCCGCC/GUCGGCUU | R6-157 | AAGCAGCC/GGCGGCUU |
| R6-22 | AUGCUGCC/GGCGGCAU | R6-162 | AUGCCGCC/GUCGGCCU |
| R6-25 | AUGCUGCC/GGCCGCAU | R6-166 | AGUCCGCC/GGCUGACU |
| R6-31 | AGGCAGCC/GGCUGCUU | R6-169 | AGUCCGCC/GGCGGAUU |
| R6-34 | AGGCUGCC/GGCUGCUU | R6-170 | CUGCUGCC/GGCGGCAU |
| R6-36 | AUGCCGCC/GUCGGCAU | R6-171 | ACUCAGCC/GGCUGCGU |
| R6-39 | AGGCAUCC/GGCUGCCU | R6-172 | AGGCUGCC/GGCAUCCU |
| R6-42 | AAGCUGCC/GGCGGCUU | R6-173 | UUGCUGCC/GGCUGCAU |
| R6-45 | AGUCAGCC/GGCUGCCU | R6-177 | UGUCCGCC/GGCGGCUU |
| R6-48 | AUGCCGCC/GGUGGCAU | R6-178 | CUGCAGCC/GGCUGCUU |
| R6-49 | AUGCUGCC/GGCGGCUU | R6-179 | AGUCCGCC/GGCGUACU |
| R6-50 | AUGCAUCC/GGCUGCAU | R6-181 | AGCCCGCC/GGCGUGCU |
| R6-53 | AGGCCACC/GGUGGCUU | R6-182 | AGUCCACC/GGUGGCUA |
| R6-54 | AGUCCGCC/GGCGGCUA | R6-197 | AUGCAGCC/GGCUGCCU |
| R6-57 | AAGCAGCC/GGCUGCUU | R6-198 | AGGCCGCC/GGCUGCAU |
| R6-58 | AUGCAGCC/GGCUGCAU | R6-201 | AUUCAGCC/GGCUGCUU |
| R6-67 | AGGCCACC/GGUGUCCU | R6-203 | AUGCCGCC/GGCUGCGU |
| R6-70 | UUGCCGCC/GGCUGCUU | R6-204 | AUUCCGCC/GGCGGCAU |
| R6-72 | ACGCAGCC/GGCUGCUU | R6-205 | AUGUCGCC/GGCGGCUU |
| R6-76 | UUGCUGCC/GGCCGCAU | R6-208 | ACUCAGCC/GGCUGAUU |
| R6-79 | AAGCCGCC/GGCGGCUU | R6-210 | AAGCCACC/GGUGGCUU |
| R6-80 | AAUCAGCC/GGCUGCUU | R6-214 | AGGCCGCC/GGCGUCCU |

TABLE 10-continued

| Doped selection sequence variation observed in stem S1 (S1) (Full sequences and truncated sequences are described in Table 1). | | | |
|---|---|---|---|
| | Sequence (5' to 3') | | Sequence (5' to 3') |
| R6-83 | **UU**GCCGCC/GGCGGCUU | R6-221 | AG**U**CC**A**CC/GG**U**GGC**C**U |
| R6-85 | **CU**GCCGCC/GGCGGCUU | R6-227 | **CU**GC**U**GCC/GGC**U**GC**A**U |
| R6-88 | A**U**GC**U**GCC/GGC**U**GCUU | R6-241 | AGGC**U**GCC/GGC**A**GCUU |

Differences from the parent (Aptamer 26) stem Si are denoted in bold. Unpaired residues are underlined.

The identity of loop L1 was found to be 100% conserved across the top 250 stacks of sequences analyzed in the doped selection (FIG. 6). Thus, the nucleotide sequence of loop L1 was 5'-U-3'.

The identity of stem S2 was found to be 100% conserved across the top 250 stacks of sequences analyzed in the doped selection (FIG. 6). Thus, the nucleotide sequence of stem S2 was 5'-CC/GG-3'.

The identity of loop L2 was found to be 100% conserved across the top 250 stacks of sequences analyzed in the doped selection (FIG. 6). Thus, the nucleotide sequence of loop L2 was 5'-GCGC-3'.

The identity of loop L3 was found to be 100% conserved across the top 250 stacks of sequences analyzed in the doped selection (FIG. 6). Thus, the nucleotide sequence of loop L3 was 5'-A-3'.

A comparison of sequences observed in stem S3 suggested that the preferred length of stem S3 was four, five, or six base pairs. When stem S3 was six base pairs in length, the 5' side of the stem may be seven nucleotides in length. As such, the six base pair stem S3 may contain a single mis-match at the penultimate nucleotide in the 5' side of the stem. These data provided additional support of the formation of stem S3, as indicated by the sequence covariation in this region (Table 11). The variation between four, five, and six base pairs in stem S3 directly related to the variation of loop L4 between eight, six, four and three nucleotides. When stem S3 was four base pairs in length, loop L4 was eight nucleotides in length. When stem S3 was five base pairs in length, loop L4 was six nucleotides in length. When stem S3 was six base pairs in length, loop L4 was four nucleotides in length. When stem S3 was six base pairs in length and contained a mismatch, loop L4 was three nucleotides in length.

Together, these data suggested that the consensus sequence of stem S3 for all variants observed with the top 250 stacks of Aptamer 26 was 5'-GGGRUD-3' for the 5' side of stem S3 and 5'-HWYCCC-3' for the 3' side of stem S3, where R is A or U; D is A, G, or U; H is A, C, or U; W is A or U; and Y is C or U. In some cases, when stem S3 was four base pairs, the consensus sequence was 5'-GGGG-3' for the 5' side of stem S3 and 5'-CCCC-3' for the 3' side of stem S3. In some cases, when stem S3 was 5 base pairs, the consensus sequence was 5'-GGGRU-3' for the 5' side of stem S3 and 5'-AYCCC-3' for the 3' side, where R is A or G; and Y is C or U. In some cases, when stem S3 was six base pairs, the consensus sequence was 5'-GGGGUD-3' for the 5' side of stem S3 and 5'-HAUCCC-3' for the 3' side, where D is A, G or U; and H is A, C, or U. In some cases, when stem S3 was six base pairs long and contained a single mis-matched nucleotide, the consensus was 5'-GGGRUUR-3' for the 5' side of stem S3 and 5'-UAUCCC-3' for the 3' side, where the underlined U is the single mis-matched nucleotide; and R is A or G.

TABLE 11

| Doped selection sequence variation observed in stern S3 (Full sequences and truncated sequences are described in Table 1). | |
|---|---|
| | Sequence (5' to 3') |
| Aptamer 26 | GGGGU/AUCCC |
| R6-9 | GGGGU**UA**/**U**AUCCC |
| R6-33 | GGG**A**U**UA**/**U**AUCCC |
| R6-43 | GGGGU**UG**/**U**AUCCC |
| R6-68 | GGG**A**U**UG**/**U**AUCCC |
| R6-5 | GGGGU**U**/**A**AUCCC |
| R6-6 | GGGGU**A**/**U**AUCCC |
| R6-61 | GGGGU**G**/**C**AUCCC |
| R6-1 | GGG**A**U/AUCCC |
| R6-65 | GGGGU/A**C**CCC |
| R6-62 | GGGG/**C**CCC |

Differences from the parent (Aptamer 26) stem S3 are denoted in bold.

A comparison of sequences observed in loop L4 suggested that the preferred length of loop L4 was eight, six, four, or three nucleotides (Table 12). The variation between eight, six, four and three nucleotides in loop L4 directly related to the variation in the length of stem S3 between four, five, six base pairs, or six base pairs and a single mismatch. Together, these data suggested that when loop L4 was three nucleotides in length, the consensus sequence for loop L4 was 5'-MAU-3', where M is A or C. When loop L4 was four nucleotides in length, the consensus sequence for loop L4 was 5'-DNAH-3', where D is A, G or U; H is A, C, or U; and N is A, C, G, or U. In some cases, when loop L4 was six nucleotides in length, the consensus sequence for loop L4 was 5'-UDNDHU-3', where D is A, G or U; H is A, C, or U; and N is A, C, G, or U. In some cases, when loop L4 was eight nucleotides in length, the consensus sequence for loop L4 was 5'-UUUCAUUU-3'.

TABLE 12

Doped selection sequence variation observed in loop L4 (Full sequences and truncated sequences are described in Table 1).

| | Sequence (5' to 3') | | Sequence (5' to 3') |
|---|---|---|---|
| Aptamer 26 | UUCAUU | R6-186 | UUC**G**UU |
| R6-62 | UUUCAUUU | R6-5 | UCAU |
| R6-27 | U**A**CAUU | R6-24 | UCA**C** |
| R6-43 | U**G**CAUU | R6-29 | **A**CAU |
| R6-75 | UUCA**C**U | R6-117 | U**GA**U |
| R6-99 | UU**A**AUU | R6-200 | U**UA**U |
| R6-110 | UU**U**AUU | R6-228 | **GCAA** |
| R6-119 | UUC**U**UU | R6-229 | U**AA**U |
| R6-131 | UUCA**A**U | R6-9 | CAU |
| R6-142 | UU**G**AUU | R6-211 | **A**AU |

Differences from the parent (Aptamer 26) loop L4 are denoted in bold.

A comparison of sequences observed in loop L5 suggested that the preferred length of loop L5 was four bases (Table 13). Together, these data suggest the consensus sequence for loop L5 was 5'-GYUU-3', where Y is C or U.

TABLE 13

Doped selection sequence variation observed in loop L5 (Full sequences and truncated sequences are described in Table 1).

| | Sequence (5' to 3') |
|---|---|
| Aptamer 26 | GUUU |
| R6-139 | G**C**UU |

Differences from the parent (Aptamer 26) loop L5 are denoted in bold.

Using the data from the degenerate selection, the consensus sequence for all sequence variants within the top 250 stacks of the Aptamer 26 family of sequence members was 5'-HNBYHDCC-U-CC-GCGC-GG-A-GGGRUD-DNDH-HWYCCC-GYUU-GKYNKVNW-3' (SEQ ID NO: 1), where H is A, C, or U; N is A, C, G, or U; B is C, G, or U; Y is C or U; D is A, G, or U; R is A or G; W is A or U; K is G or U; and V is A, C, or G; and is represented with a six base pair stem S3 and a four nucleotide loop L4 in FIG. 7. The alternate pairings of stem S3 and loop L4 are highlighted by dashed boxes. When stem S3 was five base pairs and loop L4 was six nucleotides in length, the consensus sequence for the Aptamer 26 family of sequence members was 5'-HNBYHDCC-U-CC-GCGC-GG-A-GGGRU-UDNDHU-AYCCC-GYUU-GKYNKVNW-3' (SEQ ID NO: 2), where H is A, C, or U; N is A, C, G, or U; B is C, G, or U; Y is C or U; D is A, G, or U; R is A or G; K is G or U; V is A, C, or G; and W is A or U. When stem S3 was six base pairs and loop L4 was four nucleotides in length, the consensus sequence for the Aptamer 26 family of sequence members was 5'-WNKYHDCC-U-CC-GCGC-GG-A-GGGGUD-DNAH-HAUCCC-GUUU-GGYBKMHW-3' (SEQ ID NO: 3), where W is A or U; N is A, C, G, or U; K is G or U; Y is C or U; H is A, C, or U; D is A, G, or U; B is C, G, or U; and M is A or C. When stem S3 was four base pairs and loop L4 was eight nucleotides in length, the consensus sequence for the Aptamer 26 family of sequence members was 5'-AUGCCGCC-U-CC-GCGC-GG-A-GGGG-UUUCAUUU-CCCC-GUUU-GGCUGCAU-3' (SEQ ID NO: 4).

FIG. 7 also depicts the motif variations for each structural element (e.g., stem S1, loop L1, stem S2, loop L2, loop L3, stem S3, loop L4, loop L5) observed within the top 250 sequence stacks from the selection. By combining the provided motifs in the proper order for the respective structural elements of this aptamer family, one can assemble extant or novel Aptamer 26-like variants with anti-VEGF-A activity.

Example 7. Linker Scanning Aptamer 26

Figure 8:
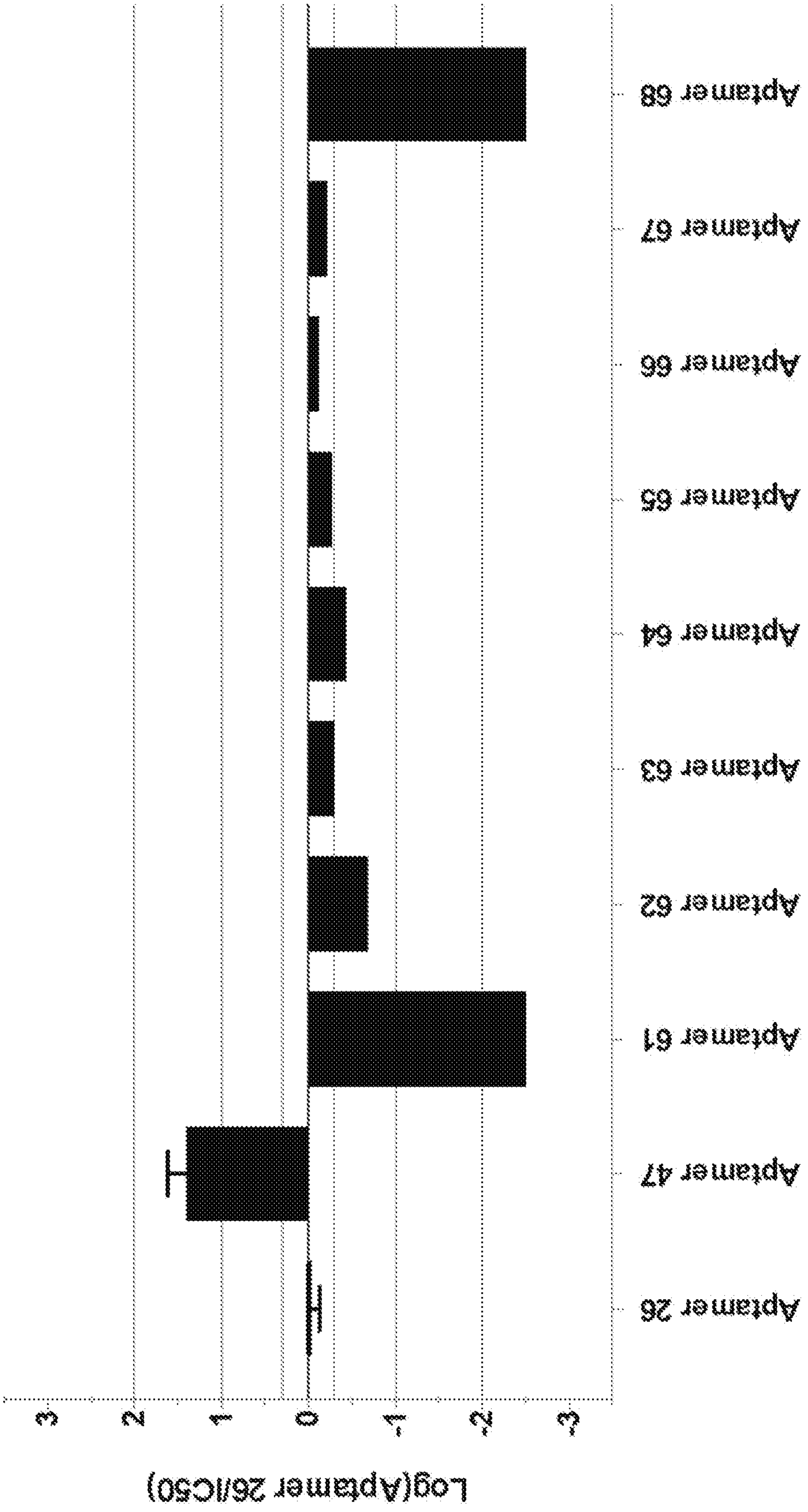
FIG. 8 depicts competitive TR-FRET data demonstrating the relative affinity of linker-containing anti-VEGF-A aptamers according to embodiments of the disclosure. Data is represented as the log of fold change in $IC_{50}$ as compared to parent aptamer.

To better understand the nucleotide dependence and secondary structure of Aptamer 26, variants of the parent aptamer were synthesized in which every position from U9 to U38 was replaced, individually, with a non-nucleotide 3-carbon spacer (SP3; 1,3-propanediol) and assayed for activity using a receptor phosphorylation AlphaLISA® and competition TR-FRET (Table 14 and FIG. 8).

Briefly, for competition TR-FRET, 2-fold dilutions of thermally equilibrated aptamers were made in TR-FRET Buffer (50 mM MOPS, pH 7.4, 125 mM NaCl, 5 mM KCl, 50 μM CHAPS, 0.1 mg/mL BSA, 1 mM $CaCl_2$, and 1 mM $MgCl_2$). 5 μL of aptamer or control solution was added to a 15 μL mix of glycan biotinylated VEGF-$A_{21}$ (5 nM final), ALEXA FLUOR® 647-labeled Aptamer (30 nM final), and Streptavidin-Eu (Perkin Elmer; 2.5 nM final) in a black wall low volume 384 well plate (Greiner). For control, 5 μl of 1000-fold excess of unlabeled parent aptamer or 5 μl TR-FRET buffer alone was added to the mix of ALEXA FLUOR® 647-labeled aptamer, biotin-VEGF-A, and Streptavidin-Eu. The plate was covered with a plate seal and subsequently incubated in the dark for 1 hour at room temperature. The plate was read on a Biotek CYTATION™ 5 plate reader. Samples were excited at 330 nm and fluorescent values were collected at 665 nm. Data analysis was performed by subtracting the background value and plotting as percent inhibition, normalized to baseline in the absence of competitor. The values were fit by [Inhibitor] vs. response-Variable slope (four parameters) using GraphPad Prism Version 7.0 and then normalized to aptamer control to obtain an $IC_{50}$ relative to parent aptamer. Data is presented as log values of relative $IC_{50}$.

Consistent with the high level of conservation observed during the degenerate selection (FIG. 6), the majority of positions could not be replaced with a linker without a substantial loss in activity (>10-fold worse). Interestingly, positions 24 through 29 (see Table 14; Aptamers 62, 63, 64, 65, 66, and 67), tolerated replacement by SP3 with relatively equal activity to the parent. This further supported the secondary structure proposed in Example 5 and shown in FIG. 7, demonstrating that these positions were in a loop or at the end of a stem and not essential for structure. More surprisingly, replacement of loop L1 (position 9) with an SP3 linker led to a >10-fold enhancement of activity against VEGF-$A_{121}$, even though it was found to be 100% conserved in the degenerate selection (Table 14 and FIG. 8; Aptamer 47).

TABLE 14

Linker Scan Analysis

| SEQ ID NO with modifications: | Aptamer Number | Sequence (5' to 3') S1 L1 S2 L2 S2 L3 S3 L4 S3 L5 S1 | pRDR | TR-FRET |
|---|---|---|---|---|
| 220 | Aptamer 26 | $C6NH_2$-AGGCCGCC-U-CC-GCGC-GG-A-GGGGU-UUCAUU-AUCCC-GUUU-GGCGGCUU-idT | parent | parent |
| 227 | Aptamer 47 | $C6NH_2$-AGGCCGCC-**3**-CC-GCGC-GG-A-GGGGU-UUCAUU-AUCCC-GUUU-GGCGGCUU-idT | ++ | ++ |
| 228 | Aptamer 48 | $C6NH_2$-AGGCCGCC-U-**3**C-GCGC-GG-A-GGGGU-UUCAUU-AUCCC-GUUU-GGCGGCUU-idT | --- | nd |
| 229/230 | Aptamer 49 | $C6NH_2$-AGGCCGCC-U-C**3**-GCGC-GG-A-GGGGU-UUCAUU-AUCCC-GUUU-GGCGGCUU-idT | --- | nd |
| 231/232 | Aptamer 50 | $C6NH_2$-AGGCCGCC-U-CC-**3**CGC-GG-A-GGGGU-UUCAUU-AUCCC-GUUU-GGCGGCUU-idT | --- | nd |
| 233/234 | Aptamer 51 | $C6NH_2$-AGGCCGCC-U-CC-G**3**GC-GG-A-GGGGU-UUCAUU-AUCCC-GUUU-GGCGGCUU-idT | --- | nd |
| 235/236 | Aptamer 52 | $C6NH_2$-AGGCCGCC-U-CC-GC**3**C-GG-A-GGGGU-UUCAUU-AUCCC-GUUU-GGCGGCUU-idT | --- | nd |
| 237/238 | Aptamer 53 | $C6NH_2$-AGGCCGCC-U-CC-GCG**3**-GG-A-GGGGU-UUCAUU-AUCCC-GUUU-GGCGGCUU-idT | --- | nd |
| 239/240 | Aptamer 54 | $C6NH_2$-AGGCCGCC-U-CC-GCGC-**3**G-A-GGGGU-UUCAUU-AUCCC-GUUU-GGCGGCUU-idT | --- | nd |
| 241/242 | Aptamer 55 | $C6NH_2$-AGGCCGCC-U-CC-GCGC-G**3**-A-GGGGU-UUCAUU-AUCCC-GUUU-GGCGGCUU-idT | --- | nd |
| 243/244 | Aptamer 56 | $C6NH_2$-AGGCCGCC-U-CC-GCGC-GG-**3**-GGGGU-UUCAUU-AUCCC-GUUU-GGCGGCUU-idT | --- | nd |
| 245/246 | Aptamer 57 | $C6NH_2$-AGGCCGCC-U-CC-GCGC-GG-A-**3**GGGU-UUCAUU-AUCCC-GUUU-GGCGGCUU-idT | --- | nd |
| 247/248 | Aptamer 58 | $C6NH_2$-AGGCCGCC-U-CC-GCGC-GG-A-G**3**GGU-UUCAUU-AUCCC-GUUU-GGCGGCUU-idT | --- | nd |
| 249/250 | Aptamer 59 | $C6NH_2$-AGGCCGCC-U-CC-GCGC-GG-A-GG**3**GU-UUCAUU-AUCCC-GUUU-GGCGGCUU-idT | --- | nd |
| 251/252 | Aptamer 60 | $C6NH_2$-AGGCCGCC-U-CC-GCGC-GG-A-GGG**3**U-UUCAUU-AUCCC-GUUU-GGCGGCUU-idT | --- | nd |
| 253/254 | Aptamer 61 | $C6NH_2$-AGGCCGCC-U-CC-GCGC-GG-A-GGGG**3**-UUCAUU-AUCCC-GUUU-GGCGGCUU-idT | --- | --- |
| 255/256 | Aptamer 62 | $C6NH_2$-AGGCCGCC-U-CC-GCGC-GG-A-GGGGU-**3**UCAUU-AUCCC-GUUU-GGCGGCUU-idT | ~ | - |
| 257/258 | Aptamer 63 | $C6NH_2$-AGGCCGCC-U-CC-GCGC-GG-A-GGGGU-U**3**CAUU-AUCCC-GUUU-GGCGGCUU-idT | ~ | ~ |
| 259/260 | Aptamer 64 | $C6NH_2$-AGGCCGCC-U-CC-GCGC-GG-A-GGGGU-UU**3**AUU-AUCCC-GUUU-GGCGGCUU-idT | ~ | - |
| 261/262 | Aptamer 65 | $C6NH_2$-AGGCCGCC-U-CC-GCGC-GG-A-GGGGU-UUC**3**UU-AUCCC-GUUU-GGCGGCUU-idT | ~ | ~ |
| 263/264 | Aptamer 66 | $C6NH_2$-AGGCCGCC-U-CC-GCGC-GG-A-GGGGU-UUCA**3**U-AUCCC-GUUU-GGCGGCUU-idT | ~ | ~ |
| 265/266 | Aptamer 67 | $C6NH_2$-AGGCCGCC-U-CC-GCGC-GG-A-GGGGU-UUCAU**3**-AUCCC-GUUU-GGCGGCUU-idT | ~ | ~ |
| 267/268 | Aptamer 68 | $C6NH_2$-AGGCCGCC-U-CC-GCGC-GG-A-GGGGU-UUCAUU-**3**UCCC-GUUU-GGCGGCUU-idT | -- | --- |

TABLE 14-continued

Linker Scan Analysis

| SEQ ID NO with modifications: | Aptamer Number | Sequence (5' to 3')<br>S1 L1 S2 L2 S2 L3 S3 L4 S3 L5 S1 | pRDR | TR-FRET |
|---|---|---|---|---|
| 269/270 | Aptamer 69 | C6NH$_2$-AGGCCGCC-U-CC-GCGC-GG-A-GGGGU-UUCAUU-A**3**CCC-GUUU-GGCGGCUU-idT | --- | nd |
| 271/272 | Aptamer 70 | C6NH$_2$-AGGCCGCC-U-CC-GCGC-GG-A-GGGGU-UUCAUU-AU**3**CC-GUUU-GGCGGCUU-idT | --- | nd |
| 273/274 | Aptamer 71 | C6NH$_2$-AGGCCGCC-U-CC-GCGC-GG-A-GGGGU-UUCAUU-AUC**3**C-GUUU-GGCGGCUU-idT | --- | nd |
| 275/276 | Aptamer 72 | C6NH$_2$-AGGCCGCC-U-CC-GCGC-GG-A-GGGGU-UUCAUU-AUCC**3**-GUUU-GGCGGCUU-idT | --- | nd |
| 277/278 | Aptamer 73 | C6NH$_2$-AGGCCGCC-U-CC-GCGC-GG-A-GGGGU-UUCAUU-AUCCC-**3**UUU-GGCGGCUU-idT | --- | nd |
| 279/280 | Aptamer 74 | C6NH$_2$-AGGCCGCC-U-CC-GCGC-GG-A-GGGGU-UUCAUU-AUCCC-G**3**UU-GGCGGCUU-idT | --- | nd |
| 281/282 | Aptamer 75 | C6NH$_2$-AGGCCGCC-U-CC-GCGC-GG-A-GGGGU-UUCAUU-AUCCC-GU**3**U-GGCGGCUU-idT | -- | nd |
| 283 | Aptamer 76 | C6NH$_2$-AGGCCGCC-U-CC-GCGC-GG-A-GGGGU-UUCAUU-AUCCC-GUU**3**-GGCGGCUU-idT | --- | nd |

where G is 2'F, and A, C, and U are 2'OMe modified RNA;
C6NH$_2$ is a hexylamine linker;
idT is an inverted deoxythymidine residue;
3 is the SP3 spacer (1,3-propanediol); and
bold letters denote differences from the parent Aptamer 26.
Dashes (-) delineate the structural features of the aptamers (e,g, stems, loops).
Key:
~ = 2 fold worse to 2 fold better,
+ = 2-10 fold better,
++ = 10-100 fold better,
+++ more than 100 fold better,
– = 2-10 fold worse,
10-100 fold worse,
––– = more than 100 fold worse.
nd = not determined.

Example 8. Structure Validation and Analysis by Selective Mutagenesis

To better understand the sequence requirements and to confirm the stem structures of the Aptamer 26 family as determined from sequence covariation analysis from the secondary (degenerate) selection, a series of variants that included mutations and deletions to the predicted stems were synthesized and screened. Activity of each of these variants were tested using a time resolved competition TR-FRET assay, as described in Example 7, in which a labeled parent was competed with increasing concentrations of unlabeled variants for binding to VEGF-A$_{121}$.

Figure 9:
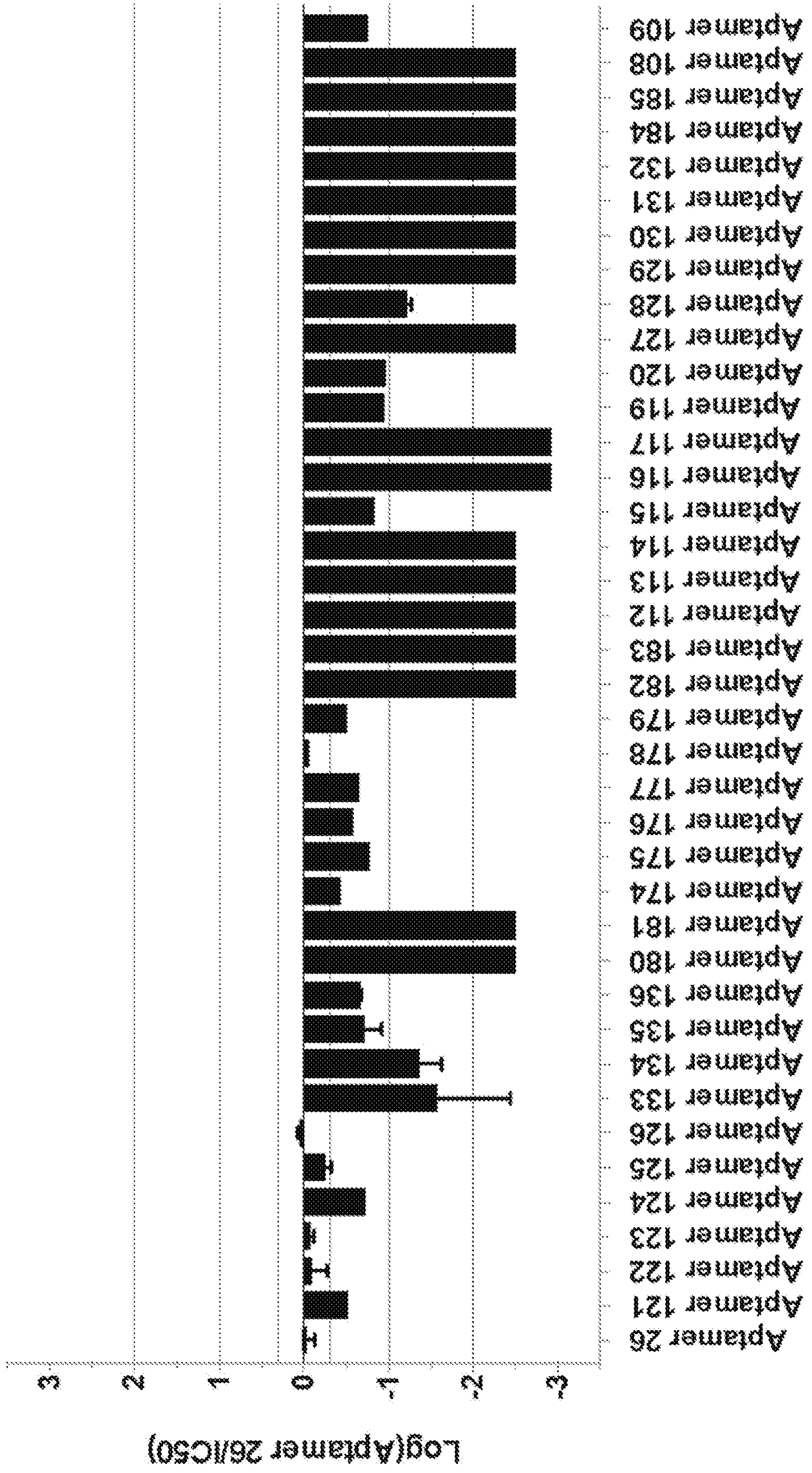
FIG. 9 depicts competitive TR-FRET data demonstrating the relative affinity of anti-VEGF-A aptamers according to embodiments of the disclosure. Data is represented as the log of fold change in $IC_{50}$ as compared to parent aptamer.

Replacing the sequence of stem S1 found in Aptamer 26, 5'-AGGCCGCC/GGCGGCUU-3', with single base pair A/U or U/A covariations in positions 7/40 and 8/39 (Table 15 and FIG. 9; Aptamers 122, 123, 125, and 126) showed activity within approximately 2-fold of the parent molecule, confirming the presence of a stem. Other modifications in these positions resulted in only a modest loss in activity (approximately 2-10 fold; Aptamers 124, 135 and 136) further supporting stem formation. Importantly, mutations leading to intentional mispairing of the terminal base pairs in stem S1 led to a complete loss of activity (>100-fold; Table 15 and FIG. 9; Aptamers 180 and 181). Together with the data from the doped selection (Table 10), these data further support the formation of stem S1, and the requirement for the formation of a base pair between positions 8 and 39 of the stem. Therefore, stem S1 may be composed of two to eight contiguous base pairs that end in a base pair at positions 8 and 39. The identity of the nucleotides can be varied with little effect on activity provided pairing is maintained. When combined with consensus sequence from the degenerate selection, the consensus sequence was 5'-HNBYHDNN-3' for the 5' side of the stem and 5'-NNYNKVNW-3' for the 3' complementary side of stem S1, where N is A, C, G, or U; B is C, G or U; Y is C or U; H is A, C, or U; D is A, G or U; K is G or U; V is A, C, or G; and W is A or U.

The identity of stem S2 was found to be 100% conserved during the degenerate selection (FIG. 6). To confirm the identity of this stem, we replaced nucleotides to assess the effect of alternate base pairings on aptamer function. Replacing nucleotides at positions 10 and 17, or 11 and 16, resulted in only a modest loss of aptamer activity (approximately 2-10 fold; Table 15 and FIG. 9; Aptamers 174-179) provided that base pairing was maintained. Mutations leading to mispairing of the stem S2 led to a complete loss of activity (>100-fold; Table 15 and FIG. 9; Aptamers 182 and 183), thus confirming the requirement of a stem. When combined with consensus sequence from the degenerate selection, this expanded the consensus for stem S2. Thus, Stem S2 was composed of 2 base pairs with a consensus sequence of 5'-NN-3' for both the 5' and 3' sides of the stem, where N is A, C, G, or U.

A comparison of sequences observed in stem S3 suggested that the preferred length of stem S3 was four, five, or six base pairs and that the variation between four, five, and six base pairs in stem S3 was directly related to the length of loop L4, which varied between eight, six, and four nucleotides, respectively. To confirm the identity of this stem, the effect of alternate base pairings on aptamer function was assessed. For simplicity, replacements were done in the context of Aptamer 26, which had a five base pair stem S3 and six nucleotides in loop L4.

Replacing the G:C base pair formed between positions 19 and 34 within this stem with any other canonical pairing resulted in a complete loss of activity (>100-fold; Table 15 and FIG. 9, Aptamers 112, 113 and 114). Similarly, replacing the G:C base pair formed between positions 20 and 33 with either a U:A or a C:G pair resulted in a complete loss of activity (>100 fold; Table 15 and FIG. 9, Aptamers 116 and 117). When replaced with an A:U, however, the resulting molecule (Aptamer 115) demonstrated only a modest loss in activity (approximately 7-fold) supporting the formation of a stem, albeit one with a preference for a purine at position 20 and a pyrimidine at position 33. Interestingly, other modifications to these within the center of the stem (paired positions 21:32 and 22:31) proved refractory to change leading to significant (>10-fold; Aptamer 128) or complete (>100-fold; Aptamers 127, 129, 130, 131 and 132) loss of activity. It was unclear if this was the result of a preference for a specific base pairing within the stem (as with position 19 and 34) or due to misfolding. Indeed, it was possible that modification of the primary sequence elsewhere in the molecule or within the stem itself could compensate for this observation and overcome these negative effects. For example, when the deleterious C:G pairing at positions 19 and 34, and 20 and 33 were combined with a U to C mutation at position 32, the resultant molecule only demonstrated a modest loss in activity (Aptamer 119; approximately 9-fold). Similar results were observed from the combination of an A:U pair at positions 20 and 33 with a G:C at positions 23 and 30 and a U to C mutation at position 31 (Aptamer 120; approximately 9-fold). These results, together with the high degree of conservation of pairing within this stem observed during the primary and degenerate selections and the observation that intentional mispairings in stem S3 resulted in molecules with no activity (>100-fold; Aptamer 184 and 185), strongly supported the formation of a stem. Finally, because shortened versions of stem S3 had been observed during the degenerate selection (Table 11), the effects of truncations in stem S3 were tested. Removal of the terminal A:U at positions 23 and 30 (Aptamer 108) resulted in the complete loss of activity (>100-fold), whereas removal of the penultimate pair, positions 22 and 31 (Aptamer 109), only resulted in a modest loss in activity.

These data, when combined with sequence data observed in the primary and degenerate selections, supported the observation that stem S3 can be four, five or six base pairs in length, but expanded the observation that a four base pair stem S3 can be combined with a six or eight nucleotide loop L4. These data also further expanded the consensus for stem S3. When stem S3 was five base pairs long and loop L4 was six nucleotides in length, the consensus sequence was 5'-SVVVK-3' for the 5 side of the stem and 5'-MBBBS-3' for the complementary region of stem S3, where S is G or C; V is A, C, or G; K is G or U; M is A or C; and B is C, G, or U.

TABLE 15

Analysis of Stems 1, 2, and 3

| SEQ ID NO with modifications: | Aptamer Number | Sequence (5' to 3')<br>S1 L1 S2 L2 S2 L3 S3 L4 S3 L5 S1 | TR-FRET |
|---|---|---|---|
| 220 | Aptamer 26 | C6NH$_2$-AGGCCGCC-U-CC-GCGC-GG-A-GGGGU-UUCAUU-AUCCC-GUUU-GGCGGCUU-idT | parent |
| 295 | Aptamer 121 | C6NH$_2$-AGGCCGC**G**-U-CC-GCGC-GG-A-GGGGU-UUCAUU-AUCCC-GUUU-**C**GCGGCUU-idT | - |
| 296 | Aptamer 122 | C6NH$_2$-AGGCCGC**A**-U-CC-GCGC-GG-A-GGGGU-UUCAUU-AUCCC-GUUU-**U**GCGGCUU-idT | ~ |
| 297 | Aptamer 123 | C6NH$_2$-AGGCCGC**U**-U-CC-GCGC-GG-A-GGGGU-UUCAUU-AUCCC-GUUU-**A**GCGGCUU-idT | ~ |
| 298 | Aptamer 124 | C6NH$_2$-AGGCCG**G**C-U-CC-GCGC-GG-A-GGGGU-UUCAUU-AUCCC-GUUU-G**C**CGGCUU-idT | - |
| 299 | Aptamer 125 | C6NH$_2$-AGGCCG**A**C-U-CC-GCGC-GG-A-GGGGU-UUCAUU-AUCCC-GUUU-G**U**CGGCUU-idT | ~ |
| 300 | Aptamer 126 | C6NH$_2$-AGGCCG**U**C-U-CC-GCGC-GG-A-GGGGU-UUCAUU-AUCCC-GUUU-G**A**CGGCUU-idT | ~ |
| 307 | Aptamer 133 | C6NH$_2$-AGGCCG**AA**-U-CC-GCGC-GG-A-GGGGU-UUCAUU-AUCCC-GUUU-**UU**CGGCUU-idT | -- |
| 308 | Aptamer 134 | C6NH$_2$-AGGCCG**AU**-U-CC-GCGC-GG-A-GGGGU-UUCAUU-AUCCC-GUUU-**AU**CGGCUU-idT | -- |
| 309 | Aptamer 135 | C6NH$_2$-AGGCCG**UA**-U-CC-GCGC-GG-A-GGGGU-UUCAUU-AUCCC-GUUU-**UA**CGGCUU-idT | - |
| 310 | Aptamer 136 | C6NH$_2$-AGGCCG**UU**-U-CC-GCGC-GG-A-GGGGU-UUCAUU-AUCCC-GUUU-**AA**CGGCUU-idT | - |

TABLE 15-continued

Analysis of Stems 1, 2, and 3

| SEQ ID NO with modifications: | Aptamer Number | Sequence (5' to 3 ) S1 L1 S2 L2 S2 L3 S3 L4 S3 L5 S1 | TR-FRET |
|---|---|---|---|
| 354 | Aptamer 180 | $C6NH_2$-AGGCCGC**A**-U-CC-GCGC-GG-A-GGGGU-UUCAUU-AUCCC-GUUU-**AA**C**C**GCUU-idT | --- |
| 355 | Aptamer 181 | $C6NH_2$-AGGCCGC**A**-U-CC-GCGC-GG-A-GGGGU-UUCAUU-AUCCC-GUUU-**AA**C**C**G**A**UU-idT | --- |
| 348 | Aptamer 174 | $C6NH_2$-AGGCCGCC-U-**G**C-GCGC-G**C**-A-GGGGU-UUCAUU-AUCCC-GUUU-GGCGGCUU-idT | - |
| 349 | Aptamer 175 | $C6NH_2$-AGGCCGCC-U-**A**C-GCGC-G**U**-A-GGGGU-UUCAUU-AUCCC-GUUU-GGCGGCUU-idT | - |
| 350 | Aptamer 176 | $C6NH_2$-AGGCCGCC-U-**U**C-GCGC-G**A**-A-GGGGU-UUCAUU-AUCCC-GUUU-GGCGGCUU-idT | - |
| 351 | Aptamer 177 | $C6NH_2$-AGGCCGCC-U-C**G**-GCGC-**C**G-A-GGGGU-UUCAUU-AUCCC-GUUU-GGCGGCUU-idT | - |
| 352 | Aptamer 178 | $C6NH_2$-AGGCCGCC-U-C**A**-GCGC-**U**G-A-GGGGU-UUCAUU-AUCCC-GUUU-GGCGGCUU-idT | ~ |
| 353 | Aptamer 179 | $C6NH_2$-AGGCCGCC-U-C**U**-GCGC-**A**G-A-GGGGU-UUCAUU-AUCCC-GUUU-GGCGGCUU-idT | - |
| 356 | Aptamer 182 | $C6NH_2$-AGGCCGCC-U-**UU**-GCGC-**UU**-A-GGGGU-UUCAUU-AUCCC-GUUU-GGCGGCUU-idT | --- |
| 357 | Aptamer 183 | $C6NH_2$-AGGCCGCC-U-CC-GCGC-**CC**-A-GGGGU-UUCAUU-AUCCC-GUUU-GGCGGCUU-idT | --- |
| 287 | Aptamer 112 | $C6NH_2$-AGGCCGCC-U-CC-GCGC-GG-A-**A**GGGU-UUCAUU-AUCC**U**-GUUU-GGCGGCUU-idT | --- |
| 288 | Aptamer 113 | $C6NH_2$-AGGCCGCC-U-CC-GCGC-GG-A-**U**GGGU-UUCAUU-AUCC**A**-GUUU-GGCGGCUU-idT | --- |
| 289 | Aptamer 114 | $C6NH_2$-AGGCCGCC-U-CC-GCGC-GG-A-**C**GGGU-UUCAUU-AUCC**G**-GUUU-GGCGGCUU-idT | --- |
| 290 | Aptamer 115 | $C6NH_2$-AGGCCGCC-U-CC-GCGC-GG-A-G**A**GGU-UUCAUU-AUC**U**C-GUUU-GGCGGCUU-idT | - |
| 291 | Aptamer 116 | $C6NH_2$-AGGCCGCC-U-CC-GCGC-GG-A-G**U**GGU-UUCAUU-AUC**A**C-GUUU-GGCGGCUU-idT | --- |
| 292 | Aptamer 117 | $C6NH_2$-AGGCCGCC-U-CC-GCGC-GG-A-G**C**GGU-UUCAUU-AUC**G**C-GUUU-GGCGGCUU-idT | --- |
| 293 | Aptamer 119 | $C6NH_2$-AGGCCGCC-U-CC-GCGC-GG-A-**CC**GGU-UUCAUU-A**C**C**GG**-GUUU-GGCGGCUU-idT | - |
| 294 | Aptamer 120 | $C6NH_2$-AGGCCGCC-U-CC-GCGC-GG-A-G**A**GG**G**-UUCAUU-**CC**C**U**C-GUUU-GGCGGCUU-idT | - |
| 301 | Aptamer 127 | $C6NH_2$-AGGCCGCC-U-CC-GCGC-GG-A-GGG**C**U-UUCAUU-A**G**CCC-GUUU-GGCGGCUU-idT | --- |
| 302 | Aptamer 128 | $C6NH_2$-AGGCCGCC-U-CC-GCGC-GG-A-GG**AC**U-UUCAUU-A**GU**CC-GUUU-GGCGGCUU-idT | -- |
| 303 | Aptamer 129 | $C6NH_2$-AGGCCGCC-U-CC-GCGC-GG-A-GG**UC**U-UUCAUU-A**GA**CC-GUUU-GGCGGCUU-idT | --- |
| 304 | Aptamer 130 | $C6NH_2$-AGGCCGCC-U-CC-GCGC-GG-A-GG**U**GU-UUCAUU-A**CA**CC-GUUU-GGCGGCUU-idT | --- |
| 305 | Aptamer 131 | $C6NH_2$-AGGCCGCC-U-CC-GCGC-GG-A-GG**A**GU-UUCAUU-A**CU**CC-GUUU-GGCGGCUU-idT | --- |
| 306 | Aptamer 132 | $C6NH_2$-AGGCCGCC-U-CC-GCGC-GG-A-GG**C**GU-UUCAUU-A**CG**CC-GUUU-GGCGGCUU-idT | --- |

TABLE 15-continued

| SEQ ID NO with modifications: | Aptamer Number | Sequence (5' to 3 ) S1 L1 S2 L2 S2 L3 S3 L4 S3 L5 S1 | TR-FRET |
|---|---|---|---|
| | | Analysis of Stems 1, 2, and 3 | |
| 358 | Aptamer 184 | $C6NH_2$-AGGCCGCC-U-CC-GCGC-GG-A-G**CC**GU-UUCAUU-AUCCC-GUUU-GGCGGCUU-idT | --- |
| 359 | Aptamer 185 | $C6NH_2$-AGGCCGCC-U-CC-GCGC-GG-A-GGGGU-UUCAUU-AU**AA**C-GUUU-GGCGGCUU-idT | --- |
| 285 | Aptamer 108 | $C6NH_2$-AGGCCGCC-U-CC-GCGC-GG-A-GGGG_-UUCAUU-_UCCC-GUUU-GGCGGCUU-idT | --- |
| 286 | Aptamer 109 | $C6NH_2$-AGGCCGCC-U-CC-GCGC-GG-A-GGGG_-UUCAUU-_ACCC-GUUU-GGCGGCUU-idT | - |

where G is 2'F and A, C, and U are 2'OMe modified RNA;
$C6NH_2$ is a hexylamine linker;
idT is an inverted deoxythymidine residue; and
bold letters denote differences from the parent Aptamer 26.
Dashes (-) delineate the structural features of the aptamers (e.g., stems, loops) and underline (_) denotes a deletion.
Key:
~ = 2 fold worse to 2 fold better,
+ = 2-10 fold better,
++ = 10-100 fold better,
+++ more than 100 fold better,
- = 2-10 fold worse,
10-100 fold worse,
--- = more than 100 fold worse.

To better understand the role of loops in the Aptamer 26 sequence family, residues in loop L1, loop L2, loop L3, loop L4, and loop L5 were replaced with alternate base identities and the effects of substitutions on activity were determined.

Figure 10:
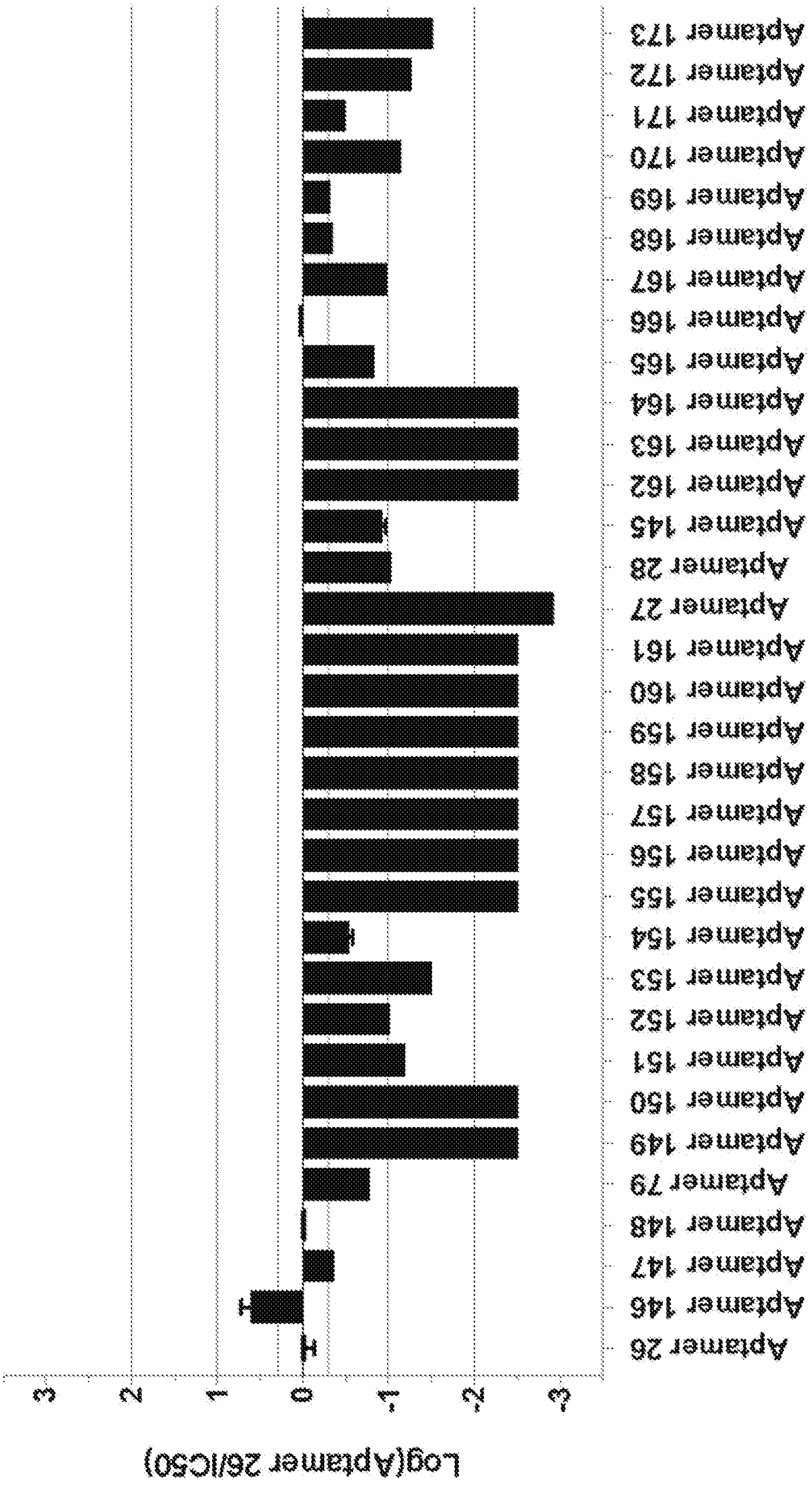
FIG. 10 depicts competitive TR-FRET data demonstrating the relative affinity of anti-VEGF-A aptamers according to embodiments of the disclosure. Data is represented as the log of fold change in $IC_{50}$ as compared to parent aptamer.

During the degenerate selection, the identity of loop L1 (position 9) was a highly conserved U (100%; FIG. 6). Interestingly, this position could be replaced with any other base (C, G, or A) or deleted entirely with only modest effects on activity (Table 16 and FIG. 10, Aptamers 146, 147, 148 and 79). For example, replacement with an A lead to a modest (~3-fold) increase in activity. Together, this data indicated that the identity or even the presence of a nucleotide at this position was not necessary for activity, and suggested that loop L1 could be a flexible linker joining stems S1 and S2. Thus, the consensus for loop L1 can be expanded to 5'-N*-3', where N* is A, C, G, U, a non-nucleotidyl spacer 3 modification (Sp3), or can be deleted entirely.

The identity of loop L2 was found to be 100% conserved during the degenerate selection (FIG. 6). Consistent with this, base modifications to positions within this loop were poorly tolerated. For example, replacement of position 12 within the loop with an A or C resulted in >100-fold loss in activity (Table 16 and FIG. 10; Aptamers 149 and 150). Replacement with a U was slightly less detrimental, but still resulted in >10-fold loss in activity (Aptamer 151). Position 13 proved to be the most tolerant but still resulted in a significant (>10-fold) loss in activity for substitution with A and G (Table 16 and FIG. 10; Aptamers 152 and 153). Replacement with U was the least detrimental to activity, resulting in only a 4-fold loss in activity (Aptamer 154). For both positions 14 and 15, replacement with any nucleotide other than that found in the parent resulted in >100-fold loss in activity (Table 16 and FIG. 10; Aptamers 155-160). Thus, the nucleotide sequence of loop L2 may be expanded to 5'-KNGC-3', where K is G or U; and N is A, C, G, or U. In a preferred embodiment, loop L2 is 5'-GYGC-3', where Y is C or U. In another preferred embodiment, loop L2 is 5'-GCGC-3'. The identity of loop L3 was found to be 100% conserved during the degenerate selection (FIG. 6). Consistent with this observation, when the conserved A was mutated to a C or a G, the resultant molecules (Aptamers 27 and 161) lost >100-fold activity. Additionally, when mutated to a U, the resultant molecule (Aptamer 28) only demonstrated a 10-fold loss of activity. Thus, the nucleotide sequence of L3 may be 5'-W-3', where W is A or U.

A comparison of sequences observed in loop L4 suggested that positions 24, 25, and 29 within the loop were not highly conserved and remained equal to the composition of the staring library, ~85%. Positions 26, 27, and 28, on the other hand, were more conserved (97%, 99%, and 96%, respectively). The identity of loop L4 was explored by deletion analysis to assess if all nucleotides in the position were required for function. To this end, when the nucleotides at positions 24 and 29 were removed, only a modest loss in activity was observed (Aptamer 145; approximately 8-fold). Together with data from the primary and degenerate selections, these data further expand the relationship between stem S3 and loop L4. Stem S3 can be four, five or six base pairs in length. When stem S3 is four base pairs in length, loop L4 may be six or eight nucleotides in length. When stem S3 is five base pairs in length, loop L4 may be four or six nucleotides in length and when stem S3 is six base pairs, loop L4 may be four nucleotides in length. When loop L4 is four nucleotides in length, the consensus sequence for loop L4 may be 5'-DNAH-3', where D is A, G or U; H is A, C, or U; and N is A, C, G, or U. In some cases, when loop L4 is six nucleotides in length, the consensus sequence for loop L4 may be 5'-UDNDHU-3', where D is A, G or U; H is A, C, or U; and N is A, C, G, or U. In some cases, when loop L4 is eight nucleotides in length, the consensus sequence for loop L4 may be 5'-UUUCAUUU-3'.

A comparison of sequences observed in loop L5 from the degenerate selection suggested a high degree of conservation for all positions in this domain (FIG. 6). Consistent with this, replacement of the parental G at position 35 with any other nucleotide resulted in a complete loss in activity (>100-fold; Aptamers 162, 163, and 164). Surprisingly, similar replacements in other positions of the loop were tolerated much better (2-10 fold and 10-100 fold; Aptamers 165-173). Consistent with observations from the degenerate selection, the most tolerant substitutions were allowed at position 36, where replacement of the parental U with C had almost no effect on activity (Aptamer 166). Together, these data expanded the consensus sequence of loop L5 to 5'-GNNN-3', where N is A, C, G, or U. In a preferred embodiment, the consensus sequence of loop L5 may be 5'-GNHW-3', where N is A, C, G, or U; H is A, C, or U; and W is A or U. In another preferred embodiment, the consensus sequence of loop L5 may be 5'-GYUU-3', where Y is C or U.

TABLE 16

Analysis and optimization of Loops 1, 2,3, 4, and 5

| SEQ ID NO with modifications: | Aptamer Number | Sequence (5' to 3') S1 L1 S2 L2 S2 L3 S3 L4 S3 L5 S1 | TR-FRET |
|---|---|---|---|
| 220 | Aptamer 26 | C6NH$_2$-AGGCCGCC-U-CC-GCGC-GG-A-GGGGU-UUCAUU-AUCCC-GUUU-GGCGGCUU-idT | parent |
| 320 | Aptamer 146 | C6NH$_2$-AGGCCGCC-**A**-CC-GCGC-GG-A-GGGGU-UUCAUU-AUCCC-GUUU-GGCGGCUU-idT | + |
| 321 | Aptamer 147 | C6NH$_2$-AGGCCGCC-**C**-CC-GCGC-GG-A-GGGGU-UUCAUU-AUCCC-GUUU-GGCGGCUU-idT | - |
| 322 | Aptamer 148 | C6NH$_2$-AGGCCGCC-**G**-CC-GCGC-GG-A-GGGGU-UUCAUU-AUCCC-GUUU-GGCGGCUU-idT | ~ |
| 284 | Aptamer 79 | C6NH$_2$-AGGCCGCC-_-CC-GCGC-GG-A-GGGGU-UUCAUU-AUCCC-GUUU-GGCGGCUU-idT | - |
| 323 | Aptamer 149 | C6NH$_2$-AGGCCGCC-U-CC-**A**CGC-GG-A-GGGGU-UUCAUU-AUCCC-GUUU-GGCGGCUU-idT | --- |
| 324 | Aptamer 150 | C6NH$_2$-AGGCCGCC-U-CC-**C**CGC-GG-A-GGGGU-UUCAUU-AUCCC-GUUU-GGCGGCUU-idT | --- |
| 325 | Aptamer 151 | C6NH$_2$-AGGCCGCC-U-CC-**U**CGC-GG-A-GGGGU-UUCAUU-AUCCC-GUUU-GGCGGCUU-idT | -- |
| 326 | Aptamer 152 | C6NH$_2$-AGGCCGCC-U-CC-G**A**GC-GG-A-GGGGU-UUCAUU-AUCCC-GUUU-GGCGGCUU-idT | -- |
| 327 | Aptamer 153 | C6NH$_2$-AGGCCGCC-U-CC-G**G**GC-GG-A-GGGGU-UUCAUU-AUCCC-GUUU-GGCGGCUU-idT | -- |
| 328 | Aptamer 154 | C6NH$_2$-AGGCCGCC-U-CC-G**U**GC-GG-A-GGGGU-UUCAUU-AUCCC-GUUU-GGCGGCUU-idT | - |
| 329 | Aptamer 155 | C6NH$_2$-AGGCCGCC-U-CC-GC**A**C-GG-A-GGGGU-UUCAUU-AUCCC-GUUU-GGCGGCUU-idT | --- |
| 330 | Aptamer 156 | C6NH$_2$-AGGCCGCC-U-CC-GC**C**C-GG-A-GGGGU-UUCAUU-AUCCC-GUUU-GGCGGCUU-idT | --- |
| 331 | Aptamer 157 | C6NH$_2$-AGGCCGCC-U-CC-GC**U**C-GG-A-GGGGU-UUCAUU-AUCCC-GUUU-GGCGGCUU-idT | --- |
| 332 | Aptamer 158 | C6NH$_2$-AGGCCGCC-U-CC-GCG**A**-GG-A-GGGGU-UUCAUU-AUCCC-GUUU-GGCGGCUU-idT | --- |
| 333 | Aptamer 159 | C6NH$_2$-AGGCCGCC-U-CC-GCG**G**-GG-A-GGGGU-UUCAUU-AUCCC-GUUU-GGCGGCUU-idT | --- |
| 334 | Aptamer 160 | C6NH$_2$-AGGCCGCC-U-CC-GCG**U**-GG-A-GGGGU-UUCAUU-AUCCC-GUUU-GGCGGCUU-idT | --- |
| 335 | Aptamer 161 | C6NH$_2$-AGGCCGCC-U-CC-GCGC-GG-**C**-GGGGU-UUCAUU-AUCCC-GUUU-GGCGGCUU-idT | --- |
| 221 | Aptamer 27 | C6NH$_2$-**U**AGGCCGCC-U-CC-GC-GCGG-**G**-GGGGU-UUCAUU-AUCCC-GUUU-GGCGGCUU**U**-idT | --- |

TABLE 16-continued

Analysis and optimization of Loops 1, 2,3, 4, and 5

| SEQ ID NO with modifications: | Aptamer Number | Sequence (5' to 3')<br>S1 L1 S2 L2 S2 L3 S3 L4 S3 L5 S1 | TR-FRET |
|---|---|---|---|
| 222 | Aptamer 28 | C6NH$_2$-**U**AGGCCGCC-U-CC-GC-GCGG-**U**-GGGGU-UUCAUU-AUCCC-GUUU-GGCGGCUU**U**-idT | -- |
| 319 | Aptamer 145 | C6NH$_2$-AGGCCGCC-U-CC-GCGC-GG-A-GGGGU-_UCAU_-AUCCC-GUUU-GGCGGCUU-idT | - |
| 336 | Aptamer 162 | C6NH$_2$-AGGCCGCC-U-CC-GCGC-GG-A-GGGGU-UUCAUU-AUCCC-**A**UUU-GGCGGCUU-idT | --- |
| 337 | Aptamer 163 | C6NH$_2$-AGGCCGCC-U-CC-GCGC-GG-A-GGGGU-UUCAUU-AUCCC-**C**UUU-GGCGGCUU-idT | --- |
| 338 | Aptamer 164 | C6NH$_2$-AGGCCGCC-U-CC-GCGC-GG-A-GGGGU-UUCAUU-AUCCC-**U**UUU-GGCGGCUU-idT | --- |
| 339 | Aptamer 165 | C6NH$_2$-AGGCCGCC-U-CC-GCGC-GG-A-GGGGU-UUCAUU-AUCCC-G**A**UU-GGCGGCUU-idT | - |
| 340 | Aptamer 166 | C6NH$_2$-AGGCCGCC-U-CC-GCGC-GG-A-GGGGU-UUCAUU-AUCCC-G**C**UU-GGCGGCUU-idT | ~ |
| 341 | Aptamer 167 | C6NH$_2$-AGGCCGCC-U-CC-GCGC-GG-A-GGGGU-UUCAUU-AUCCC-G**G**UU-GGCGGCUU-idT | - |
| 342 | Aptamer 168 | C6NH$_2$-AGGCCGCC-U-CC-GCGC-GG-A-GGGGU-UUCAUU-AUCCC-GU**A**U-GGCGGCUU-idT | - |
| 343 | Aptamer 169 | C6NH$_2$-AGGCCGCC-U-CC-GCGC-GG-A-GGGGU-UUCAUU-AUCCC-GU**C**U-GGCGGCUU-idT | - |
| 344 | Aptamer 170 | C6NH$_2$-AGGCCGCC-U-CC-GCGC-GG-A-GGGGU-UUCAUU-AUCCC-GU**G**U-GGCGGCUU-idT | -- |
| 345 | Aptamer 171 | C6NH$_2$-AGGCCGCC-U-CC-GCGC-GG-A-GGGGU-UUCAUU-AUCCC-GUU**A**-GGCGGCUU-idT | - |
| 346 | Aptamer 172 | C6NH$_2$-AGGCCGCC-U-CC-GCGC-GG-A-GGGGU-UUCAUU-AUCCC-GUU**C**-GGCGGCUU-idT | -- |
| 347 | Aptamer 173 | C6NH$_2$-AGGCCGCC-U-CC-GCGC-GG-A-GGGGU-UUCAUU-AUCCC-GUU**G**-GGCGGCUU-idT | -- |

where G is 2'F and A, C, and U are 2'OMe modified RNA;
C6NH$_2$ is a hexylamine linker;
idT is an inverted deoxythymidine residue;
an underscore (_) denotes an internal deletion; and
bold letters denote differences from the parent Aptamer 26.
Dashes (-) delineate the structural features of the aptamers (e.g, stems, loops).
Key:
~ = 2 fold worse to 2 fold better,
+ = 2-10 fold better,
++ = 10-100 fold better,
+++ more than 100 fold better,
- = 2-10 fold worse,
10-100 fold worse,
--- = more than 100 fold worse.

Example 9A. Lead Optimization and Characterization

Figure 11:
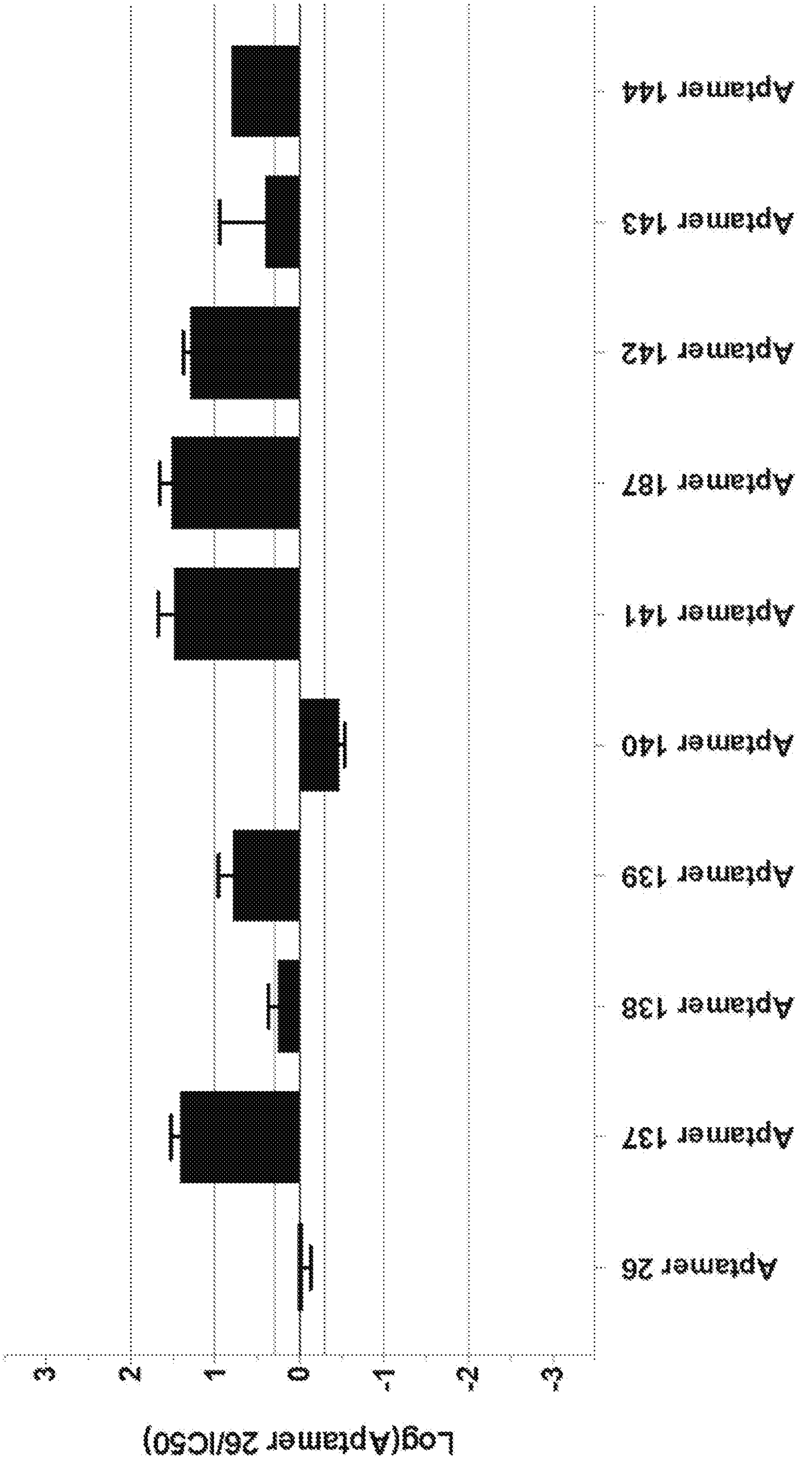
FIG. 11 depicts competitive TR-FRET data demonstrating the relative affinity of anti-VEGF-A aptamers according to embodiments of the disclosure. Data is represented as the log of fold change in $IC_{50}$ as compared to parent aptamer.

Linker scanning analysis (Table 14 and FIG. 8) revealed that replacement of the parental U in loop L1 (position 9) with a non-nucleotidyl spacer 3 modification, lead to a significant improvement in aptamer activity (10-100 fold) as determined by competition TR-FRET. To better characterize this substitution, we assessed the effect of this modification on stem S3 modifications that were previously tested for function (Table 15). As shown in Table 17 and FIG. 11, replacement of position 9 with a non-nucleotidyl spacer 3 modification lead to an improvement in the activity of all molecules tested (compare the activities of Aptamer 137, 138, 139, 141, 142, 143, and 144 with Aptamers 133, 134, 135, 125, 126, 122, and 123 in FIG. 9). Only Aptamer 140 failed to show any improvement in activity. These data support the assertion that a non-nucleotidyl spacer 3 modification is a beneficial mutation and that the consensus for loop L1 is 5'-N*-3', where N* is A, C, G, U, a non-nucleotidyl spacer 3 modification or deleted entirely. In a preferred embodiment, loop L1 is 5'-A-3'. Loop L1 can also be a non-nucleotide spacer. In another preferred embodiment, loop L1 is 5'-U-3'. In another preferred embodiment, loop L1 is 5'-Sp3-3', where Sp3 is non-nucleotidyl spacer 3 modification.

TABLE 17

Optimization of lead consensus mutations

| SEQ ID NO with modifications: | Aptamer Number | Sequence (5' to 3') | TR-FRET |
|---|---|---|---|
| | | S1 L1 S2 L2 S2 L3 S3 L4 S3 L5 S1 | |
| 220 | Aptamer 26 | C6NH$_2$-AGGCCGCC-U-CC-GCGC-GG-A-GGGGU-UUCAUU-AUCCC-GUUU-GGCGGCUU-idT | parent |
| 311 | Aptamer 137 | C6NH$_2$-AGGCCG**AA**-**3**-CC-GCGC-GG-A-GGGGU-UUCAUU-AUCCC-GUUU-**UU**CGGCUU-idT | ++ |
| 312 | Aptamer 138 | C6NH$_2$-AGGCCG**AU**-**3**-CC-GCGC-GG-A-GGGGU-UUCAUU-AUCCC-GUUU-**AU**CGGCUU-idT | ~ |
| 313 | Aptamer 139 | C6NH$_2$-AGGCCG**UA**-**3**-CC-GCGC-GG-A-GGGGU-UUCAUU-AUCCC-GUUU-**UA**CGGCUU-idT | + |
| 314 | Aptamer 140 | C6NH$_2$-AGGCCG**UU**-**3**-CC-GCGC-GG-A-GGGGU-UUCAUU-AUCCC-GUUU-**AA**CGGCUU-idT | - |
| 315 | Aptamer 141 | C6NH$_2$-AGGCCG**A**C-**3**-CC-GCGC-GG-A-GGGGU-UUCAUU-AUCCC-GUUU-G**U**CGGCUU-idT | ++ |
| 360 | Aptamer 187 | C6NH$_2$-AGGCCG**A**C-**3**-CC-GCGC-GG-A-GGGGU-UUCAUU-A**C**CCC-GUUU-G**U**CGGCUU-idT | ++ |
| 316 | Aptamer 142 | C6NH$_2$-AGGCCG**U**C-**3**-CC-GCGC-GG-A-GGGGU-UUCAUU-AUCCC-GUUU-G**A**CGGCUU-idT | ++ |
| 317 | Aptamer 143 | C6NH$_2$-AGGCCGC**A**-**3**-CC-GCGC-GG-A-GGGGU-UUCAUU-AUCCC-GUUU-**U**GCGGCUU-idT | + |
| 318 | Aptamer 144 | C6NH$_2$-AGGCCGC**U**-**3**-CC-GCGC-GG-A-GGGGU-UUCAUU-AUCCC-GUUU-**A**GCGGCUU-idT | + |

where G is 2'F and A, C, and U are 2'OMe modified RNA;
C6NH$_2$ is a hexylamine linker,
idT is an inverted deoxythymidine residue;
3 is the SP3 spacer (1,3-propanediol); and bold letters denote differences from the parent Aptamer 26.
Dashes (-) delineate the structural features of the aptamers (e.g., stems; loops).
Key:
~ = 2 fold worse to 2 fold better,
+ = 2-10 fold better,
++ = 10-100 fold better,
+++ more than 100 fold better,
- = 2-10 fold worse,
10-100 fold worse,
--- = more than 100 fold worse.

Example 9B. Lead Characterization by TR-FRET

To characterize the binding affinities of lead aptamers and an anti-VEGF-A mAb to VEGF-$A_{165}$ and VEGF-$A_{121}$, a time resolved FRET (TR-FRET) assay was performed. Briefly, ALEXA FLUOR® 647-labeled aptamers were heated to 90° C. for 3 minutes and cooled to room temperature. Titrations of ALEXA FLUOR® 647-labeled aptamers and ALEXA FLUOR® 647-labeled anti-VEGF-A antibody were made in TR-FRET buffer (50 mM MOPS, pH 7.4, 125 mM NaCl, 5 mM KCl, 50 μM CHAPS, 0.1 mg/mL BSA, 1 mM $CaCl_2$, and 1 mM $MgCl_2$) in a polypropylene plate. 5 μL of aptamers or antibody were transferred to the black wall low volume 384 well assay plate (Greiner), followed by 5 μL glycan biotinylated VEGF-$A_{121}$ (2.5 nM final), and 5 μL Streptavidin-Eu (Perkin Elmer; 2.5 nM final). The plate was covered with a plate seal and subsequently incubated in the dark for 2 hours at room temperature. The plate was read on a Biotek CYTATION™ 5 plate reader. Samples were excited at 330 nm and fluorescent values were collected at 665 nm.

Figure 12A:
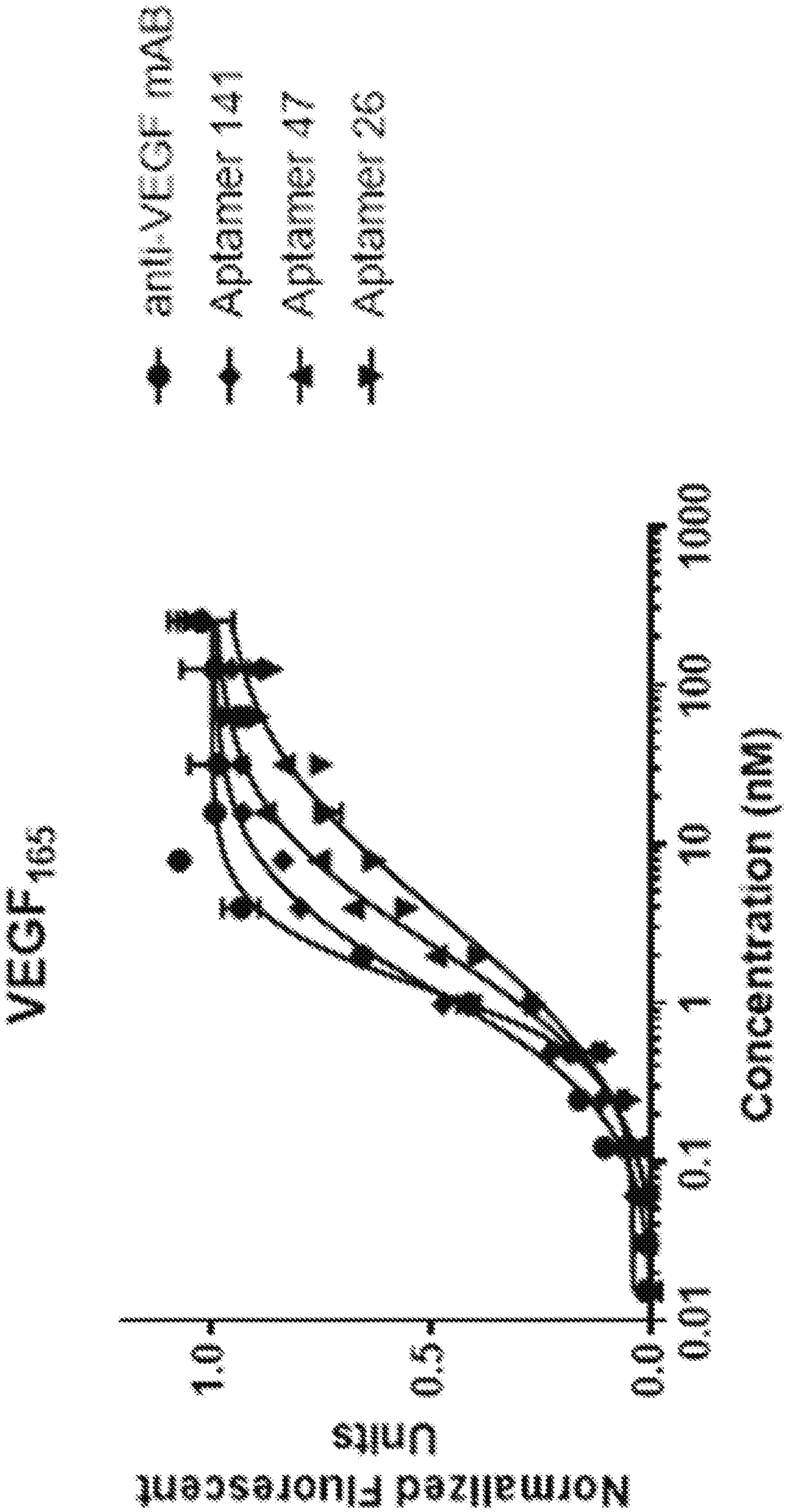
FIG. 12A depicts non-limiting examples of TR-FRET data demonstrating the affinity of Aptamers 26, 47, 141, and the anti-VEGF-A mAb for VEGF-$A_{1G}$s. Compounds were tested in a dose-dependent fashion to determine a $K_d$ against each isoform according to embodiments of the disclosure.
Figure 12B:
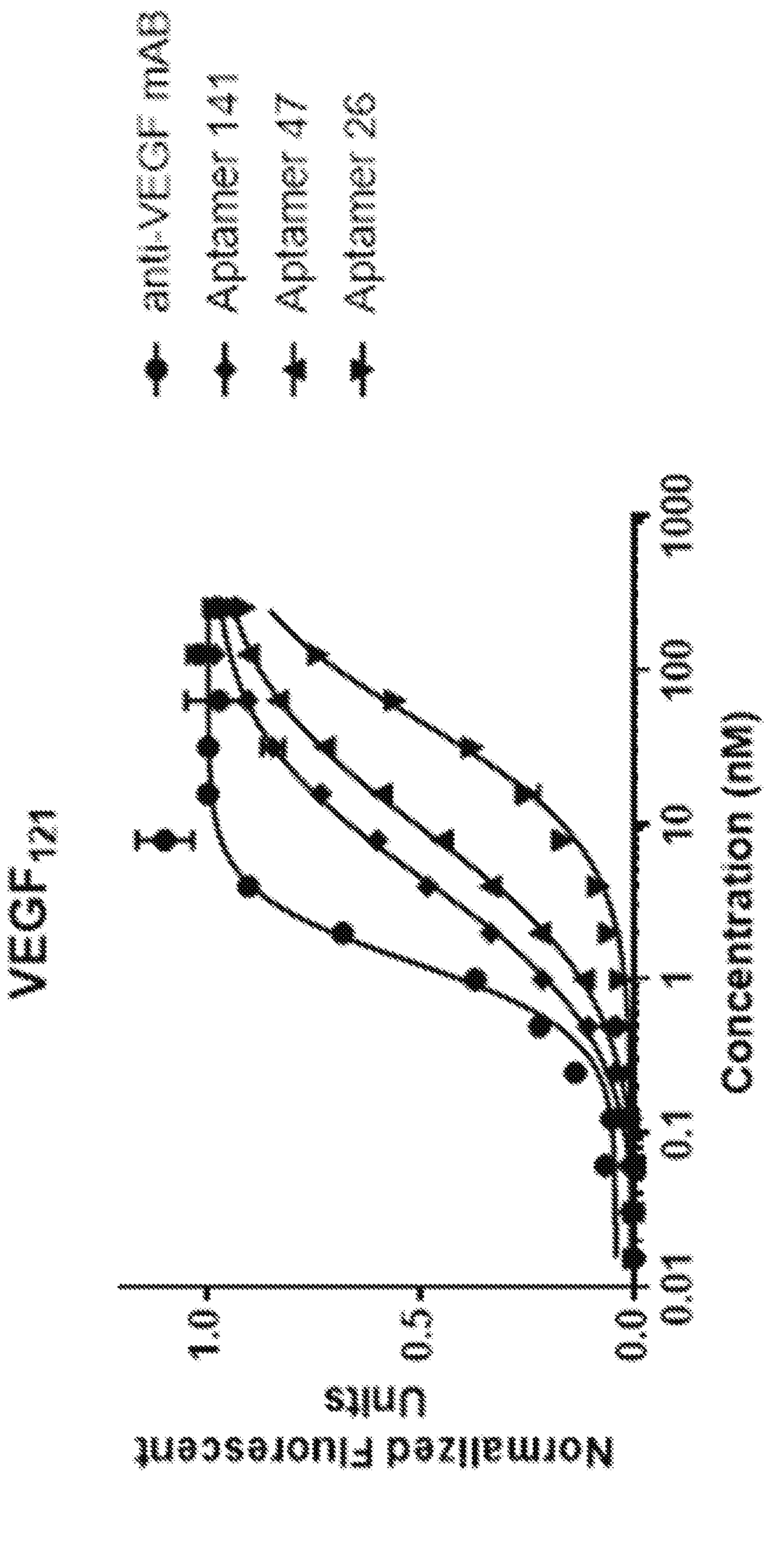
FIG. 12B depicts non-limiting examples of TR-FRET data demonstrating the affinity of Aptamers 26, 47, 141, and the anti-VEGF-A mAb for VEGF-$A_{121}$. Compounds were tested in a dose-dependent fashion to determine a $K_d$ against each isoform according to embodiments of the disclosure.

No protein background fluorescent values were averaged and subtracted from test compounds, with data normalized as a fold change to highest concentrations of aptamers and antibody. These values were fit using a four-parameter non-linear fit in GraphPad Prism Version 7.0. Representative binding affinity curves of Aptamers 26, 47, and 141, compared to the anti-VEGF-A mAb described in Table 8, is shown in FIG. 12A and FIG. 12B. Results indicated that Aptamers 26, 47, and 141 have a binding affinity to VEGF-$A_{165}$ with calculated $K_d$ values of 4.0±0.64 nM, 2.1±0.21 nM, and 1.2±0.21 nM, respectively, which is comparable to the anti-VEGF-A mAb tested, with a $K_d$ of 1.2±0.07 nM. For VEGF-$A_{121}$, Aptamers 26, 47, and 141 demonstrated calculated $K_d$ values of 46±nM, 11±2.1 nM, and 4.3 nM, respectively, with the anti-VEGF-A mAb with a $K_d$ of 1.3 nM. Importantly, the calculated $K_d$ values for Aptamer 141 (for VEGF-$A_{165}$) and the anti-VEGF-A mAb (for both VEGF-$A_{165}$ and VEGF-$A_{121}$) were limited by the input VEGF-A concentration. These results were consistent with binding affinity SPR data from Example 2 and supported the pan-isoform specificity of the lead aptamers.

Example 9C. Lead Characterization by Receptor Inhibition AlphaLISA®

The mechanism of action of lead aptamers was characterized by interrogating their ability to inhibit the VEGF-A:

KDR interaction with both VEGF-$A_{165}$ and VEGF-$A_{121}$. To do this, Aptamers 26, 47, 141 and a comparator anti-VEGF-A mAb were tested and analyzed by an AlphaLISA® assay, as described in Example 3.

Figure 13A:
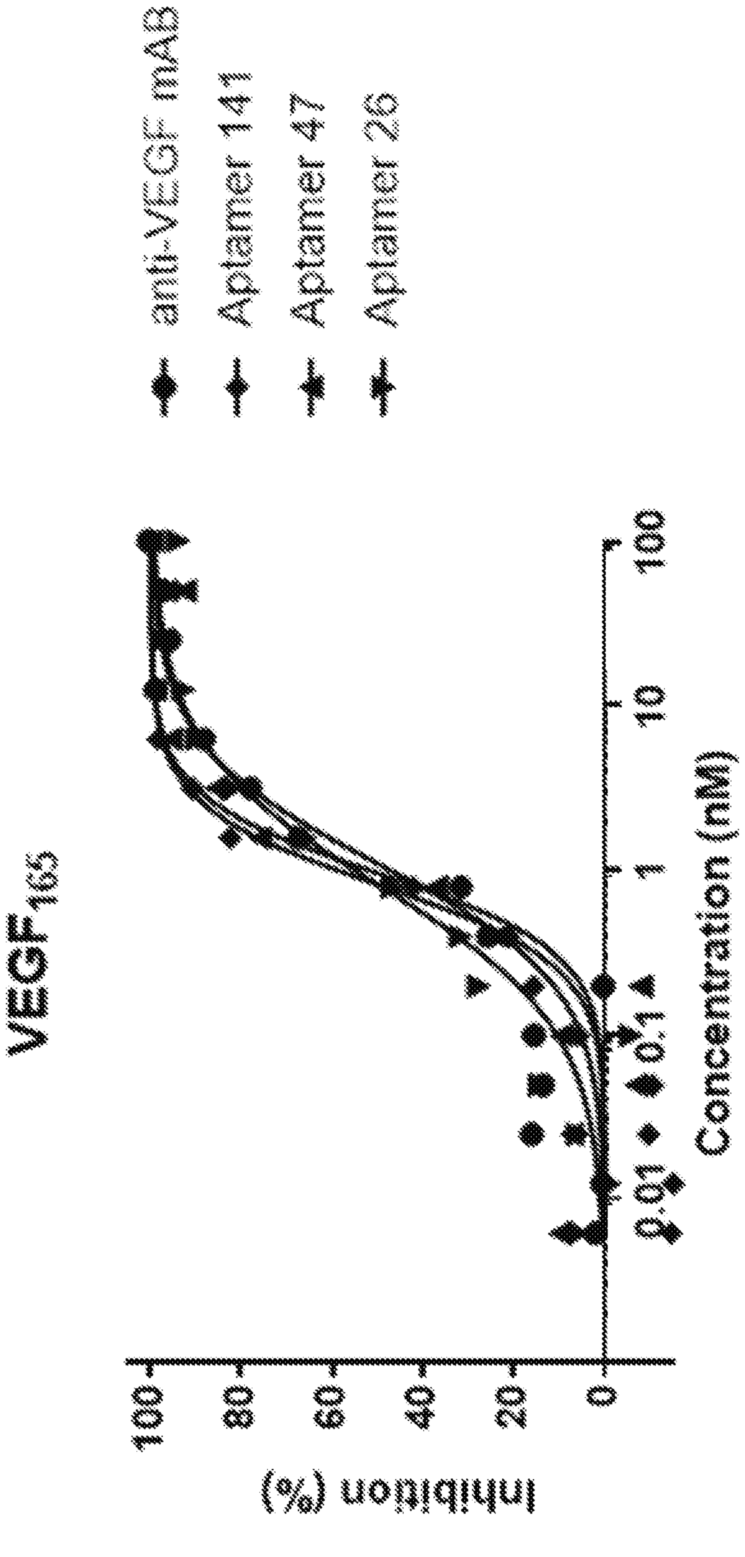
FIG. 13A depicts non-limiting examples of AlphaLISA® data demonstrating inhibition VEGF-$A_{165}$, binding to KDR by Aptamers 26, 47, or 141, compared to an anti-VEGF-A mAb. Compounds were tested in a dose-dependent fashion to determine an $IC_{50}$ against each isoform according to embodiments of the disclosure.
Figure 13B:
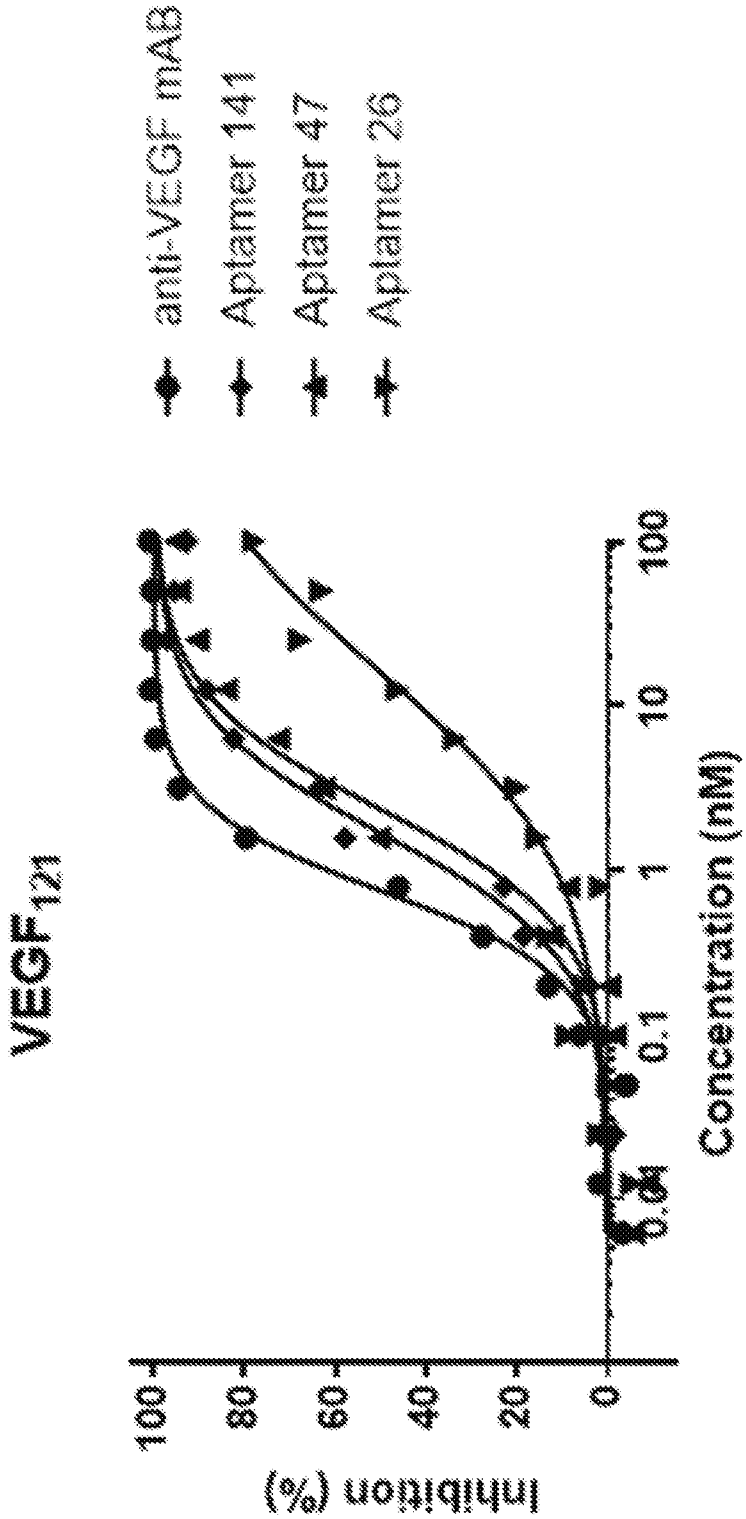
FIG. 13B depicts non-limiting examples of AlphaLISA® data demonstrating inhibition VEGF-$A_{121}$ binding to KDR by Aptamers 26, 47, or 141, compared to an anti-VEGF-A mAb. Compounds were tested in a dose-dependent fashion to determine an $IC_{50}$ against each isoform according to embodiments of the disclosure.

Representative curves of Aptamers 26, 47, 141 and comparator anti-VEGF-A mAb is shown in FIG. 13A and FIG. 13B. Results indicated that Aptamers 26, 47, 141 and the anti-VEGF-A mAb directly blocked the interaction of VEGF-A (VEGF-$A_{165}$ or VEGF-$A_{121}$) with KDR. Aptamers 26, 47, and 141 blocked the interaction of VEGF-$A_{165}$ with KDR with $IC_{50}$ values of 3.7±2.4 nM, 0.84±0.50 nM, and 0.81±0.22 nM, respectively, which is in line with the anti-VEGF-A mAb comparator that demonstrated an $IC_{50}$ of 0.71±0.48 nM. Similarly, Aptamers 26, 47, and 141 blocked the interaction of VEGF-$A_{121}$ with KDR with $IC_{50}$ values of 19±19 nM, 3.6±2.3 nM, and 3.2±1.6 nM, respectively, which is in line with the anti-VEGF-A mAb comparator that demonstrated an $IC_{50}$ of 0.63±0.22 nM. Importantly, the calculated $IC_{50}$ values for all aptamers (for VEGF-$A_{165}$) and the anti-VEGF-A mAb (for both VEGF-$A_{165}$ and VEGF-$A_{121}$) were limited by the input VEGF-A concentration.

The data presented in FIG. 13A and FIG. 13B demonstrates that these aptamers bound to an epitope consisting of or overlapping with the receptor binding face contained within the RBD of VEGF-A, and thus directly blocked the interaction of VEGF-A with its cognate receptor.

Example 9D. Lead Characterization by Receptor Phosphorylation

When the RBD of VEGF-A binds to KDR, the receptor dimerizes leading to trans-autophosphorylation and activation of VEGF-A signaling. To determine if lead aptamers bound to the RBD of VEGF-A and resulted in inhibition of VEGF-A activity, Aptamers 26, 47, and 141 were tested for their ability to inhibit KDR phosphorylation induced by VEGF-$A_{165}$ as compared to an anti-VEGF-A antibody. This characterization was performed by a KDR phosphorylation AlphaLISA®, as described in Example 4.

Figure 14:
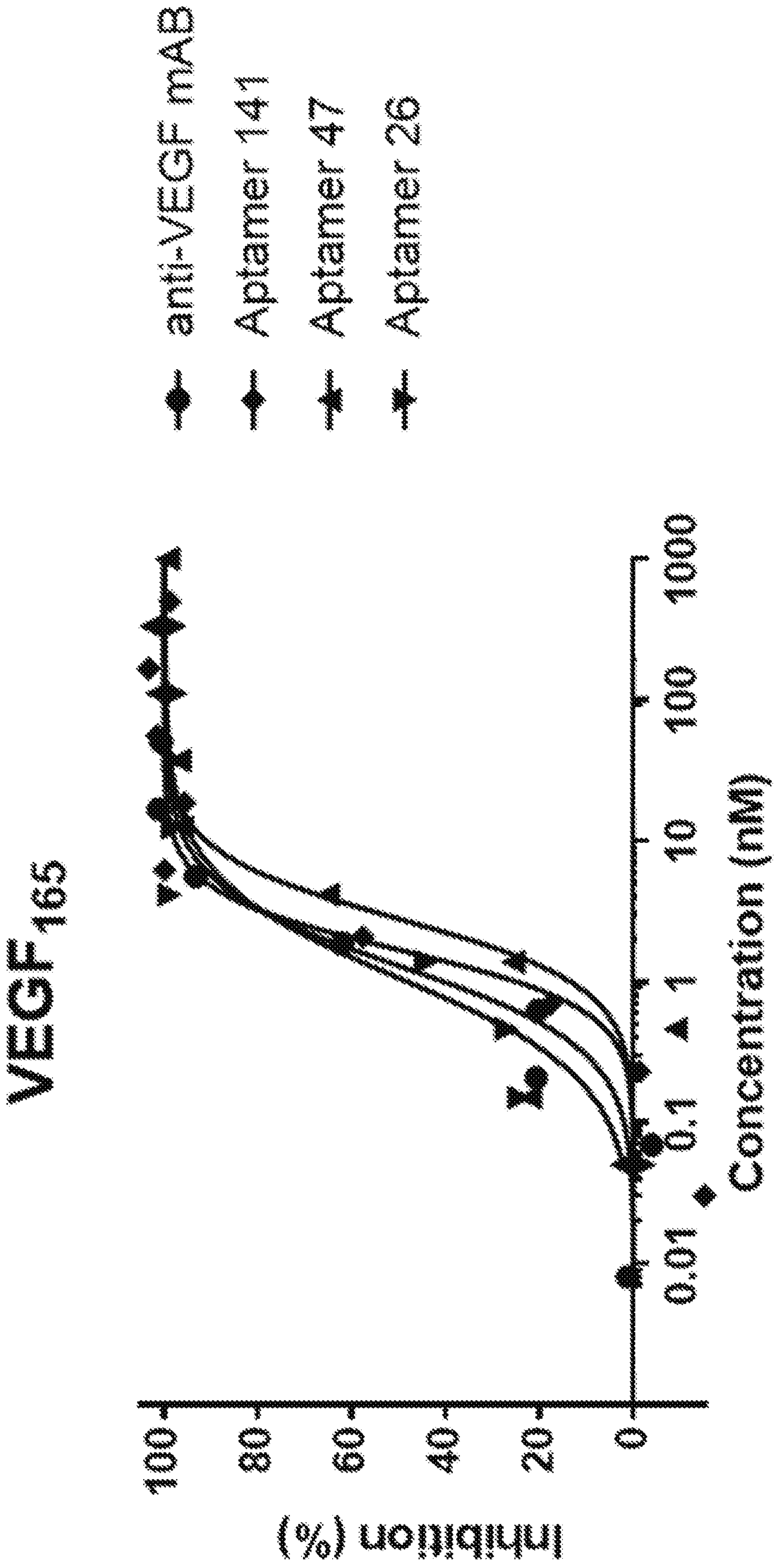
FIG. 14 depicts non-limiting examples of AlphaLISA® data demonstrating inhibition of VEGF-$A_{165}$-stimulated KDR phosphorylation by Aptamers 26, 47, or 141, compared to an anti-VEGF-A mAb. Compounds were tested in a dose-dependent fashion to determine an $IC_{50}$ against each isoform according to embodiments of the disclosure.

Representative curves of Aptamers 26, 47, 141 and comparator anti-VEGF-A mAb is shown in FIG. 14. Results indicated that Aptamers 26, 47, 141 and the anti-VEGF-A mAb achieved full inhibition of the phosphorylation of KDR by inhibiting its interaction with VEGF-$A_{165}$. Calculated $IC_{50}$ values for Aptamers 26, 47, and 141 and the comparator anti-VEGF-A mAb were 1.5±0.60 nM, 2.6±0.26 nM, 1.7±0.46 nM, and 1.1±0.02 nM, respectively. The potency and complete inhibition of VEGF-$A_{165}$-induced phosphorylation of KDR by Aptamers 26, 47, and 141 and their comparable activity profile to an anti-VEGF-A mAb, is consistent with the ability of Aptamers 26, 47, and 141 to bind to the receptor binding face present within the RBD of VEGF-A and directly block the interaction between VEGF-A and KDR.

Example 9E. Lead Characterization by Inhibition of Angiogenesis

VEGF-A plays an important role in inducing angiogenesis in both normal tissues and diseased pathologies (Ferrara, 2004). It is therefore of interest to evaluate potential VEGF-A antagonists in an angiogenesis assay. In vitro models have been established to study VEGF-A-stimulated angiogenesis. These models can therefore be used with the selected aptamers to determine their ability to inhibit angiogenesis via binding to either VEGF-$A_{165}$ or VEGF-$A_{121}$ and inhibiting VEGF-A induced signal transduction via KDR activation.

Co-culture of fibroblasts and endothelial cells leads to the formation of tubes after stimulation with either VEGF-$A_{165}$ or VEGF-$A_{121}$. Briefly, at Day 0, primary human dermal fibroblasts (ATCC) were plated at 20 k cells/well in 100 µL fibroblast growth media (ATCC) and incubated at room temperature for 1 hour. GFP-infected HUVEC cells (Lonza, infected in-house) were then plated at 10 k cells/well with 100 µL HUVEC growth media (without VEGF-A supplement, PromoCell) and incubated at room temperature for 1 hour. The plate was then placed in the IncuCyte® Zoom (Essen Bioscience) set to the default angiogenesis analysis definition with imaging programmed every 4 hours. After 24 hours of incubation (Day 1), old media was removed and replaced with 150 µL/well of IncuCyte® Angiogenesis Prime Kit Optimized Assay Medium (Essen Bioscience). After 24 hours (Day 2), media was changed with fresh media with or without treatment. Treatment included 400 µM VEGF-$A_{165}$ or 800 pM VEGF-$A_{121}$ premixed with or without a dilution of aptamer or the anti-VEGF-A mAb. Assays were carried out for 6 days with media changes and subsequent treatments performed on Days 4 and 6.

Figure 15A:
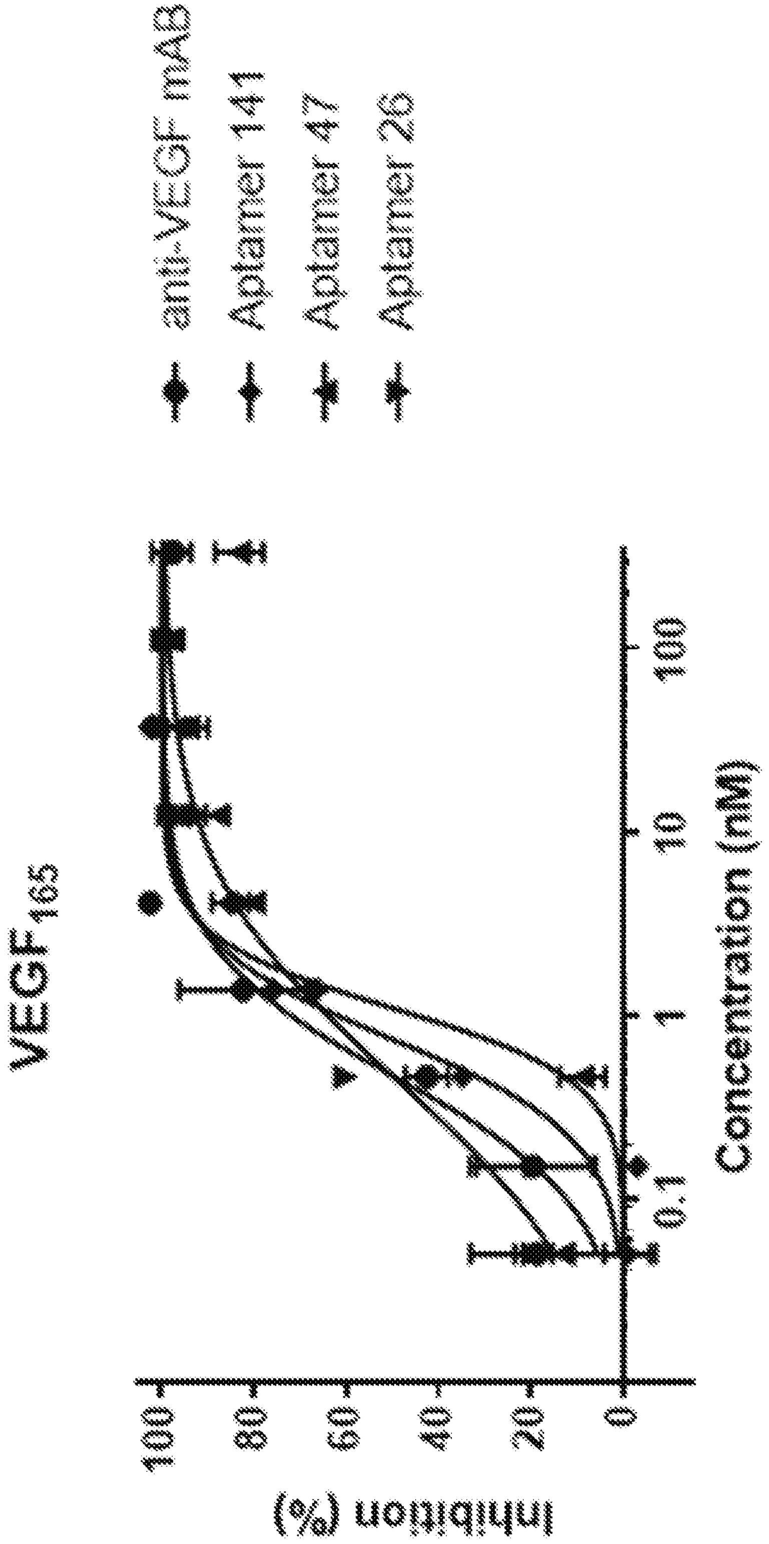
FIG. 15A depicts non-limiting examples of tube formation data demonstrating inhibition of VEGF-$A_{165}$-stimulated angiogenesis by Aptamers 26, 47, or 141, compared to an anti-VEGF-A mAb. Aptamers were tested in a dose-dependent fashion to determine an $IC_{50}$ against each isoform according to embodiments of the disclosure.
Figure 15B:
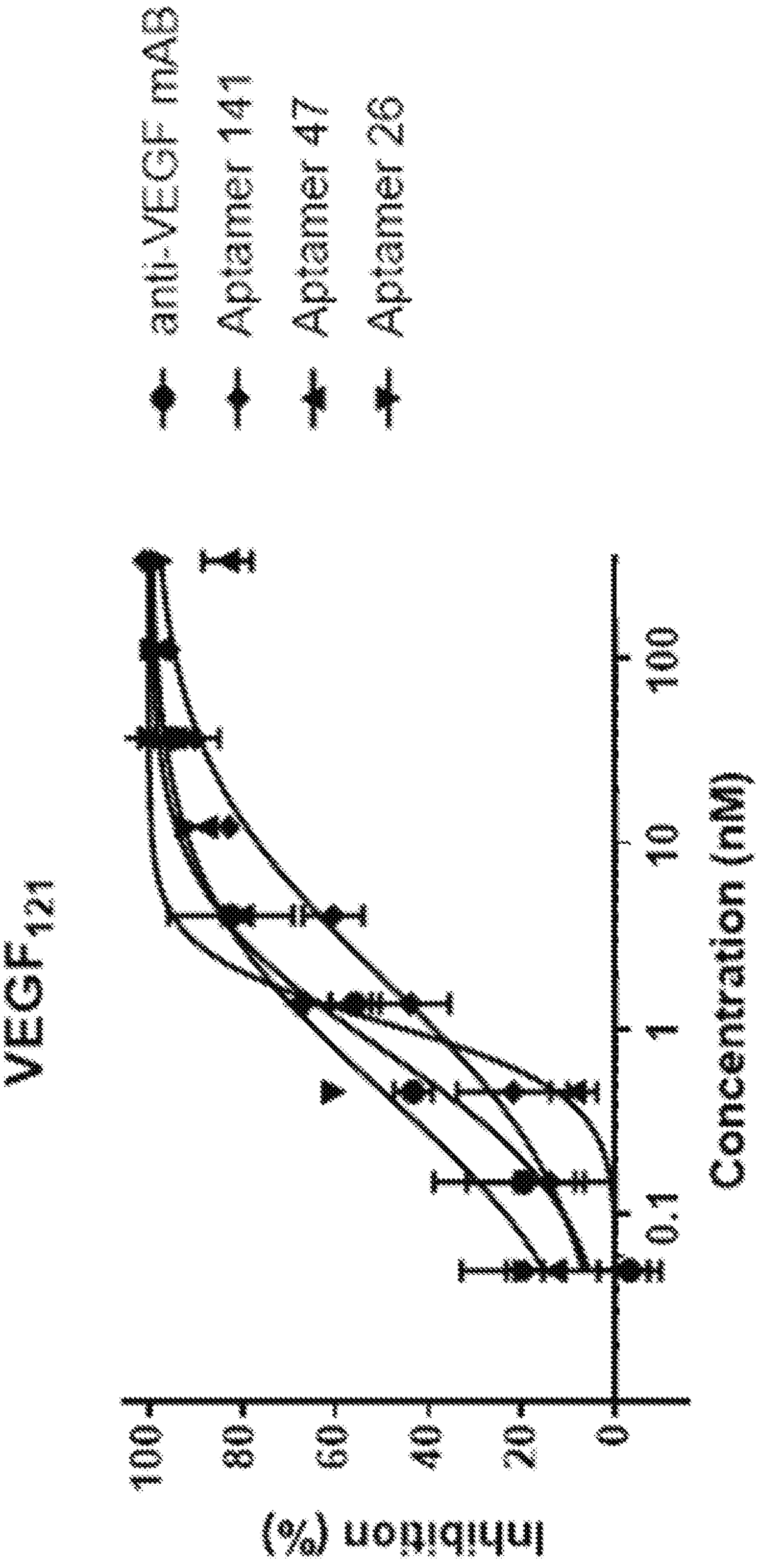
FIG. 15B depicts non-limiting examples of tube formation data demonstrating inhibition of VEGF-$A_{121}$-stimulated angiogenesis by Aptamers 26, 47, or 141, compared to an anti-VEGF-A mAb. Aptamers were tested in a dose-dependent fashion to determine an $IC_{50}$ against each isoform according to embodiments of the disclosure.
Figure 16A:
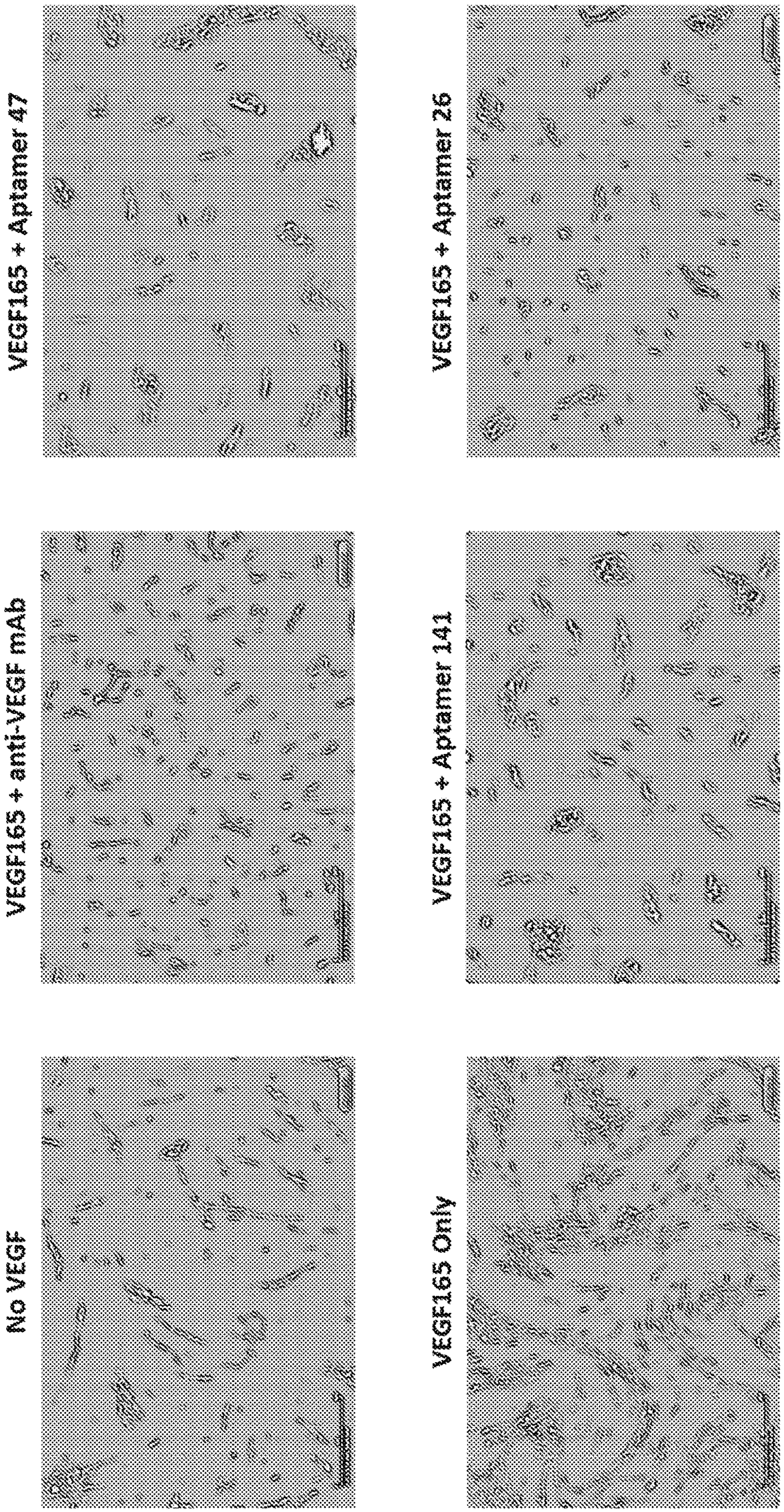
FIG. 16A depicts non-limiting examples of representative images of the inhibition of VEGF-$A_{165}$-stimulated angiogenesis by Aptamers 26, 47, or 141, compared to an anti-VEGF-A mAb. Images depict the VEGF-A-induced and inhibition of VEGF-A-induced tube formation of GFP-HUVEC cells according to embodiments of the disclosure.
Figure 16B:
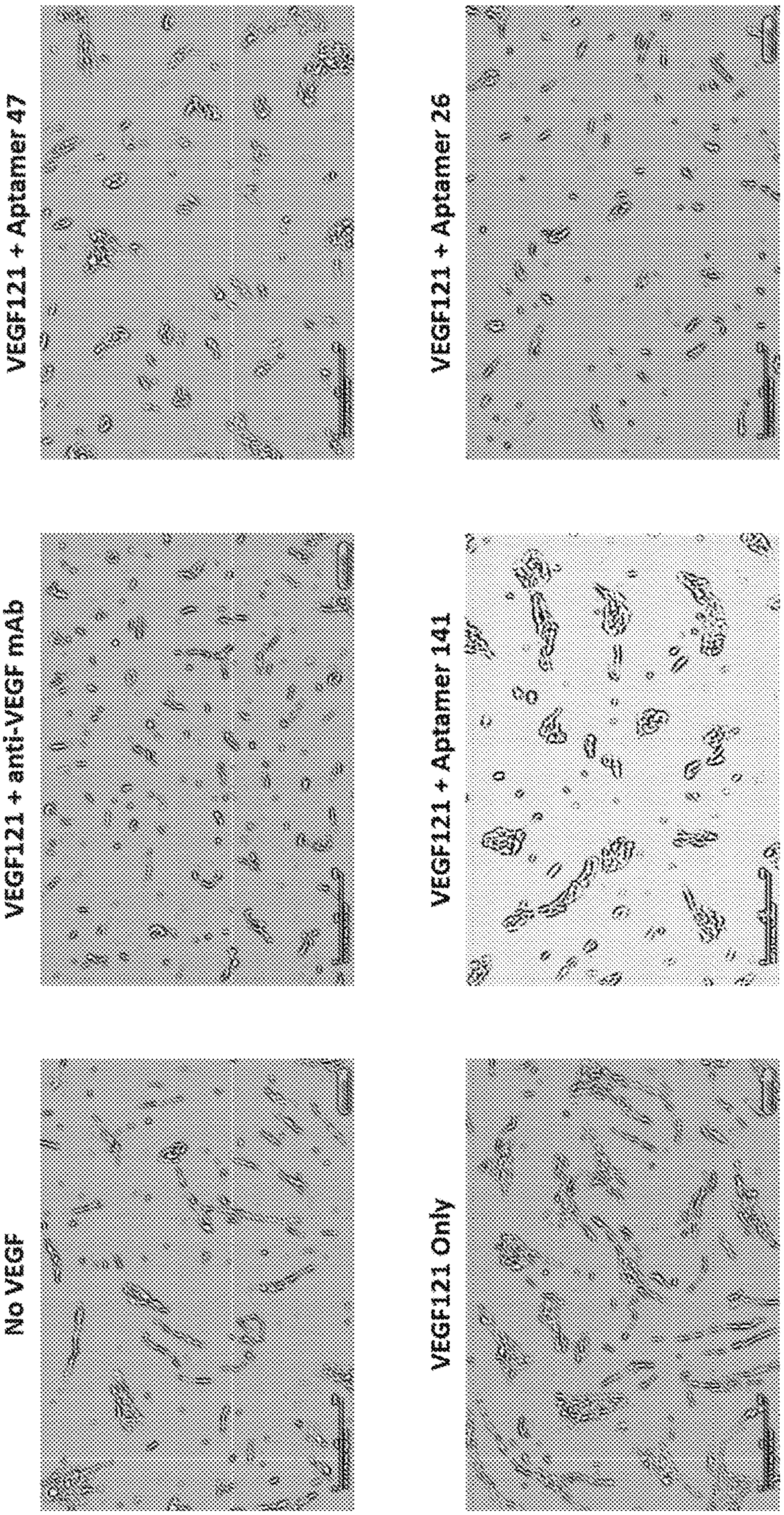
FIG. 16B depicts non-limiting examples of representative images of the inhibition of VEGF-$A_{121}$-stimulated angiogenesis by Aptamers 26, 47, or 141, compared to an anti-VEGF-A mAb. Images depict the VEGF-A-induced and inhibition of VEGF-A-induced tube formation of GFP-HUVEC cells according to embodiments of the disclosure.

Network length ($mm/mm^3$) of the tubes formed from the GFP-HUVEC cells was measured as a primary indication of angiogenesis. Percent inhibition was calculated by subtracting assay media background from each value and normalizing to VEGF-A only controls. The values were fit using a four-parameter non-linear fit in GraphPad Prism Version 7.0. $IC_{50}$ values for VEGF-$A_{165}$ and VEGF-$A_{121}$ were calculated at a time point that reflected an $EC_{90}$-$EC_{100}$ of the VEGF-A alone induction of tube formation. Representative dose response curves of Aptamers 26, 47, and 141, compared to the anti-VEGF-A mAb described in Table 8, are shown in FIG. 15A and FIG. 15B. Data indicated that all aptamers had an inhibitory effect against VEGF-$A_{16}$ with $IC_{50}$ values of 1.9±0.85 nM, 0.64±0.17 nM, and 0.50±0.21 nM, respectively which was comparable to the anti-VEGF-A mAb tested, with an $IC_{50}$ of 0.51±0.05 nM. When angiogenesis was stimulated by VEGF-$A_{121}$, Aptamers 26, 47, and 141 likewise had an inhibitory effect with $IC_{50}$ values of 18±5.6 nM, 5.5±2.4 nM, and 3.1±1.8 nM, respectively, with the anti-VEGF-A mAb inhibiting at 0.91±0.06 nM. This is also represented qualitatively in FIG. 16A and FIG. 16B, in which Aptamers 26, 47, and 141 as well as the anti-VEGF-A mAb were shown to inhibit tube formation when GFP-HUVEC cells (shown) were treated with either VEGF-$A_{165}$ or VEGF-$A_{121}$. These data supported the notion that lead aptamers could inhibit both VEGF-$A_{165}$ and VEGF-$A_{121}$-induced angiogenesis.

Example 10. Lead Stabilization and Truncation

2'OMe modifications are known to impart higher duplex stability and have greater coupling efficiency during synthesis compared to 2'F-containing nucleotides. The use of these nucleotides also avoids the potential loss of the 2'F group, which can happen in production during the deprotection step and during exposure to heat. The effect of 2'F-G to 2'OMe-G substitution on target binding was probed, using Aptamer 141, an improved variant of Aptamer 26 that contained a non-nucleotidyl spacer 3 modification, and an A:U base pair at positions 7 and 40 within stem S1.

Figure 17:
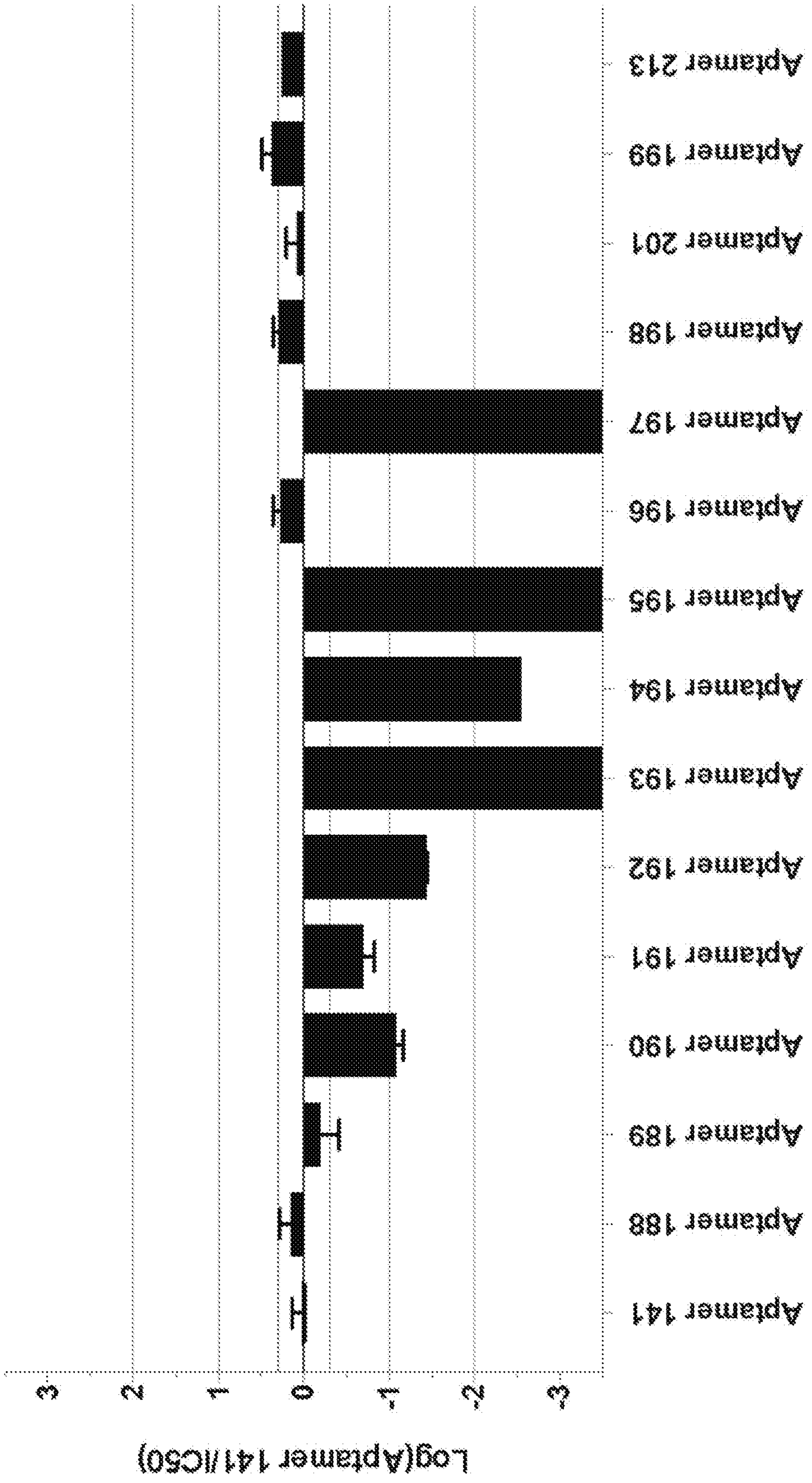
FIG. 17 depicts competitive TR-FRET data demonstrating the relative affinity of anti-VEGF-A aptamers according to embodiments of the disclosure. Data is represented as the log of fold change in $IC_{50}$ as compared to parent aptamer.

Starting at position 6, 2'F-G residues were systematically replaced, one at a time, and the activity of the resultant molecule was assessed by competition TR-FRET, as described in Example 7, against the parent molecule, Aptamer 141. As shown in Table 18 and FIG. 17, the 2'OMe-G substitution was tolerated at numerous positions throughout the molecule, including positions 6, 12, 14, 16, 17, 22, 39 and 40 (Aptamers 188-198), with modification at some of these positions (positions 22 and 39) leading to a modest improvement in activity (~2-fold; Aptamer 196 and Aptamer 198).

In addition, an initial attempt at truncating stem S1 of Aptamer 141 to six base pairs resulted in a ~2-fold increase in activity (Aptamer 199). In the context of Aptamer 199, the replacement of the terminal 2'F-G residues outside of the region systematically examined by Aptamers 188-198 was tested. As shown in Table 18 and FIG. 17, replacement of the terminal stem S1 positions (Aptamer 213) had no effect on aptamer activity relative to Aptamer 199 (~2-fold improvement in activity over Aptamer 141).

In summary, 2'OMe-G substitution was tolerated at numerous positions throughout the molecule and was particularly well tolerated in all of the positions within stem S1 as well as positions 12, 22, and 39 (Aptamers 189, 196, and 198).

TABLE 18

O-Methyl G substitution analysis

| SEQ ID NO with modifications: | Aptamer Number | Sequence (5' to 3')<br>S1 L1 S2 L2 S2 L3 S3 L4 S3 L5 S1 | TR-FRET |
|---|---|---|---|
| 315 | Aptamer 141 | $C6NH_2$-AGGCCG**A**C-**3**-CC-GCGC-GG-A-GGGGU-UUCAUU-AUCCC-GUUU-G**U**CGGCUU-idT | parent |
| 361 | Aptamer 188 | $C6NH_2$-AGGCC**XA**C-**3**-CC-GCGC-GG-A-GGGGU-UUCAUU-AUCCC-GUUU-G**U**CGGCUU-idT | ~ |
| 362 | Aptamer 189 | $C6NH_2$-AGGCCG**A**C-**3**-CC-**X**CGC-GG-A-GGGGU-UUCAUU-AUCCC-GUUU-G**U**CGGCUU-idT | ~ |
| 363 | Aptamer 190 | $C6NH_2$-AGGCCG**A**C-**3**-CC-GC**X**C-GG-A-GGGGU-UUCAUU-AUCCC-GUUU-G**U**CGGCUU-idT | -- |
| 364 | Aptamer 191 | $C6NH_2$-AGGCCG**A**C-**3**-CC-GCGC-**X**G-A-GGGGU-UUCAUU-AUCCC-GUUU-G**U**CGGCUU-idT | - |
| 365 | Aptamer 192 | $C6NH_2$-AGGCCG**A**C-**3**-CC-GCGC-G**X**-A-GGGGU-UUCAUU-AUCCC-GUUU-G**U**CGGCUU-idT | -- |
| 366 | Aptamer 193 | $C6NH_2$-AGGCCG**A**C-**3**-CC-GCGC-GG-A-**X**GGGU-UUCAUU-AUCCC-GUUU-G**U**CGGCUU-idT | --- |
| 367 | Aptamer 194 | $C6NH_2$-AGGCCG**A**C-**3**-CC-GCGC-GG-A-G**X**GGU-UUCAUU-AUCCC-GUUU-G**U**CGGCUU-idT | --- |
| 368 | Aptamer 195 | $C6NH_2$-AGGCCG**A**C-**3**-CC-GCGC-GG-A-GG**X**GU-UUCAUU-AUCCC-GUUU-G**U**CGGCUU-idT | --- |
| 369 | Aptamer 196 | $C6NH_2$-AGGCCG**A**C-**3**-CC-GCGC-GG-A-GGG**X**U-UUCAUU-AUCCC-GUUU-G**U**CGGCUU-idT | ~ |
| 370 | Aptamer 197 | $C6NH_2$-AGGCCG**A**C-**3**-CC-GCGC-GG-A-GGGGU-UUCAUU-AUCCC-**X**UUU-G**U**CGGCUU-idT | --- |
| 371 | Aptamer 198 | $C6NH_2$-AGGCCG**A**C-**3**-CC-GCGC-GG-A-GGGGU-UUCAUU-AUCCC-GUUU-**XU**CGGCUU-idT | + |
| 373 | Aptamer 201 | $C6NH_2$-AGGCC**XA**C-**3**-CC-GCGC-GG-A-GGG**X**U-UUCAUU-A**C**CCC-GUUU-**XU**CGGCUU-idT | ~ |
| 372 | Aptamer 199 | $C6NH_2$-__GCCG**A**C-**3**-CC-GCGC-GG-A-GGGGU-UUCAUU-ACCCC-GUUU-G**U**CGGC__-idT | + |
| 374 | Aptamer 213 | $C6NH_2$-__**X**CCG**A**C-**3**-CC-GCGC-GG-A-GGGGU-UUCAUU-ACCCC-GUUU-G**U**C**XX**C__-idT | ~ |

where G is 2'F and A, C, and U are 2'OMe modified RNA;
X is 2'OMe-G modified RNA;
$C6NH_2$ is a hexylamine linker;
idT is an inverted deoxythymidine residue;
3 is the SP3 spacer (1,3-propanediol); and
bold letters denote differences from the parent Aptamer 26.
Dashes (-) delineate the structural features of the aptamers (e.g., stems, loops).
Key:
~ = 2 fold worse to 2 fold better,
+ = 2-10 fold better,
++ = 10-100 fold better,
+++ more than 100 fold better,
– = 2-10 fold worse, 10-100 fold worse,
––– = more than 100 fold worse.

Figure 18:
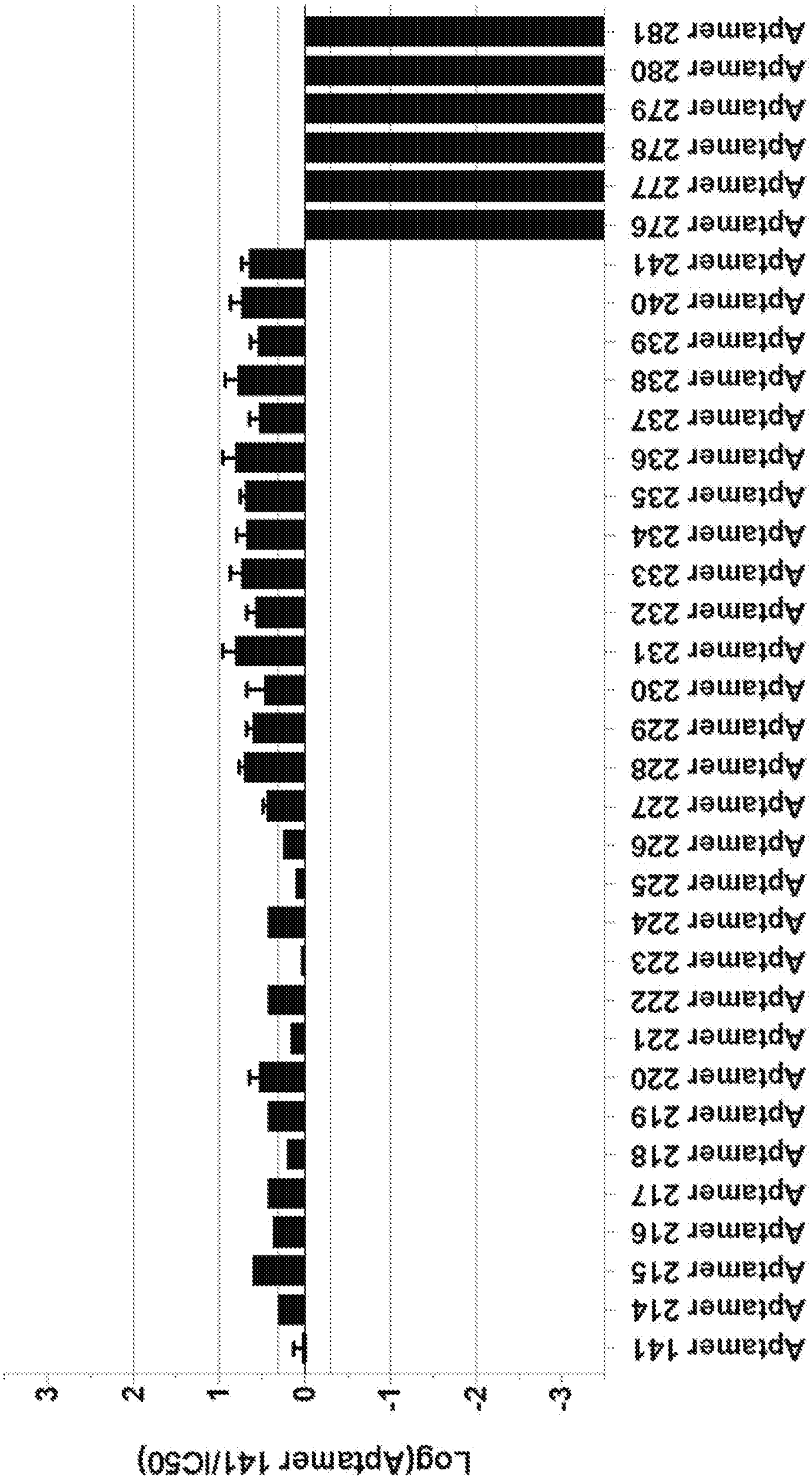
FIG. 18 depicts competitive TR-FRET data demonstrating the relative affinity of anti-VEGF-A aptamers according to embodiments of the disclosure. Data is represented as the log of fold change in $IC_{50}$ as compared to parent aptamer.

To further probe the relationship between 2'F-G to 2'OMe-G replacement and aptamer length, a series of constructs bearing stem S1 lengths of six, five, four, three, two, and one nucleotide were synthesized and the combinatorial effect of 2'F-G to 2'OMe-G replacements that were previously observed to be permissible were explored (Table 19 and FIG. 18). The length of stem S1 could be reduced to three base pairs in length without any adverse effect on activity (Aptamers 233-241). Moreover, the 2'F-G to 2'OMe-G substitutions could be readily accommodated into all these molecules. Shortening the length of stem S1 to less than three base pairs in length (Aptamers 276-281) resulted in a significant loss in activity (>100-fold). Together, these data support the finding that the 2'F-G residues at positions 6, 22, 39, and 40 could be replaced with a 2'OMe-G without negatively affecting the activity of Aptamer 141. Moreover, 2'OMe-G replacements at positions 6, 22, and 40 could be combined without negatively affecting the activity of Aptamer 141. Finally, stem S1 of aptamer 141, or variants bearing 2'F-G to 2'OMe-G replacements could be eight, six, five, four, or three base pairs in length.

TABLE 19

O-Methyl G consensus and truncation analysis

| SEQ ID NO with modifications: | Aptamer Number | Sequence (5' to 3')<br>S1 L1 S2 L2 S2 L3 S3 L4 S3 L5 S1 | TR-FRET |
|---|---|---|---|
| 315 | Aptamer 141 | C6NH$_2$-AGGCCGAC-3-CC-GCGC-GG-A-GGGGU-UUCAUU-AUCCC-GUUU-GUCGGCUU-idT | parent |
| 375 | Aptamer 214 | C6NH$_2$-XCCXAC-3-CC-GCGC-GG-A-GGGGU-UUCAUU-AUCCC-GUUU-GUCXXC-idT | + |
| 376 | Aptamer 215 | C6NH$_2$-XCCGAC-3-CC-GCGC-GG-A-GGGXU-UUCAUU-AUCCC-GUUU-GUCXXC-idT | + |
| 377 | Aptamer 216 | C6NH$_2$-XCCGAC-3-CC-GCGC-GG-A-GGGGU-UUCAUU-AUCCC-GUUU-XUCXXC-idT | + |
| 378 | Aptamer 217 | C6NH$_2$-XCCXAC-3-CC-GCGC-GG-A-GGGXU-UUCAUU-AUCCC-GUUU-GUCXXC-idT | + |
| 379 | Aptamer 218 | C6NH$_2$-XCCXAC-3-CC-GCGC-GG-A-GGGGU-UUCAUU-AUCCC-GUUU-XUCXXC-idT | ~ |
| 380 | Aptamer 219 | C6NH$_2$-XCCGAC-3-CC-GCGC-GG-A-GGGXU-UUCAUU-AUCCC-GUUU-XUCXXC-idT | + |
| 381 | Aptamer 220 | C6NH$_2$-XCCXAC-3-CC-GCGC-GG-A-GGGXU-UUCAUU-AUCCC-GUUU-XUCXXC-idT | + |
| 382 | Aptamer 221 | C6NH$_2$-CCXAC-3-CC-GCGC-GG-A-GGGGU-UUCAUU-AUCCC-GUUU-GUCXXC-idT | ~ |
| 383 | Aptamer 222 | C6NH$_2$-CCGAC-3-CC-GCGC-GG-A-GGGXU-UUCAUU-AUCCC-GUUU-GUCXXC-idT | + |
| 384 | Aptamer 223 | C6NH$_2$-CCGAC-3-CC-GCGC-GG-A-GGGGU-UUCAUU-AUCCC-GUUU-XUCXXC-idT | ~ |
| 385 | Aptamer 224 | C6NH$_2$-CCXAC-3-CC-GCGC-GG-A-GGGXU-UUCAUU-AUCCC-GUUU-GUCXXC-idT | + |
| 386 | Aptamer 225 | C6NH$_2$-CCXAC-3-CC-GCGC-GG-A-GGGGU-UUCAUU-AUCCC-GUUU-XUCXXC-idT | ~ |
| 387 | Aptamer 226 | C6NH$_2$-CCGAC-3-CC-GCGC-GG-A-GGGXU-UUCAUU-AUCCC-GUUU-XUCXXC-idT | ~ |
| 388 | Aptamer 227 | C6NH$_2$-CCXAC-3-CC-GCGC-GG-A-GGGXU-UUCAUU-AUCCC-GUUU-XUCXXC-idT | + |
| 389 | Aptamer 228 | C6NH$_2$-CXAC-3-CC-GCGC-GG-A-GGGGU-UUCAUU-AUCCC-GUUU-GUCX-idT | + |
| 390 | Aptamer 229 | C6NH$_2$-CGAC-3-CC-GCGC-GG-A-GGGXU-UUCAUU-AUCCC-GUUU-GUCX-idT | + |
| 391 | Aptamer 230 | C6NH$_2$-CGAC-3-CC-GCGC-GG-A-GGGGU-UUCAUU-AUCCC-GUUU-XUCX-idT | + |
| 392 | Aptamer 231 | C6NH$_2$-CXAC-3-CC-GCGC-GG-A-GGGXU-UUCAUU-AUCCC-GUUU-GUCX-idT | + |
| 393 | Aptamer 232 | C6NH$_2$-CXAC-3-CC-GCGC-GG-A-GGGGU-UUCAUU-AUCCC-GUUU-XUCX-idT | + |

TABLE 19-continued

| O-Methyl G consensus and truncation analysis | | | |
|---|---|---|---|
| SEQ ID NO with modifications: | Aptamer Number | Sequence (5' to 3')<br>S1 L1 S2 L2 S2 L3 S3 L4 S3 L5 S1 | TR-FRET |
| 394 | Aptamer 233 | C6NH$_2$-CG**A**C-**3**-CC-GCGC-GG-A-GGG**X**U-UUCAUU-AUCCC-GUUU-**XU**C**X**-idT | + |
| 395 | Aptamer 234 | C6NH$_2$-C**XA**C-**3**-CC-GCGC-GG-A-GGG**X**U-UUCAUU-AUCCC-GUUU-**XU**C**X**-idT | + |
| 396 | Aptamer 235 | C6NH$_2$-**XA**C-**3**-CC-GCGC-GG-A-GGGGU-UUCAUU-AUCCC-GUUU-G**U**C-idT | + |
| 397 | Aptamer 236 | C6NH$_2$-G**A**C-**3**-CC-GCGC-GG-A-GGG**X**U-UUCAUU-AUCCC-GUUU-G**U**C-idT | + |
| 398 | Aptamer 237 | C6NH$_2$-G**A**C-**3**-CC-GCGC-GG-A-GGGGU-UUCAUU-AUCCC-GUUU-**XU**C-idT | + |
| 399 | Aptamer 238 | C6NH$_2$-**XA**C-**3**-CC-GCGC-GG-A-GGG**X**U-UUCAUU-AUCCC-GUUU-G**U**C-idT | + |
| 400 | Aptamer 239 | C6NH$_2$-**XA**C-**3**-CC-GCGC-GG-A-GGGGU-UUCAUU-AUCCC-GUUU-**XU**C-idT | + |
| 401 | Aptamer 240 | C6NH$_2$-G**A**C-**3**-CC-GCGC-GG-A-GGG**X**U-UUCAUU-AUCCC-GUUU-**XU**C-idT | + |
| 402 | Aptamer 241 | C6NH$_2$-**XA**C-**3**-CC-GCGC-GG-A-GGG**X**U-UUCAUU-AUCCC-GUUU-**XU**C-idT | + |
| 403 | Aptamer 276 | C6NH$_2$-**A**C-**3**-CC-GCGC-GG-A-GGG**X**U-UUCAUU-AUCCC-GUUU-G**U**-idT | --- |
| 404 | Aptamer 277 | C6NH$_2$-**A**C-**3**-CC-GCGC-GG-A-GGGGU-UUCAUU-AUCCC-GUUU-**XU**-idT | --- |
| 405 | Aptamer 278 | C6NH$_2$-**A**C-**3**-CC-GCGC-GG-A-GGG**X**U-UUCAUU-AUCCC-GUUU-**XU**-idT | --- |
| 406 | Aptamer 279 | C6NH$_2$-C-**3**-CC-GCGC-GG-A-GGG**X**U-UUCAUU-AUCCC-GUUU-G-idT | --- |
| 407 | Aptamer 280 | C6NH$_2$-C-**3**-CC-GCGC-GG-A-GGGGU-UUCAUU-AUCCC-GUUU-**X**-idT | --- |
| 408 | Aptamer 281 | C6NH$_2$-C-**3**-CC-GCGC-GG-A-GGG**X**U-UUCAUU-AUCCC-GUUU-**X**-idT | --- |

where G is 2'F and A, C, and U are 2'OMe modified RNA;
X is 2'OMe-G modified RNA;
C6NH$_2$ is a hexylamine linker;
idT is an inverted deoxythmidine residue;
3 is the SP3 spacer (1,3-propanediol); and
bold letters denote differences from the parent Aptamer 26.
Dashes (-) delineate the structural features of the aptamers (e.g., stems, loops).
Key:
~ = 2 fold worse to 2 fold better,
+ = 2-10 fold better,
++ = 10-100 fold better,
+++ more than 100 fold better,
− = 2-10 fold worse,
10-100 fold worse,
--- = more than 100 fold worse.

Figure 19:
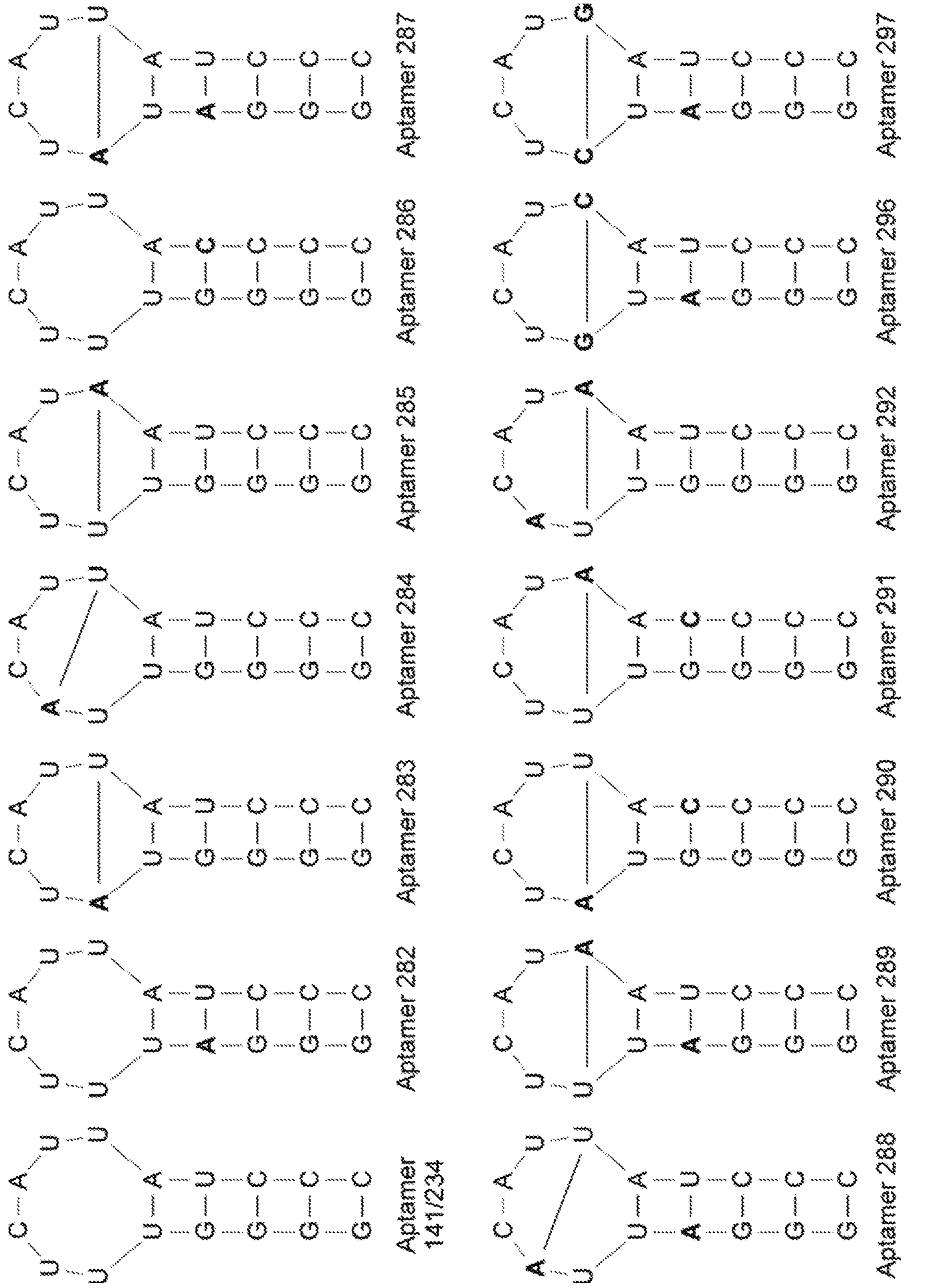
FIG. 19 depicts a non-limiting example of secondary structures of stem S3 and loop L4 of anti-VEGF-A aptamers according to embodiments of the disclosure.

Aptamer 234, a 2'OMe-G bearing variant of Aptamer 141 with a four base pair stem S1, was used to further explore the effects of various stem S3/loop L4 mutations identified in the degenerate selection on aptamer function. The proposed effect of these substitutions on the stem/loop structure are illustrated in FIG. 19. As shown in Table 20 and FIG. 20, almost all of these substitutions were well tolerated, providing molecules with activity levels comparable to Aptamer 234; a 2-10 fold improvement over Aptamer 141. Of particular note, the replacement of the U at position 29 (numbering based on Aptamer 141) with an A, generating a predicted six base pair stem S3 and a four nucleotide loop L4, resulted in an approximately 10-fold improvement in activity over Aptamer 141 (Aptamer 285). Additionally, these data demonstrated that a six base pair stem S3 could contain a single mis-matched nucleotide (e.g., Aptamer 284, and 288). Thus, when stem S3 is six base pairs long and contains a single mis-matched nucleotide, the length of loop L4 may be three nucleotides in length.

These data further highlighted the relationship between stem S3 and loop L4. When combined with sequence data observed in the primary and degenerate selections, these data further supported the observation that stem S3 could be four, five, or six base pairs in length. When stem S3 is six base pairs in length, it may contain a single mis-match at the penultimate nucleotide in the 5' side of the stem. When stem S3 is four base pairs in length, loop L4 may be six or eight nucleotides in length. When stem S3 is five base pairs in length, loop L4 may be four or six nucleotides in length and when stem S3 is six base pairs, loop L4 may be four nucleotides in length. When stem S3 is six base pairs long and contains a single mis-matched nucleotide, the length of loop L4 may be three nucleotides in length.

Together these data expand the consensus sequence of stem S3 for all of the variants observed or tested for Aptamer 26. Stem S3 may be expanded to 5'-GGGRUN3' for the 5' side of stem S3 and 5'-NWYCCC-3' for the 3' side of stem S3, where R is A or G; N is A, C, G, or U; W is A or U; and Y is C or U. When stem S3 is four base pairs, the consensus sequence may be 5'-GGGG-3' for the 5' side of stem S3 and 5'-CCCC-3' for the 3' side of stem S3. In some cases, when stem S3 is five base pairs, the consensus sequence may be 5'-GGGRU-3' for the 5' side of stem S3 and 5'-AYCCC-3' for the 3' side, where R is A or G; and Y is C or U. In some cases, when stem S3 is six base pairs, the consensus sequence may be 5'-GGGRUN-3' for the 5' side of stem S3 and 5'-NAYCCC-3' for the 3' side, where R is A or G; N is A, C, G, or U; D is A, G, or U; and H is A, C, or U. When stem S3 is six base pairs long and contains a single mis-matched nucleotide, the consensus sequence may be 5'-GG-GRUUR-3' for the 5' side of stem S3 and 5'-UAUCCC-3' for the 3' side, where U is the single mis-matched nucleotide; and R is A or G. When stem S3 is six base pairs long and contains a single mis-matched nucleotide, loop L4 may be three nucleotides long. When loop L4 is three nucleotides long, the sequence may be 5'-CUA-3'.

Aptamer 234 was also used to examine the effects of an alternate pairing at positions 10 and 17 in stem S2 (numbering based on Aptamer 141) and the effect of an additional 2'F-G to 2'OMe substitution at position 12 in loop L2 (numbering based on Aptamer 141) on aptamer function (Aptamers 293, 294, and 295). Consistent with the secondary structure prediction, the C:G pair at positions 10 and 17 could be replaced with an A:U pair with only a modest loss in activity relative to Aptamer 141 (Aptamers 293; approximately 6-fold loss). Interestingly, while the effect of the 2'F-G to 2'OMe substitution at position 12 was well tolerated (Aptamer 294; 1-2 fold loss), the combination of both the base pair substitution and the 2'OMe substitution resulted in a more significant loss of activity (Aptamer 295; 12-fold loss). The data further supported the consensus sequence for stem S2. Stem S2 may be composed of two base pairs with a consensus sequence of 5'-NN-3' for both the 5' and 3' sides of the stem.

Figure 20:
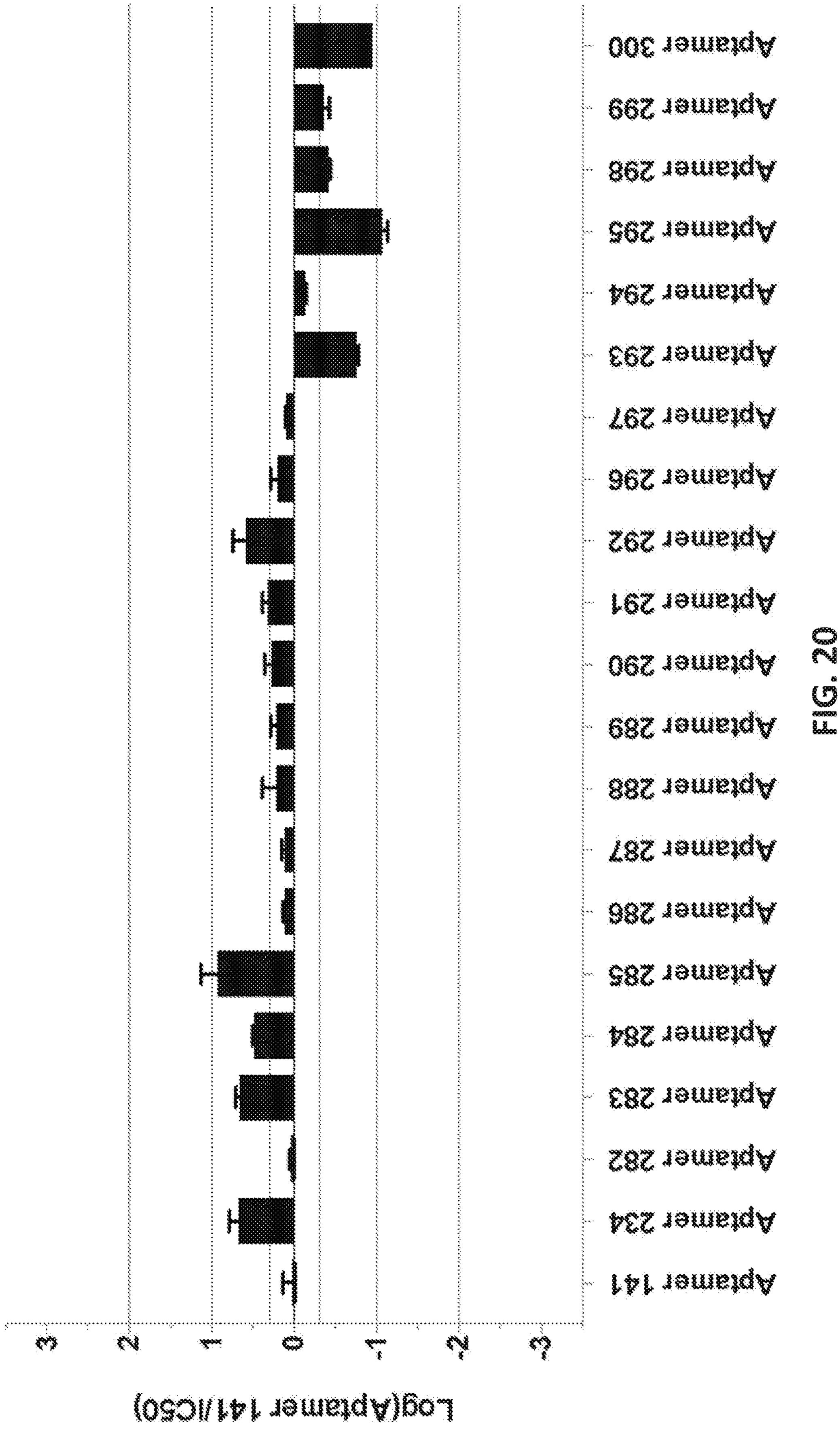
FIG. 20 depicts competitive TR-FRET data demonstrating the relative affinity of anti-VEGF-A aptamers according to embodiments of the disclosure. Data is represented as the log of fold change in $IC_{50}$ as compared to parent aptamer.

Finally, using Aptamer 234, the effects of linker length on loop L1 (position 7; numbering based on Aptamer 141; Aptamers 298-300) was explore. Increasing the length of the non-nucleotidyl linker in loop L1 resulted in a loss in activity relative to Aptamer 141. The longer the linker, the less potent the molecule (compare Aptamers 298, 299, and 300; FIG. 20). Together, these data further expanded the range of moieties that could be substituted into loop L1. Thus, the expanded consensus for loop L1 is 5'-N*-3', where N* is A, C, G, U, can be deleted entirely, or is a non-nucleotidyl spacer 3 (1,3-propanediol) modification (Table 20; 3), two spacer 3 modifications (Table 20; 33), a 6 carbon alkyl linker (1,6-hexanediol) (Table 20; 6), or a spacer 9 (triethyleneglycol) modification (Table 20; 9).

TABLE 20

Lead optimization by loop L4/stem S3 mutations discovered in degenerate selection

| SEQ ID NO with modifications: | Aptamer Number | Sequence (5' to 3')<br>S1 L1 S2 L2 S2 L3 S3 L4 S3 L5 S1 | TR-FRET |
|---|---|---|---|
| 315 | Aptamer 141 | C6NH$_2$-AGGCCGAC-3--CC-GCGC-GG-A-GGGGU-UUCAUU-AUCCC-GUUU-GUCGGCUU-idT | parent |
| 395 | Aptamer 234 | C6NH$_2$-CXAC-3--CC-GCGC-GG-A-GGGXU-UUCAUU-AUCCC-GUUU-XUCX-idT | + |
| 409 | Aptamer 282 | C6NH$_2$-CXAC-3--CC-GCGC-GG-A-GGGAU-UUCAUU-AUCCC-GUUU-XUCX-idT | ~ |
| 410 | Aptamer 283 | C6NH$_2$-CXAC-3--CC-GCGC-GG-A-GGGXU-AUCAUU-AUCCC-GUUU-XUCX-idT | + |
| 411 | Aptamer 284 | C6NH$_2$-CXAC-3--CC-GCGC-GG-A-GGGXU-UACAUU-AUCCC-GUUU-XUCX-idT | + |
| 412 | Aptamer 285 | C6NH$_2$-CXAC-3--CC-GCGC-GG-A-GGGXU-UUCAUA-AUCCC-GUUU-XUCX-idT | ++ |
| 413 | Aptamer 286 | C6NH$_2$-CXAC-3--CC-GCGC-GG-A-GGGXU-UUCAUU-ACCCC-GUUU-XUCX-idT | ~ |
| 414 | Aptamer 287 | C6NH$_2$-CXAC-3--CC-GCGC-GG-A-GGGAU-AUCAUU-AUCCC-GUUU-XUCX-idT | ~ |

TABLE 20-continued

Lead optimization by loop L4/stem S3 mutations discovered in degenerate selection

| SEQ ID NO with modifications: | Aptamer Number | Sequence (5' to 3') S1 L1 S2 L2 S2 L3 S3 L4 S3 L5 S1 | TR-FRET |
|---|---|---|---|
| 415 | Aptamer 288 | C6NH$_2$-CXAC-3--CC-GCGC-GG-A-GGGAU-UACAUU-AUCCC-GUUU-XUCX-idT | + |
| 416 | Aptamer 289 | C6NH$_2$-CXAC-3--CC-GCGC-GG-A-GGGAU-UUCAUA-AUCCC-GUUU-XUCX-idT | ~ |
| 417 | Aptamer 290 | C6NH$_2$-CXAC-3--CC-GCGC-GG-A-GGGXU-AUCAUU-ACCCC-GUUU-XUCX-idT | + |
| 418 | Aptamer 291 | C6NH$_2$-CXAC-3--CC-GCGC-GG-A-GGGXU-UUCAUA-ACCCC-GUUU-XUCX-idT | + |
| 419 | Aptamer 292 | C6NH$_2$-CXAC-3--CC-GCGC-GG-A-GGGXU-UACAUA-AUCCC-GUUU-XUCX-idT | + |
| 423 | Aptamer 296 | C6NH$_2$-CXAC-3--CC-GCGC-GG-A-GGGAU-XUCAUC-AUCCC-GUUU-XUCX-idT | ~ |
| 424 | Aptamer 297 | C6NH$_2$-CXAC-3--CC-GCGC-GG-A-GGGAU-CUCAUX-AUCCC-GUUU-XUCX-idT | ~ |
| 420 | Aptamer 293 | C6NH$_2$-CXAC-3--CA-GCGC-UG-A-GGGXU-UUCAUU-AUCCC-GUUU-XUCX-idT | - |
| 421 | Aptamer 294 | C6NH$_2$-CXAC-3--CC-XCGC-GG-A-GGGXU-UUCAUU-AUCCC-GUUU-XUCX-idT | ~ |
| 422 | Aptamer 295 | C6NH$_2$-CXAC-3--CA-XCGC-UG-A-GGGXU-UUCAUU-AUCCC-GUUU-XUCX-idT | -- |
| 425 | Aptamer 298 | C6NH$_2$-CXAC-33-CC-GCGC-GG-A-GGGXU-UUCAUU-AUCCC-GUUU-XUCX-idT | - |
| 426 | Aptamer 299 | C6NH$_2$-CXAC-6--CC-GCGC-GG-A-GGGXU-UUCAUU-AUCCC-GUUU-XUCX-idT | - |
| 427 | Aptamer 300 | C6NH$_2$-CXAC-9--CC-GCGC-GG-A-GGGXU-UUCAUU-AUCCC-GUUU-XUCX-idT | - |

where G is 2'F and A, C, and U are 2'OMe modified RNA;
X is 2'OMe-G modified RNA;
C6NH$_2$ is a hexylamine linker;
idT is an inverted deoxythymidine residue;
3 is the SP3 spacer (1,3-propanediol);
6 is the SP6 spacer (1,6-hexanediol);
9 is the SP9 spacer (triethyleneglycol); and
bold letters denote differences from the parent Aptamer 26.
Dashes (-) delineate the structural features of the aptamers (e.g., stems, loops).
Key:
~ = 2 fold worse to 2 fold better,
+ = 2-10 fold better,
++ = 10-100 fold better,
+++ more than 100 fold better,
- = 2-10 fold worse,
10-100 fold worse,
--- = more than 100 fold worse.

In total, when the data from the degenerate selection (Example 6) is combined with the data from our structure activity relationship studies (Examples 7, 8, 9 and 10), the consensus sequences for the Aptamer 26 family of molecules is 5'-HNBYHDNNN*NNKNGCNNWGGG-RUNDNDHNWYCCCGNNNNNYNKVNW-3 (SEQ ID NO:5) where H is A, C, or U, N is A, C, G, or U, Bis C, G, or U, Y is C or U; N* is A, C, G, U, can be deleted entirely, or is a non-nucleotidyl spacer 3 modification, a 6 carbon alkyl linker (1,6-hexanediol), or a spacer 9 (triethyleneglycol) modification; D is A, G, or U; K is G or U; W is A or U; R is A or G; and V is A, C, or G; and is represented with a six base pair stem S3 and a four nucleotide loop L4 in FIG. 7.

Example 11 Optimization of S3/L4 by SELEX

To better understand the roles of S3 and L4 in aptamer function we generated two different randomized libraries based on the sequence and structure of Aptamer 285, in which the non-nucleotidyl linker was replaced with a random nucleotide, N, where N is A, G, U or C, and where the entirety of Stem S3 and Loop L4 (S3-L4) was replaced with a library composed of 16 or 14 random positions. The sequence of the libraries used were:

GGGAGAGTCGGTAGCCTCAACGACNCCGCGCGGAN16GTTTGTCGCTAT

GTGGAAATGGCGCTGT,

GGGAGAGTCGGTAGCCTCAACGACNCCGCGCGGAN14GTTTGTCGCTAT

GTGGAAATGGCGCTGT (N16, N14; where N16 is 16 N positions, N14 is 14 N positions and Nis A, G, U or C).

Using these libraries, we performed two separate selections targeting human VEGF 121 in a manner similar to that described for the original selection (Example 1). Following 3 rounds of selection, each library was found to demonstrate significant VEGF binding activity (~10-fold signal over background) as determined by flow cytometry. The libraries were subsequently adapted for sequencing and sequenced on a an Illimuna MiSeq sequencer. Sequence analysis was performed as described previously.

For the S3-L4 N16 library, we analyzed the sequence data from 174,583 reads. An alignment of the sequences corresponding to the top 20 stacks from this library are shown in Table 21. These 20 stacks correspond to the top 44% of the enriched library sequences.

As shown in Table 21, the sequences from these top 20 stacks from the S3-L4 N16 library strongly support the structural and sequence requirements summarized in FIG. 7 in which the preferred identity of nucleotide in loop L1 is U, and stem S3 is composed of 4, 5 or 6 base pairs with a corresponding loop L4 of 8, 6 or 4 nucleotides, respectively. The results also demonstrate that S3 contains a significant degree of covariation, is not highly conserved in sequence identity except for the first base pair in the stem which prefers to be G:C pair. The consensus sequence for this randomized region (S3-L4) within the N16 library from the top 20 stacks is GDSBHDNNNNHNNBNC. When S3 is composed of 4 base pairs, the consensus sequence for the S3-L4 region is GGGT-TRVWGGYT-ACCC. When S3 is composed of 5 base pairs, consensus sequence for the S3-L4 region is GKSCY-KNNNNW-RKKVC, and when S3 is composed of 6 base pairs consensus sequence for the S3-L4 region is GRGGAG-GYWA-CYYCYC. When stem S3 is 4 based pairs long, loop L4 is 8 nucleotides long and the consensus is 5'-URVWGGY-3'. When stem S3 is 5 base pairs long, loop L4 is 6 nucleotides long and the consensus is 5'-KNNNNW-3'. When stem S3 is 6 base pairs long loop L4 is 4 nucleotides long and the consensus is 5'GYWA-3'.

TABLE 21

Top 20 sequence stacks identified in from the S3-L4 N16 library.

| SEQ ID NO: | S1 | **L1** | S2 | L2 | S2 | L3 | **S3** | **L4** | **S3** | L6 | S1 |
|---|---|---|---|---|---|---|---|---|---|---|---|
| 439: | CGAC | **U** | CC | GCGC | GG | A | **GGGU** | **UGGAGGUU** | **ACCC** | GUUU | GUCG |
| 441: | CGAC | **U** | CC | GCGC | GG | A | **GUCCC** | **UAAUUU** | **GGGGC** | GUUU | GUCG |
| 443: | CGAC | **U** | CC | GCGC | GG | A | **GUCCC** | **UUCAUU** | **GGGGC** | GUUU | GUCG |
| 445: | CGAC | **U** | CC | GCGC | GG | A | **GGGU** | **UAAUGGCU** | **ACCC** | GUUU | GUCG |
| 447: | CGAC | **U** | CC | GCGC | GG | A | **GUCCC** | **UGUAAU** | **GGGGC** | GUUU | GUCG |
| 449: | CGAC | **U** | CC | GCGC | GG | A | **GUCCC** | **UAUUUU** | **GGGGC** | GUUU | GUCG |
| 451: | CGAC | **U** | CC | GCGC | GG | A | **GAGGAG** | **GUUA** | **CCCCUC** | GUUU | GUCG |
| 453: | CGAC | **U** | CC | GCGC | GG | A | **GUCCC** | **UUGAUU** | **GGGGC** | GUUU | GUCG |
| 455: | CGAC | **U** | CC | GCGC | GG | A | **GGGU** | **UACUGGCU** | **ACCC** | GUUU | GUCG |
| 457: | CGAC | **U** | CC | GCGC | GG | A | **GUCCC** | **UAACAU** | **GGGGC** | GUUU | GUCG |
| 459: | CGAC | **U** | CC | GCGC | GG | A | **GGGGAG** | **GCAA** | **CUUCCC** | GUUU | GUCG |
| 461: | CGAC | **U** | CC | GCGC | GG | A | **GUCCC** | **UUUAUU** | **GGGGC** | GUUU | GUCG |
| 463: | CGAC | **U** | CC | GCGC | GG | A | **GUCCC** | **UACAAU** | **GGGGC** | GUUU | GUCG |
| 465: | CGAC | **U** | CC | GCGC | GG | A | **GUGCC** | **GUUUGA** | **GGUAC** | GUUU | GUCG |
| 467: | CGAC | **U** | CC | GCGC | GG | A | **GGGCU** | **GAGGCAAUGCCC** | | GUUU | GUCG |
| 469: | CGAC | **U** | CC | GCGC | GG | A | **GUCCC** | **UACUUU** | **GGGGC** | GUUU | GUCG |
| 471: | CGAC | **U** | CC | GCGC | GG | A | **GUCCC** | **UCACAU** | **GGGGC** | GUUU | GUCG |
| 473: | CGAC | **U** | CC | GCGC | GG | A | **GGGU** | **UACAGGCU** | **ACCC** | GUUU | GUCG |
| 475: | CGAC | **U** | CC | GCGC | GG | A | **GUCCC** | **UUUGUU** | **GGGGC** | GUUU | GUCG |
| 477: | CGAC | **U** | CC | GCGC | GG | A | **GUCCC** | **UAAAAU** | **GGGGC** | GUUU | GUCG |

Sequences in bold indicated randomized positions in the library.

For the S3-L4 N14 library, we analyzed the sequence data from 1,644,139 reads. An alignment of the sequences corresponding to the top 20 stacks from this library are shown in Table 22. These 20 stacks correspond to the top 80% of the enriched library sequences.

When S3 is composed of 5 base pairs, consensus sequence for the S3-L4 region is GYBYC-DNWD-GRKRC. When stem S3 is 4 base pairs long, loop L4 is 6 nucleotides long and the consensus is 5'-UDRGBU-3'. When stem S3 is 5 base pairs long, loop L4 is 4 nucleotides long and the consensus is 5'-DNWD-3'.

TABLE 22

Top 20 sequence stacks identified in from the S3-L4 N14 library.

| SEQ ID NO: | S1 | L1 | S2 | L2 | S2 | L3 | S3 | L4 | S3 | L6 | S1 |
|---|---|---|---|---|---|---|---|---|---|---|---|
| 479: | CGAC | **U** | CC | GCGC | GG | A | **GGGU** | **UUGGCU** | **ACCC** | GUUU | GUCG |
| 481: | CGAC | **U** | CC | GCGC | GG | A | **GGCU** | **UGAGGU** | **AGCC** | GUUU | GUCG |
| 483: | CGAC | **U** | CC | GCGC | GG | A | **GUCCC** | **ACAU** | **GGGGC** | GUUU | GUCG |
| 485: | CGAC | **U** | CC | GCGC | GG | A | **GGGA** | **UGAGGU** | **UCCC** | GUUU | GUCG |
| 487: | CGAC | **U** | CC | GCGC | GG | A | **GGCA** | **UGAGGU** | **UGCC** | GUUU | GUCG |
| 489: | CGAC | **U** | CC | GCGC | GG | A | **GUGC** | **UGAGGU** | **GCAC** | GUUU | GUCG |
| 491: | CGAC | **U** | CC | GCGC | GG | A | **GUCCC** | **UAUU** | **GGGGC** | GUUU | GUCG |
| 493: | CGAC | **U** | CC | GCGC | GG | A | **GGGU** | **UAGGCU** | **ACCC** | GUUU | GUCG |
| 495: | CGAC | **U** | CC | GCGC | GG | A | **GCUUC** | **GGAU** | **GAGGC** | GUUU | GUCG |
| 497: | CGAC | **U** | CC | GCGC | GG | A | **GUCCC** | **UCAU** | **GGGGC** | GUUU | GUCG |
| 499: | CGAC | **U** | CC | GCGC | GG | A | **GUCCC** | **GUAU** | **GGGGC** | GUUU | GUCG |
| 501: | CGAC | **U** | CC | GCGC | GG | A | **GUCCC** | **AAUU** | **GGGGC** | GUUU | GUCG |
| 503: | CGAC | **U** | CC | GCGC | GG | A | **GGGU** | **UUGGUU** | **ACCC** | GUUU | GUCG |
| 505: | CGAC | **U** | CC | GCGC | GG | A | **GUCCC** | **AUUU** | **GGGGC** | GUUU | GUCG |
| 507: | CGAC | **U** | CC | GCGC | GG | A | **GUCCC** | **ACAA** | **GGGGC** | GUUU | GUCG |
| 509: | CGAC | **U** | CC | GCGC | GG | A | **GCUUC** | **GGAA** | **GAGGC** | GUUU | GUCG |
| 511: | CGAC | **U** | CC | GCGC | GG | A | **GUCCC** | **AUUA** | **GGGGC** | GUUU | GUCG |
| 513: | CGAC | **U** | CC | GCGC | GG | A | **GUGCC** | **AACU** | **GGUAC** | GUUU | GUCG |
| 515: | CGAC | **U** | CC | GCGC | GG | A | **GUCCC** | **UAUA** | **GGGGC** | GUUU | GUCG |
| 517: | CGAC | **U** | CC | GCGC | GG | A | **GUCCC** | **UAAU** | **GGGGC** | GUUU | GUCG |

Sequences in bold indicated randomized positions in the library.

As sown in Table 22, the sequences from the top 20 stacks from the S3-L4 N14 library strongly support the structural and sequence requirements summarized in FIG. 7 in which the preferred identity of nucleotide in loop L1 is U, and the stem S3 is capable of forming 4 or 5 or base pairs with a corresponding loop L4 of 6 or 4 nucleotides respectively. We note that while some sequences appear capable of forming up to a 6 base pairs in stem S3 (M33-3, M33-10, M33-13, M33-14, M33-19, M33-27, M33-28 and M33-29), such pairing would result the formation of an unfavorable two nucleotide loop L4. Thus, we have chosen to draw all these sequences with a 5 base pair stem S3. These results further support the finding that S3 is a stem as indicated by the degree of covariation and that stem S3 is not highly conserved in sequence identity except for the first base pair in the stem which prefers to be G:C pair. The consensus sequence for this randomized region (S3-L4) within the N14 library from the top 20 stacks is GKBHYDNNNKDBVC. When S3 is composed of 4 base pairs, the consensus sequence for the S3-L4 region is GKSH-UDRGBU-DSMC.

When combined the data both the S3-L4 N16 and S3-L4 N14 further broaden the observed consensus sequences for stem S3 and loop L4. When the data from the N16 selection is combined with data from the primary selection, degenerate selection and SAR analysis broadens the observed consensus when stem S3 is 6 base pairs long expands to 5'-GRGGWN-3' on the 5' side and 5'-NHYCYC-3' on the 3' side. When stem S3 is 5 base pairs long, the consensus from the outcome of the N16 and N14 selections combined with data from the primary selection, degenerate selection and SAR analysis broadens the observed consensus to 5'-GBBNY-3' on the 5' side and 5'-RNBNC-3' on the 3' side. When stem S3 is 4 base pairs long, the consensus from the outcome of the N16 and N14 selections combined with data from the primary selection, degenerate selection and SAR analysis broadens the observed consensus to 5'-GKGN-3' on the 5' side and 5'-NSMC-3' on the 3' side. Similarly, when combined with data from the primary selection, degenerate selection and SAR analysis, when loop L4 is 6 nucleotides long, 5 nucleotides long or 4 nucleotides long the consensus sequences expand to 5'UDUHRKYU-3', 5'KNNNNW-3' and 5'DNDN-3'.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
<160> NUMBER OF SEQ ID NOS: 518

<210> SEQ ID NO 1
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(46)
<223> OTHER INFORMATION: H is A, C, or U; N is A, C, G, or U; B is C, G,
      or U; Y is C or U; D is A, G, or U; R is A or G; W is A or U; K is
      G or U; and V is A, C, or G

<400> SEQUENCE: 1

hnbyhdccuc cgcgcggagg gruddndhhw ycccgyuugk ynkvnw                  46


<210> SEQ ID NO 2
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(46)
<223> OTHER INFORMATION: H is A, C, or U; N is A, C, G, or U; B is C, G,
      or U; Y is C or U; D is A, G, or U; R is A or G; K is G or U; V is
      A, C, or G; and W is A or U

<400> SEQUENCE: 2

hnbyhdccuc cgcgcggagg gruudndhua ycccgyuugk ynkvnw                  46


<210> SEQ ID NO 3
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(46)
<223> OTHER INFORMATION: W is A or U; N is A, C, G, or U; K is G or U; Y
      is C or U; H is A, C, or U; D is A, G, or U; B is C, G, or U; and
      M is A or C

<400> SEQUENCE: 3

wnkyhdccuc cgcgcggagg gguddnahha ucccguuugg ybkmhw                  46


<210> SEQ ID NO 4
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 4

augccgccuc cgcgcggagg gguuucauuu ccccguuugg cugcau                  46
```

<210> SEQ ID NO 5
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(46)
<223> OTHER INFORMATION: H is A, C, or U; N is A, C, G, or U; B is C, G, or U; Y is C or U; D is A, G, or U; K is G or U; W is A or U; R is A or G; and V is A, C, or G
<220> FEATURE:
<221> NAME/KEY: misc_feature
<222> LOCATION: (9)..(9)
<223> OTHER INFORMATION: N at residue 9 is A, C, G, U, deleted entirely, or a non-nucleotidyl spacer 3 modification, a 6 carbon alkyl linker (1,6-hexanediol), or a spacer 9 (triethyleneglycol) modification

<400> SEQUENCE: 5
hnbyhdnnnn nkngcnnwgg grundndhnw ycccgnnnnn ynkvnw 46

<210> SEQ ID NO 6
<211> LENGTH: 206
<212> TYPE: PRT
<213> ORGANISM: Homo sapiens

<400> SEQUENCE: 6

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Tyr Val Gly Ala Arg
    130                 135                 140

Cys Cys Leu Met Pro Trp Ser Leu Pro Gly Pro His Pro Cys Gly Pro
145                 150                 155                 160

Cys Ser Glu Arg Arg Lys His Leu Phe Val Gln Asp Pro Gln Thr Cys
                165                 170                 175

Lys Cys Ser Cys Lys Asn Thr Asp Ser Arg Cys Lys Ala Arg Gln Leu
            180                 185                 190

Glu Leu Asn Glu Arg Thr Cys Arg Cys Asp Lys Pro Arg Arg
        195                 200                 205
```

<210> SEQ ID NO 7
<211> LENGTH: 189
<212> TYPE: PRT
<213> ORGANISM: Homo sapiens

<400> SEQUENCE: 7

-continued

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Pro Cys Gly Pro Cys
    130                 135                 140

Ser Glu Arg Arg Lys His Leu Phe Val Gln Asp Pro Gln Thr Cys Lys
145                 150                 155                 160

Cys Ser Cys Lys Asn Thr Asp Ser Arg Cys Lys Ala Arg Gln Leu Glu
                165                 170                 175

Leu Asn Glu Arg Thr Cys Arg Cys Asp Lys Pro Arg Arg
            180                 185
```

<210> SEQ ID NO 8
<211> LENGTH: 165
<212> TYPE: PRT
<213> ORGANISM: Homo sapiens

<400> SEQUENCE: 8

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165
```

<210> SEQ ID NO 9
<211> LENGTH: 121
<212> TYPE: PRT
<213> ORGANISM: Homo sapiens

<400> SEQUENCE: 9

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Cys Asp Lys Pro Arg Arg
        115                 120

<210> SEQ ID NO 10
<211> LENGTH: 110
<212> TYPE: PRT
<213> ORGANISM: Homo sapiens

<400> SEQUENCE: 10

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg
            100                 105                 110

<210> SEQ ID NO 11
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 11
aggccgccuc cgcgcggagg gauuucauua ucccguuugg cugcuu                    46

<210> SEQ ID NO 12
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 12
gggagugugu acgaggcauu aaggccgccu ccgcgcggag ggauuucauu aucccguuug 60
gcugcuuuga uacuugaucg cccuagaagc 90

<210> SEQ ID NO 13
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 13
augccgccuc cgcgcggagg gauuucauua ucccguuugg cugcuu 46

<210> SEQ ID NO 14
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 14
gggagugugu acgaggcauu aaugccgccu ccgcgcggag ggauuucauu aucccguuug 60
gcugcuuuga uacuugaucg cccuagaagc 90

<210> SEQ ID NO 15
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 15
augccgccuc cgcgcggagg gguuucauua ucccguuugg cugcau 46

<210> SEQ ID NO 16
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 16
gggagugugu acgaggcauu aaugccgccu ccgcgcggag ggguuucauu aucccguuug 60
gcugcauuga uacuugaucg cccuagaagc 90

<210> SEQ ID NO 17
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 17
augccgccuc cgcgcggagg gguuucauua ucccguuugg cggcuu 46

<210> SEQ ID NO 18
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 18
gggagugugu acgaggcauu aaugccgccu ccgcgcggag ggguuucauu aucccguuug 60
gcggcuuuga uacuugaucg cccuagaagc 90

<210> SEQ ID NO 19
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 19
augccgccuc cgcgcggagg gguuucauaa ucccguuugg cugcau 46

<210> SEQ ID NO 20
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 20
gggagugugu acgaggcauu aaugccgccu ccgcgcggag ggguuucaua aucccguuug 60
gcugcauuga uacuugaucg cccuagaagc 90

<210> SEQ ID NO 21
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 21
augccgccuc cgcgcggagg gguaucauua ucccguuugg cugcau 46

<210> SEQ ID NO 22
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 22
gggagugugu acgaggcauu aaugccgccu ccgcgcggag ggguaucauu aucccguuug 60
gcugcauuga uacuugaucg cccuagaagc 90

<210> SEQ ID NO 23
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 23
aagccgccuc cgcgcggagg gguaucauua ucccguuugg cugcuu 46

<210> SEQ ID NO 24
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 24
gggagugugu acgaggcauu aaagccgccu ccgcgcggag gguaucauu aucccguuug 60 gcugcuuuga uacuugaucg cccuagaagc 90

<210> SEQ ID NO 25
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 25
aagcugccuc cgcgcggagg gguuucauua ucccguuugg cugcuu 46

<210> SEQ ID NO 26
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 26
gggagugugu acgaggcauu aaagcugccu ccgcgcggag ggguuucauu aucccguuug 60
gcugcuuuga uacuugaucg cccuagaagc 90

<210> SEQ ID NO 27
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 27
augccgccuc cgcgcggagg gguuacauua ucccguuugg cugcau 46

<210> SEQ ID NO 28
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 28
gggagugugu acgaggcauu aaugccgccu ccgcgcggag ggguuacauu aucccguuug 60
gcugcauuga uacuugaucg cccuagaagc 90

<210> SEQ ID NO 29
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 29
augccgccuc cgcgcggagg gauuucauua ucccguuugu cggcuu 46

<210> SEQ ID NO 30
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 30
gggagugugu acgaggcauu aaugccgccu ccgcgcggag ggauuucauu aucccguuug 60
ucggcuuuga uacuugaucg cccuagaagc 90

<210> SEQ ID NO 31
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 31
augcugccuc cgcgcggagg gguuucauua ucccguuugg cugcau 46

<210> SEQ ID NO 32
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 32
gggagugugu acgaggcauu aaugcugccu ccgcgcggag ggguuucauu aucccguuug 60
gcugcauuga uacuugaucg cccuagaagc 90

<210> SEQ ID NO 33
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 33
aagcugccuc cgcgcggagg gguuucauua ucccguuugg ccgcuu 46

<210> SEQ ID NO 34
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 34
gggagugugu acgaggcauu aaagcugccu ccgcgcggag ggguuucauu aucccguuug 60
gccgcuuuga uacuugaucg cccuagaagc 90

<210> SEQ ID NO 35
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 35
aagcauccuc cgcgcggagg gguuucauua ucccguuugg cugcuu 46

<210> SEQ ID NO 36
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 36
gggagugugu acgaggcauu aaagcauccu ccgcgcggag ggguuucauu aucccguuug 60
gcugcuuuga uacuugaucg cccuagaagc 90

<210> SEQ ID NO 37
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 37
augcagccuc cgcgcggagg gguuucauua ucccguuugg cugcuu 46

<210> SEQ ID NO 38
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 38
gggagugugu acgaggcauu aaugcagccu ccgcgcggag ggguuucauu aucccguuug 60
gcugcuuuga uacuugaucg cccuagaagc 90

<210> SEQ ID NO 39
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 39
augccgccuc cgcgcggagg gguuucauua ucccguuugg cggcau 46

<210> SEQ ID NO 40
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 40
gggagugugu acgaggcauu aaugccgccu ccgcgcggag ggguuucauu aucccguuug 60
gcggcauuga uacuugaucg cccuagaagc 90

<210> SEQ ID NO 41
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 41
augucgccuc cgcgcggagg gguuucauua ucccguuugg cggcau 46

<210> SEQ ID NO 42
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 42
gggagugugu acgaggcauu aaugucgccu ccgcgcggag ggguuucauu aucccguuug 60
gcggcauuga uacuugaucg cccuagaagc 90

<210> SEQ ID NO 43
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 43
aggccgccuc cgcgcggagg gauuucauua ucccguuugg cugccu 46

<210> SEQ ID NO 44
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 44
gggagugugu acgaggcauu aaggccgccu ccgcgcggag ggauuucauu aucccguuug 60
gcugccuuga uacuugaucg cccuagaagc 90

<210> SEQ ID NO 45
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 45
aggccgccuc cgcgcggagg gauuucauua ucccguuugu cggcuu 46

<210> SEQ ID NO 46
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 46
gggagugugu acgaggcauu aaggccgccu ccgcgcggag ggauuucauu aucccguuug 60
ucggcuuuga uacuugaucg cccuagaagc 90

<210> SEQ ID NO 47
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 47
augcugccuc cgcgcggagg gguuucauua ucccguuugg cggcau 46

<210> SEQ ID NO 48
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 48
gggagugugu acgaggcauu aaugcugccu ccgcgcggag ggguuucauu aucccguuug 60
gcggcauuga uacuugaucg cccuagaagc 90

<210> SEQ ID NO 49
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 49
augccgccuc cgcgcggagg gguuucacaa ucccguuugg cugcau 46

<210> SEQ ID NO 50
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 50
gggagugugu acgaggcauu aaugccgccu ccgcgcggag ggguuucaca aucccguuug 60
gcugcauuga uacuugaucg cccuagaagc 90

<210> SEQ ID NO 51
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 51
augcugccuc cgcgcggagg gguuucauua ucccguuugg ccgcau 46

<210> SEQ ID NO 52
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 52
gggagugugu acgaggcauu aaugcugccu ccgcgcggag ggguuucauu aucccguuug 60
gccgcauuga uacuugaucg cccuagaagc 90

<210> SEQ ID NO 53
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 53
augccgccuc cgcgcggagg gguuacauua ucccguuugg cggcuu 46

<210> SEQ ID NO 54
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 54
gggagugugu acgaggcauu aaugccgccu ccgcgcggag ggguuacauu aucccguuug 60
gcggcuuuga uacuugaucg cccuagaagc 90

<210> SEQ ID NO 55
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 55
augccgccuc cgcgcggagg gguuacauaa ucccguuugg cugcau 46

<210> SEQ ID NO 56
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 56
gggagugugu acgaggcauu aaugccgccu ccgcgcggag ggguuacaua aucccguuug 60
gcugcauuga uacuugaucg cccuagaagc 90

<210> SEQ ID NO 57
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 57
aggcagccuc cgcgcggagg gguuucauua ucccguuugg cugcuu 46

<210> SEQ ID NO 58
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 58
gggagugugu acgaggcauu aaggcagccu ccgcgcggag ggguuucauu aucccguuug 60
gcugcuuuga uacuugaucg cccuagaagc 90

<210> SEQ ID NO 59
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 59
aggccgccuc cgcgcggagg gauuacauua ucccguuugg cugcuu 46

<210> SEQ ID NO 60
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 60
gggagugugu acgaggcauu aaggccgccu ccgcgcggag ggauuacauu aucccguuug 60
gcugcuuuga uacuugaucg cccuagaagc 90

-continued

<210> SEQ ID NO 61
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 61
aggcugccuc cgcgcggagg gguuucauua ucccguuugg cugcuu 46

<210> SEQ ID NO 62
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 62
gggagugugu acgaggcauu aaggcugccu ccgcgcggag ggguuucauu aucccguuug 60
gcugcuuuga uacuugaucg cccuagaagc 90

<210> SEQ ID NO 63
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 63
augccgccuc cgcgcggagg gauuucauua ucccguuugu cggcau 46

<210> SEQ ID NO 64
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 64
gggagugugu acgaggcauu aaugccgccu ccgcgcggag ggauuucauu aucccguuug 60
ucggcauuga uacuugaucg cccuagaagc 90

<210> SEQ ID NO 65
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 65
aggcauccuc cgcgcggagg gguuucauua ucccguuugg cugccu 46

<210> SEQ ID NO 66
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 66
gggagugugu acgaggcauu aaggcauccu ccgcgcggag ggguuucauu aucccguuug 60
gcugccuuga uacuugaucg cccuagaagc 90

<210> SEQ ID NO 67

<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 67
aagcugccuc cgcgcggagg gguuucauua ucccguuugg cggcuu 46

<210> SEQ ID NO 68
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 68
gggagugugu acgaggcauu aaagcugccu ccgcgcggag ggguuucauu aucccguuug 60
gcggcuuuga uacuugaucg cccuagaagc 90

<210> SEQ ID NO 69
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 69
aagcugccuc cgcgcggagg gguugcauua ucccguuugg cugcuu 46

<210> SEQ ID NO 70
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 70
gggagugugu acgaggcauu aaagcugccu ccgcgcggag ggguugcauu aucccguuug 60
gcugcuuuga uacuugaucg cccuagaagc 90

<210> SEQ ID NO 71
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 71
agucagccuc cgcgcggagg gguuucauua ucccguuugg cugccu 46

<210> SEQ ID NO 72
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 72
gggagugugu acgaggcauu aagucagccu ccgcgcggag ggguuucauu aucccguuug 60
gcugccuuga uacuugaucg cccuagaagc 90

<210> SEQ ID NO 73
<211> LENGTH: 46

<212> TYPE: RNA
<213> ORGANISM: Artificial Sequence
<220> FEATURE:
<223> OTHER INFORMATION: Synthetic Oligonucleotide

<400> SEQUENCE: 73
augccgccuc cgcgcggagg gguuucauua ucccguuugg uggcau 46

<210> SEQ ID NO 74
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 74
gggagugugu acgaggcauu aaugccgccu ccgcgcggag ggguuucauu aucccguuug 60
guggcauuga uacuugaucg cccuagaagc 90

<210> SEQ ID NO 75
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 75
augcugccuc cgcgcggagg gguuucauua ucccguuugg cggcuu 46

<210> SEQ ID NO 76
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 76
gggagugugu acgaggcauu aaugcugccu ccgcgcggag ggguuucauu aucccguuug 60
gcggcuuuga uacuugaucg cccuagaagc 90

<210> SEQ ID NO 77
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 77
augcauccuc cgcgcggagg gguuucauua ucccguuugg cugcau 46

<210> SEQ ID NO 78
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 78
gggagugugu acgaggcauu aaugcauccu ccgcgcggag ggguuucauu aucccguuug 60
gcugcauuga uacuugaucg cccuagaagc 90

<210> SEQ ID NO 79
<211> LENGTH: 46
<212> TYPE: RNA

<213> ORGANISM: Artificial Sequence
<220> FEATURE:
<223> OTHER INFORMATION: Synthetic Oligonucleotide

<400> SEQUENCE: 79
aggccaccuc cgcgcggagg gguuucauua ucccguuugg uggcuu 46

<210> SEQ ID NO 80
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 80
gggagugugu acgaggcauu aaggccaccu ccgcgcggag ggguuucauu aucccguuug 60
guggcuuuga uacuugaucg cccuagaagc 90

<210> SEQ ID NO 81
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 81
aguccgccuc cgcgcggagg gguuucauua ucccguuugg cggcua 46

<210> SEQ ID NO 82
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 82
gggagugugu acgaggcauu aaguccgccu ccgcgcggag ggguuucauu aucccguuug 60
gcggcuauga uacuugaucg cccuagaagc 90

<210> SEQ ID NO 83
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 83
aagcagccuc cgcgcggagg gguuucauua ucccguuugg cugcuu 46

<210> SEQ ID NO 84
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 84
gggagugugu acgaggcauu aaagcagccu ccgcgcggag ggguuucauu aucccguuug 60
gcugcuuuga uacuugaucg cccuagaagc 90

<210> SEQ ID NO 85
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 85
augcagccuc cgcgcggagg gguuucauua ucccguuugg cugcau 46

<210> SEQ ID NO 86
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 86
gggagugugu acgaggcauu aaugcagccu ccgcgcggag ggguuucauu aucccguuug 60
gcugcauuga uacuugaucg cccuagaagc 90

<210> SEQ ID NO 87
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 87
aagcauccuc cgcgcggagg ggugucauca ucccguuugg cugcuu 46

<210> SEQ ID NO 88
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 88
gggagugugu acgaggcauu aaagcauccu ccgcgcggag gggugucauc aucccguuug 60
gcugcuuuga uacuugaucg cccuagaagc 90

<210> SEQ ID NO 89
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 89
augccgccuc cgcgcggagg gguuucauuu ccccguuugg cugcau 46

<210> SEQ ID NO 90
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 90
gggagugugu acgaggcauu aaugccgccu ccgcgcggag ggguuucauu uccccguuug 60
gcugcauuga uacuugaucg cccuagaagc 90

<210> SEQ ID NO 91
<211> LENGTH: 46
<212> TYPE: RNA
<213> ORGANISM: Artificial Sequence
<220> FEATURE:

<223> OTHER INFORMATION: Synthetic Oligonucleotide

<400> SEQUENCE: 91
augccgccuc cgcgcggagg gguuucauua ccccguuugg cugcuu 46

<210> SEQ ID NO 92
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 92
gggagugugu acgaggcauu aaugccgccu ccgcgcggag ggguuucauu accccguuug 60
gcugcuuuga uacuugaucg cccuagaagc 90

<210> SEQ ID NO 93
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 93
aggccaccuc cgcgcggagg gguuucauua ucccguuugg uguccu 46

<210> SEQ ID NO 94
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 94
gggagugugu acgaggcauu aaggccaccu ccgcgcggag ggguuucauu aucccguuug 60
guguccuuga uacuugaucg cccuagaagc 90

<210> SEQ ID NO 95
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 95
augccgccuc cgcgcggagg gauugcauua ucccguuugg cugcau 46

<210> SEQ ID NO 96
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 96
gggagugugu acgaggcauu aaugccgccu ccgcgcggag ggauugcauu aucccguuug 60
gcugcauuga uacuugaucg cccuagaagc 90

<210> SEQ ID NO 97
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 97
uugccgccuc cgcgcggagg gauuucauua ucccguuugg cugcuu 46

<210> SEQ ID NO 98
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 98
gggagugugu acgaggcauu auugccgccu ccgcgcggag ggauuucauu aucccguuug 60
gcugcuuuga uacuugaucg cccuagaagc 90

<210> SEQ ID NO 99
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 99
acgcagccuc cgcgcggagg gguuucauua ucccguuugg cugcuu 46

<210> SEQ ID NO 100
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 100
gggagugugu acgaggcauu aacgcagccu ccgcgcggag ggguuucauu aucccguuug 60
gcugcuuuga uacuugaucg cccuagaagc 90

<210> SEQ ID NO 101
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 101
augccgccuc cgcgcggagg gguuucacua ucccguuugg cggcuu 46

<210> SEQ ID NO 102
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 102
gggagugugu acgaggcauu aaugccgccu ccgcgcggag ggguuucacu aucccguuug 60
gcggcuuuga uacuugaucg cccuagaagc 90

<210> SEQ ID NO 103
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 103
uugcugccuc cgcgcggagg gguuucauua ucccguuugg ccgcau 46

<210> SEQ ID NO 104
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 104
gggagugugu acgaggcauu auugcugccu ccgcgcggag ggguuucauu aucccguuug 60
gccgcauuga uacuugaucg cccuagaagc 90

<210> SEQ ID NO 105
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 105
aagccgccuc cgcgcggagg gguuucauua ucccguuugg cggcuu 46

<210> SEQ ID NO 106
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 106
gggagugugu acgaggcauu aaagccgccu ccgcgcggag ggguuucauu aucccguuug 60
gcggcuuuga uacuugaucg cccuagaagc 90

<210> SEQ ID NO 107
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 107
aaucagccuc cgcgcggagg gguuucauua ucccguuugg cugcuu 46

<210> SEQ ID NO 108
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 108
gggagugugu acgaggcauu aaaucagccu ccgcgcggag ggguuucauu aucccguuug 60
gcugcuuuga uacuugaucg cccuagaagc 90

<210> SEQ ID NO 109
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 109
uugccgccuc cgcgcggagg gguuucauua ucccguuugg cggcuu 46

<210> SEQ ID NO 110
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 110
gggagugugu acgaggcauu auugccgccu ccgcgcggag ggguuucauu aucccguuug 60
gcggcuuuga uacuugaucg cccuagaagc 90

<210> SEQ ID NO 111
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 111
cugccgccuc cgcgcggagg gguuucauua ucccguuugg cggcuu 46

<210> SEQ ID NO 112
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 112
gggagugugu acgaggcauu acugccgccu ccgcgcggag ggguuucauu aucccguuug 60
gcggcuuuga uacuugaucg cccuagaagc 90

<210> SEQ ID NO 113
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 113
augcugccuc cgcgcggagg gguuucauaa ucccguuugg cugcuu 46

<210> SEQ ID NO 114
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 114
gggagugugu acgaggcauu aaugcugccu ccgcgcggag ggguuucaua aucccguuug 60
gcugcuuuga uacuugaucg cccuagaagc 90

<210> SEQ ID NO 115
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 115
acgcauccuc cgcgcggagg gguuucauua ucccguuugg cugcgu 46

<210> SEQ ID NO 116
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 116
gggagugugu acgaggcauu aacgcauccu ccgcgcggag ggguuucauu aucccguuug 60
gcugcguuga uacuugaucg cccuagaagc 90

<210> SEQ ID NO 117
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 117
augccgccuc cgcgcggagg gguuuaauua ucccguuugg cggcuu 46

<210> SEQ ID NO 118
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 118
gggagugugu acgaggcauu aaugccgccu ccgcgcggag ggguuuaauu aucccguuug 60
gcggcuuuga uacuugaucg cccuagaagc 90

<210> SEQ ID NO 119
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 119
aagccgccuc cgcgcggagg gauuucauua ucccguuugu cggcuu 46

<210> SEQ ID NO 120
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 120
gggagugugu acgaggcauu aaagccgccu ccgcgcggag ggauuucauu aucccguuug 60
ucggcuuuga uacuugaucg cccuagaagc 90

<210> SEQ ID NO 121
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 121
uugcugccuc cgcgcggagg gguuucauua ucccguuugg cugcuu 46

<210> SEQ ID NO 122
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 122
gggagugugu acgaggcauu auugcugccu ccgcgcggag ggguuucauu aucccguuug 60
gcugcuuuga uacuugaucg cccuagaagc 90

<210> SEQ ID NO 123
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 123
uggccgccuc cgcgcggagg gauuucauua ucccguuugg cugcuu 46

<210> SEQ ID NO 124
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 124
gggagugugu acgaggcauu auggccgccu ccgcgcggag ggauuucauu aucccguuug 60
gcugcuuuga uacuugaucg cccuagaagc 90

<210> SEQ ID NO 125
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 125
augccgccuc cgcgcggagg gguuuuauua ucccguuugg cugcau 46

<210> SEQ ID NO 126
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 126
gggagugugu acgaggcauu aaugccgccu ccgcgcggag ggguuuuauu aucccguuug 60
gcugcauuga uacuugaucg cccuagaagc 90

<210> SEQ ID NO 127
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 127
aggcauccuc cgcgcggagg gauuucauua ucccguuugg cugcuu 46

```
<210> SEQ ID NO 128
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 128

gggagugugu acgaggcauu aaggcauccu ccgcgcggag ggauuucauu aucccguuug     60

gcugcuuuga uacuugaucg cccuagaagc                                      90


<210> SEQ ID NO 129
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 129

aggccgccuc cgcgcggagg gauuucauua ucccguuugu cguccu                    46


<210> SEQ ID NO 130
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 130

gggagugugu acgaggcauu aaggccgccu ccgcgcggag ggauuucauu aucccguuug     60

ucguccuuga uacuugaucg cccuagaagc                                      90


<210> SEQ ID NO 131
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 131

augccgccuc cgcgcggagg gguuugauaa ucccguuugg cugcau                    46


<210> SEQ ID NO 132
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 132

gggagugugu acgaggcauu aaugccgccu ccgcgcggag gguuugauaa aucccguuug     60

gcugcauuga uacuugaucg cccuagaagc                                      90


<210> SEQ ID NO 133
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 133

aggccgccuc cgcgcggagg gauuucuuua ucccguuugg cugcuu                    46
```

-continued

<210> SEQ ID NO 134
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 134
gggagugugu acgaggcauu aaggccgccu ccgcgcggag ggauuucuuu aucccguuug 60
gcugcuuuga uacuugaucg cccuagaagc 90

<210> SEQ ID NO 135
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 135
aauccgccuc cgcgcggagg gguuucauua ucccguuugg cggauu 46

<210> SEQ ID NO 136
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 136
gggagugugu acgaggcauu aaauccgccu ccgcgcggag ggguuucauu aucccguuug 60
gcggauuuga uacuugaucg cccuagaagc 90

<210> SEQ ID NO 137
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 137
aggcugccuc cgcgcggagg gguuucauua ucccguuugg cugccu 46

<210> SEQ ID NO 138
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 138
gggagugugu acgaggcauu aaggcugccu ccgcgcggag ggguuucauu aucccguuug 60
gcugccuuga uacuugaucg cccuagaagc 90

<210> SEQ ID NO 139
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 139
aauccgccuc cgcgcggagg gguaucauua ucccguuugg cggcuu 46

<210> SEQ ID NO 140

<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 140
gggagugugu acgaggcauu aaauccgccu ccgcgcggag ggguaucauu aucccguuug 60
gcggcuuuga uacuugaucg cccuagaagc 90

<210> SEQ ID NO 141
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 141
augccgccuc cgcgcggagg gguuucaaua ucccguuugg cugcau 46

<210> SEQ ID NO 142
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 142
gggagugugu acgaggcauu aaugccgccu ccgcgcggag ggguuucaau aucccguuug 60
gcugcauuga uacuugaucg cccuagaagc 90

<210> SEQ ID NO 143
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 143
augcugccuc cgcgcggagg gguuucauua ucccguuugg cagcuu 46

<210> SEQ ID NO 144
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 144
gggagugugu acgaggcauu aaugcugccu ccgcgcggag ggguuucauu aucccguuug 60
gcagcuuuga uacuugaucg cccuagaagc 90

<210> SEQ ID NO 145
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 145
aggcugccuc cgcgcggagg gguuucauua ucccguuugg cggcuu 46

<210> SEQ ID NO 146
<211> LENGTH: 90

<212> TYPE: RNA
<213> ORGANISM: Artificial Sequence
<220> FEATURE:
<223> OTHER INFORMATION: Synthetic Oligonucleotide

<400> SEQUENCE: 146
gggagugugu acgaggcauu aaggcugccu ccgcgcggag ggguuucauu aucccguuug 60
gcggcuuuga uacuugaucg cccuagaagc 90

<210> SEQ ID NO 147
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 147
augcugccuc cgcgcggagg gguuucauua ucccguuugg cagcau 46

<210> SEQ ID NO 148
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 148
gggagugugu acgaggcauu aaugcugccu ccgcgcggag ggguuucauu aucccguuug 60
gcagcauuga uacuugaucg cccuagaagc 90

<210> SEQ ID NO 149
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 149
aggccgccuc cgcgcggagg gauuucauua ucccgcuugg cugcuu 46

<210> SEQ ID NO 150
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 150
gggagugugu acgaggcauu aaggccgccu ccgcgcggag ggauuucauu aucccgcuug 60
gcugcuuuga uacuugaucg cccuagaagc 90

<210> SEQ ID NO 151
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 151
augccgccuc cgcgcggagg gguuugauua ucccguuugg cugcau 46

<210> SEQ ID NO 152
<211> LENGTH: 90
<212> TYPE: RNA

<213> ORGANISM: Artificial Sequence
<220> FEATURE:
<223> OTHER INFORMATION: Synthetic Oligonucleotide

<400> SEQUENCE: 152
gggagugugu acgaggcauu aaugccgccu ccgcgcggag ggguuugauu aucccguuug 60
gcugcauuga uacuugaucg cccuagaagc 90

<210> SEQ ID NO 153
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 153
uugcugccuc cgcgcggagg gguuucauua ucccguuugg cggcuu 46

<210> SEQ ID NO 154
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 154
gggagugugu acgaggcauu auugcugccu ccgcgcggag ggguuucauu aucccguuug 60
gcggcuuuga uacuugaucg cccuagaagc 90

<210> SEQ ID NO 155
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 155
cugccgccuc cgcgcggagg gguuucauua ucccguuugg cggcau 46

<210> SEQ ID NO 156
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 156
gggagugugu acgaggcauu acugccgccu ccgcgcggag ggguuucauu aucccguuug 60
gcggcauuga uacuugaucg cccuagaagc 90

<210> SEQ ID NO 157
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 157
auucagccuc cgcgcggagg gguuucauua ucccguuugg cugcau 46

<210> SEQ ID NO 158
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 158
gggagugugu acgaggcauu aauucagccu ccgcgcggag ggguuucauu aucccguuug 60
gcugcauuga uacuugaucg cccuagaagc 90

<210> SEQ ID NO 159
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 159
aagcagccuc cgcgcggagg gguuucauua ucccguuugg cggcuu 46

<210> SEQ ID NO 160
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 160
gggagugugu acgaggcauu aaagcagccu ccgcgcggag ggguuucauu aucccguuug 60
gcggcuuuga uacuugaucg cccuagaagc 90

<210> SEQ ID NO 161
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 161
augccgccuc cgcgcggagg gauuucauua ucccguuugu cggccu 46

<210> SEQ ID NO 162
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 162
gggagugugu acgaggcauu aaugccgccu ccgcgcggag ggauuucauu aucccguuug 60
ucggccuuga uacuugaucg cccuagaagc 90

<210> SEQ ID NO 163
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 163
aguccgccuc cgcgcggagg gguuucauua ucccguuugg cugacu 46

<210> SEQ ID NO 164
<211> LENGTH: 90
<212> TYPE: RNA
<213> ORGANISM: Artificial Sequence
<220> FEATURE:

<223> OTHER INFORMATION: Synthetic Oligonucleotide

<400> SEQUENCE: 164
gggagugugu acgaggcauu aaguccgccu ccgcgcggag ggguuucauu aucccguuug 60
gcugacuuga uacuugaucg cccuagaagc 90

<210> SEQ ID NO 165
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 165
aguccgccuc cgcgcggagg gguuucauua ucccguuugg cggauu 46

<210> SEQ ID NO 166
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 166
gggagugugu acgaggcauu aaguccgccu ccgcgcggag ggguuucauu aucccguuug 60
gcggauuuga uacuugaucg cccuagaagc 90

<210> SEQ ID NO 167
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 167
cugcugccuc cgcgcggagg gguuucauua ucccguuugg cggcau 46

<210> SEQ ID NO 168
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 168
gggagugugu acgaggcauu acugcugccu ccgcgcggag ggguuucauu aucccguuug 60
gcggcauuga uacuugaucg cccuagaagc 90

<210> SEQ ID NO 169
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 169
acucagccuc cgcgcggagg gguuucauua ucccguuugg cugcgu 46

<210> SEQ ID NO 170
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 170
gggagugugu acgaggcauu aacucagccu ccgcgcggag ggguuucauu aucccguuug 60
gcugcguuga uacuugaucg cccuagaagc 90

<210> SEQ ID NO 171
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 171
aggcugccuc cgcgcggagg gguuucauua ucccguuugg cauccu 46

<210> SEQ ID NO 172
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 172
gggagugugu acgaggcauu aaggcugccu ccgcgcggag ggguuucauu aucccguuug 60
gcauccuuga uacuugaucg cccuagaagc 90

<210> SEQ ID NO 173
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 173
uugcugccuc cgcgcggagg gguuucauua ucccguuugg cugcau 46

<210> SEQ ID NO 174
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 174
gggagugugu acgaggcauu auugcugccu ccgcgcggag ggguuucauu aucccguuug 60
gcugcauuga uacuugaucg cccuagaagc 90

<210> SEQ ID NO 175
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 175
uguccgccuc cgcgcggagg gguuucauua ucccguuugg cggcuu 46

<210> SEQ ID NO 176
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 176
gggagugugu acgaggcauu auguccgccu ccgcgcggag ggguuucauu aucccguuug 60
gcggcuuuga uacuugaucg cccuagaagc 90

<210> SEQ ID NO 177
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 177
cugcagccuc cgcgcggagg gguuucauua ucccguuugg cugcuu 46

<210> SEQ ID NO 178
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 178
gggagugugu acgaggcauu acugcagccu ccgcgcggag ggguuucauu aucccguuug 60
gcugcuuuga uacuugaucg cccuagaagc 90

<210> SEQ ID NO 179
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 179
aguccgccuc cgcgcggagg gguaucauua ucccguuugg cguacu 46

<210> SEQ ID NO 180
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 180
gggagugugu acgaggcauu aaguccgccu ccgcgcggag ggguaucauu aucccguuug 60
gcguacuuga uacuugaucg cccuagaagc 90

<210> SEQ ID NO 181
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 181
agcccgccuc cgcgcggagg gguuucauua ucccguuugg cgugcu 46

<210> SEQ ID NO 182
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 182
gggagugugu acgaggcauu aagcccgccu ccgcgcggag ggguuucauu aucccguuug 60
gcgugcuuga uacuugaucg cccuagaagc 90

<210> SEQ ID NO 183
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 183
aguccaccuc cgcgcggagg gguuucauaa ucccguuugg uggcua 46

<210> SEQ ID NO 184
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 184
gggagugugu acgaggcauu aaguccaccu ccgcgcggag ggguuucaua aucccguuug 60
guggcuauga uacuugaucg cccuagaagc 90

<210> SEQ ID NO 185
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 185
augccgccuc cgcgcggagg gauuucguua ucccguuugg cugcuu 46

<210> SEQ ID NO 186
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 186
gggagugugu acgaggcauu aaugccgccu ccgcgcggag ggauuucguu aucccguuug 60
gcugcuuuga uacuugaucg cccuagaagc 90

<210> SEQ ID NO 187
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 187
augcagccuc cgcgcggagg gguuucauua ucccguuugg cugccu 46

<210> SEQ ID NO 188
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 188
gggagugugu acgaggcauu aaugcagccu ccgcgcggag ggguuucauu aucccguuug 60
gcugccuuga uacuugaucg cccuagaagc 90

<210> SEQ ID NO 189
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 189
aggccgccuc cgcgcggagg gauuucauua ucccguuugg cugcau 46

<210> SEQ ID NO 190
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 190
gggagugugu acgaggcauu aaggccgccu ccgcgcggag ggauuucauu aucccguuug 60
gcugcauuga uacuugaucg cccuagaagc 90

<210> SEQ ID NO 191
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 191
augccgccuc cgcgcggagg gguauuauua ucccguuugg cugcau 46

<210> SEQ ID NO 192
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 192
gggagugugu acgaggcauu aaugccgccu ccgcgcggag ggguauuauu aucccguuug 60
gcugcauuga uacuugaucg cccuagaagc 90

<210> SEQ ID NO 193
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 193
auucagccuc cgcgcggagg gguuucauua ucccguuugg cugcuu 46

<210> SEQ ID NO 194
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 194
gggagugugu acgaggcauu aauucagccu ccgcgcggag ggguuucauu aucccguuug 60
gcugcuuuga uacuugaucg cccuagaagc 90

<210> SEQ ID NO 195
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 195
augccgccuc cgcgcggagg gauuucauua ucccguuugg cugcgu 46

<210> SEQ ID NO 196
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 196
gggagugugu acgaggcauu aaugccgccu ccgcgcggag ggauuucauu aucccguuug 60
gcugcguuga uacuugaucg cccuagaagc 90

<210> SEQ ID NO 197
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 197
auuccgccuc cgcgcggagg gguaucauua ucccguuugg cggcau 46

<210> SEQ ID NO 198
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 198
gggagugugu acgaggcauu aauuccgccu ccgcgcggag ggguaucauu aucccguuug 60
gcggcauuga uacuugaucg cccuagaagc 90

<210> SEQ ID NO 199
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 199
augucgccuc cgcgcggagg gguuucauua ucccguuugg cggcuu 46

<210> SEQ ID NO 200
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 200
gggagugugu acgaggcauu aaugucgccu ccgcgcggag ggguuucauu aucccguuug 60
gcggcuuuga uacuugaucg cccuagaagc 90

<210> SEQ ID NO 201
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 201
acucagccuc cgcgcggagg gguuucauua ucccguuugg cugauu 46

<210> SEQ ID NO 202
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 202
gggagugugu acgaggcauu aacucagccu ccgcgcggag ggguuucauu aucccguuug 60
gcugauuuga uacuugaucg cccuagaagc 90

<210> SEQ ID NO 203
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 203
aagccaccuc cgcgcggagg gguuucauua ucccguuugg uggcuu 46

<210> SEQ ID NO 204
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 204
gggagugugu acgaggcauu aaagccaccu ccgcgcggag ggguuucauu aucccguuug 60
guggcuuuga uacuugaucg cccuagaagc 90

<210> SEQ ID NO 205
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 205
augccgccuc cgcgcggagg gguugaauua ucccguuugg cugcau 46

<210> SEQ ID NO 206
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 206
gggagugugu acgaggcauu aaugccgccu ccgcgcggag ggguugaauu aucccguuug 60
gcugcauuga uacuugaucg cccuagaagc 90

<210> SEQ ID NO 207
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 207
aggccgccuc cgcgcggagg gguuucauua ucccguuugg cguccu 46

<210> SEQ ID NO 208
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 208
gggagugugu acgaggcauu aaggccgccu ccgcgcggag ggguuucauu aucccguuug 60
gcguccuuga uacuugaucg cccuagaagc 90

<210> SEQ ID NO 209
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 209
aguccaccuc cgcgcggagg gguuucauua ucccguuugg uggccu 46

<210> SEQ ID NO 210
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 210
gggagugugu acgaggcauu aaguccaccu ccgcgcggag ggguuucauu aucccguuug 60
guggccuuga uacuugaucg cccuagaagc 90

<210> SEQ ID NO 211
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 211
cugcugccuc cgcgcggagg gguuucauua ucccguuugg cugcau 46

<210> SEQ ID NO 212
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 212
gggagugugu acgaggcauu acugcugccu ccgcgcggag ggguuucauu aucccguuug 60
gcugcauuga uacuugaucg cccuagaagc 90

<210> SEQ ID NO 213
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 213
augccgccuc cgcgcggagg gguagcaaua ucccguuugg cugcuu 46

<210> SEQ ID NO 214
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 214
gggagugugu acgaggcauu aaugccgccu ccgcgcggag ggguagcaau aucccguuug 60
gcugcuuuga uacuugaucg cccuagaagc 90

<210> SEQ ID NO 215
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 215
aagccgccuc cgcgcggagg gguauaauua ucccguuugg cugcuu 46

<210> SEQ ID NO 216
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 216
gggagugugu acgaggcauu aaagccgccu ccgcgcggag ggguauaauu aucccguuug 60
gcugcuuuga uacuugaucg cccuagaagc 90

<210> SEQ ID NO 217
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 217
aggcugccuc cgcgcggagg gguuucauua ucccguuugg cagcuu 46

<210> SEQ ID NO 218
<211> LENGTH: 90
<212> TYPE: RNA
<213> ORGANISM: Artificial Sequence
<220> FEATURE:
<223> OTHER INFORMATION: Synthetic Oligonucleotide

<400> SEQUENCE: 218
gggagugugu acgaggcauu aaggcugccu ccgcgcggag ggguuucauu aucccguuug 60
gcagcuuuga uacuugaucg cccuagaagc 90

<210> SEQ ID NO 219
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 219
aggccgccuc cgcgcggagg gguuucauua ucccguuugg cggcuu 46

<210> SEQ ID NO 220
<211> LENGTH: 48
<212> TYPE: RNA
<213> ORGANISM: Artificial Sequence
<220> FEATURE:
<223> OTHER INFORMATION: Synthetic Oligonucleotide

<400> SEQUENCE: 220
uaggccgccu ccgcgcggag ggguuucauu aucccguuug gcggcuuu 48

<210> SEQ ID NO 221
<211> LENGTH: 48
<212> TYPE: RNA
<213> ORGANISM: Artificial Sequence
<220> FEATURE:
<223> OTHER INFORMATION: Synthetic Oligonucleotide

<400> SEQUENCE: 221
uaggccgccu ccgcgcgggg ggguuucauu aucccguuug gcggcuuu 48

<210> SEQ ID NO 222
<211> LENGTH: 48
<212> TYPE: RNA
<213> ORGANISM: Artificial Sequence
<220> FEATURE:
<223> OTHER INFORMATION: Synthetic Oligonucleotide

<400> SEQUENCE: 222
uaggccgccu ccgcgcggug ggguuucauu aucccguuug gcggcuuu 48

<210> SEQ ID NO 223
<211> LENGTH: 48
<212> TYPE: RNA
<213> ORGANISM: Artificial Sequence
<220> FEATURE:
<223> OTHER INFORMATION: Synthetic Oligonucleotide

<400> SEQUENCE: 223
uaguccgccu ccgcgcggag ggguuucauu aucccguuug gcggcuuu 48

<210> SEQ ID NO 224
<211> LENGTH: 49
<212> TYPE: RNA
<213> ORGANISM: Artificial Sequence
<220> FEATURE:
<223> OTHER INFORMATION: Synthetic Oligonucleotide

<400> SEQUENCE: 224
uaggccgccu ccgcgcggag ggguuucauu uaucccguuu ggcggcuuu 49

<210> SEQ ID NO 225
<211> LENGTH: 48
<212> TYPE: RNA
<213> ORGANISM: Artificial Sequence
<220> FEATURE:
<223> OTHER INFORMATION: Synthetic Oligonucleotide

<400> SEQUENCE: 225
uagaccgccu ccgcgcggag ggguuucauu aucccguuug gcggcuuu 48

<210> SEQ ID NO 226
<211> LENGTH: 48
<212> TYPE: RNA
<213> ORGANISM: Artificial Sequence
<220> FEATURE:
<223> OTHER INFORMATION: Synthetic Oligonucleotide

<400> SEQUENCE: 226
uaggccgccu ccgcgcggag ggguuucauu aucccguuug gcggccuu 48

<210> SEQ ID NO 227
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 227
aggccgccnc cgcgcggagg gguuucauua ucccguuugg cggcuu 46

<210> SEQ ID NO 228
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: n is SP3 spacer (1,3-propanediol)

<400> SEQUENCE: 228
aggccgccun cgcgcggagg gguuucauua ucccguuugg cggcuu 46

<210> SEQ ID NO 229
<211> LENGTH: 10
<212> TYPE: RNA
<213> ORGANISM: Artificial Sequence
<220> FEATURE:
<223> OTHER INFORMATION: Synthetic Oligonucleotide

<400> SEQUENCE: 229
aggccgccuc 10

<210> SEQ ID NO 230
<211> LENGTH: 35
<212> TYPE: RNA
<213> ORGANISM: Artificial Sequence
<220> FEATURE:
<223> OTHER INFORMATION: Synthetic Oligonucleotide

<400> SEQUENCE: 230
gcgcggaggg guuucauuau cccguuuggc ggcuu 35

<210> SEQ ID NO 231
<211> LENGTH: 11
<212> TYPE: RNA
<213> ORGANISM: Artificial Sequence
<220> FEATURE:
<223> OTHER INFORMATION: Synthetic Oligonucleotide

<400> SEQUENCE: 231
aggccgccuc c 11

<210> SEQ ID NO 232
<211> LENGTH: 34
<212> TYPE: RNA
<213> ORGANISM: Artificial Sequence
<220> FEATURE:
<223> OTHER INFORMATION: Synthetic Oligonucleotide

<400> SEQUENCE: 232
cgcggagggg uuucauuauc ccguuuggcg gcuu 34

<210> SEQ ID NO 233
<211> LENGTH: 12
<212> TYPE: RNA
<213> ORGANISM: Artificial Sequence
<220> FEATURE:
<223> OTHER INFORMATION: Synthetic Oligonucleotide

<400> SEQUENCE: 233
aggccgccuc cg 12

<210> SEQ ID NO 234
<211> LENGTH: 33
<212> TYPE: RNA
<213> ORGANISM: Artificial Sequence
<220> FEATURE:
<223> OTHER INFORMATION: Synthetic Oligonucleotide

<400> SEQUENCE: 234
gcggaggggu uucauuaucc cguuuggcgg cuu 33

<210> SEQ ID NO 235
<211> LENGTH: 13
<212> TYPE: RNA
<213> ORGANISM: Artificial Sequence
<220> FEATURE:
<223> OTHER INFORMATION: Synthetic Oligonucleotide

<400> SEQUENCE: 235
aggccgccuc cgc 13

<210> SEQ ID NO 236
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 236
cggaggggUU ucauuauccc guuuggcggc uu 32

<210> SEQ ID NO 237
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 237
aggccgccuc cgcg 14

<210> SEQ ID NO 238

<211> LENGTH: 31
<212> TYPE: RNA
<213> ORGANISM: Artificial Sequence
<220> FEATURE:
<223> OTHER INFORMATION: Synthetic Oligonucleotide

<400> SEQUENCE: 238
ggagggguuu cauuaucccg uuuggcggcu u 31

<210> SEQ ID NO 239
<211> LENGTH: 15
<212> TYPE: RNA
<213> ORGANISM: Artificial Sequence
<220> FEATURE:
<223> OTHER INFORMATION: Synthetic Oligonucleotide

<400> SEQUENCE: 239
aggccgccuc cgcgc 15

<210> SEQ ID NO 240
<211> LENGTH: 30
<212> TYPE: RNA
<213> ORGANISM: Artificial Sequence
<220> FEATURE:
<223> OTHER INFORMATION: Synthetic Oligonucleotide

<400> SEQUENCE: 240 gaggguuuc auuaucccgu uuggcggcuu 30

<210> SEQ ID NO 241
<211> LENGTH: 16
<212> TYPE: RNA
<213> ORGANISM: Artificial Sequence
<220> FEATURE:
<223> OTHER INFORMATION: Synthetic Oligonucleotide

<400> SEQUENCE: 241
aggccgccuc cgcgcg 16

<210> SEQ ID NO 242
<211> LENGTH: 29
<212> TYPE: RNA
<213> ORGANISM: Artificial Sequence
<220> FEATURE:
<223> OTHER INFORMATION: Synthetic Oligonucleotide

<400> SEQUENCE: 242 aggguuuca uuaucccguu uggcggcuu 29

<210> SEQ ID NO 243
<211> LENGTH: 17
<212> TYPE: RNA
<213> ORGANISM: Artificial Sequence
<220> FEATURE:
<223> OTHER INFORMATION: Synthetic Oligonucleotide

<400> SEQUENCE: 243
aggccgccuc cgcgcgg 17

<210> SEQ ID NO 244
<211> LENGTH: 28
<212> TYPE: RNA
<213> ORGANISM: Artificial Sequence
<220> FEATURE:
<223> OTHER INFORMATION: Synthetic Oligonucleotide

<400> SEQUENCE: 244
gggguuucau uaucccguuu ggcggcuu 28

<210> SEQ ID NO 245
<211> LENGTH: 18
<212> TYPE: RNA
<213> ORGANISM: Artificial Sequence
<220> FEATURE:
<223> OTHER INFORMATION: Synthetic Oligonucleotide

<400> SEQUENCE: 245
aggccgccuc cgcgcgga 18

<210> SEQ ID NO 246
<211> LENGTH: 27
<212> TYPE: RNA
<213> ORGANISM: Artificial Sequence
<220> FEATURE:
<223> OTHER INFORMATION: Synthetic Oligonucleotide

<400> SEQUENCE: 246
ggguuucauu aucccguuug gcggcuu 27

<210> SEQ ID NO 247
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 247
aggccgccuc cgcgcggag 19

<210> SEQ ID NO 248
<211> LENGTH: 26
<212> TYPE: RNA
<213> ORGANISM: Artificial Sequence
<220> FEATURE:
<223> OTHER INFORMATION: Synthetic Oligonucleotide

<400> SEQUENCE: 248
gguuucauua ucccguuugg cggcuu 26

<210> SEQ ID NO 249
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 249
aggccgccuc cgcgcggagg 20

<210> SEQ ID NO 250
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 250
guuucauuau cccguuuggc ggcuu 25

<210> SEQ ID NO 251
<211> LENGTH: 21
<212> TYPE: RNA

<213> ORGANISM: Artificial Sequence
<220> FEATURE:
<223> OTHER INFORMATION: Synthetic Oligonucleotide

<400> SEQUENCE: 251
aggccgccuc cgcgcggagg g 21

<210> SEQ ID NO 252
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 252
uuucauuauc ccguuuggcg gcuu 24

<210> SEQ ID NO 253
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 253
aggccgccuc cgcgcggagg gg 22

<210> SEQ ID NO 254
<211> LENGTH: 23
<212> TYPE: RNA
<213> ORGANISM: Artificial Sequence
<220> FEATURE:
<223> OTHER INFORMATION: Synthetic Oligonucleotide

<400> SEQUENCE: 254
uucauuaucc cguuuggcgg cuu 23

<210> SEQ ID NO 255
<211> LENGTH: 23
<212> TYPE: RNA
<213> ORGANISM: Artificial Sequence
<220> FEATURE:
<223> OTHER INFORMATION: Synthetic Oligonucleotide

<400> SEQUENCE: 255
aggccgccuc cgcgcggagg ggu 23

<210> SEQ ID NO 256
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 256
ucauuauccc guuuggcggc uu 22

<210> SEQ ID NO 257
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 257
aggccgccuc cgcgcggagg gguu 24

<210> SEQ ID NO 258
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 258
cauuaucccg uuuggcggcu u 21

<210> SEQ ID NO 259
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 259
aggccgccuc cgcgcggagg gguuu 25

<210> SEQ ID NO 260
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 260
auuaucccgu uuggcggcuu 20

<210> SEQ ID NO 261
<211> LENGTH: 26
<212> TYPE: RNA
<213> ORGANISM: Artificial Sequence
<220> FEATURE:
<223> OTHER INFORMATION: Synthetic Oligonucleotide

<400> SEQUENCE: 261
aggccgccuc cgcgcggagg gguuuc 26

<210> SEQ ID NO 262
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 262
uuaucccguu uggcggcuu 19

<210> SEQ ID NO 263
<211> LENGTH: 27
<212> TYPE: RNA
<213> ORGANISM: Artificial Sequence
<220> FEATURE:
<223> OTHER INFORMATION: Synthetic Oligonucleotide

<400> SEQUENCE: 263
aggccgccuc cgcgcggagg gguuuca 27

<210> SEQ ID NO 264
<211> LENGTH: 18
<212> TYPE: RNA
<213> ORGANISM: Artificial Sequence
<220> FEATURE:

<223> OTHER INFORMATION: Synthetic Oligonucleotide

<400> SEQUENCE: 264
uaucccguuu ggcggcuu 18

<210> SEQ ID NO 265
<211> LENGTH: 28
<212> TYPE: RNA
<213> ORGANISM: Artificial Sequence
<220> FEATURE:
<223> OTHER INFORMATION: Synthetic Oligonucleotide

<400> SEQUENCE: 265
aggccgccuc cgcgcggagg gguuucau 28

<210> SEQ ID NO 266
<211> LENGTH: 17
<212> TYPE: RNA
<213> ORGANISM: Artificial Sequence
<220> FEATURE:
<223> OTHER INFORMATION: Synthetic Oligonucleotide

<400> SEQUENCE: 266
aucccguuug gcggcuu 17

<210> SEQ ID NO 267
<211> LENGTH: 29
<212> TYPE: RNA
<213> ORGANISM: Artificial Sequence
<220> FEATURE:
<223> OTHER INFORMATION: Synthetic Oligonucleotide

<400> SEQUENCE: 267
aggccgccuc cgcgcggagg gguuucauu 29

<210> SEQ ID NO 268
<211> LENGTH: 16
<212> TYPE: RNA
<213> ORGANISM: Artificial Sequence
<220> FEATURE:
<223> OTHER INFORMATION: Synthetic Oligonucleotide

<400> SEQUENCE: 268
ucccguuugg cggcuu 16

<210> SEQ ID NO 269
<211> LENGTH: 30
<212> TYPE: RNA
<213> ORGANISM: Artificial Sequence
<220> FEATURE:
<223> OTHER INFORMATION: Synthetic Oligonucleotide

<400> SEQUENCE: 269
aggccgccuc cgcgcggagg gguuucauua 30

<210> SEQ ID NO 270
<211> LENGTH: 15
<212> TYPE: RNA
<213> ORGANISM: Artificial Sequence
<220> FEATURE:
<223> OTHER INFORMATION: Synthetic Oligonucleotide

<400> SEQUENCE: 270
cccguuuggc ggcuu 15

<210> SEQ ID NO 271
<211> LENGTH: 31
<212> TYPE: RNA
<213> ORGANISM: Artificial Sequence
<220> FEATURE:
<223> OTHER INFORMATION: Synthetic Oligonucleotide

<400> SEQUENCE: 271
aggccgccuc cgcgcggagg gguuucauua u 31

<210> SEQ ID NO 272
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 272
ccguuuggcg gcuu 14

<210> SEQ ID NO 273
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 273
aggccgccuc cgcgcggagg gguuucauua uc 32

<210> SEQ ID NO 274
<211> LENGTH: 13
<212> TYPE: RNA
<213> ORGANISM: Artificial Sequence
<220> FEATURE:
<223> OTHER INFORMATION: Synthetic Oligonucleotide

<400> SEQUENCE: 274
cguuuggcgg cuu 13

<210> SEQ ID NO 275
<211> LENGTH: 33
<212> TYPE: RNA
<213> ORGANISM: Artificial Sequence
<220> FEATURE:
<223> OTHER INFORMATION: Synthetic Oligonucleotide

<400> SEQUENCE: 275
aggccgccuc cgcgcggagg gguuucauua ucc 33

<210> SEQ ID NO 276
<211> LENGTH: 12
<212> TYPE: RNA
<213> ORGANISM: Artificial Sequence
<220> FEATURE:
<223> OTHER INFORMATION: Synthetic Oligonucleotide

<400> SEQUENCE: 276
guuuggcggc uu 12

<210> SEQ ID NO 277
<211> LENGTH: 34
<212> TYPE: RNA
<213> ORGANISM: Artificial Sequence
<220> FEATURE:
<223> OTHER INFORMATION: Synthetic Oligonucleotide

<400> SEQUENCE: 277
aggccgccuc cgcgcggagg gguuucauua uccc 34

<210> SEQ ID NO 278
<211> LENGTH: 11
<212> TYPE: RNA
<213> ORGANISM: Artificial Sequence
<220> FEATURE:
<223> OTHER INFORMATION: Synthetic Oligonucleotide

<400> SEQUENCE: 278
uuuggcggcu u 11

<210> SEQ ID NO 279
<211> LENGTH: 35
<212> TYPE: RNA
<213> ORGANISM: Artificial Sequence
<220> FEATURE:
<223> OTHER INFORMATION: Synthetic Oligonucleotide

<400> SEQUENCE: 279
aggccgccuc cgcgcggagg gguuucauua ucccg 35

<210> SEQ ID NO 280
<211> LENGTH: 10
<212> TYPE: RNA
<213> ORGANISM: Artificial Sequence
<220> FEATURE:
<223> OTHER INFORMATION: Synthetic Oligonucleotide

<400> SEQUENCE: 280
uuggcggcuu 10

<210> SEQ ID NO 281
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 281
aggccgccuc cgcgcggagg gguuucauua ucccgu 36

<210> SEQ ID NO 282
<211> LENGTH: 9
<212> TYPE: RNA
<213> ORGANISM: Artificial Sequence
<220> FEATURE:
<223> OTHER INFORMATION: Synthetic Oligonucleotide

<400> SEQUENCE: 282 uggcggcuu 9

<210> SEQ ID NO 283
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (38)..(38)
<223> OTHER INFORMATION: n is SP3 spacer (1,3-propanediol)

<400> SEQUENCE: 283
aggccgccuc cgcgcggagg gguuucauua ucccguungg cggcuu 46

<210> SEQ ID NO 284
<211> LENGTH: 45
<212> TYPE: RNA
<213> ORGANISM: Artificial Sequence
<220> FEATURE:
<223> OTHER INFORMATION: Synthetic Oligonucleotide

<400> SEQUENCE: 284
aggccgcccc gcgcggaggg guuucauuau cccguuuggc ggcuu 45

<210> SEQ ID NO 285
<211> LENGTH: 44
<212> TYPE: RNA
<213> ORGANISM: Artificial Sequence
<220> FEATURE:
<223> OTHER INFORMATION: Synthetic Oligonucleotide

<400> SEQUENCE: 285
aggccgccuc cgcgcggagg gguucauuuc ccguuuggcg gcuu 44

<210> SEQ ID NO 286
<211> LENGTH: 44
<212> TYPE: RNA
<213> ORGANISM: Artificial Sequence
<220> FEATURE:
<223> OTHER INFORMATION: Synthetic Oligonucleotide

<400> SEQUENCE: 286
aggccgccuc cgcgcggagg guuucauuac ccguuuggcg gcuu 44

<210> SEQ ID NO 287
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 287
aggccgccuc cgcgcggaag gguuucauua uccuguuugg cggcuu 46

<210> SEQ ID NO 288
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 288
aggccgccuc cgcgcggaug gguuucauua uccaguuugg cggcuu 46

<210> SEQ ID NO 289
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 289
aggccgccuc cgcgcggacg gguuucauua uccgguuugg cggcuu 46

<210> SEQ ID NO 290
<211> LENGTH: 46
<212> TYPE: RNA
<213> ORGANISM: Artificial Sequence
<220> FEATURE:

<223> OTHER INFORMATION: Synthetic Oligonucleotide

<400> SEQUENCE: 290
aggccgccuc cgcgcggaga gguuucauua ucucguuugg cggcuu 46

<210> SEQ ID NO 291
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 291
aggccgccuc cgcgcggagu gguuucauua ucacguuugg cggcuu 46

<210> SEQ ID NO 292
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 292
aggccgccuc cgcgcggagc gguuucauua ucgcguuugg cggcuu 46

<210> SEQ ID NO 293
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 293
aggccgccuc cgcgcggacc gguuucauua ccggguuugg cggcuu 46

<210> SEQ ID NO 294
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 294
aggccgccuc cgcgcggaga ggguucauuc ccucguuugg cggcuu 46

<210> SEQ ID NO 295
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 295
aggccgcguc cgcgcggagg gguuucauua ucccguuucg cggcuu 46

<210> SEQ ID NO 296
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 296
aggccgcauc cgcgcggagg gguuucauua ucccguuuug cggcuu 46

<210> SEQ ID NO 297
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 297
aggccgcuuc cgcgcggagg gguuucauua ucccguuuag cggcuu 46

<210> SEQ ID NO 298
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 298
aggccggcuc cgcgcggagg gguuucauua ucccguuugc cggcuu 46

<210> SEQ ID NO 299
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 299
aggccgacuc cgcgcggagg gguuucauua ucccguuugu cggcuu 46

<210> SEQ ID NO 300
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 300
aggccgucuc cgcgcggagg gguuucauua ucccguuuga cggcuu 46

<210> SEQ ID NO 301
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 301
aggccgccuc cgcgcggagg gcuuucauua gcccguuugg cggcuu 46

<210> SEQ ID NO 302
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 302
aggccgccuc cgcgcggagg acuuucauua guccguuugg cggcuu 46

<210> SEQ ID NO 303
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 303
aggccgccuc cgcgcggagg ucuuucauua gaccguuugg cggcuu 46

<210> SEQ ID NO 304
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 304
aggccgccuc cgcgcggagg uguuucauua caccguuugg cggcuu 46

<210> SEQ ID NO 305
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 305
aggccgccuc cgcgcggagg aguuucauua cuccguuugg cggcuu 46

<210> SEQ ID NO 306
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 306
aggccgccuc cgcgcggagg cguuucauua cgccguuugg cggcuu 46

<210> SEQ ID NO 307
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 307
aggccgaauc cgcgcggagg gguuucauua ucccguuuuu cggcuu 46

<210> SEQ ID NO 308
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 308
aggccgauuc cgcgcggagg gguuucauua ucccguuuau cggcuu 46

<210> SEQ ID NO 309
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 309
aggccguauc cgcgcggagg gguuucauua ucccguuuua cggcuu 46

<210> SEQ ID NO 310
<211> LENGTH: 46

<212> TYPE: RNA
<213> ORGANISM: Artificial Sequence
<220> FEATURE:
<223> OTHER INFORMATION: Synthetic Oligonucleotide

<400> SEQUENCE: 310
aggccguuuc cgcgcggagg gguuucauua ucccguuuaa cggcuu 46

<210> SEQ ID NO 311
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 311
aggccgaanc cgcgcggagg gguuucauua ucccguuuuu cggcuu 46

<210> SEQ ID NO 312
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 312
aggccgaunc cgcgcggagg gguuucauua ucccguuuau cggcuu 46

<210> SEQ ID NO 313
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 313
aggccguanc cgcgcggagg gguuucauua ucccguuuua cggcuu 46

<210> SEQ ID NO 314
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 314
aggccguunc cgcgcggagg gguuucauca ucccguuuaa cggcuu 46

<210> SEQ ID NO 315
<211> LENGTH: 46
<212> TYPE: RNA
<213> ORGANISM: Artificial Sequence
<220> FEATURE:

<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 315
aggccgacnc cgcgcggagg gguuucauua ucccguuugu cggcuu 46

<210> SEQ ID NO 316
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 316
aggccgucnc cgcgcggagg gguuucauua ucccguuuga cggcuu 46

<210> SEQ ID NO 317
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 317
aggccgcanc cgcgcggagg gguuucauua ucccguuuug cggcuu 46

<210> SEQ ID NO 318
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 318
aggccgcunc cgcgcggagg gguuucauua ucccguuuag cggcuu 46

<210> SEQ ID NO 319
<211> LENGTH: 44
<212> TYPE: RNA
<213> ORGANISM: Artificial Sequence
<220> FEATURE:
<223> OTHER INFORMATION: Synthetic Oligonucleotide

<400> SEQUENCE: 319
aggccgccuc cgcgcggagg gguucauauc ccguuuggcg gcuu 44

<210> SEQ ID NO 320
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 320
aggccgccac cgcgcggagg gguuucauua ucccguuugg cggcuu 46

<210> SEQ ID NO 321
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 321
aggccgcccc cgcgcggagg gguuucauua ucccguuugg cggcuu 46

<210> SEQ ID NO 322
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 322
aggccgccgc cgcgcggagg gguuucauua ucccguuugg cggcuu 46

<210> SEQ ID NO 323
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 323
aggccgccuc cacgcggagg gguuucauua ucccguuugg cggcuu 46

<210> SEQ ID NO 324
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 324
aggccgccuc cccgcggagg gguuucauua ucccguuugg cggcuu 46

<210> SEQ ID NO 325
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 325
aggccgccuc cucgcggagg gguuucauua ucccguuugg cggcuu 46

<210> SEQ ID NO 326
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 326
aggccgccuc cgagcggagg gguuucauua ucccguuugg cggcuu 46

<210> SEQ ID NO 327
<211> LENGTH: 46
<212> TYPE: RNA

<213> ORGANISM: Artificial Sequence
<220> FEATURE:
<223> OTHER INFORMATION: Synthetic Oligonucleotide

<400> SEQUENCE: 327
aggccgccuc cgggcggagg gguuucauua ucccguuugg cggcuu 46

<210> SEQ ID NO 328
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 328
aggccgccuc cgugcggagg gguuucauua ucccguuugg cggcuu 46

<210> SEQ ID NO 329
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 329
aggccgccuc cgcacggagg gguuucauua ucccguuugg cggcuu 46

<210> SEQ ID NO 330
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 330
aggccgccuc cgcccggagg gguuucauua ucccguuugg cggcuu 46

<210> SEQ ID NO 331
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 331
aggccgccuc cgcucggagg gguuucauua ucccguuugg cggcuu 46

<210> SEQ ID NO 332
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 332
aggccgccuc cgcgaggagg gguuucauua ucccguuugg cggcuu 46

<210> SEQ ID NO 333
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 333
aggccgccuc cgcggggagg gguuucauua ucccguuugg cggcuu 46

<210> SEQ ID NO 334
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 334
aggccgccuc cgcguggagg gguuucauua ucccguuugg cggcuu 46

<210> SEQ ID NO 335
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 335
aggccgccuc cgcgcggcgg gguuucauua ucccguuugg cggcuu 46

<210> SEQ ID NO 336
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 336
aggccgccuc cgcgcggagg gguuucauua ucccauuugg cggcuu 46

<210> SEQ ID NO 337
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 337
aggccgccuc cgcgcggagg gguuucauua uccccuuugg cggcuu 46

<210> SEQ ID NO 338
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 338
aggccgccuc cgcgcggagg gguuucauua ucccuuuugg cggcuu 46

<210> SEQ ID NO 339
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 339
aggccgccuc cgcgcggagg gguuucauua ucccgauugg cggcuu 46

<210> SEQ ID NO 340
<211> LENGTH: 46
<212> TYPE: RNA
<213> ORGANISM: Artificial Sequence
<220> FEATURE:

<223> OTHER INFORMATION: Synthetic Oligonucleotide

<400> SEQUENCE: 340
aggccgccuc cgcgcggagg gguuucauua ucccgcuugg cggcuu 46

<210> SEQ ID NO 341
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 341
aggccgccuc cgcgcggagg gguuucauua ucccgguugg cggcuu 46

<210> SEQ ID NO 342
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 342
aggccgccuc cgcgcggagg gguuucauua ucccguaugg cggcuu 46

<210> SEQ ID NO 343
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 343
aggccgccuc cgcgcggagg gguuucauua ucccgucugg cggcuu 46

<210> SEQ ID NO 344
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 344
aggccgccuc cgcgcggagg gguuucauua ucccgugugg cggcuu 46

<210> SEQ ID NO 345
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 345
aggccgccuc cgcgcggagg gguuucauua ucccguuagg cggcuu 46

<210> SEQ ID NO 346
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 346
aggccgccuc cgcgcggagg gguuucauua ucccguucgg cggcuu 46

<210> SEQ ID NO 347
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 347
aggccgccuc cgcgcggagg gguuucauua ucccguuggg cggcuu 46

<210> SEQ ID NO 348
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 348
aggccgccug cgcgcgcagg gguuucauua ucccguuugg cggcuu 46

<210> SEQ ID NO 349
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 349
aggccgccua cgcgcguagg gguuucauua ucccguuugg cggcuu 46

<210> SEQ ID NO 350
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 350
aggccgccuu cgcgcgaagg gguuucauua ucccguuugg cggcuu 46

<210> SEQ ID NO 351
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 351
aggccgccuc ggcgccgagg gguuucauua ucccguuugg cggcuu 46

<210> SEQ ID NO 352
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 352
aggccgccuc agcgcugagg gguuucauua ucccguuugg cggcuu 46

<210> SEQ ID NO 353
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 353
aggccgccuc ugcgcagagg gguuucauua ucccguuugg cggcuu 46

<210> SEQ ID NO 354
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 354
aggccgcauc cgcgcggagg gguuucauua ucccguuuaa ccgcuu 46

<210> SEQ ID NO 355
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 355
aggccgcauc cgcgcggagg gguuucauua ucccguuuaa ccgauu 46

<210> SEQ ID NO 356
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 356
aggccgccuu ugcgcuuagg gguuucauua ucccguuugg cggcuu 46

<210> SEQ ID NO 357
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 357
aggccgccuc cgcgcccagg gguuucauua ucccguuugg cggcuu 46

<210> SEQ ID NO 358
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 358
aggccgccuc cgcgcggagc cguuucauua ucccguuugg cggcuu 46

<210> SEQ ID NO 359
<211> LENGTH: 46
<212> TYPE: RNA
<213> ORGANISM: Artificial Sequence
<220> FEATURE:
<223> OTHER INFORMATION: Synthetic Oligonucleotide

<400> SEQUENCE: 359
aggccgccuc cgcgcggagg gguuucauua uaacguuugg cggcuu 46

<210> SEQ ID NO 360
<211> LENGTH: 46

<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 360
aggccgacnc cgcgcggagg gguuucauua ccccguuugu cggcuu 46

<210> SEQ ID NO 361
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 361
aggccgacnc cgcgcggagg gguuucauua ucccguuugu cggcuu 46

<210> SEQ ID NO 362
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 362
aggccgacnc cgcgcggagg gguuucauua ucccguuugu cggcuu 46

<210> SEQ ID NO 363
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is the SP3 spacer (1,3-propanediol)

<400> SEQUENCE: 363
aggccgacnc cgcgcggagg gguuucauua ucccguuugu cggcuu 46

<210> SEQ ID NO 364
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 364
aggccgacnc cgcgcggagg gguuucauua ucccguuugu cggcuu 46

<210> SEQ ID NO 365

<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 365
aggccgacnc cgcgcggagg gguuucauua ucccguuugu cggcuu 46

<210> SEQ ID NO 366
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 366
aggccgacnc cgcgcggagg gguuucauua ucccguuugu cggcuu 46

<210> SEQ ID NO 367
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol).

<400> SEQUENCE: 367
aggccgacnc cgcgcggagg gguuucauua ucccguuugu cggcuu 46

<210> SEQ ID NO 368
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 368
aggccgacnc cgcgcggagg gguuucauua ucccguuugu cggcuu 46

<210> SEQ ID NO 369
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 369
aggccgacnc cgcgcggagg gguuucauua ucccguuugu cggcuu 46

<210> SEQ ID NO 370
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 370
aggccgacnc cgcgcggagg gguuucauua ucccguuugu cggcuu 46

<210> SEQ ID NO 371
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 371
aggccgacnc cgcgcggagg gguuucauua ucccguuugu cggcuu 46

<210> SEQ ID NO 372
<211> LENGTH: 42
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is SP3 spacer (1,3-propanediol)

<400> SEQUENCE: 372
gccgacnccg cgcggagggg uuucauuauc ccguuugucg gc 42

<210> SEQ ID NO 373
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is SP3 spacer (1,3-propanediol)

<400> SEQUENCE: 373
aggccgacnc cgcgcggagg gguuucauua ccccguuugu cggcuu 46

<210> SEQ ID NO 374
<211> LENGTH: 42
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is SP3 spacer (1,3-propanediol)

<400> SEQUENCE: 374
gccgacnccg cgcggagggg uuucauuauc ccguuugucg gc 42

<210> SEQ ID NO 375
<211> LENGTH: 42
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is SP3 spacer (1,3-propanediol)

<400> SEQUENCE: 375
gccgacnccg cgcggagggg uuucauuauc ccguuugucg gc 42

<210> SEQ ID NO 376
<211> LENGTH: 42
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is SP3 spacer (1,3-propanediol)

<400> SEQUENCE: 376
gccgacnccg cgcggagggg uuucauuauc ccguuugucg gc 42

<210> SEQ ID NO 377
<211> LENGTH: 42
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: SP3 spacer (1,3-propanediol)

<400> SEQUENCE: 377
gccgacnccg cgcggagggg uuucauuauc ccguuugucg gc 42

<210> SEQ ID NO 378
<211> LENGTH: 42
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is SP3 spacer (1,3-propanediol)

<400> SEQUENCE: 378
gccgacnccg cgcggagggg uuucauuauc ccguuugucg gc 42

<210> SEQ ID NO 379
<211> LENGTH: 42
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is SP3 spacer (1,3-propanediol)

<400> SEQUENCE: 379
gccgacnccg cgcggagggg uuucauuauc ccguuugucg gc 42

<210> SEQ ID NO 380
<211> LENGTH: 42
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is SP3 spacer (1,3-propanediol)

<400> SEQUENCE: 380
gccgacnccg cgcggagggg uuucauuauc ccguuugucg gc 42

<210> SEQ ID NO 381
<211> LENGTH: 41
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is SP3 spacer (1,3-propanediol)

<400> SEQUENCE: 381
gccgacnccg cgcggagggg uuucauuauc ccguuugucg g 41

<210> SEQ ID NO 382
<211> LENGTH: 40
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (3)..(3)
<223> OTHER INFORMATION: 2?OMe
<220> FEATURE:
<221> NAME/KEY: misc_feature
<222> LOCATION: (6)..(6)
<223> OTHER INFORMATION: n is SP3 spacer (1,3-propanediol)
<220> FEATURE:
<221> NAME/KEY: modified_base
<222> LOCATION: (39)..(40)
<223> OTHER INFORMATION: 2?OMe

<400> SEQUENCE: 382
ccgacnccgc gcggaggggu uucauuaucc cguuugucgg 40

<210> SEQ ID NO 383
<211> LENGTH: 40
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: n is SP3 spacer (1,3-propanediol)

<400> SEQUENCE: 383
ccgacnccgc gcggaggggu uucauuaucc cguuugucgg 40

<210> SEQ ID NO 384
<211> LENGTH: 40
<212> TYPE: RNA
<213> ORGANISM: Artificial Sequence
<220> FEATURE:

<223> OTHER INFORMATION: Synthetic Oligonucleotide
<220> FEATURE:
<221> NAME/KEY: misc_feature
<222> LOCATION: (6)..(6)
<223> OTHER INFORMATION: n is SP3 spacer (1,3-propanediol)

<400> SEQUENCE: 384
ccgacnccgc gcggaggggu uucauuaucc cguuugucgg 40

<210> SEQ ID NO 385
<211> LENGTH: 40
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: n is SP3 spacer (1,3-propanediol)

<400> SEQUENCE: 385
ccgacnccgc gcggaggggu uucauuaucc cguuugucgg 40

<210> SEQ ID NO 386
<211> LENGTH: 40
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: n is SP3 spacer (1,3-propanediol)

<400> SEQUENCE: 386
ccgacnccgc gcggaggggu uucauuaucc cguuugucgg 40

<210> SEQ ID NO 387
<211> LENGTH: 40
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: n is SP3 spacer (1,3-propanediol)

<400> SEQUENCE: 387
ccgacnccgc gcggaggggu uucauuaucc cguuugucgg 40

<210> SEQ ID NO 388
<211> LENGTH: 40
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: n is SP3 spacer (1,3-propanediol)

<400> SEQUENCE: 388
ccgacnccgc gcggaggggu uucauuaucc cguuugucgg 40

<210> SEQ ID NO 389
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 389
cgacnccgcg cggaggggguu ucauuauccc guuugucg 38

<210> SEQ ID NO 390
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 390
cgacnccgcg cggaggggguu ucauuauccc guuugucg 38

<210> SEQ ID NO 391
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 391
cgacnccgcg cggaggggguu ucauuauccc guuugucg 38

<210> SEQ ID NO 392
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 392
cgacnccgcg cggaggggguu ucauuauccc guuugucg 38

<210> SEQ ID NO 393
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 393
cgacnccgcg cggaggggguu ucauuauccc guuugucg 38

<210> SEQ ID NO 394
<211> LENGTH: 38
<212> TYPE: RNA

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 394

cgacnccgcg cggaggguu ucauuauccc guuugucg                      38


<210> SEQ ID NO 395
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 395

cgacnccgcg cggaggguu ucauuauccc guuugucg                      38


<210> SEQ ID NO 396
<211> LENGTH: 36
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: n is SP3 spacer (1,3-propanediol)

<400> SEQUENCE: 396

gacnccgcgc ggaggguuu cauuaucccg uuuguc                        36


<210> SEQ ID NO 397
<211> LENGTH: 36
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: n is SP3 spacer (1,3-propanediol)

<400> SEQUENCE: 397

gacnccgcgc ggaggguuu cauuaucccg uuuguc                        36


<210> SEQ ID NO 398
<211> LENGTH: 36
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: is SP3 spacer (1,3-propanediol)

<400> SEQUENCE: 398

gacnccgcgc ggaggguuu cauuaucccg uuuguc                        36


<210> SEQ ID NO 399
<211> LENGTH: 36
```

<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: n is SP3 spacer (1,3-propanediol)

<400> SEQUENCE: 399
gacnccgcgc ggagggguuu cauuaucccg uuuguc 36

<210> SEQ ID NO 400
<211> LENGTH: 36
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: n is SP3 spacer (1,3-propanediol)

<400> SEQUENCE: 400
gacnccgcgc ggagggguuu cauuaucccg uuuguc 36

<210> SEQ ID NO 401
<211> LENGTH: 36
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: n is SP3 spacer (1,3-propanediol)

<400> SEQUENCE: 401
gacnccgcgc ggagggguuu cauuaucccg uuuguc 36

<210> SEQ ID NO 402
<211> LENGTH: 36
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(4)
<223> OTHER INFORMATION: n is SP3 spacer (1,3-propanediol)

<400> SEQUENCE: 402
gacnccgcgc ggagggguuu cauuaucccg uuuguc 36

<210> SEQ ID NO 403
<211> LENGTH: 34
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n is SP3 spacer (1,3-propanediol)

<400> SEQUENCE: 403
acnccgcgcg gaggggguuuc auuaucccgu uugu 34

<210> SEQ ID NO 404

<211> LENGTH: 34
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n is SP3 spacer (1,3-propanediol)

<400> SEQUENCE: 404
acnccgcgcg gagggguuuc auuaucccgu uugu 34

<210> SEQ ID NO 405
<211> LENGTH: 34
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n is SP3 spacer (1,3-propanediol)

<400> SEQUENCE: 405
acnccgcgcg gagggguuuc auuaucccgu uugu 34

<210> SEQ ID NO 406
<211> LENGTH: 32
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is SP3 spacer (1,3-propanediol)

<400> SEQUENCE: 406
cnccgcgcgg aggggguuuca uuaucccguu ug 32

<210> SEQ ID NO 407
<211> LENGTH: 32
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is SP3 spacer (1,3-propanediol)

<400> SEQUENCE: 407
cnccgcgcgg agggguuuca uuaucccguu ug 32

<210> SEQ ID NO 408
<211> LENGTH: 32
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is SP3 spacer (1,3-propanediol)

<400> SEQUENCE: 408
cnccgcgcgg agggguuuca uuaucccguu ug 32

<210> SEQ ID NO 409
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 409
cgacnccgcg cggagggauu ucauuauccc guuugucg 38

<210> SEQ ID NO 410
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 410
cgacnccgcg cggaggggua ucauuauccc guuugucg 38

<210> SEQ ID NO 411
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 411
cgacnccgcg cggagggguu acauuauccc guuugucg 38

<210> SEQ ID NO 412
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 412
cgacnccgcg cggagggguu ucauaauccc guuugucg 38

<210> SEQ ID NO 413
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 413
cgacnccgcg cggagggguu ucauuacccc guuugucg 38

<210> SEQ ID NO 414
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 414
cgacnccgcg cggagggaua ucauuauccc guuugucg 38

<210> SEQ ID NO 415
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 415
cgacnccgcg cggagggauu acauuauccc guuugucg 38

<210> SEQ ID NO 416
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 416
cgacnccgcg cggagggauu ucauaauccc guuugucg 38

<210> SEQ ID NO 417
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 417
cgacnccgcg cggaggggua ucauuacccc guuugucg 38

<210> SEQ ID NO 418
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 418
cgacnccgcg cggaggggu ucauaacccc guuugucg 38

<210> SEQ ID NO 419
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 419
cgacnccgcg cggaggggguu acauaaaucccc guuugucg 38

<210> SEQ ID NO 420
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 420
cgacncagcg cugaggggguu ucauuauccc guuugucg 38

<210> SEQ ID NO 421
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 421
cgacnccgcg cggaggggguu ucauuauccc guuugucg 38

<210> SEQ ID NO 422
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 422
cgacncagcg cugaggggguu ucauuauccc guuugucg 38

<210> SEQ ID NO 423
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 423
cgacnccgcg cggagggaug ucaucauccc guuugucg 38

<210> SEQ ID NO 424
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP3 spacer (1,3-propanediol)

<400> SEQUENCE: 424
cgacnccgcg cggagggauc ucaugauccc guuugucg 38

<210> SEQ ID NO 425
<211> LENGTH: 39
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(6)
<223> OTHER INFORMATION: n is SP3 spacer (1,3-propanediol)

<400> SEQUENCE: 425
cgacnnccgc gcggaggggu uucauuaucc cguuugucg 39

<210> SEQ ID NO 426
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP6 spacer (1,6-hexanediol)

<400> SEQUENCE: 426
cgacnccgcg cggaggguu ucauuauccc guuugucg 38

<210> SEQ ID NO 427
<211> LENGTH: 38
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is SP9 spacer (triethyleneglycol)

<400> SEQUENCE: 427
cgacnccgcg cggaggguu ucauuauccc guuugucg 38

<210> SEQ ID NO 428
<211> LENGTH: 89
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (28)..(58)
<223> OTHER INFORMATION: N is G, A, C, or T

<400> SEQUENCE: 428
gggagtgtgt acgaggcatt aggccgccnn nnnnnnnnnn nnnnnnnnnn nnnnnnnngg 60
cggctttgat acttgatcgc cctagaagc 89

<210> SEQ ID NO 429
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 429
gggagtgtgt acgaggcatt a 21

<210> SEQ ID NO 430
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 430
gcttctaggg cgatcaagta tca 23

<210> SEQ ID NO 431
<211> LENGTH: 27
<212> TYPE: RNA
<213> ORGANISM: Artificial Sequence
<220> FEATURE:
<223> OTHER INFORMATION: Synthetic Oligonucleotide

<400> SEQUENCE: 431
cggaaucagu gaaugcuuau acauccg 27

<210> SEQ ID NO 432
<211> LENGTH: 214
<212> TYPE: PRT
<213> ORGANISM: Artificial Sequence
<220> FEATURE:
<223> OTHER INFORMATION: Light Chain

<400> SEQUENCE: 432

Asp Ile Gln Met Thr Gln Ser Pro Ser Ser Leu Ser Ala Ser Val Gly
1 5 10 15

Asp Arg Val Thr Ile Thr Cys Ser Ala Ser Gln Asp Ile Ser Asn Tyr
20 25 30

Leu Asn Trp Tyr Gln Gln Lys Pro Gly Lys Ala Pro Lys Val Leu Ile
35 40 45

Tyr Phe Thr Ser Ser Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Thr Val Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 433
<211> LENGTH: 453
<212> TYPE: PRT
<213> ORGANISM: Artificial Sequence
<220> FEATURE:
<223> OTHER INFORMATION: Heavy Chain

<400> SEQUENCE: 433

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
```

```
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 434
<211> LENGTH: 89
<212> TYPE: DNA
<213> ORGANISM: Artificial Sequence
<220> FEATURE:
<223> OTHER INFORMATION: Synthetic Oligonucleotide

<400> SEQUENCE: 434

gggagagtcg gtagcatact aggccgcctc cgcgcggagg ggtttcatta tcccgtttgg      60

cggctttgat acttgatcgc cctagaagc                                         89


<210> SEQ ID NO 435
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 435

gggagagtcg gtagcatact                                                   20


<210> SEQ ID NO 436
<211> LENGTH: 46
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(46)
<223> OTHER INFORMATION: H is A, C, or U; N is A, C, G, or U; B is C, G,
      or U; Y is C or U; D is A, G, or U; R is A or G; W is A or U; K is
      G or U; and V is A, C, or G

<400> SEQUENCE: 436

hnbyhdccuc cgcgcggagd sbhdnnnnhn nbncgyuugk ynkvnw                      46


<210> SEQ ID NO 437
<211> LENGTH: 44
```

<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(44)
<223> OTHER INFORMATION: H is A, C, or U; N is A, C, G, or U; B is C, G, or U; Y is C or U; D is A, G, or U; R is A or G; W is A or U; K is G or U; and V is A, C, or G

<400> SEQUENCE: 437
hnbyhdccuc cgcgcggagk bhydnnnkdb vcgyuugkyn kvnw 44

<210> SEQ ID NO 438
<211> LENGTH: 44
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(44)
<223> OTHER INFORMATION: H is A, C, or U; N is A, C, G, or U; B is C, G, or U; Y is C or U; D is A, G, or U; R is A or G; W is A or U; K is G or U; M is A or C; and V is A, C, or G

<400> SEQUENCE: 438
hnbyhdccuc cgcgcggagk shudrgbuds mcgyuugkyn kvnw 44

<210> SEQ ID NO 439
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 439
cgacuccgcg cggaggguug gagguuaccc guuugucg 38

<210> SEQ ID NO 440
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 440
gggagagucg guagccucaa cgacuccgcg cggaggguug gagguuaccc guuugucgcu 60
auguggaaau ggcgcugu 78

<210> SEQ ID NO 441
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 441
cgacuccgcg cggagucccu aauuuggggc guuugucg 38

<210> SEQ ID NO 442
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 442
gggagagucg guagccucaa cgacuccgcg cggagucccu aauuuggggc guuugucgcu 60
auguggaaau ggcgcugu 78

<210> SEQ ID NO 443
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 443
cgacuccgcg cggagucccu ucauuggggc guuugucg 38

<210> SEQ ID NO 444
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 444
gggagagucg guagccucaa cgacuccgcg cggagucccu ucauuggggc guuugucgcu 60
auguggaaau ggcgcugu 78

<210> SEQ ID NO 445
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 445
cgacuccgcg cggaggguua auggcuaccc guuugucg 38

<210> SEQ ID NO 446
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 446
gggagagucg guagccucaa cgacuccgcg cggaggguua auggcuaccc guuugucgcu 60
auguggaaau ggcgcugu 78

<210> SEQ ID NO 447
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 447
cgacuccgcg cggagucccu guaauggggc guuugucg 38

<210> SEQ ID NO 448
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 448
gggagagucg guagccucaa cgacuccgcg cggagucccu guaaugggc guuugucgcu 60 auguggaaau ggcgcugu 78

<210> SEQ ID NO 449
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 449
cgacuccgcg cggagucccu auuuuggggc guuugucg 38

<210> SEQ ID NO 450
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 450
gggagagucg guagccucaa cgacuccgcg cggagucccu auuuuggggc guuugucgcu 60
auguggaaau ggcgcugu 78

<210> SEQ ID NO 451
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 451
cgacuccgcg cggagaggag guuaccccuc guuugucg 38

<210> SEQ ID NO 452
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 452
gggagagucg guagccucaa cgacuccgcg cggagaggag guuaccccuc guuugucgcu 60
auguggaaau ggcgcugu 78

<210> SEQ ID NO 453
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 453
cgacuccgcg cggagucccu ugauuggggc guuugucg 38

<210> SEQ ID NO 454
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 454
gggagagucg guagccucaa cgacuccgcg cggagucccu ugauuggggc guuugucgcu 60
auguggaaau ggcgcugu 78

<210> SEQ ID NO 455
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 455
cgacuccgcg cggaggguua cuggcuaccc guuugucg 38

<210> SEQ ID NO 456
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 456
gggagagucg guagccucaa cgacuccgcg cggaggguua cuggcuaccc guuugucgcu 60
auguggaaau ggcgcugu 78

<210> SEQ ID NO 457
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 457
cgacuccgcg cggagucccu aacaugggc guuugucg 38

<210> SEQ ID NO 458
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 458
gggagagucg guagccucaa cgacuccgcg cggagucccu aacaugggc guuugucgcu 60 auguggaaau ggcgcugu 78

<210> SEQ ID NO 459
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 459
cgacuccgcg cggaggggag gcaacuuccc guuugucg 38

<210> SEQ ID NO 460
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 460
gggagagucg guagccucaa cgacuccgcg cggaggggag gcaacuuccc guuugucgcu 60
auguggaaau ggcgcugu 78

<210> SEQ ID NO 461
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 461
cgacuccgcg cggagucccu uuauuggggc guuugucg 38

<210> SEQ ID NO 462
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 462
gggagagucg guagccucaa cgacuccgcg cggagucccu uuauuggggc guuugucgcu 60
auguggaaau ggcgcugu 78

<210> SEQ ID NO 463
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 463
cgacuccgcg cggagucccu acaauggggc guuugucg 38

<210> SEQ ID NO 464
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 464
gggagagucg guagccucaa cgacuccgcg cggagucccu acaauggggc guuugucgcu 60
auguggaaau ggcgcugu 78

<210> SEQ ID NO 465
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 465
cgacuccgcg cggagugccg uuugagguac guuugucg 38

<210> SEQ ID NO 466
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 466
gggagagucg guagccucaa cgacuccgcg cggagugccg uuugagguac guuugucgcu 60
auguggaaau ggcgcugu 78

<210> SEQ ID NO 467
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 467
cgacuccgcg cggagggcug aggcaaugcc cguuuguc 38

<210> SEQ ID NO 468
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 468
gggagagucg guagccucaa cgacuccgcg cggagggcug aggcaaugcc cguuuguccu 60
auguggaaau ggcgcugu 78

<210> SEQ ID NO 469
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 469
cgacuccgcg cggaguccu acuuuggggc guuugucg 38

<210> SEQ ID NO 470
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 470
gggagagucg guagccucaa cgacuccgcg cggaguccu acuuuggggc guuugucgcu 60
auguggaaau ggcgcugu 78

<210> SEQ ID NO 471
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 471
cgacuccgcg cggaguccu cacaugggc guuugucg 38

<210> SEQ ID NO 472
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 472
gggagagucg guagccucaa cgacuccgcg cggaguccu cacaugggc guuugucgcu 60 auguggaaau ggcgcugu 78

<210> SEQ ID NO 473
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 473
cgacuccgcg cggaggguua caggcuaccc guuugucg 38

<210> SEQ ID NO 474
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 474
gggagagucg guagccucaa cgacuccgcg cggaggguua caggcuaccc guuugucgcu 60
auguggaaau ggcgcugu 78

<210> SEQ ID NO 475
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 475
cgacuccgcg cggagucccu uuguuggggc guuugucg 38

<210> SEQ ID NO 476
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 476
gggagagucg guagccucaa cgacuccgcg cggagucccu uuguuggggc guuugucgcu 60
auguggaaau ggcgcugu 78

<210> SEQ ID NO 477
<211> LENGTH: 38
<212> TYPE: RNA
<213> ORGANISM: Artificial Sequence
<220> FEATURE:
<223> OTHER INFORMATION: Synthetic Oligonucleotide

<400> SEQUENCE: 477
cgacuccgcg cggagucccu aaaaaugggc guuugucg 38

<210> SEQ ID NO 478
<211> LENGTH: 78
<212> TYPE: RNA
<213> ORGANISM: Artificial Sequence
<220> FEATURE:
<223> OTHER INFORMATION: Synthetic Oligonucleotide

<400> SEQUENCE: 478
gggagagucg guagccucaa cgacuccgcg cggagucccu aaaaaugggc guuugucgcu 60
auguggaaau ggcgcugu 78

<210> SEQ ID NO 479
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 479
cgacuccgcg cggaggguuu ggcuacccgu uugucg 36

<210> SEQ ID NO 480
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 480
gggagagucg guagccucaa cgacuccgcg cggaggguuu ggcuacccgu uugucgcuau 60
guggaaaugg cgcugu 76

<210> SEQ ID NO 481
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 481
cgacuccgcg cggaggcuug agguagccgu uugucg 36

<210> SEQ ID NO 482
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 482
gggagagucg guagccucaa cgacuccgcg cggaggcuug agguagccgu uugucgcuau 60
guggaaaugg cgcugu 76

<210> SEQ ID NO 483
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 483
cgacuccgcg cggaguccca cauggggcgu uugucg 36

<210> SEQ ID NO 484
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 484
gggagagucg guagccucaa cgacuccgcg cggaguccca cauggggcgu uugucgcuau 60
guggaaaugg cgcugu 76

<210> SEQ ID NO 485
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 485
cgacuccgcg cggagggaug agguucccgu uugucg 36

<210> SEQ ID NO 486
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 486
gggagagucg guagccucaa cgacuccgcg cggagggaug agguucccgu uugucgcuau 60
guggaaaugg cgcugu 76

<210> SEQ ID NO 487
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 487
cgacuccgcg cggaggcaug agguugccgu uugucg 36

<210> SEQ ID NO 488
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 488
gggagagucg guagccucaa cgacuccgcg cggaggcaug agguugccgu uugucgcuau 60
guggaaaugg cgcugu 76

<210> SEQ ID NO 489
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 489
cgacuccgcg cggagugcug aggugcacgu uugucg 36

<210> SEQ ID NO 490
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 490
gggagagucg guagccucaa cgacuccgcg cggagugcug aggugcacgu uugucgcuau 60
guggaaaugg cgcugu 76

<210> SEQ ID NO 491

<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 491
cgacuccgcg cggagucccu auuggggcgu uugucg 36

<210> SEQ ID NO 492
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 492
gggagagucg guagccucaa cgacuccgcg cggagucccu auuggggcgu uugucgcuau 60
guggaaaugg cgcugu 76

<210> SEQ ID NO 493
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 493
cgacuccgcg cggaggguua ggcuacccgu uugucg 36

<210> SEQ ID NO 494
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 494
gggagagucg guagccucaa cgacuccgcg cggaggguua ggcuacccgu uugucgcuau 60
guggaaaugg cgcugu 76

<210> SEQ ID NO 495
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 495
cgacuccgcg cggagcuucg gaugaggcgu uugucg 36

<210> SEQ ID NO 496
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 496
gggagagucg guagccucaa cgacuccgcg cggagcuucg gaugaggcgu uugucgcuau 60
guggaaaugg cgcugu 76

<210> SEQ ID NO 497
<211> LENGTH: 36

<212> TYPE: RNA
<213> ORGANISM: Artificial Sequence
<220> FEATURE:
<223> OTHER INFORMATION: Synthetic Oligonucleotide

<400> SEQUENCE: 497
cgacuccgcg cggagucccu caugggcgu uugucg 36

<210> SEQ ID NO 498
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 498
gggagagucg guagccucaa cgacuccgcg cggaguccu caugggcgu uugucgcuau 60 guggaaaugg cgcugu 76

<210> SEQ ID NO 499
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 499
cgacuccgcg cggagucccg uaugggcgu uugucg 36

<210> SEQ ID NO 500
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 500
gggagagucg guagccucaa cgacuccgcg cggagucccg uaugggcgu uugucgcuau 60 guggaaaugg cgcugu 76

<210> SEQ ID NO 501
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 501
cgacuccgcg cggaguccca auugggcgu uugucg 36

<210> SEQ ID NO 502
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 502
gggagagucg guagccucaa cgacuccgcg cggaguccca auugggcgu uugucgcuau 60 guggaaaugg cgcugu 76

<210> SEQ ID NO 503
<211> LENGTH: 36
<212> TYPE: RNA

<213> ORGANISM: Artificial Sequence
<220> FEATURE:
<223> OTHER INFORMATION: Synthetic Oligonucleotide

<400> SEQUENCE: 503
cgacuccgcg cggaggguuu gguuacccgu uugucg 36

<210> SEQ ID NO 504
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 504
gggagagucg guagccucaa cgacuccgcg cggaggguuu gguuacccgu uugucgcuau 60
guggaaaugg cgcugu 76

<210> SEQ ID NO 505
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 505
cgacuccgcg cggaguccca uuuggggcgu uugucg 36

<210> SEQ ID NO 506
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 506
gggagagucg guagccucaa cgacuccgcg cggaguccca uuuggggcgu uugucgcuau 60
guggaaaugg cgcugu 76

<210> SEQ ID NO 507
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 507
cgacuccgcg cggaguccca caaggggcgu uugucg 36

<210> SEQ ID NO 508
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 508
gggagagucg guagccucaa cgacuccgcg cggaguccca caaggggcgu uugucgcuau 60
guggaaaugg cgcugu 76

<210> SEQ ID NO 509
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 509
cgacuccgcg cggagcuucg gaagaggcgu uugucg 36

<210> SEQ ID NO 510
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 510
gggagagucg guagccucaa cgacuccgcg cggagcuucg gaagaggcgu uugucgcuau 60
guggaaaugg cgcugu 76

<210> SEQ ID NO 511
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 511
cgacuccgcg cggaguccca uuaggggcgu uugucg 36

<210> SEQ ID NO 512
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 512
gggagagucg guagccucaa cgacuccgcg cggaguccca uuaggggcgu uugucgcuau 60
guggaaaugg cgcugu 76

<210> SEQ ID NO 513
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 513
cgacuccgcg cggagugcca acugguacgu uugucg 36

<210> SEQ ID NO 514
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 514
gggagagucg guagccucaa cgacuccgcg cggagugcca acugguacgu uugucgcuau 60
guggaaaugg cgcugu 76

<210> SEQ ID NO 515
<211> LENGTH: 36
<212> TYPE: RNA
<213> ORGANISM: Artificial Sequence
<220> FEATURE:

-continued

```
<223> OTHER INFORMATION: Synthetic Oligonucleotide

<400> SEQUENCE: 515

cgacuccgcg cggagucccu auaggggcgu uugucg                            36


<210> SEQ ID NO 516
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 516

gggagagucg guagccucaa cgacuccgcg cggagucccu auaggggcgu uugucgcuau    60

guggaaaugg cgcugu                                                   76


<210> SEQ ID NO 517
<211> LENGTH: 36
<212> TYPE: RNA
<213> ORGANISM: Artificial Sequence
<220> FEATURE:
<223> OTHER INFORMATION: Synthetic Oligonucleotide

<400> SEQUENCE: 517

cgacuccgcg cggagucccu aauggggcgu uugucg                            36


<210> SEQ ID NO 518
<211> LENGTH: 76
<212> TYPE: RNA
<213> ORGANISM: Artificial Sequence
<220> FEATURE:
<223> OTHER INFORMATION: Synthetic Oligonucleotide

<400> SEQUENCE: 518

gggagagucg guagccucaa cgacuccgcg cggagucccu aauggggcgu uugucgcuau    60

guggaaaugg cgcugu                                                   76
```

What is claimed is:

1. An aptamer having a nucleic acid sequence, wherein said aptamer comprises a stem-loop secondary structure which specifically binds to and inhibits at least one of VEGF-$A_{121}$ and VEGF-$A_{110}$, wherein said aptamer comprises, in a 5' to 3' direction: (i) a first side of a first base paired stem (S1); (ii) optionally, a first loop (L1); (iii) a first side of a second base paired stern (S2); (iv) a second loop (L2); (v) a second side of said second base paired stem (S2'); (vi) a third loop (L3); (vii) a first side of a third base paired stem (S3); (vii) a fourth loop (L4); (viii) a second side of said third base paired stem (S3'); (ix) a fifth loop (L5); and (x) a second side of said first base paired stem (S1'), wherein the aptamer comprises a consensus 5'-nucleic acid sequence comprising HNBYHDNNN*NNKNGCNNWGG-GRUNDNDHNWYCCCGNNNNNYNKVNW-3' (SEQ ID NO: 5), where H is A, C, or U; N is A, C, G, or U; Bis C, G, or U; Y is Cor U; N* is A, C, G, U, deleted entirely, or a non-nucleotidyl spacer 3 modification, a 6 carbon alkyl linker (1,6-hexanediol), or a spacer 9 (triethyleneglycol) modification; D is A, G, or U; K is G or U; W is A or U; R is A or G; and V is A, C, or G.

2. The aptamer of claim 1, wherein S1' comprises between two and eight nucleotides and forms at least one base pair with S1.

3. The aptamer of claim 1, wherein S1 comprises a consensus nucleic acid sequence comprising 5'-HN-BYHDNN-3', and S1' comprises a consensus nucleic acid sequence comprising 5'-NNYNKVNW-3', where His A, C, or U; N is A, C, G, or U; B is C, G, or U; Y is C or U; Dis A, G, or U; K is G or U; and W is A or U.

4. The aptamer of claim 1, wherein L1 comprises a consensus nucleic acid sequence comprising 5'-N *-3', wherein N* is A, C, G, U, a 3-carbon non-nucleotidyl spacer, two 3 carbon non-nucleotidyl spacers, a 6-carbon non-nucleotidyl spacer, or a 9-carbon non-nucleotidyl spacer.

5. The aptamer of claim 1, wherein S2 comprises a consensus nucleic acid sequence comprising 5'-NN-3', and S2' comprises a consensus nucleic acid sequence comprising 5'-NN-3', where N is A, C, G, or U.

6. The aptamer of claim 1, wherein L2 comprises up to four nucleotides.

7. The aptamer of claim 1, wherein L2 comprises a consensus nucleic acid sequence comprising 5'-KNGC-3', where K is G or U; and N is A, C, G or U.

8. The aptamer of claim 1, wherein S3' comprises between four and eight nucleotides and forms at least one base pair with said S1.

9. The aptamer of claim 1, wherein S3 comprises a consensus nucleic acid sequence comprising 5'-GRGRWN-3', and S3' comprises a consensus nucleic acid sequence comprising 5'-NHYCYC-3', where R is A or G; N is A, C, G, or U; W is A or U; and Y is C or U.

10. The aptamer of claim 1, wherein L3 comprises up to one nucleotide and comprises a consensus nucleic acid sequence comprising 5'-W-3', where W is A or U.

11. The aptamer of claim 1, wherein L4 comprises three, four, six, or eight nucleotides.

12. The aptamer of claim 1, wherein L4 comprises a consensus nucleic acid sequence comprising 5'-KNNNNW-3', where K is G or U; N is A, C, G, or U; and Wis A or U.

13. The aptamer of claim 1, wherein L5 comprises up to four nucleotides.

14. The aptamer of claim 1, wherein L5 comprises a consensus nucleic acid sequence comprising 5'-GNNN-3', where N is A, C, G, or U.

15. The aptamer of claim 1, wherein the 3-carbon non-nucleotidyl spacer is 1,3-propanediol.

16. The aptamer of claim 1, wherein the aptamer is conjugated to a polyethylene glycol (PEG) molecule.

17. A method of treating an ocular disease or disorder in a subject in need thereof, comprising administering to the subject an aptamer of claim 1, thereby treating said ocular disease or disorder.

18. The method of claim 17, wherein the ocular disease or disorder is selected from the group consisting of diabetic retinopathy, retinopathy of prematurity, central retinal vein occlusion, macular edema, choroidal neovascularization, neovascular age-related macular degeneration, myopic choroidal neovascularization, punctate inner choroidopathy, ocular histoplasmosis syndrome, familial exudative vitreoretinopathy, retinoblastoma, or combinations thereof.

19. The method of claim 17, wherein the subject is a human.

* * * * *